United States Patent
Chan et al.

(10) Patent No.: US 10,889,593 B2
(45) Date of Patent: *Jan. 12, 2021

(54) COMPOUNDS TARGETING PROTEINS, COMPOSITIONS, METHODS, AND USES THEREOF

(71) Applicant: BioTheryX, Inc., Chappaqua, NY (US)

(72) Inventors: Kyle W. H. Chan, San Diego, CA (US); Paul E. Erdman, San Diego, CA (US); Leah Fung, San Diego, CA (US); Frank Mercurio, Rancho Santa Fe, CA (US); Robert Sullivan, Vista, CA (US); Eduardo Torres, San Diego, CA (US)

(73) Assignee: BioTheryX, Inc., Chappaqua, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/457,409

(22) Filed: Jun. 28, 2019

(65) Prior Publication Data

US 2019/0322683 A1    Oct. 24, 2019

Related U.S. Application Data

(63) Continuation of application No. 16/011,090, filed on Jun. 18, 2018, now Pat. No. 10,336,771, which is a continuation of application No. 15/847,628, filed on Dec. 19, 2017, now Pat. No. 10,040,804.

(60) Provisional application No. 62/437,400, filed on Dec. 21, 2016, provisional application No. 62/485,563, filed on Apr. 14, 2017, provisional application No. 62/538,203, filed on Jul. 28, 2017.

(51) Int. Cl.
| | |
|---|---|
| *C07D 495/04* | (2006.01) |
| *C07D 519/00* | (2006.01) |
| *A61P 29/00* | (2006.01) |
| *A61P 19/02* | (2006.01) |
| *A61P 35/00* | (2006.01) |
| *A61P 1/00* | (2006.01) |
| *A61P 11/00* | (2006.01) |
| *A61P 25/28* | (2006.01) |
| *A61P 17/06* | (2006.01) |

(52) U.S. Cl.
CPC .............. *C07D 495/04* (2013.01); *A61P 1/00* (2018.01); *A61P 11/00* (2018.01); *A61P 17/06* (2018.01); *A61P 19/02* (2018.01); *A61P 25/28* (2018.01); *A61P 29/00* (2018.01); *A61P 35/00* (2018.01); *C07D 519/00* (2013.01)

(58) Field of Classification Search
CPC ........ C07D 495/04; A61P 17/06; A61P 25/28; A61P 19/02; A61P 1/00; A61P 29/00; A61P 35/00

See application file for complete search history.

(56) References Cited

U.S. PATENT DOCUMENTS

| | | |
|---|---|---|
| 5,153,192 A | 10/1992 | Dean et al. |
| 5,240,923 A | 8/1993 | Dean et al. |
| 5,276,009 A | 1/1994 | Muenster et al. |
| 5,378,703 A | 1/1995 | Dean et al. |
| 5,386,036 A | 1/1995 | Muenster et al. |
| 5,420,923 A | 5/1995 | Beyers, II et al. |
| 5,463,063 A | 10/1995 | Muller |
| 5,585,377 A | 12/1996 | Dean et al. |
| 5,605,914 A | 2/1997 | Muller |
| 5,679,670 A | 10/1997 | Dean et al. |
| 5,698,579 A | 12/1997 | Muller |
| 5,877,200 A | 3/1999 | Muller |
| 6,570,070 B1 | 5/2003 | Nakajima et al. |
| 6,906,245 B1 | 6/2005 | Nakajima et al. |
| 7,247,736 B2 | 7/2007 | Leban et al. |
| 7,485,777 B2 | 2/2009 | Nakajima et al. |
| 7,973,219 B2 | 7/2011 | Nakajima et al. |
| 8,183,260 B2 | 5/2012 | Zhang |
| 10,040,804 B2 | 8/2018 | Chan et al. |
| 10,336,771 B2 | 7/2019 | Chan et al. |

(Continued)

FOREIGN PATENT DOCUMENTS

| | | |
|---|---|---|
| CA | 2270448 C | 6/2012 |
| CN | 1597680 | 3/2005 |

(Continued)

OTHER PUBLICATIONS

Cancer and Metastasis Reviews (1998), 17(1), 91-106.*
Science (1999), vol. 286, 531-537.*
Amit et al., 2002, Axin-mediated CKI phosphorylation of β-catenin at Ser 45: a molecular switch for the Wnt pathway, Genes & Development, 16:1066-1076.
Brenner et al., 2008, The protective role of melanin against UV damage in human skin, Photochem. Photobiol., 84:539-549.
Brito et al., 2005, Polyglycine expansions in eRF3/GSPT1 are associated with gastric cancer susceptibility, Carcinogenesis, 26(12):2046-2049.

(Continued)

*Primary Examiner* — Rebecca L Anderson
(74) *Attorney, Agent, or Firm* — Lin Yu, Esq.; Juniv LLP

(57) ABSTRACT

The present invention provides compounds that modulate protein function, to restore protein homeostasis, including cytokine, CK1α, GSPT1, aiolos, and/or ikaros activity, and cell-cell adhesion. The invention provides methods of modulating protein-mediated diseases, such as cytokine-mediated diseases, disorders, conditions, or responses. Compositions, including in combination with other cytokine and inflammatory mediators, are provided. Methods of treatment, amelioration, or prevention of diseases, disorders, or conditions associated with a protein, such as diseases, disorders, and conditions associated with cytokines, including inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer, are provided.

27 Claims, 13 Drawing Sheets

(56) References Cited

U.S. PATENT DOCUMENTS

| | | | |
|---|---|---|---|
| 2005/0257284 | A1 | 11/2005 | Nakajima et al. |
| 2007/0027193 | A1 | 2/2007 | Leban et al. |
| 2010/0152240 | A1 | 6/2010 | Zhang |
| 2010/0184597 | A1 | 7/2010 | Nakajima et al. |
| 2012/0085992 | A1 | 4/2012 | Beaujuge et al. |
| 2016/0362397 | A1 | 12/2016 | Chan |

FOREIGN PATENT DOCUMENTS

| | | |
|---|---|---|
| CN | 103664916 | 3/2014 |
| CN | 105294536 | 2/2016 |
| CN | 105693745 | 6/2016 |
| EP | 1 964 842 | 9/2008 |
| EP | 2 093 228 | 8/2009 |
| JP | 10-264532 | 10/1998 |
| JP | 2000-159761 | 6/2000 |
| JP | 2001-190168 | 7/2001 |
| JP | 2001-120092 | 8/2001 |
| JP | 2004-018434 | 1/2004 |
| JP | 2008-273924 | 11/2008 |
| JP | 2014-047192 | 3/2014 |
| JP | 2014-047196 | 3/2014 |
| JP | 2014-178650 | 9/2014 |
| JP | 2014-185147 | 10/2014 |
| JP | 2015-013989 | 1/2015 |
| KR | 10-2015-0027344 | 3/2015 |
| KR | 10-2015-0113631 | 10/2015 |
| WO | WO 94/26745 | 11/1974 |
| WO | WO 91/15486 | 10/1991 |
| WO | WO 93/16701 | 9/1993 |
| WO | WO 95/01348 A2 | 1/1995 |
| WO | WO 95/01348 A3 | 1/1995 |
| WO | WO 95/33746 | 12/1995 |
| WO | WO 96/11201 | 4/1996 |
| WO | WO 97/30704 A2 | 8/1997 |
| WO | WO 97/30704 A3 | 8/1997 |
| WO | WO 98/33927 | 8/1998 |
| WO | WO 00/69828 | 11/2000 |
| WO | WO 00/69829 | 11/2000 |
| WO | WO 03/006443 A2 | 1/2003 |
| WO | WO 03/006443 A3 | 1/2003 |
| WO | WO 04/056797 | 7/2004 |
| WO | WO 04/065351 | 8/2004 |
| WO | WO 05/100351 | 10/2005 |
| WO | WO 06/065480 A2 | 6/2006 |
| WO | WO 06/065480 A3 | 6/2006 |
| WO | WO 07/036138 | 4/2007 |
| WO | WO 08/028168 A2 | 3/2008 |
| WO | WO 08/028168 A3 | 3/2008 |
| WO | WO 08/045529 | 4/2008 |
| WO | WO 08/058449 | 5/2008 |
| WO | WO 08/116881 | 10/2008 |
| WO | WO 08/127029 | 10/2008 |
| WO | WO 10/042674 | 4/2010 |
| WO | WO 10/052027 | 5/2010 |
| WO | WO 10/114971 | 10/2010 |
| WO | WO 12/030990 | 3/2012 |
| WO | WO 12/082893 A2 | 6/2012 |
| WO | WO 12/082893 A3 | 6/2012 |
| WO | WO 12/142460 | 10/2012 |
| WO | WO 12/156948 | 11/2012 |
| WO | WO 13/052153 | 4/2013 |
| WO | WO 14/057422 | 4/2014 |
| WO | WO 14/076650 | 5/2014 |
| WO | WO 14/076662 | 5/2014 |
| WO | WO 14/089324 | 6/2014 |
| WO | WO 14/204082 | 12/2014 |
| WO | WO 15/038671 A2 | 3/2015 |
| WO | WO 15/038671 A3 | 3/2015 |
| WO | 2016029004 A1 | 2/2016 |
| WO | WO 16/029843 | 3/2016 |
| WO | WO 16/061751 | 4/2016 |
| WO | WO 16/064935 | 4/2016 |
| WO | WO 16/191178 | 12/2016 |

OTHER PUBLICATIONS

Chauvin et al., Aug. 2007, Human eukaryotic release factor 3a depletion causes cell cycle arrest at $G_1$ phase through inhibition of the mTOR pathway, Mol. Cell. Bio., 27(16):5619-5629.
Cheong et al., 2011, Casein kinase 1: complexity in the family, J. Biochem. Cell Biol., 43:465-469.
Costin et al., 2007, Human skin pigmentation: melanocytes modulate skin color in response to stress, FASEB J., 21(4):976-994.
Cui et al., Mar. 9, 2007, Central role of p53 in the suntan response and pathologic hyperpigmentation, Cell, 128:853-864.
D'Orazio et al., Sep. 21, 2006, Topical drug rescue stratecy and skin protection based on the role of Mc1r in UV-Induced tanning, Nature, 443:340-344.
Ding et al., 2013, Discovery of RG7388, a potent and selective p53-MDM2 inhibitor in clinical development, Journal of Medicinal Chemistry, 56(14):5979-5983, and Supplementary Material.
Ding et al., Dec. 22, 2015, BRD4 is a novel therapeutic target for liver fibrosis, Proceedings of the National Academy of Sciences of the United States of America, 112(51):15713-15718.
Elyada et al., Feb. 17, 2011, CK1α ablation highlights a critical role for p53 in invasiveness control, Nature, 470:409-413.
Gorczynski et al., 2007, Allosteric inhibition of the protein-protein interaction between the leukemia-associated proteins RUnx1 and CBFβ, Chemistry & Biology, 14(10):1186-1197.
Hashimoto et al., 2012, Translation termination factor eRF3 is targeted for caspase-mediated proteolytic cleavage and degradation during DNA damage-induced apoptosis, Apoptosis, 17:1287-1299.
Huart et al., Nov. 20, 2009, CK1α plays a central role in mediating MDM2 control of p53 and E2F-1 protein stability, J. Biol. Chem., 284(47):32384-32394.
Hyter et al., Mar. 2013, Endothelin-1 is a transcriptional target of p53 in epidermal keratinocytes and regulates UV induced melanocyte homeostasis, Pigment. Cell Melanoma Res., 26(2):247-258.
Ishii et al., Jan. 27, 2017, A novel Rac1-GSPT1 signaling pathway controls astrogliosis following central nervous system injury, J. Biol. Chem., 292(4):1240-1250.
Jung et al., Apr. 9, 2010, Structure-activity relationship for thiohydantoin androgen receptor antagonists for castration-resistant prostate cancer ICRPC), Journal of Medicinal Chemistry, 53(7):2779-2796.
Kadekaro et al., 2003, Cutaneous photobiology. The melanocyte vs. the sun: who will win the final round? Pigment Cell Res., 16:434-447.
Kesarwani et al., 2015, Targeting substrate-site in Jak2 kinase prevents emergence of genetic resistance, Scientific Reports, 5:14538.
Kondo, 1999, The roles of keratinocyte-derived cytokines in the epidermis and their possible responses to UVA-irradiation, J. Invest. Dermatol. Symp. Proc., 4:177-183.
Levine et al., Oct. 2009, The first 30 years of p53: growing ever more complex, Nat. Rev. Cancer, 9(10):749-758.
Li et. al., Jan. 2014, eRF3b, a biomarker for hepatocellular carcinoma, influences cell cycle and phosphoralation status of 4E-BP1, PLOS One, 9(1):e86371.
Lountos et al., Dec. 2011, Structural characterization of inhibitor complexes with check point kinase 2(Chk2), a drug target for cancer therapy, J. Struct. Biol., 176(3):292-301.
Malta-Vacas et al., 2009, Differential expression of GSPT1 $GGC_n$ alleles in cancer, Canc. Geneti. Cytogen., 195:132-142.
Matysklela et al., Jul. 14, 2016, A novel cereblon modulator recruits GSPT1 to the CRL4$^{CRBN}$ ubiquitin ligase, Nature, 535:252-257.
Millan et al., 2011, Design and synthesis of inhaled p38 inhibitors for the treatment of chronic obstructive pulmonary disease, J. Med. Chem., 54:7797-7814, and supporting information.
Miri et al., 2012, GGCn polymorphism of eRF3a/GSPT1 gene and breast cancer susceptibility, Med. Oncol., 29:1581-1585.
Mitra et al., Nov. 15, 2012, A UV-independent pathway to melanoma carcinogenesis in the redhair-fairskin background, Nature, 491:449-453.
Murase et al., Feb. 13, 2009, The essential role of p53 in hyperpigmentation of the skin via regulation of paracrine melanogenic cytokine receptor signaling, J. Biol. Chem., 284(7):4343-4353.

(56) References Cited

OTHER PUBLICATIONS

Nasti et al., 2015, MC1R, eumelanin and pheomelanin: their role in determining the susceptibility to skin cancer, Photochem. Photobiol., 91:188-200.
Natarajan et al., Jul. 2014, Multifaceted pathways protect human skin from UV radiation, Nat. Chem. Biol., 10:542-551.
Ogmundsdottir et al., 2014, Selection, p53, and pigmentation, Pigment Cell Melanoma Res., 27:154-155.
Patch et al., 2011, Identification of diaryl ether-based ligands for estrogen-related receptor α as potential antidiabetic agents, Journal of Medicinal Chemistry, 54(3):788-808, and Supplementary Information.
Prota, 1992, The role of peroxidase in melanogenesis revisited, Pigment. Cell Res., Suppl. 2:25-31.
Rehan et al., Oct. 2014, Computational insights into the inhibitory mechanism of human AKT1 by an orally active inhibitor, MK-2206, PLoS One, 9(10):e109705/1-e109705/12.
Rodriguez-Gonzalez et al., 2008, Targeting steroid hormone receptors for ubiquitination and degradation in breast and prostate cancer, Oncogene, 27:7201-7211.
Sakamoto, et al., 2003, Development of Protacs to target cancer-promoting proteins for ubiquitination and degradation, Mol Cell Proteomics, 2(12):1350-1358.
Schenkel et al., 2011, Discovery of potent and highly selective thienopyridine janus kinase 2 inhibitors, J. Med. Chem., 54(24):8440-8450, and Supporting Information.
Schittek et al., 2014 Biological functions of casein kinase 1 isoforms and putative roles in tumorigenesis, Mol. Cancer., 13:231.
Schneekloth et al., 2008, Targeted intracellular protein degradation induced by a small molecule: en route to chemical proteomics, Bioorg. Med. Chem. Lett., 18:5904-5908.
Schneider et al., Oct. 13, 2014, Role of casein kinase 1A1 in the biology and targeted therapy of del(5q) MDS, Cancer Cell, 26:509-520.
Slominski et al., 2004, Melanin pigmentation in mammalian skin and its hormonal regulation, Physiol. Rev., 84:1155-1228.
Stern, Mar. 2010, Prevalence of a history of skin cancer in 2007, Arch Dermatol., 146(3):279-282.
Thody et al., 1991, Pheomelanin as well as eumelanin is present in human epidermis, J. Invest. Dermatol., 97:340-344.
Tokarski et al., Jun. 1, 2006, The structure of dasatinib (BMS-354825) bound to activated ABL kinase domain elucidates its inhibitory activity against imatinib-resistant ABL mutants, Cancer Research, 66(11):5790-5797.
Van Eis et al., 2011; 2,6-Naphthyridines as potent and selective inhibitors of the novel protein kinase C isozymes, Biorg. Med. Chem. Lett., 21(24):7367-7372.
Vassilev et al., Feb. 6, 2004, In vivo activation of the p53 pathway by small-molecule antagonists of MDM2, Science, 303:844-848.
Wright et al., 2007, Newer potential biomarkers in prostate cancer, Rev. Urol., 9(4):207-213.
International Search Report and Written Opinion dated May 4, 2018 in application No. PCT/US2017/067353.

* cited by examiner

COMPOUNDS TARGETING PROTEINS, COMPOSITIONS, METHODS, AND USES THEREOF

CROSS-REFERENCE TO RELATED APPLICATIONS

This application is a continuation of U.S. patent application Ser. No. 16/011,090, filed Jun. 18, 2018 and to be issued as U.S. Pat. No. 10,336,771, which is a continuation of U.S. patent application Ser. No. 15/847,628, filed Dec. 19, 2017, now U.S. Pat. No. 10,040,804, which claims the benefit of priority to U.S. Provisional Patent Application Nos. 62/437,400 filed Dec. 21, 2016, 62/485,563 filed Apr. 14, 2017, and 62/538,203 filed Jul. 28, 2017, all of which are incorporated by reference herein in their entireties.

BACKGROUND OF THE INVENTION

Field of the Invention

Compounds, methods of making such compounds, pharmaceutical compositions and medicaments comprising such compounds, and methods of using such compounds to treat, prevent or diagnose diseases, disorders, or conditions associated with protein malfunction are provided.

Description of the Related Technology

Aberrant protein function, and/or protein imbalance is a hallmark of many disease states. For example, the functioning of the immune system is finely balanced by the activities of pro-inflammatory and anti-inflammatory mediators or cytokines. Some cytokines promote inflammation (pro-inflammatory cytokines), whereas other cytokines suppress the activity of the pro-inflammatory cytokines (anti-inflammatory cytokines). For example, IL-4, IL-10, and IL-13 are potent activators of B lymphocytes, and also act as anti-inflammatory agents. They are anti-inflammatory cytokines by virtue of their ability to suppress genes for pro-inflammatory cytokines such as IL-1, TNF, and chemokines.

Unregulated activities of these mediators can lead to the development of serious inflammatory conditions. For example, autoimmune diseases arise when immune system cells (lymphocytes, macrophages) become sensitized against the "self." Lymphocytes, as well as macrophages, are usually under control in this system. However, a misdirection of the system toward the body's own tissues may happen in response to still unexplained triggers. One hypothesis is that lymphocytes recognize an antigen which mimics the "self" and a cascade of activation of different components of the immune system takes place, ultimately leading to tissue destruction. Genetic predisposition has also been postulated to be responsible for autoimmune disorders.

Tumor necrosis factor-alpha (TNF-alpha, or TNF-α) and interleukin-1 (IL-1) are pro-inflammatory cytokines that mediate inflammatory responses associated with infectious agents and other cellular stresses. Overproduction of these cytokines is believed to underlie the progression of many inflammatory diseases including rheumatoid arthritis (RA), Crohn's disease, inflammatory bowel disease, multiple sclerosis, endotoxin shock, osteoporosis, Alzheimer's disease, congestive heart failure, and psoriasis among others.

Recent data from clinical trials support the use of protein antagonists of cytokines, for example soluble TNF-α receptor fusion protein (etanercept) or the monoclonal TNF-α antibody (infliximab), for the treatment of rheumatoid arthritis, Crohn's disease, juvenile chronic arthritis and psoriatic arthritis. Thus, the reduction of pro-inflammatory cytokines such as TNF-α and interleukin-1 (IL-I) has become an accepted therapeutic approach for potential drug intervention in these conditions.

Moreover, IL-2 is now FDA approved for the treatment of renal cancer and melanoma patients, with durable, complete remissions achieved with IL-2 up to 148 months. However, the short half-life of IL-2 in serum requires that large amounts of IL-2 be injected to achieve therapeutic levels. Many attempts have been made to minimize side effects of systemic IL-2 treatment, for example, introducing IL-2 directly into the tumor, though this complicates treatment, and has largely been unsuccessful.

Local delivery of cytokines is appealing compared to systemic delivery for a variety of reasons. It takes advantage of the natural biology of cytokines that have evolved to act locally in a paracrine or autocrine fashion. Local expression also dramatically minimizes many of the side effects of systemic delivery of cytokines. Thus, compounds and methods to increase local expression of IL-2 would be better tolerated than high dose IL-2 treatment, which would expand therapeutic utility of strategies that increase IL-2.

Additional targets include several candidate genes involved in apoptosis and cell survival, including the translation termination factor GSPT1 (eRF3a), casein kinase 1α (CK1α), and the zinc-finger transcription factors aiolos, helios, and ikaros. Aiolos, helios, and ikaros are transcription factors whose expression is restricted to lymphoid lineages. For example, aiolos binds to the Bcl-2 promoter, and also interacts with the Bcl-2 and Bcl-XL proteins to promote cell survival. Upregulation of aiolos expression, for example, can reduce apoptosis of HIV-1 infected cells.

Likewise, expression of aiolos in lung and breast cancers predicts significantly reduced patient survival. Aiolos decreases expression of a large set of adhesion-related genes, disrupting cell-cell and cell-matrix interactions, facilitating metastasis. Aiolos may also function as an epigenetic driver of lymphocyte mimicry in certain metastatic epithelial cancers. Similarly, aberrant ikaros and helios expression may promote Bcl-XL expression, driving the development of hematopoetic malignancies. Thus, downregulation of aiolos, ikaros, and/or helios may reduce or eliminate metastasis.

GSPT1 mediates stop codon recognition and facilitates release of a nascent peptide from the ribosome and is also involved in several other critical cellular processes, such as cell cycle regulation, cytoskeleton organization and apoptosis. Accordingly, decreased levels of GSPT1 may impair control of cell proliferation and facilitate cell migration and scar formation. Indeed, GSPT1 has been implicated as an oncogenic driver of several different cancer types, including breast cancer, hepatocellular carcinoma, gastric cancer, and prostate cancer. See, e.g., Brito, et al., *Carcinogenesis*, Vol. 26, No. 12, pp. 2046-49 (2005); Brito, et al., *Canc. Geneti. Cytogen.*, Vol. 195, pp. 132-42 (2009); Tavassoli, et al., *Med. Oncol.*, Vol. 29, pp. 1581-85 (2011); *Wright and Lange, Rev. Urol.*, Vol. 9, No. 4, pp. 207-213 (2007); Hoshino, et al., *Apoptosis*, Vol. 17, pp. 1287-99 (2012); Liu, et. al., *PLOS One*, Vol. 9, No. 1, e86371 (2014); and Jean-Jean, et al., *Mol. Cell. Bio.*, Vol. 27, No. 16, pp. 5619-29 (2007). GSPT1 also contributes to glial scar formation and astrogliosis after a central nervous system (CNS) injury. See, e.g., Ishii et al., *J. Biol. Chem.*, Vol. 292, No. 4, pp. 1240-50 (2017).

Casein kinase 1α (CK1α) is a component of the β-catenin-degradation complex and a critical regulator of the Wnt signaling pathway, and its ablation induces both Wnt and p53 activation. Schittek and Sinnberg, *Mol. Cancer.* 2014, 13, 231; Cheong and Virshup, *J. Biochem. Cell Biol.* 2011, 43, 465-469; Elyada et al., *Nature* 2011, 470, 409-413. CK1α phosphorylates β-catenin, which is subsequently further phosphorylated by GSK-3β. This destabilizes β-catenin and marks the protein for ubiquitination and proteasomal degradation. Thus, CK1α functions as a molecular switch for the Wnt pathway. Amit et al., *Genes Dev.* 2002, 16, 1066-1076. CK1α is critical for embryogenesis and plays an important role in tissue development and response to DNA damage, at least partly coordinated with p53. Elyada et al., *Nature* 2011, 470, 409-413; Schneider et al., *Cancer Cell* 2014, 26, 509-520. Levine and Oren, *Nat. Rev. Cancer* 2009, 9, 749-758.

Indeed, CK1α also phosphorylates p53, which inhibits binding to MDM2 (a p53 inhibitor) and stabilizes p53's binding interactions with the transcriptional machinery. Huart, et al., *J. Biol. Chem.* 2009, 284, 32384-32394. Thus, inhibiting CK1α activity increases cellular levels of p53. This is of particular importance for skin cancer, which has killed more people since 1980 than all other types of cancer combined. Stern, *Arch Dermatol.* 2010, 146, 279-282.

In the skin, p53 also acts as a central player against UV damage via the p53/POMC/α-MSH/MC1R/MITF skin tanning pathway and through the DNA repair/cell cycle arrest/apoptotic pathway. Cui et al., *Cell* 2007, 128, 853-864; Ogmundsdottir and Steingrimsson, *Pigment. Cell Melanoma Res.* 2014, 27, 154-155. UV radiation can injure the skin both by indirect cellular damage via the generation of reactive oxygen species and by direct damage to the structure of DNA. This damage may cause a sunburn reaction and ultimately the development of skin cancers. Keratinocytes in the epidermis are sensitive to UV radiation and are the major responders in the skin. Upon exposure to UV radiation, keratinocytes produce various paracrine factors (for example, α-melanocyte stimulating hormone (α-MSH), adrenocorticosteroid hormone (ACTH), endothelin-1 (Edn1) and Kit) that activate adjacent melanocytes to increase melanin synthesis. Natarajan et al., *Nat. Chem. Biol.* 2014, 10, 542-551; Kondo, *J. Invest. Dermatol. Symp. Proc.* 1999, 4, 177-183; Costin and Hearing, *FASEB J.* 2007, 21, 976-994; Costin and Hearing, *FASEB J.* 2007, 21, 976-994; Cui et al., *Cell* 2007, 128, 853-864; Nasti and Timares, *Photochem. Photobiol.* 2015, 91, 188-200; Slominski et al., *Physiol. Rev.* 2004, 84, 1155-1228; Murase et al., *J. Biol. Chem.* 2009, 284, 4343-4353; Hyter et al., *Pigment. Cell Melanoma Res.* 2013, 26, 247-258; D'Orazio et al., *Nature* 2006, 443, 340-344. In particular, p53 promotes UV-induced skin pigmentation by stimulating the transcription of a melanogenic cytokine, POMC (pro-opiomelanocortin), in keratinocytes.

Skin hyperpigmentation, resulting from the increased synthesis of melanin in melanocytes followed by the distribution of melanin to neighboring keratinocytes, is one of the biological responses to exposure to UV radiation. Melanin acts as a natural sunscreen that directly protects against UV and visible light radiation from penetrating to deep skin layers, where proliferating cells reside, as well as acting as a potent antioxidant and free-radical scavenger. Kadekaro et al., *Pigment Cell Res.* 2003, 16, 434-447. Individuals with darker skin generally have a reduced incidence of UV-induced skin cancers, whereas individuals with lighter skin are more prone to UV-induced damage and tumor formation and have weak tanning responses. Brenner and Hearing, *Photochem. Photobiol.* 2008, 84, 539-549.

Melanocytes produce two distinct types of melanin pigments: black-brown eumelanin that is prevalent in individuals with black and/or brown hair, and yellow-reddish pheomelanin that is primarily produced in individuals with red hair and freckles. Costin and Hearing, *FASEB J.* 2007, 21, 976-994; Slominski et al., *Physiol. Rev.* 2004, 84, 1155-1228; Prota, *Pigment. Cell Res.* 1992, Suppl. 2, 25-31. Pheomelanin is also produced in the skin of individuals that don't have red hair and freckles. Thody et al., *J. Invest. Dermatol.* 1991, 97, 340-344. The beneficial effects of melanin are mainly due to the presence of eumelanin that absorbs most of the UV and scavenges the UV-generated free radicals, whereas pheomelanin is known to be carcinogenic. Brenner and Hearing, Photochem. Photobiol. 2008, 84, 539-549; Mitra et al., *Nature* 2012, 491, 449-453.

Therefore, there is a need for an effective method to increase the beneficial level of eumelanin selectively to prevent UV-induced DNA damage and skin cancers. Expression levels of proteins transcriptionally upregulated by p53 are demonstrably higher in pigmented skin areas relative to sun-protected controls.

One mechanism to disrupt protein drivers of disease is to decrease the cellular concentration of these proteins. For example, proteolytic degradation of cellular proteins is essential to normal cell function. Hijacking this process, by targeting specific disease-related proteins, presents a novel mechanism for the treatment of disease. The irreversible nature of proteolysis makes it well-suited to serve as a regulatory switch for controlling unidirectional processes. For example, increasing p53 levels by targeting CK1α for degradation may improve the pigmentation response to UV exposure, decreasing the risk of skin cancer.

Ubiquitin-mediated proteolysis begins with ligation of one or more ubiquitin molecules to a particular protein substrate. Ubiquitination occurs through the activity of ubiquitin-activating enzymes (E1), ubiquitin-conjugating enzymes (E2), and ubiquitin-protein ligases (E3), acting sequentially to attach ubiquitin to lysine residues of substrate proteins. The E3 ligases confer specificity to ubiquitination reactions by binding directly to particular substrates.

SUMMARY OF THE INVENTION

The compounds disclosed in the present application have been discovered to exert surprising and unexpected biological effects. Some embodiments provide protein-targeting compounds ("targeting groups"). Some embodiments provide chimeric compounds comprising a targeting group, a linker group, and an E1-binding group. Some embodiments provide chimeric compounds comprising a targeting group, a linker group, and an E2-binding group. Some embodiments provide chimeric compounds comprising a targeting group, a linker group, and an E3-binding group. Some embodiments provide chimeric compounds comprising a targeting group, a linker group, and a combination of one or more E1-, E2-, or E–3-binding groups.

Some embodiments provide compounds of Formula (II):

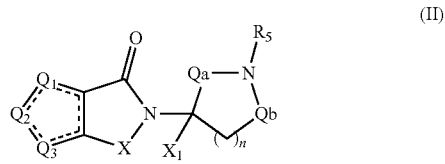

or pharmaceutically acceptable salts or solvates thereof.

In some embodiments, $Q_1$, $Q_2$, and $Q_3$ are each independently $CR_1$, $CR_2$, or —S—. In some embodiments, at least one of $Q_1$, $Q_2$, and $Q_3$ is $CR_1$ or $CR_2$. In some embodiments, each of $Q_1$, $Q_2$, and $Q_3$ cannot be —S—. In some embodiments, at least one of $Q_1$, $Q_2$, and $Q_3$, is $CR_1$ or $CR_2$.

In some embodiments, $R_1$ and $R_2$ are each independently H, deuterium, hydroxyl, halogen, cyano, nitro, optionally substituted amino, optionally substituted C-amido, optionally substituted N-amido, optionally substituted urea, optionally substituted ester, optionally substituted $C_1$-$C_6$ alkoxy, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_6$-$C_{10}$ aryl, optionally substituted 3 to 10-membered heterocyclyl, optionally substituted 5 to 10-membered heteroaryl,

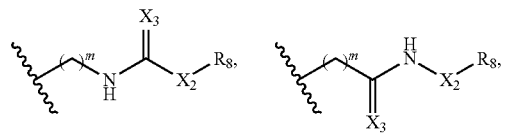

or L-Y. In some embodiments, when one of $R_1$ or $R_2$ is

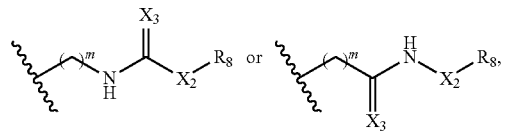

the other of $R_1$ or $R_2$ is not L-Y;

In some embodiments, $R_5$ is H, deuterium, optionally substituted $C_1$-$C_6$ alkyl, optionally substituted $C_2$-$C_6$ alkenyl.

In some embodiments, X is $C(R_5)_2$, $CH(R_5)$, $CH_2$, C=O, or C=S; when $Q_3$ is —S—, X is $C(R_5)_2$, $CH(R_5)$ or $CH_2$.

In some embodiments, $X_1$ is selected from H, deuterium, hydroxyl, halogen, cyano, nitro, optionally substituted amino, optionally substituted C-amido, optionally substituted N-amido, optionally substituted ester, optionally substituted $C_1$-$C_6$ alkoxy, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_6$-$C_{10}$ aryl, optionally substituted 3 to 10-membered heterocyclyl, and optionally substituted 5 to 10-membered heteroaryl.

In some embodiments, $X_1$ is selected from H, deuterium, halogen, and optionally substituted $C_1$-$C_6$ alkyl.

In some embodiments, $X_2$ is selected from $(CH_2)_a$, $(CF_2)_a$, $(CD_2)_a$, C=O, NH, N—(optionally substituted $C_1$-$C_6$ alkyl), and $[(CH_2)_p—O—(CH_2)_q]_r$.

In some embodiments, $X_3$ is selected from O, NH, and S.

In some embodiments, a is 0, 1, 2, 3, 4, 5, 6, 7, 8, 9, or 10. In some embodiments, n is 1, 2, or 3. In some embodiments, m is 1, 2, 3, 4, or 5. In some embodiments, p and q are independently 0, 1, 2, 3, 4, 5, or 6. In some embodiments, r is 0, 1, 2, 3, or 4.

In some embodiments, Qa and Qb are each independently C=O, C=S, or $CH_2$. In some embodiments, when n is 2, then $Q_3$ is —S—, or when n is 2, then $R_1$ is substituted $C_1$-$C_6$ alkyl, optionally substituted $C_3$-$C_8$ cycloalkyl, optionally substituted 3 to 10-membered heterocyclyl, optionally substituted 5 to 10-membered heteroaryl, optionally substituted urea, or L-Y. In some embodiments, when n is 2, then $Q_3$ is —S—. In some embodiments, when n is 2, then $R_1$ is substituted $C_1$-$C_6$ alkyl, optionally substituted $C_3$-$C_8$ cycloalkyl, optionally substituted 3 to 10-membered heterocyclyl, optionally substituted 5 to 10-membered heteroaryl, or L-Y. In some embodiments, when n is 2 and $Q_1$ is —S—, then one of $R_1$ or $R_2$ is

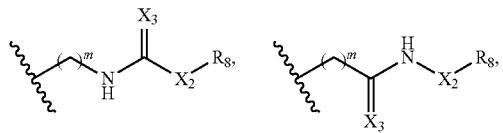

optionally substituted urea, or L-Y. In some embodiments, when n is 2 and $Q_1$ is —S—, then one of $R_1$ or $R_2$ is

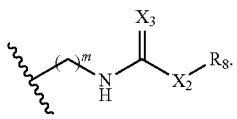

In some embodiments, when n is 2 and $Q_1$ is —S—, then one of $R_1$ or $R_2$ is

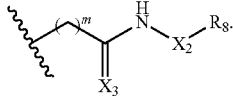

In some embodiments, when n is 2 and $Q_1$ is —S—, then one of $R_1$ or $R_2$ is L-Y. In some embodiments, wherein n is 2 and $Q_2$ is —S—, then one of $R_1$ or $R_2$ is

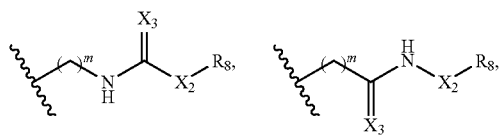

optionally substituted urea, or L-Y. In some embodiments, when n is 2 and $Q_2$ is —S—, then one of $R_1$ or $R_2$ is

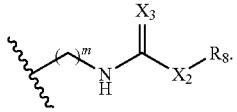

In some embodiments, when n is 2 and $Q_2$ is —S—, then one of $R_1$ or $R_2$ is

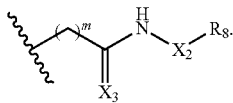

In some embodiments, when n is 2 and $Q_2$ is —S—, then one of $R_1$ or $R_2$ is L-Y. In some embodiments, when n is 2 and $Q_2$ is —S—, then one of $R_1$ or $R_2$ is optionally substituted urea.

In some embodiments, L is —$Z_1$—($R_6$—O—$R_6$)$_t$—$Z_2$—; —$Z_1$—($R_6$—NH—$R_6$)$_t$—$Z_2$—; —$Z_1$—($R_6$—S—$R_6$)$_t$—$Z_2$—; —$Z_1$—($R_6$—(C=O)—$R_6$)$_t$—$Z_2$—; —$Z_1$—($R_6$—(CO$_2$)—$R_6$)$_t$—$Z_2$—; —$Z_1$—($R_6$—(NHCO)—$R_6$)$_t$—$Z_2$—; —$Z_1$—($R_6$—(CONH)—$R_6$)$_t$—$Z_2$—; —$Z_1$—($R_6$—(SO)—$R_6$)$_t$—$Z_2$—; —$Z_1$—($R_6$—(SO$_2$)—$R_6$)$_t$—$Z_2$—; —$Z_1$—($R_6$—NH(C=NH)NH—$R_6$)$_t$—$Z_2$—; —$Z_1$—($R_6$—(NHSO$_2$)—$R_6$)$_t$—$Z_2$—; —$Z_1$—($R_6$—(SO$_2$NH)—$R_6$)$_t$—$Z_2$—; or —$Z_1$—($R_6$-$R_7$—$R_6$)$_t$—$Z_2$—. In some embodiments, each t is independently 1, 2, 3, 4, 5, 6, 7, or 8.

In some embodiments, L is —$Z_1$—($R_6$—O—$R_6$)$_t$—$Z_2$—; —$Z_1$—($R_6$—NH—$R_6$)$_t$—$Z_2$—; —$Z_1$—($R_6$—S—$R_6$)$_t$—$Z_2$—; —$Z_1$—($R_6$—(C=O)—$R_6$)$_t$—$Z_2$—; —$Z_1$—($R_6$—(CO$_2$)—$R_6$)$_t$—$Z_2$—; —$Z_1$—($R_6$—(NHCO)—$R_6$)$_t$—$Z_2$—; —$Z_1$—($R_6$—(CONH)—$R_6$)$_t$—$Z_2$—; —$Z_1$—($R_6$—(SO)—$R_6$)$_t$—$Z_2$—; —$Z_1$—($R_6$—(SO$_2$)—$R_6$)$_t$—$Z_2$—; —$Z_1$—($R_6$—(NHSO$_2$)—$R_6$)$_t$—$Z_2$—; —$Z_1$—($R_6$—(SO$_2$NH)—$R_6$)$_t$—$Z_2$—; —$Z_1$—($R_6$—NH(C=O)NH—$R_6$)$_t$—$Z_2$—; —$Z_1$—($R_6$—NH(C=NH)NH—$R_6$)$_t$—$Z_2$—; —$Z_1$—($R_6$—NH(C=S)NH—$R_6$)$_t$—$Z_2$—; or —$Z_1$—($R_6$-$R_7$—$R_6$)$_t$—$Z_2$—. In some embodiments, each t is independently 1, 2, 3, 4, 5, 6, 7, or 8.

In some embodiments, $Z_1$ and $Z_2$ are each independently —CH$_2$—; —O—; —S—; S=O; —SO$_2$—; C=O; —CO$_2$—; —NH—; —NH(CO)—; —(CO)NH—; —NH—SO$_2$—; —SO$_2$—NH—; —$R_6$CH$_2$—; —$R_6$O—; —$R_6$S—; $R_6$—S=O; —$R_6$SO$_2$—; $R_6$—C=O; —$R_6$CO$_2$—; —$R_6$NH—; —$R_6$NH(CO)—; —$R_6$(CO)NH—; —$R_6$NH—SO$_2$—; —$R_6$SO$_2$—NH—; —CH$_2$R$_6$—; —OR$_6$—; —SR$_6$—; —S=O—R$_6$; —SO$_2$R$_6$—; —C=O—R$_6$; —CO$_2$R$_6$—; —NHR$_6$—; —NH(CO)R$_6$—; —(CO)NHR$_6$—; —NH—SO$_2$R$_6$—; or —SO$_2$—NHR$_6$—.

In some embodiments, each $R_6$ is absent, or independently $C_1$-$C_6$ alkyl, $C_2$-$C_6$ alkenyl, $C_2$-$C_6$ alkynyl, $C_6$-$C_{10}$ aryl, 3 to 10-membered heterocyclyl, or 5 to 10-membered heteroaryl. In some embodiments, $R_7$ is optionally substituted $C_3$-$C_8$ cycloalkyl, optionally substituted $C_6$-$C_{10}$ aryl, optionally substituted 3 to 10-membered heterocyclyl, or optionally substituted 5 to 10-membered heteroaryl. In some embodiments, $R_8$ is selected from optionally substituted $C_3$-$C_{10}$ cycloalkyl, optionally substituted $C_6$-$C_{10}$ aryl, optionally substituted 5 to 10-membered heteroaryl, optionally substituted 3 to 10-membered heterocyclyl, optionally substituted $C_1$-$C_{10}$ alkyl, $R_{8A}$, and $R_{8B}$. In some embodiments, $R_{8A}$ is selected from hydroxyl, halogen, cyano, nitro, unsubstituted amino, mono-substituted amino, di-substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$-$C_6$ alkoxy, optionally substituted $C_1$-$C_6$ haloalkoxy, optionally substituted $C_3$-$C_{10}$ cycloalkyl($C_1$-$C_6$ alkyl), optionally substituted $C_6$-$C_{10}$ aryl($C_1$-$C_6$ alkyl), optionally substituted 5 to 10 membered heteroaryl($C_1$-$C_6$ alkyl), and optionally substituted 3 to 10 membered heterocyclyl($C_1$-$C_6$ alkyl). In some embodiments, $R_{8A}$ is selected from optionally substituted $C_3$-$C_{10}$ cycloalkyl($C_1$-$C_6$ alkyl), optionally substituted $C_6$-$C_{10}$ aryl($C_1$-$C_6$ alkyl), optionally substituted 5 to 10 membered heteroaryl($C_1$-$C_6$ alkyl), and optionally substituted 3 to 10 membered heterocyclyl($C_1$-$C_6$ alkyl). In some embodiments, $R_{8B}$ is $Y_1$.

In some embodiments, Y is

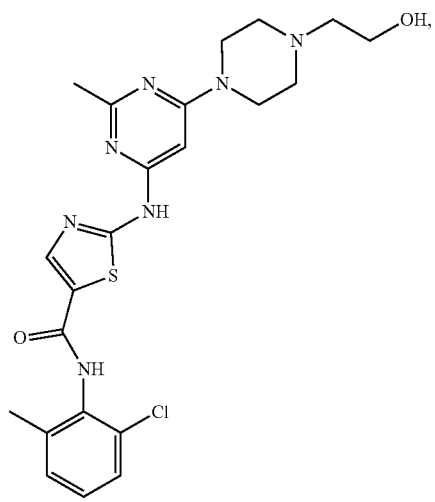

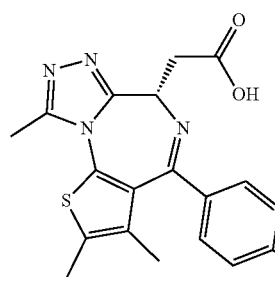

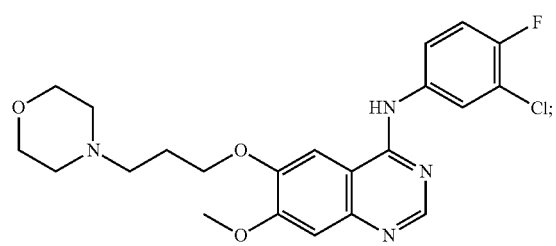

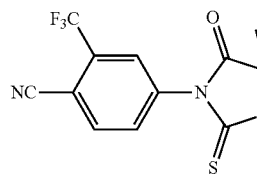

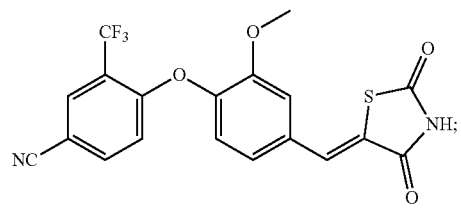

-continued
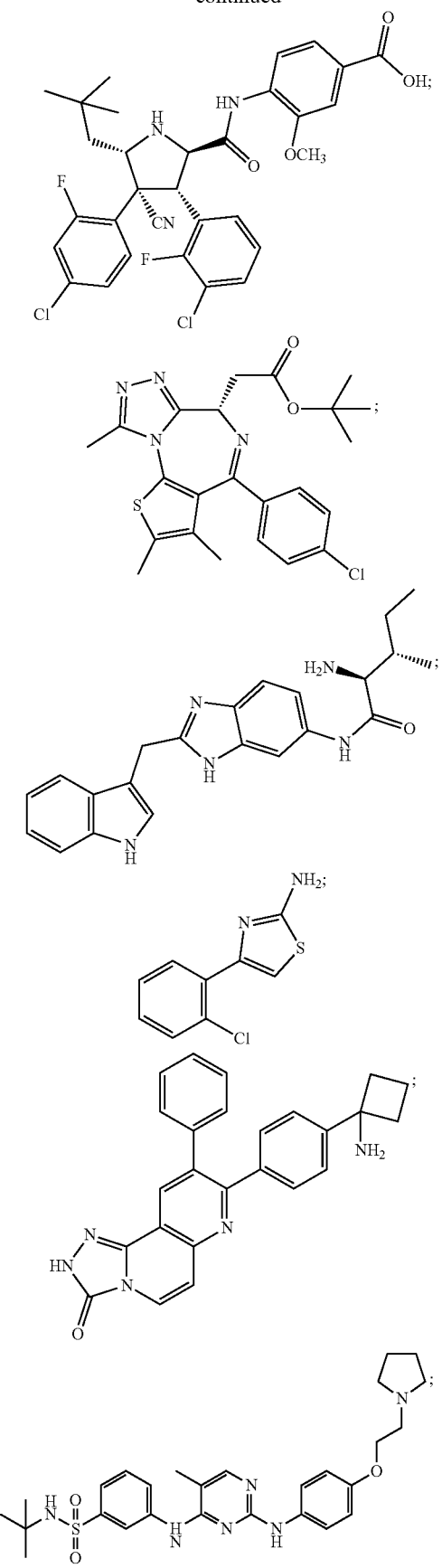
-continued
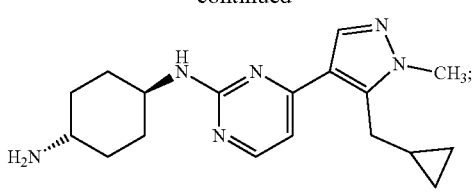
wherein Y is derivatized to attach to L.
In some embodiments, $Y_1$ is
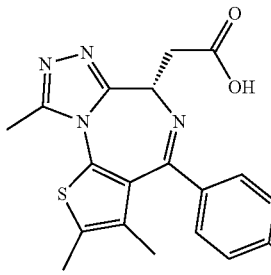
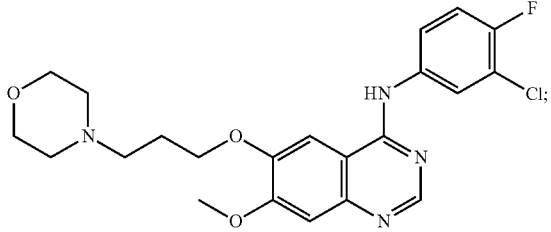
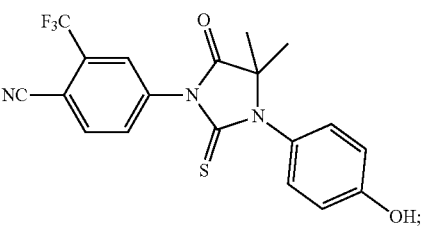

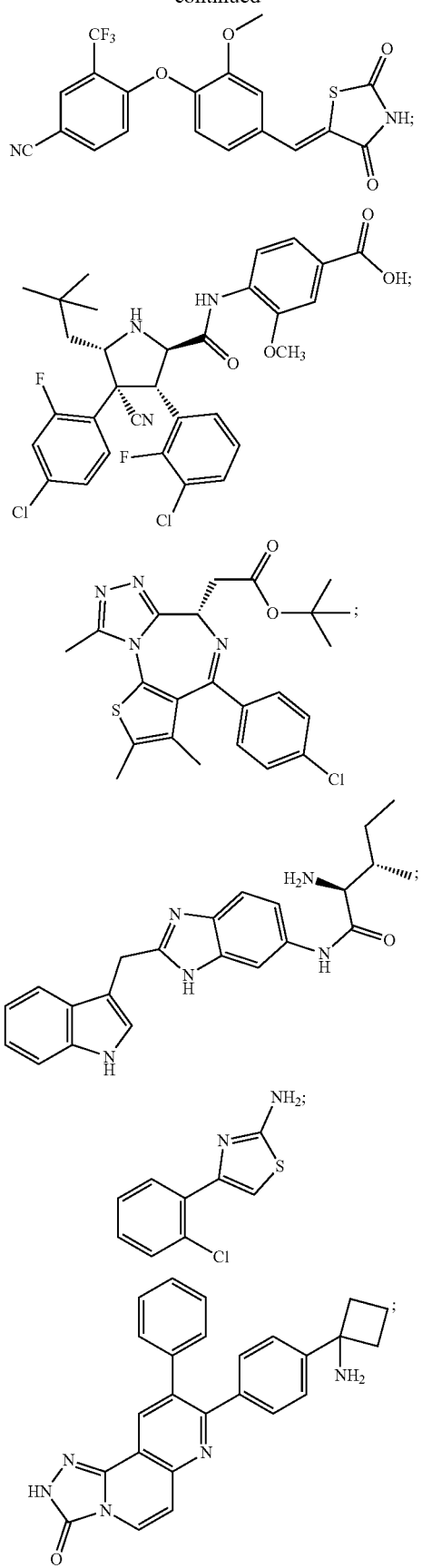

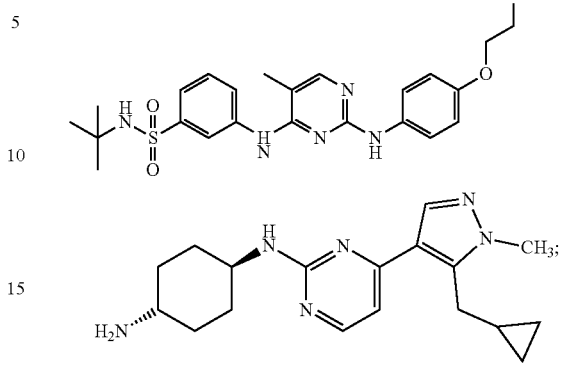

wherein $Y_1$ is derivatized to attach to $X_2$.

In some embodiments, ------ represents a carbon-carbon single bond, a carbon-carbon double bond, or a carbon-sulfur single bond. It is understood that the combinations of double and/or single bonds generated by ------ do not exceed atomic valence requirements. It is also understood that any resulting open valences are filled by hydrogen, deuterium, or are substituted as set forth herein.

In some embodiments, the compound of Formula (II) is selected from compounds of Formula (IIa)

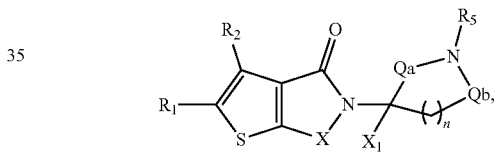

Formula (IIb)

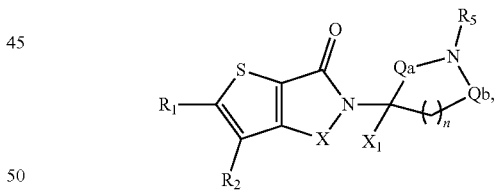

and Formula (IIc)

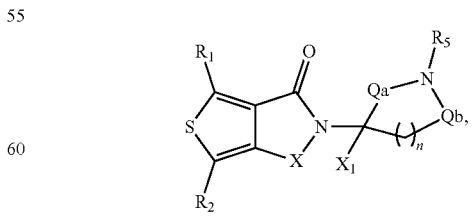

or a pharmaceutically acceptable salt thereof. In some embodiments, the compound of Formula (II) is a compound of Formula (IIa):

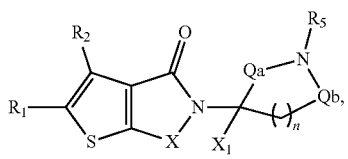

or a pharmaceutically acceptable salt thereof.

In some embodiments, the compound of Formula (II) is a compound of Formula (IIb):

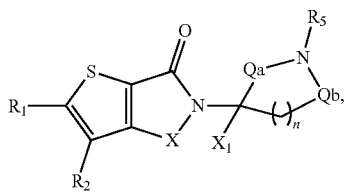

or a pharmaceutically acceptable salt thereof. In some embodiments, the compound of Formula (II) is a compound of Formula (IIc):

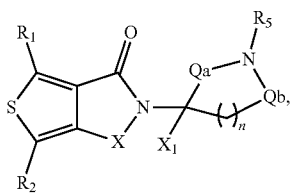

or a pharmaceutically acceptable salt thereof.

In some embodiments, the compound of Formula (II) is selected from compounds of Formula (IId)

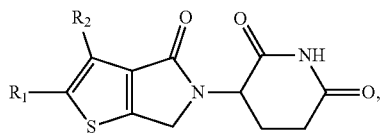

Formula (IIe)

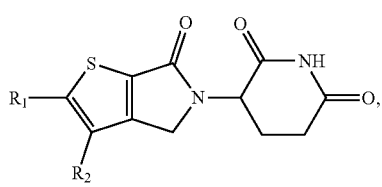

and Formula (IIf)

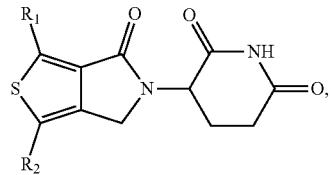

or a pharmaceutically acceptable salt thereof.

In some embodiments, the compound of Formula (II) is a compound of Formula (IId):

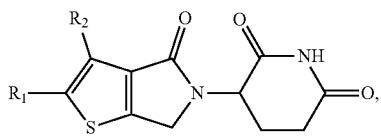

or a pharmaceutically acceptable salt thereof. In some embodiments, the compound of Formula (II) is a compound of Formula (IIe):

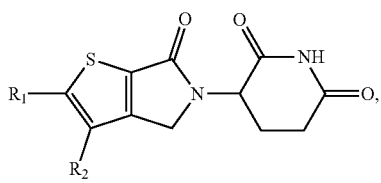

or a pharmaceutically acceptable salt thereof. In some embodiments, the compound of Formula (II) is a compound of Formula (IIf):

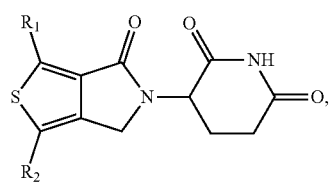

or a pharmaceutically acceptable salt thereof.

In some embodiments, Qa is C=O and Qb is C=O or $CH_2$. In some embodiments, Qa is C=O and Qb is C=O. In some embodiments, Qa is C=O and Qb is $CH_2$. In some embodiments, Qa is C=S and Qb is C=O, $CH_2$ or C=S.

In some embodiments, n is 1. In some embodiments, n is 2. In some embodiments, n is 3.

In some embodiments, $R_5$ is H. In some embodiments, $R_5$ is optionally substituted $C_1$-$C_6$ alkyl.

In some embodiments, X is $CH_2$. In some embodiments, X is C=O.

In some embodiments, $X_1$ is selected from H, deuterium, halogen, and optionally substituted $C_1$-$C_6$ alkyl. In some embodiments, $X_1$ is selected from H and fluoro. In some embodiments, $X_1$ is an unsubstituted $C_1$-$C_6$ alkyl.

In some embodiments, $R_1$ is optionally substituted $C_1$-$C_6$ alkyl. In some embodiments, $R_2$ is optionally substituted $C_1$-$C_6$ alkyl. In some embodiments, $R_1$ and $R_2$ are each independently optionally substituted $C_1$-$C_6$ alkyl.

In some embodiments, L is —Z$_1$—(R$_6$—O—R$_6$)$_t$—Z$_2$—; —Z$_1$(R$_6$—NH—R$_6$)$_t$—Z$_2$—; —Z$_1$—(R$_6$—(NHCO)—R$_6$)$_t$—Z$_2$—; —Z$_1$—(R$_6$—NH(C=O)NH—R$_6$)$_t$—Z$_2$—; —Z$_1$—(R$_6$—NH(C=S)NH—R$_6$)$_t$—Z$_2$—; —Z$_1$—(R$_6$—NH(C=NH)NH—R$_6$)$_t$—Z$_2$—; or —Z$_1$—(R$_6$—(CONH)—R$_6$)$_t$—Z$_2$—. In some embodiments, t is 1, 2, 3, or 4. In some embodiments, Z$_1$ and Z$_2$ are each independently —CH$_2$—; —O—; —NH—; —NH(CO)—; or —(CO)NH.

In some embodiments, R$_1$ is

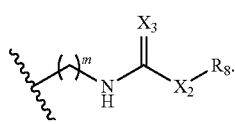

In some embodiments, R$^2$ is

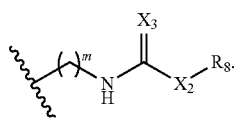

In some embodiments, R$^1$ is

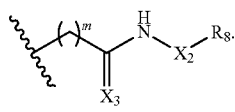

In some embodiments, R$^2$ is

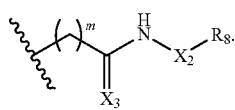

In some embodiments, one of R$_1$ and R$_2$ is an optionally substituted urea, and the other of R$_1$ and R$_2$ is H or optionally substituted C$_1$-C$_6$ alkyl.

In some embodiments, m is 1, 2, 3, or 4. In some embodiments, m is 1. In some embodiments, m is 2. In some embodiments, m is 3.

In some embodiments, X$_3$ is O. In some embodiments, X$_3$ is NH. In some embodiments, X$_3$ is S.

In some embodiments, X$_2$ is selected from (CH$_2$)$_a$, C=O, and [(CH$_2$)$_p$—O—(CH$_2$)$_q$]$_t$. In some embodiments, X$_2$ is (CH$_2$)$_a$.

In some embodiments, a is 0, 1, 2, or 3. In some embodiments, a is 0. In some embodiments, a is 1. In some embodiments, a is 2. In some embodiments, a is 3.

In some embodiments, p and q are independently 0, 1, 2, or 3. In some embodiments, p and q are independently 2 or 3. In some embodiments, p and q are independently 0, 1, or 2. In some embodiments, p and q are independently 1 or 2.

In some embodiments, t is 0, 1, 2, or 3. In some embodiments, t is 1. In some embodiments, t is 2. In some embodiments, t is 3.

In some embodiments, X$_2$ is NH or N—(an optionally substituted C$_1$-C$_6$ alkyl). In some embodiments, X$_2$ is NH.

In some embodiments, R$_8$ is selected from an optionally substituted C$_3$-C$_{10}$ cycloalkyl, an optionally substituted C$_6$-C$_{10}$ aryl, an optionally substituted 5 to 10-membered heteroaryl, and an optionally substituted 3 to 10-membered heterocyclyl. In some embodiments, the optionally substituted C$_6$-C$_{10}$ aryl is a mono-substituted phenyl group. In some embodiments, the optionally substituted C$_6$-C$_{10}$ aryl is a di-substituted phenyl group. In some embodiments, the optionally substituted C$_6$-C$_{10}$ aryl is a tri-substituted phenyl group. In some embodiments, the optionally substituted C$_6$-C$_{10}$ aryl is a phenyl group substituted with halogen. In some embodiments, the optionally substituted C$_6$-C$_{10}$ aryl is a phenyl group substituted with an unsubstituted C$_1$-C$_6$ alkyl. In some embodiments, the optionally substituted C$_6$-C$_{10}$ aryl is a phenyl group substituted with an unsubstituted C$_1$-C$_6$ alkyl and a halogen.

In some embodiments, R$_{8A}$ is selected from hydroxyl, halogen, cyano, nitro, unsubstituted amino, mono-substituted amino, di-substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted C$_1$-C$_6$ alkoxy, optionally substituted C$_1$-C$_6$ haloalkoxy, optionally substituted C$_3$-C$_{10}$ cycloalkyl(C$_1$-C$_6$ alkyl), optionally substituted C$_6$-C$_{10}$ aryl(C$_1$-C$_6$ alkyl), optionally substituted 5 to 10 membered heteroaryl(C$_1$-C$_6$ alkyl), and optionally substituted 3 to 10 membered heterocyclyl(C$_1$-C$_6$ alkyl). In some embodiments, R$_{8A}$ is selected from optionally substituted C$_3$-C$_{10}$ cycloalkyl(C$_1$-C$_6$ alkyl), optionally substituted C$_6$-C$_{10}$ aryl(C$_1$-C$_6$ alkyl), optionally substituted 5 to 10 membered heteroaryl(C$_1$-C$_6$ alkyl), and optionally substituted 3 to 10 membered heterocyclyl(C$_1$-C$_6$ alkyl). In some embodiments, R$_8$ is R$_{8B}$ and R$_{8B}$ is Y$_1$.

In some embodiments, the optionally substituted C$_6$-C$_{10}$ aryl is a phenyl group substituted with an unsubstituted C$_1$-C$_6$ alkyl and halogen. In some embodiments, the optionally substituted 5 to 10-membered heteroaryl is 5 or 6-membered heteroaryl substituted with halogen. In some embodiments, the optionally substituted 5 to 10-membered heteroaryl is 5 or 6-membered heteroaryl substituted with an unsubstituted C$_1$-C$_6$ alkyl. In some embodiments, the optionally substituted 5 to 10-membered heteroaryl is 5 or 6-membered heteroaryl substituted with an unsubstituted C$_1$-C$_6$ alkyl and halogen. In some embodiments, the optionally substituted C$_6$-C$_{10}$ aryl is a phenyl group substituted with an optionally substituted 3 to 10-membered heterocyclyl. In some embodiments, the optionally substituted 3 to 10-membered heterocyclyl is an unsubstituted 5 to 7-membered heterocyclyl group. In some embodiments, the unsubstituted 5 to 7-membered heterocyclyl group is pyrrolidinyl, morpholino, piperidinyl, piperazinyl, or azepanyl. In some embodiments, the optionally substituted 5 to 10-membered heteroaryl is 5 or 6-membered heteroaryl substituted with an optionally substituted 3 to 10-membered heterocyclyl. In some embodiments, the optionally substituted 3 to 10-membered heterocyclyl is an unsubstituted 5 to 7-membered heterocyclyl group. In some embodiments, the unsubstituted 5 to 7-membered heterocyclyl group is pyrrolidinyl, morpholino, piperidinyl, piperazinyl, or azepanyl.

In some embodiments, the compound of Formula (II) is selected from:

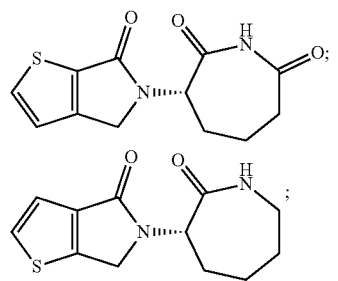
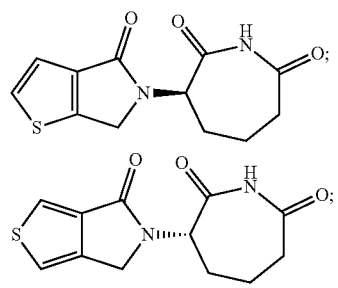
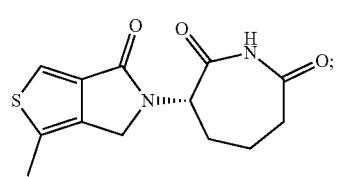
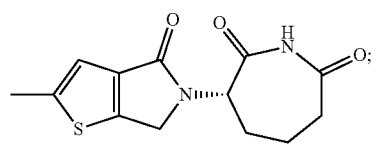
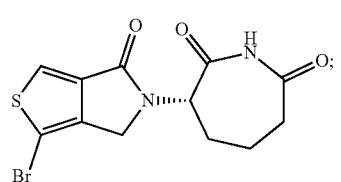
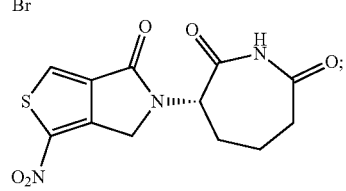
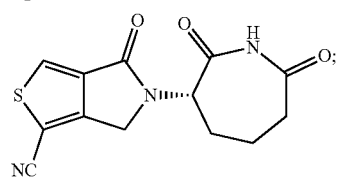
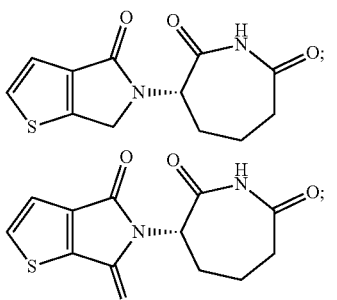
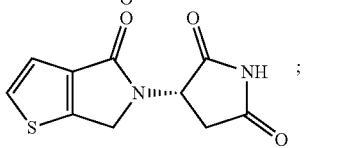
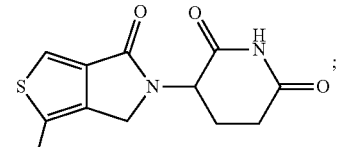
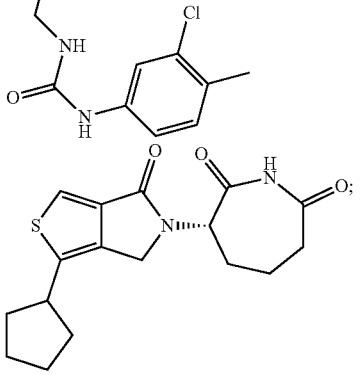
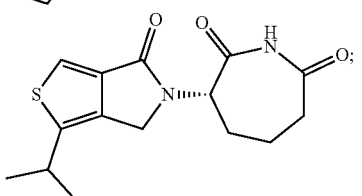
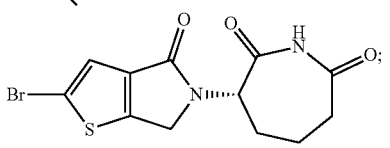
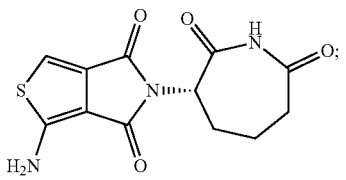
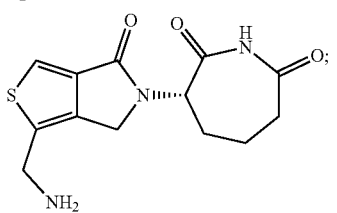

19
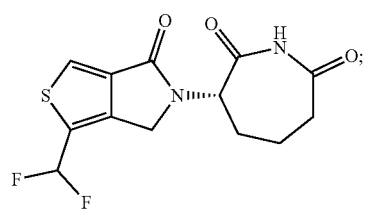
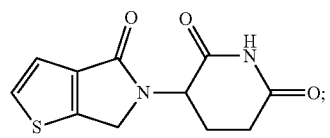
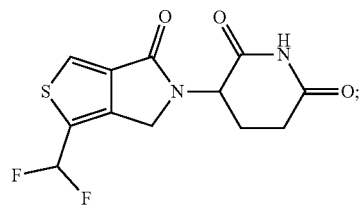
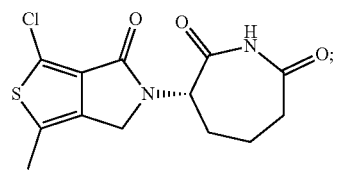
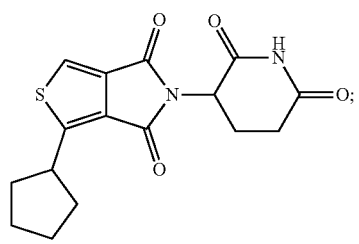
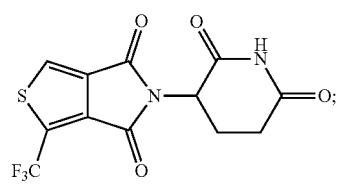
20
-continued
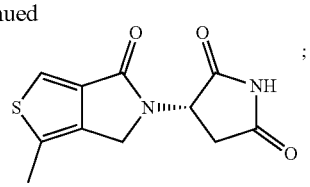
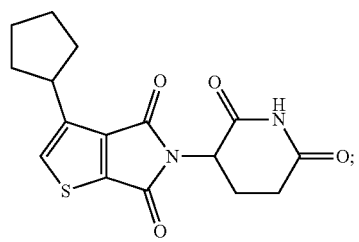
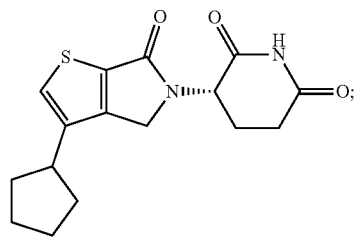
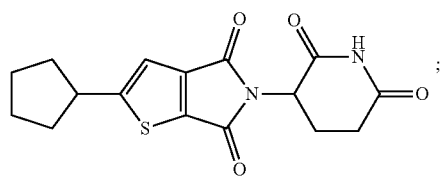
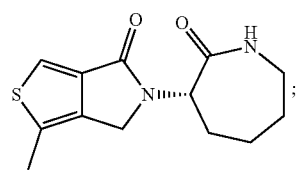
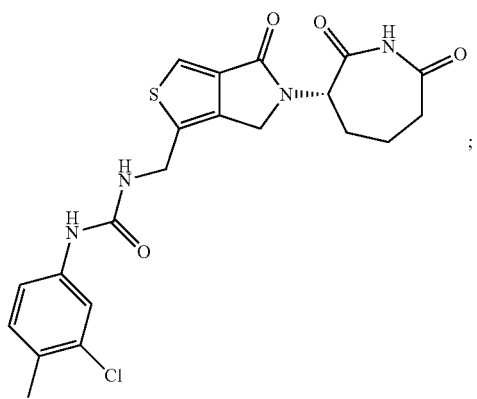

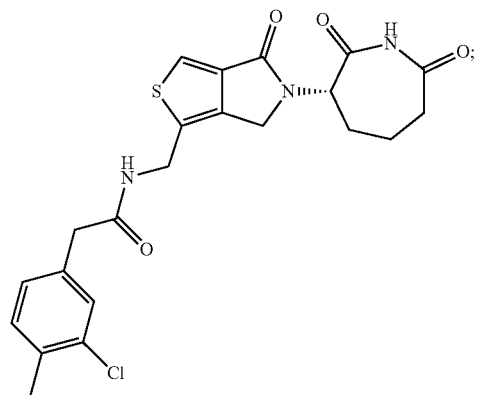
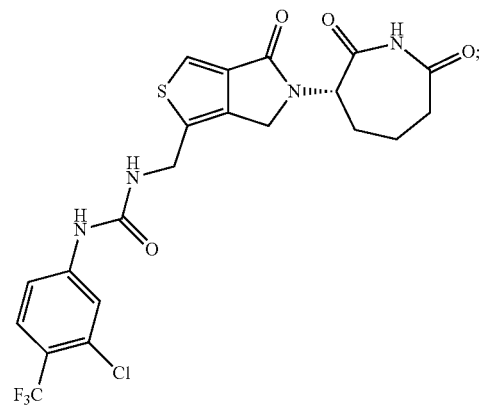
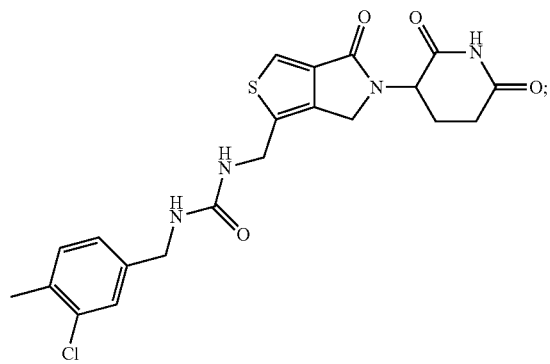
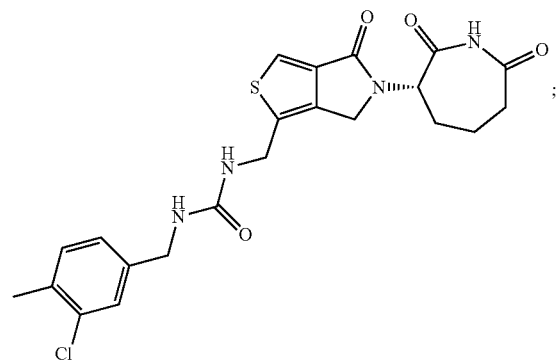
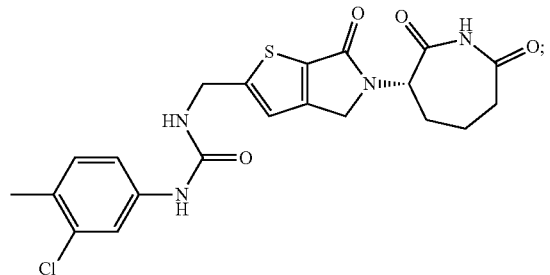
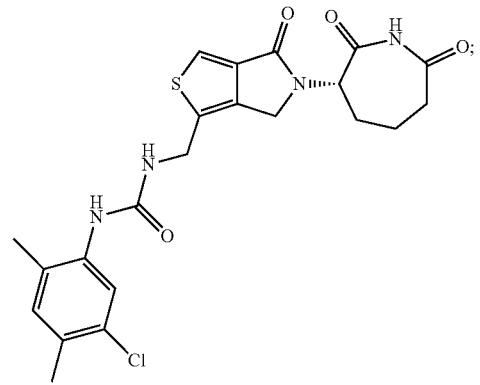
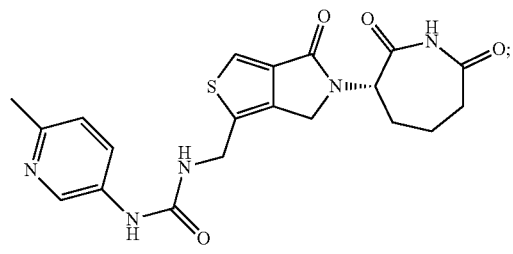
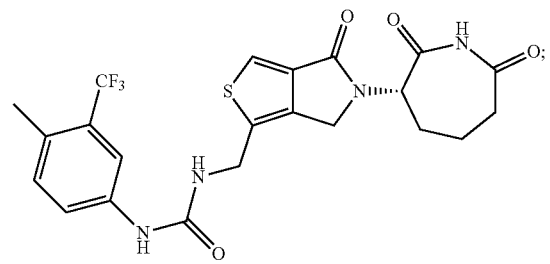

-continued
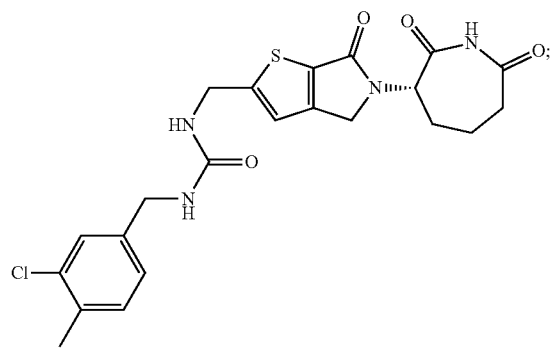
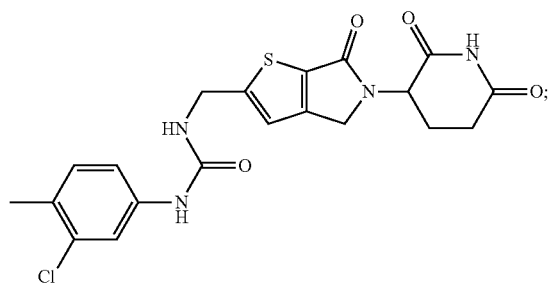
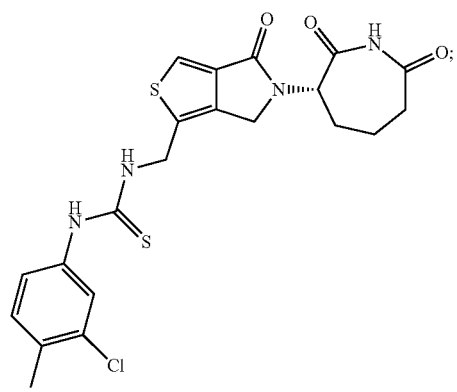
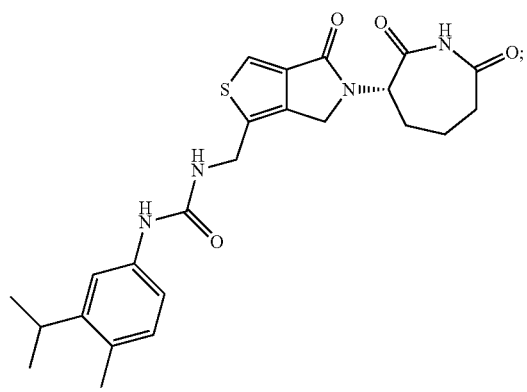
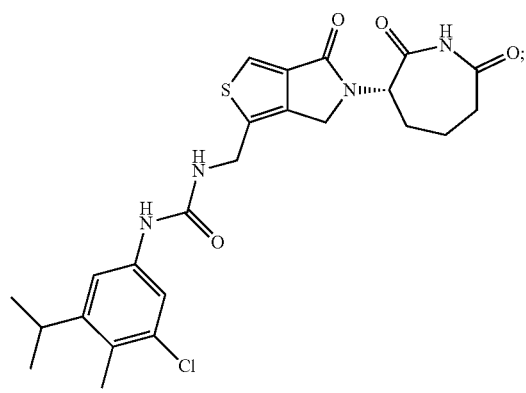
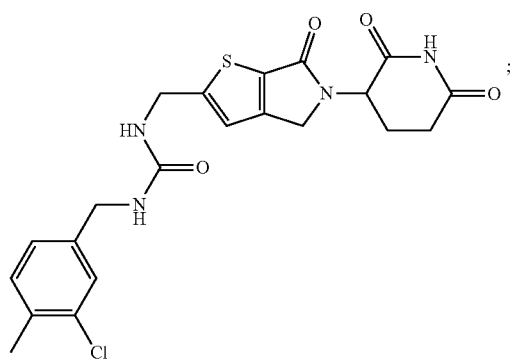
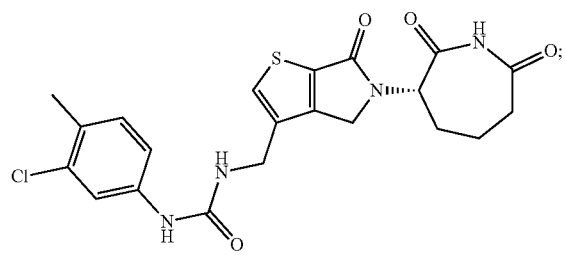
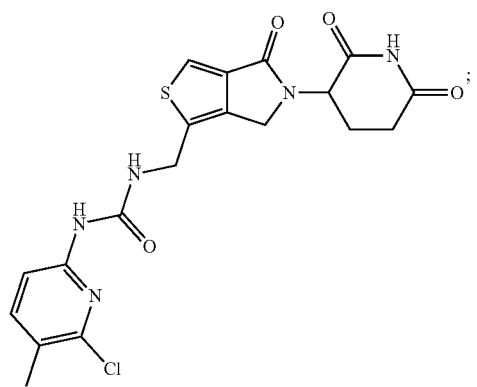

25
26
-continued
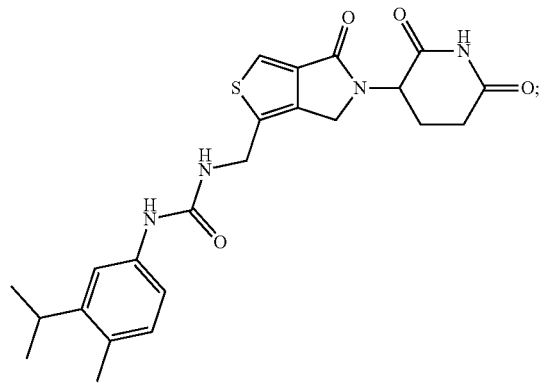
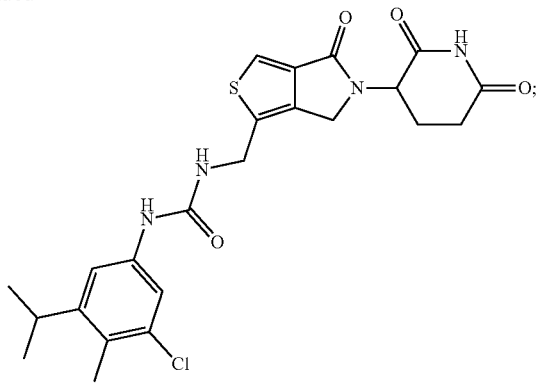
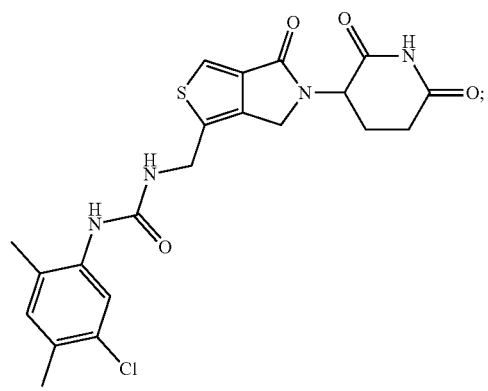
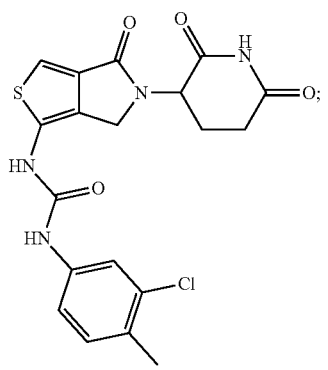
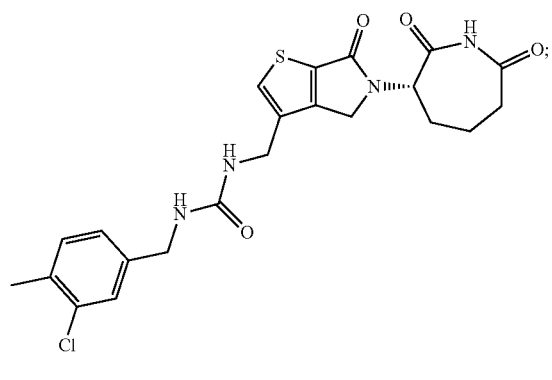
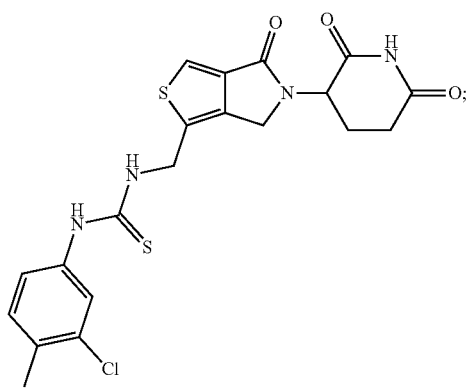
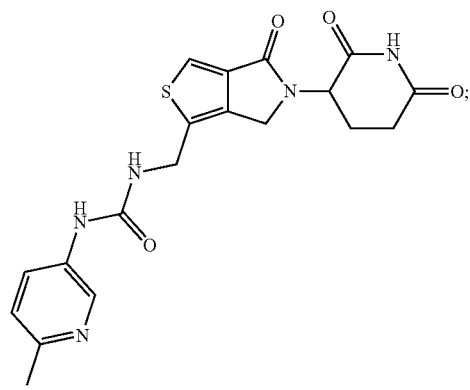
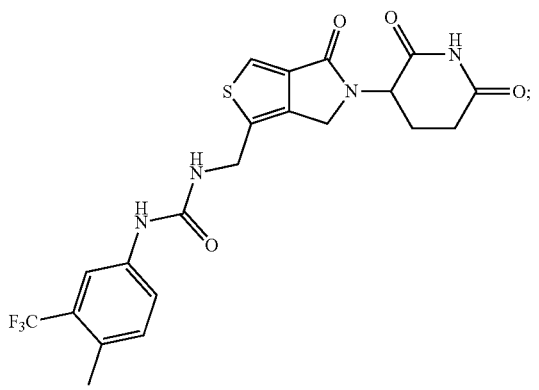

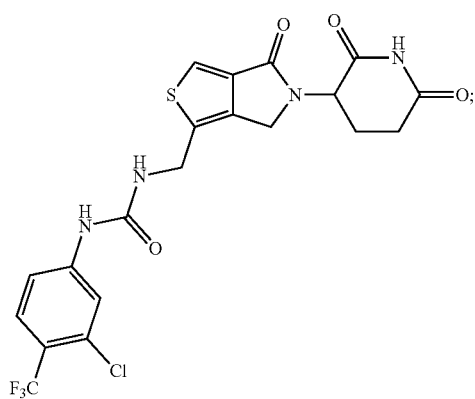
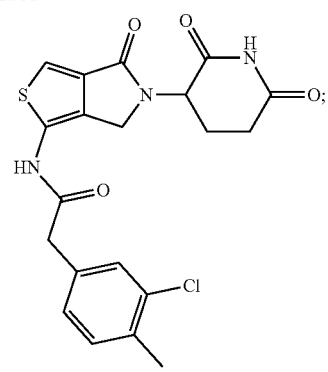
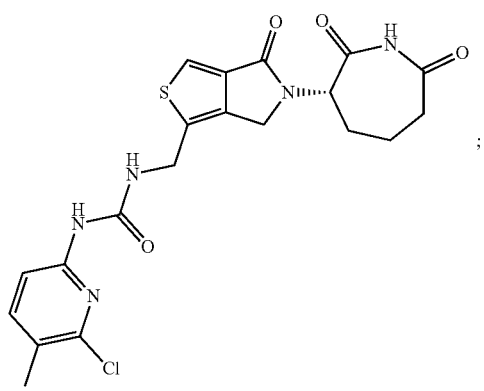
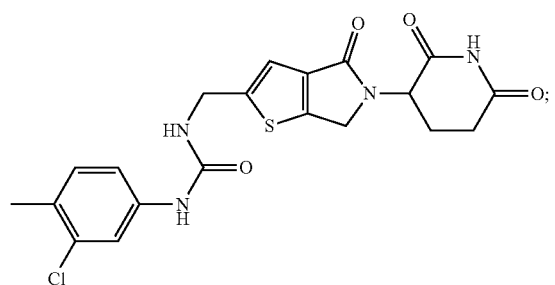
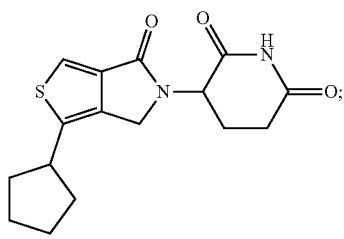
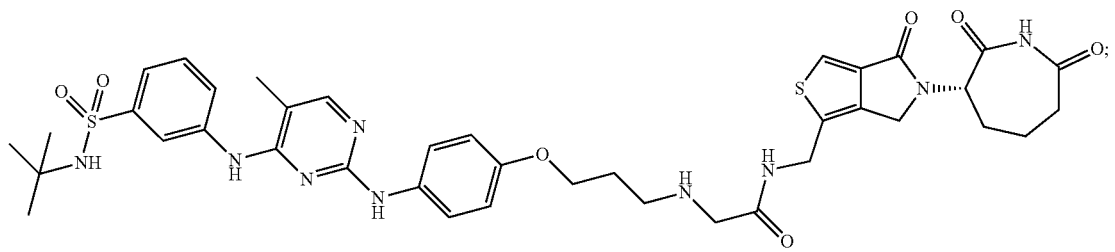
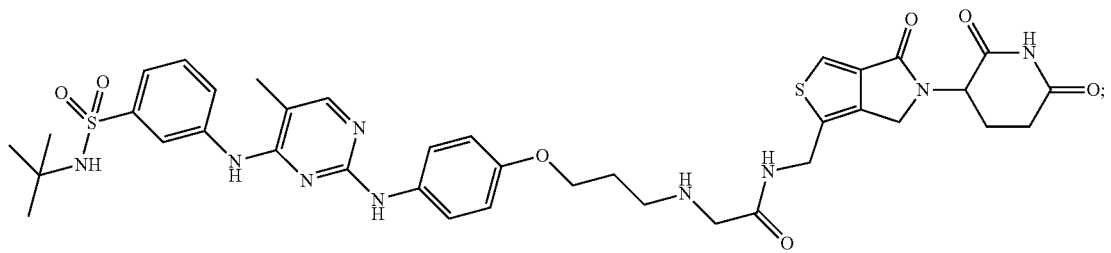

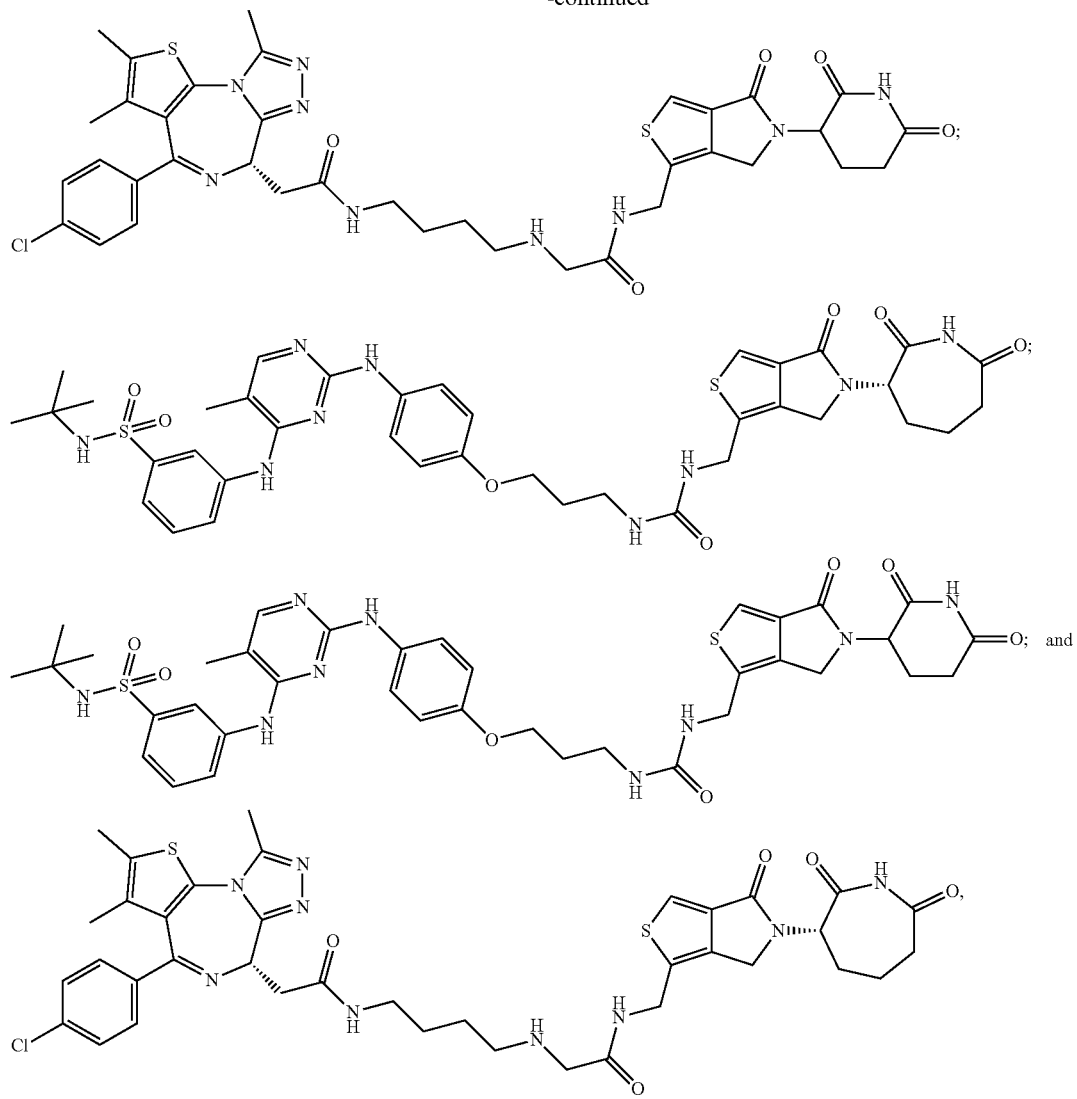
or a pharmaceutically acceptable salt or solvates of any of the foregoing.
In some embodiments, the compound of Formula (II) is selected from:
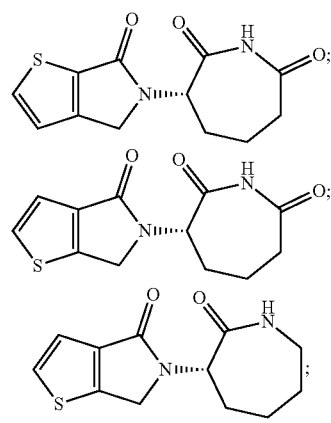
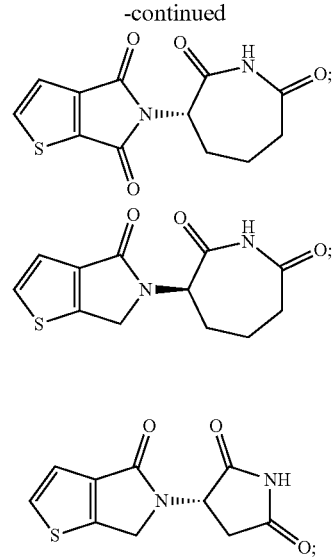

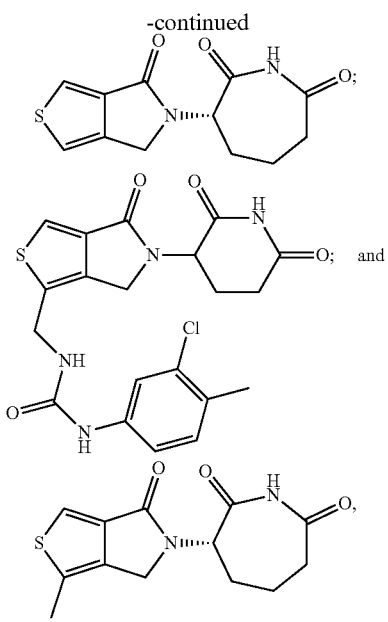

or a pharmaceutically acceptable salt or solvates of any of the foregoing. In some embodiments, the compound is a pharmaceutically acceptable salt.

Some embodiments provide a pharmaceutical composition comprising a compound of any one of Formula (II), (IIa), (IIb), (IIc), or a pharmaceutically acceptable salt thereof, and at least one pharmaceutically acceptable carrier. In some embodiments, the composition is formulated for oral, parenteral, topical, ophthalmic, inhalation, nasal, or intravenous administration.

In some embodiments, the pharmaceutical composition further comprises a second therapeutic agent. In some embodiments, the second therapeutic agent is selected from anti-inflammatory agents, anti-cancer agents, immunostimulatory agents, and immunosuppressive agents. In some embodiments, the second therapeutic agent is an anti-cancer agent.

Some embodiments provide a method of treating, ameliorating, or preventing a disease, disorder, or condition associated with a protein selected from a cytokine, aiolos, ikaros, helios, CK1α, GSPT1, and combinations of any of the foregoing, the method comprising administering a therapeutically effective amount of a compound of any one of Formula (II), (IIa), (IIb), (IIc), or a pharmaceutically acceptable salt thereof, or a pharmaceutical composition comprising Formula (II), (IIa), (IIb), (IIc), or a pharmaceutically acceptable salt thereof.

In some embodiments, the disease, disorder, or condition is selected from inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer.

In some embodiments, the disease, disorder, or condition is cancer. Examples of suitable cancers include, but are not limited to hematological malignancies and solid tumors, such as: lung cancers (e.g., small cell lung cancer and non-small cell lung cancer), breast cancers, prostate cancers, head and neck cancers (e.g., squamous cell cancer of the head and neck), pancreatic cancers (e.g., pancreatic carcinoma such as, for example, exocrine pancreatic carcinoma, or moderately differentiated metastatic pancreatic neuroendocrine tumors (pNETs)), colon cancers (e.g., colorectal carcinomas, such as, for example, colon adenocarcinoma and colon adenoma), rectal cancers, teratomas, ovarian cancers, endometrial cancers, brain cancers (e.g., recurrent, progressive, or refractory CNS tumors; gliomas, such as glioma blastoma multiforme and oligodendroglioma; astrocytomas; or progressive brain metastases), retinoblastoma, leukemias (e.g., MLL-rearranged acute leukemia or acute lymphoblastic leukemia), skin cancers (e.g., melanoma or squamous cell carcinoma), liposarcomas, lymphomas (e.g, mantle cell lymphoma), multiple myelomas, testicular cancers, liver cancers (e.g., hepatocellular carcinoma), esophageal cancers, kidney carcinomas, astrogliosis, and neuroblastoma.

In some embodiments, the compound of Formula (II) is administered in combination with a second therapeutic agent. In some embodiments, the second therapeutic agent is selected from anti-inflammatory agents, anti-cancer agents, immunostimulatory agents, and immunosuppressive agents. In some embodiments, the second therapeutic agent is an anti-cancer agent.

Some embodiments provide a method of inhibiting protein activity, comprising contacting a cell with a compound of any of Formula (II), (IIa), (IIb), (IIc), or a pharmaceutically acceptable salt thereof, wherein the protein is aiolos, ikaros, helios, CK1α, GSPT1, a cytokine, or a combination of any of the foregoing.

Some embodiments provide a method of decreasing the risk of skin cancer in a subject in need thereof, comprising administering an effective amount of a compound of any of Formula (II), (IIa), (IIb), (IIc), or a pharmaceutically acceptable salt thereof, or a composition comprising Formula (II), (IIa), (IIb), (IIc), (IId), (IIe) or (IIf), or a pharmaceutically acceptable salt thereof.

Some embodiments provide a method for treating, ameliorating, or preventing a skin disorder, disease, or condition in a subject, comprising administering to the subject a therapeutically effective amount of a compound of any of Formula (II), (IIa), (IIb), (IIc), or a pharmaceutically acceptable salt thereof, or a composition comprising Formula (II), (IIa), (IIb), (IIc), (IId), (IIe) or (IIf), or a pharmaceutically acceptable salt thereof.

In some embodiments, the skin disorder, disease, or condition is sunburn or skin hypopigmentation.

Some embodiments provide a method for treating, ameliorating, or preventing a skin disorder, disease, or condition in a subject, comprising administering to the subject a therapeutically effective amount of a compound of any of Formula (II), (IIa), (IIb), (IIc), or a pharmaceutically acceptable salt thereof, or a composition comprising Formula (II), (IIa), (IIb), (IIc), (IId), (IIe) or (IIf), or a pharmaceutically acceptable salt thereof.

Some embodiments provide a method of increasing skin pigmentation in a subject in need thereof, comprising administering a therapeutically effective amount of any of (Formula (II), (IIa), (IIb), (IIc), (IId), (IIe), (IIf), or a pharmaceutically acceptable salt thereof, or a composition comprising Formula (II), (IIa), (IIb), (IIc), (IId), (IIe) or (IIf), or a pharmaceutically acceptable salt thereof.

In some embodiments, administering comprising contacting the skin with a therapeutically effective amount of any of Formula (II), (IIa), (IIb), (IIc), (IId), (IIe), (IIf), or a pharmaceutically acceptable salt thereof, or a composition comprising Formula (II), (IIa), (IIb), (IIc), (IId), (IIe) or (IIf), or a pharmaceutically acceptable salt thereof.

Some embodiments provide a method of increasing eumelanin level in a subject in need thereof, comprising administering a therapeutically effective amount of any of Formula (II), (IIa), (IIb), (IIc), (IId), (IIe) or (IIf), or a pharmaceutically acceptable salt thereof, or a composition comprising Formula (II), (IIa), (IIb), (IIc), (IId), (IIe) or (IIf), or a pharmaceutically acceptable salt thereof.

Some embodiments provide a method of increasing p53 activity, comprising contacting a cell with a compound of any of (II), (IIa), (IIb), (IIc), (IId), (IIe) or (IIf), or a pharmaceutically acceptable salt thereof.

Some embodiments provide a method of decreasing MDM2 activity, comprising contacting a cell with a compound of any of (II), (IIa), (IIb), (IIc), (IId), (IIe) or (IIf), or a pharmaceutically acceptable salt thereof.

Any of the features of an embodiment is applicable to all embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other embodiments. Any embodiment of a method can comprise another embodiment of a compound, and any embodiment of a compound can be configured to perform a method of another embodiment.

BRIEF DESCRIPTION OF THE DRAWINGS

In FIGS. 10A and 10B, the cells were incubated for 72 hrs with Compound 9 at the indicated concentrations or DMSO. Compound activity was measured based on the signal from remaining viable cells.

DETAILED DESCRIPTION

Figure 1:
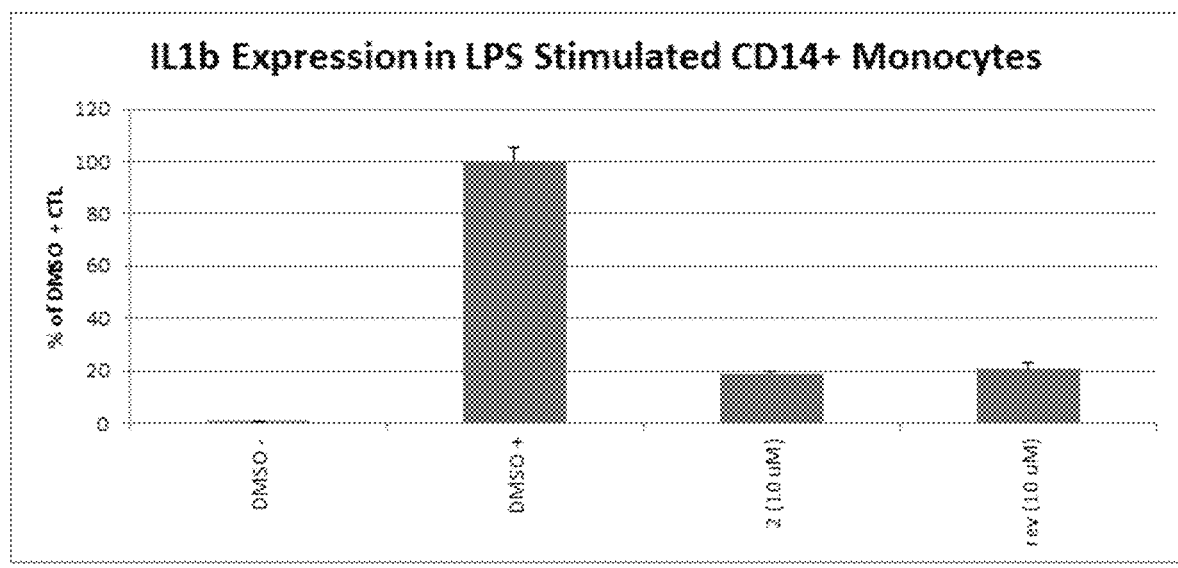
FIG. 1 is a graph showing IL-1-beta expression in LPS stimulated CD14+ monocytes. CD14+ monocytes were plated in 96-well plates and pretreated with compound (10 µM Compound 2 or 10 µm lenalidomide (rev)) for 1 h, and then induced with 100 ng/mL LPS for 18-24 h. Cytokines were measured according to MesoScale protocol. Negative control wells were treated with DMSO. Compound activity was measured as a percentage of LPS-induced activity.

Some embodiments provide a compound of Formula (II):

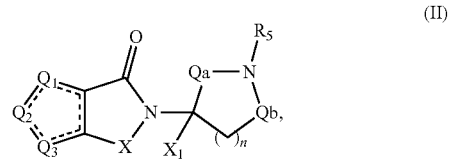

(II)

or a pharmaceutically acceptable salt or solvate thereof.

In some embodiments, compounds of Formula (II) are selected from compounds of Formula (IIa), Formula (IIb), or Formula (IIc):

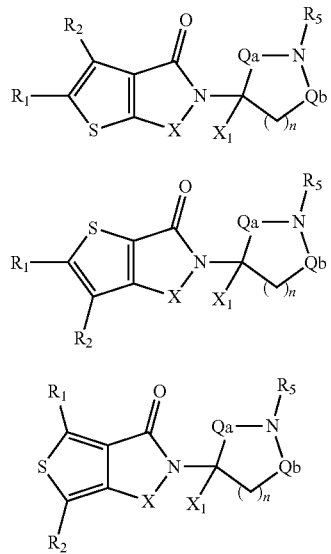

In some embodiments, $Q_1$, $Q_2$, and $Q_3$, are each independently selected from $CR_1$, $CR_2$, and —S—, with the proviso that no more than one of $Q_1$, $Q_2$, and $Q_3$, can be —S—. In some embodiments, at least one of $Q_1$, $Q_2$, and $Q_3$, is $CR_1$ or $CR_2$.

In some embodiments, $Q_1$ is $CR_1$. In some embodiments, $Q_1$ is $CR_2$. In some embodiments, $Q_1$ is —S—. In some embodiments, $Q_2$ is $CR_1$. In some embodiments, $Q_2$ is $CR_2$. In some embodiments, $Q_2$ is —S—. In some embodiments, $Q_3$ is $CR_1$. In some embodiments, $Q_3$ is $CR_2$. In some embodiments, $Q_3$ is —S—. In some embodiments, $Q_1$ is $CR_1$, $Q_2$ is $CR_2$, and $Q_3$ is —S—. In some embodiments, $Q_1$ is $CR_2$, $Q_2$ is $CR_1$, and $Q_3$ is —S—.

In some embodiments, $Q_1$ is —S—, $Q_2$ is $CR_1$, and $Q_3$ is $CR_2$. In some embodiments, $Q_1$ is —S—, $Q_2$ is $CR_2$, and $Q_3$ is $CR_1$. In some embodiments, $Q_1$ is $CR_1$, $Q_2$ is —S—, and $Q_3$ is $CR_2$. In some embodiments, $Q_1$ is $CR_2$, $Q_2$ is —S—, and $Q_3$ is $CR_1$. In some embodiments, $Q_1$ is $CR_1$, $Q_2$ is $CR_1$, and $Q_3$ is $CR_1$. In some embodiments, $Q_1$ is $CR_1$, $Q_2$ is $CR_2$, and $Q_3$ is $CR_1$. In some embodiments, $Q_1$ is $CR_1$, $Q_2$ is $CR_2$, and $Q_3$ is $CR_2$. In some embodiments, $Q_1$ is $CR_2$, $Q_2$ is $CR_2$, and $Q_3$ is $CR_1$. In some embodiments, $Q_1$ is $CR_2$, $Q_2$ is $CR_1$, and $Q_3$ is $CR_1$. In some embodiments, $Q_1$ is $CR_2$, $Q_2$ is $CR_1$, and $Q_3$ is $CR_2$. In some embodiments, $Q_1$ is $CR_2$, $Q_2$ is $CR_2$, and $Q_3$ is $CR_2$.

In some embodiments, $R_1$ and $R_2$ are each independently selected from H, deuterium, hydroxyl, halogen (for example, fluoro, chloro, bromo, and iodo), cyano, nitro, optionally substituted amino, optionally substituted C-amido, optionally substituted N-amido, optionally substituted urea, optionally substituted ester, optionally substituted $C_1$-$C_6$ alkoxy, optionally substituted $C_1$-$C_6$ alkyl (for example, methyl, ethyl, n-propyl, isopropyl, n-butyl, isobutyl, tert-butyl, pentyl (branched and straight-chained), and hexyl (branched and straight-chained)), optionally substituted $C_2$-$C_6$ alkenyl (for example, vinyl, allyl, isopropenyl, n-butenyl, isobutenyl, pentenyl (branched and straight-chained), and hexenyl (branched and straight-chained)), optionally substituted $C_2$-$C_6$ alkynyl (for example, ethynyl, propynyl, butynyl, pentynyl (branched and straight-chained), and hexynyl (branched and straight-chained)), optionally substituted $C_3$-$C_8$ cycloalkyl (for example, cyclopropyl, cyclobutyl, cyclohexyl, cycloheptyl, and cyclooctyl), optionally substituted $C_6$-$C_{10}$ aryl (for example, phenyl and naphthyl), optionally substituted 3 to 10-membered heterocyclyl (for example, monocyclic and bicyclic (including fused, bridged, and spiro) 3 to 10 membered heterocyclyl groups with one nitrogen atom, two nitrogen atoms, three nitrogen atoms, four nitrogen atoms, one oxygen atom, one sulfur atom, one oxygen atom and one or two nitrogen atoms, and one sulfur atom and one or two nitrogen atoms), optionally substituted 5 to 10-membered heteroaryl (for example, monocyclic and bicyclic 3 to 10 membered heteroaryl groups with one nitrogen atom, two nitrogen atoms, three nitrogen atoms, four nitrogen atoms, one oxygen atom, one sulfur atom, one oxygen atom and one or two nitrogen atoms, and one sulfur atom and one or two nitrogen atoms),

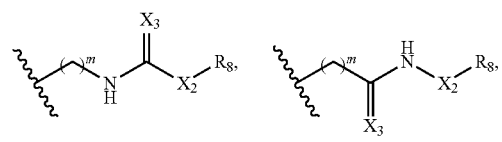

and L-Y. In some embodiments, when one of $R_1$ or $R_2$ is

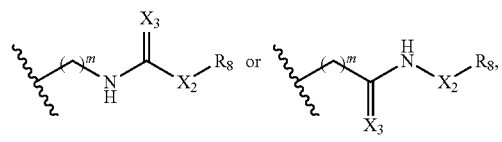

the other of $R_1$ or $R_2$ is not L-Y.

In some embodiments, $R_1$ and $R_2$ are each independently selected from H, deuterium, hydroxyl, halogen, cyano, nitro, unsubstituted amino, unsubstituted C-amido, unsubstituted N-amido, unsubstituted ester, unsubstituted $C_1$-$C_6$ alkoxy, unsubstituted $C_1$-$C_6$ alkyl, unsubstituted $C_2$-$C_6$ alkenyl, unsubstituted $C_2$-$C_6$ alkynyl, unsubstituted $C_3$-$C_8$ cycloalkyl, unsubstituted $C_6$-$C_{10}$ aryl, unsubstituted 3 to 10-membered heterocyclyl, unsubstituted 5 to 10-membered heteroaryl,

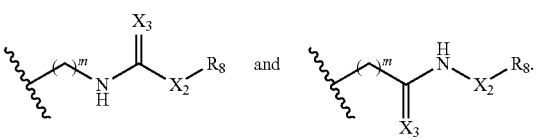

In some embodiments, $R_1$ is hydrogen and $R_2$ is L-Y. In some embodiments, $R_1$ is L-Y and $R_2$ is H. In some embodiments, $R_1$ and $R_2$ are each L-Y. In some embodiments, none of $R_1$ or $R_2$ is L-Y.

In some embodiments, $R_1$ is

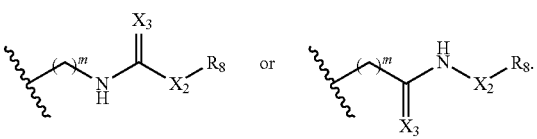

In some embodiments, $R_2$ is

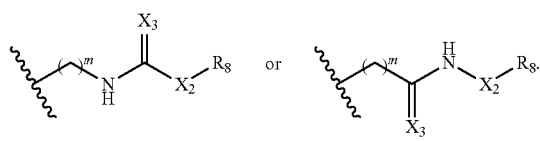

In some embodiments, $R_1$ is

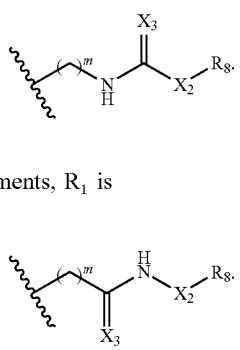

In some embodiments, $R_1$ is

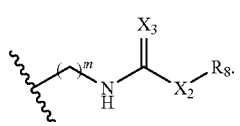

In some embodiments, $R_2$ is

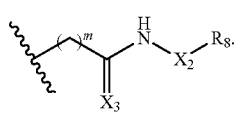

In some embodiments, $R_2$ is

For example, in some embodiments, one of $R_1$ and $R_2$ is selected from:

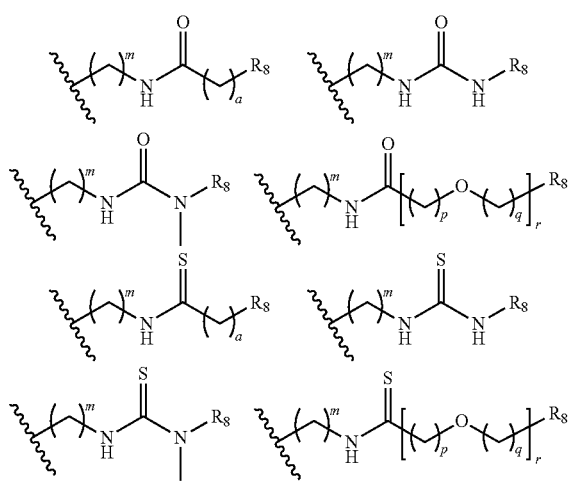

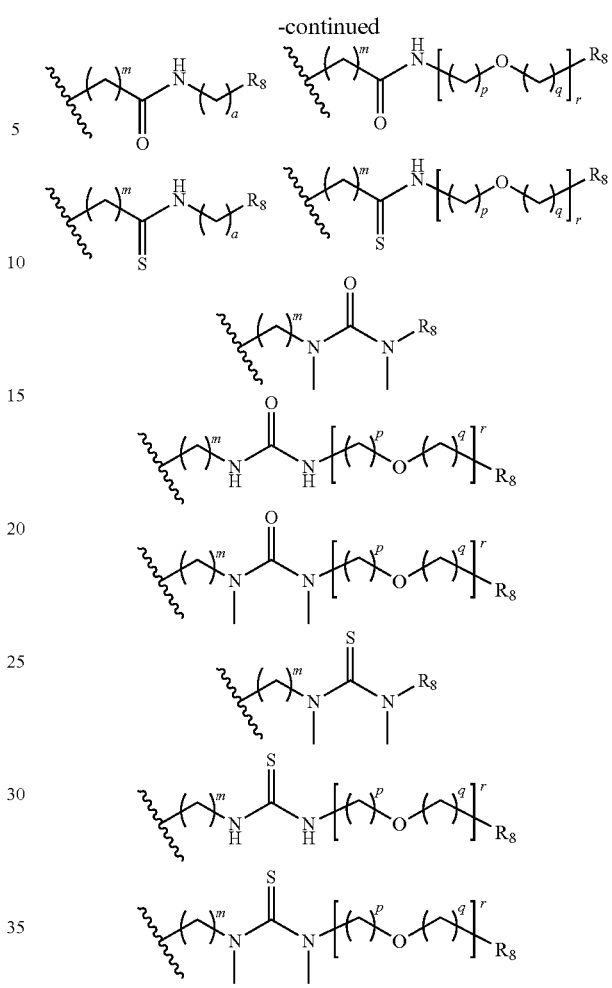

In some embodiments of this paragraph, a is 0. In some embodiments of this paragraph, a is 1. In some embodiments of this paragraph, a is 2. In some embodiments of this paragraph, a is 3. In some embodiments of this paragraph, a is 4. In some embodiments of this paragraph, a is 5. In some embodiments of this paragraph, m is 1. In some embodiments of this paragraph, m is 2. In some embodiments of this paragraph, m is 3. In some embodiments of this paragraph, m is 4. In some embodiments of this paragraph, m is 5. In some embodiments of this paragraph, p and q are independently 1 or 2. In some embodiments of this paragraph, r is 1. In some embodiments of this paragraph, r is 2. In some embodiments of this paragraph, r is 3.

In some embodiments, $R_1$ and $R_2$ are each H. In some embodiments, none of $R_1$ and $R_2$ are H. In some embodiments, $R_1$ and $R_2$ are each deuterium. In some embodiments, none of $R_1$ and $R_2$ are deuterium. In some embodiments, $R_1$ and $R_2$ are each halogen. In some embodiments, none of $R_1$ and $R_2$ are halogen.

In some embodiments, $R_1$ is optionally substituted amino. In some embodiments, $R_1$ is unsubstituted amino. In some embodiments, $R_1$ is nitro. In some embodiments, $R_1$ is optionally substituted $C_1$-$C_6$ alkoxy. In some embodiments, $R_1$ is unsubstituted $C_1$-$C_6$ alkoxy.

In some embodiments, $R_1$ is halogen. In some embodiments, $R_1$ is cyano. In some embodiments, $R_1$ is optionally substituted amido. In some embodiments, $R_1$ is optionally substituted ester.

In some embodiments, $R_1$ is optionally substituted $C_1$-$C_6$ alkyl. In some embodiments, $R_1$ is optionally substituted $C_2$-$C_6$ alkenyl. In some embodiments, $R_1$ is optionally substituted $C_2$-$C_6$ alkynyl. In some embodiments, $R_1$ is optionally substituted $C_3$-$C_8$ cycloalkyl. In some embodiments, $R_1$ is optionally substituted $C_6$-$C_{10}$ aryl. In some embodiments, $R_1$ is optionally substituted 3 to 10-membered heterocyclyl. In some embodiments, $R_1$ is optionally substituted 5 to 10-membered heteroaryl.

In some embodiments, $R_1$ is unsubstituted amido. In some embodiments, $R_1$ is unsubstituted ester.

In some embodiments, $R_1$ is unsubstituted $C_1$-$C_6$ alkoxy. In some embodiments, $R_1$ is unsubstituted $C_1$-$C_6$ alkyl. In some embodiments, $R_1$ is unsubstituted $C_2$-$C_6$ alkenyl. In some embodiments, $R_1$ is hydroxyl.

In some embodiments, $R_1$ is unsubstituted $C_2$-$C_6$ alkynyl. In some embodiments, $R_1$ is unsubstituted $C_3$-$C_8$ cycloalkyl. In some embodiments, $R_1$ is unsubstituted $C_6$-$C_{10}$ aryl. In some embodiments, $R_1$ is unsubstituted 3 to 10-membered heterocyclyl. In some embodiments, $R_1$ is unsubstituted 5 to 10-membered heteroaryl.

In some embodiments, $R_2$ is optionally substituted amino. In some embodiments, $R_2$ is unsubstituted amino. In some embodiments, $R_2$ is nitro. In some embodiments, $R_2$ is optionally substituted $C_1$-$C_6$ alkoxy. In some embodiments, $R_2$ is unsubstituted $C_1$-$C_6$ alkoxy.

In some embodiments, $R_2$ is halogen. In some embodiments, $R_2$ is cyano. In some embodiments, $R_2$ is optionally substituted amido. In some embodiments, $R_2$ is optionally substituted ester.

In some embodiments, $R_2$ is optionally substituted $C_1$-$C_6$ alkyl. In some embodiments, $R_2$ is optionally substituted $C_2$-$C_6$ alkenyl. In some embodiments, $R_2$ is optionally substituted $C_2$-$C_6$ alkynyl. In some embodiments, $R_2$ is optionally substituted $C_3$-$C_8$ cycloalkyl. In some embodiments, $R_2$ is optionally substituted $C_6$-$C_{10}$ aryl. In some embodiments, $R_2$ is optionally substituted 3 to 10-membered heterocyclyl. In some embodiments, $R_2$ is optionally substituted 5 to 10-membered heteroaryl.

In some embodiments, $R_2$ is unsubstituted amido. In some embodiments, $R_2$ is unsubstituted ester. In some embodiments, $R_2$ is unsubstituted $C_1$-$C_6$ alkoxy.

In some embodiments, $R_2$ is unsubstituted $C_1$-$C_6$ alkyl. In some embodiments, $R_2$ is unsubstituted $C_2$-$C_6$ alkenyl. In some embodiments, $R_2$ is unsubstituted $C_2$-$C_6$ alkynyl. In some embodiments, $R_2$ is unsubstituted $C_3$-$C_8$ cycloalkyl. In some embodiments, $R_2$ is unsubstituted $C_6$-$C_{10}$ aryl. In some embodiments, $R_2$ is unsubstituted 3 to 10-membered heterocyclyl. In some embodiments, $R_2$ is unsubstituted 5 to 10-membered heteroaryl.

In some embodiments, $R_1$ is hydrogen, and $R_2$ is optionally substituted $C_1$-$C_6$ alkyl. In some embodiments, $R_1$ is hydrogen, and $R_2$ is unsubstituted $C_1$-$C_6$ alkyl. In some embodiments, $R_1$ is optionally substituted $C_1$-$C_6$ alkyl, and $R_2$ is hydrogen. In some embodiments, $R_1$ is unsubstituted $C_1$-$C_6$ alkyl, and $R_2$ is hydrogen. In some embodiments, $R_1$ is hydrogen and $R_2$ is optionally substituted methyl. In some embodiments, $R_1$ is hydrogen and $R_2$ is unsubstituted methyl. In some embodiments, $R_1$ is optionally substituted methyl and $R_2$ is hydrogen. In some embodiments, $R_1$ is unsubstituted methyl and $R_2$ is hydrogen.

In some embodiments, $X_1$ is selected from H, deuterium, halogen, and optionally substituted $C_1$-$C_6$ alkyl.

In some embodiments, $X_1$ is hydrogen. In some embodiments, $X_1$ is deuterium. In some embodiments, $X_1$ is halogen, for example, chloro or fluoro.

In some embodiments, $X_1$ is optionally substituted $C_1$-$C_6$ alkyl. In some embodiments, $X_1$ is substituted $C_1$-$C_6$ alkyl. In some embodiments, $X_1$ is unsubstituted $C_1$-$C_6$ alkyl.

In some embodiments, $X_1$ is not hydrogen. In some embodiments, $X_1$ is not deuterium. In some embodiments, $X_1$ is not optionally substituted $C_1$-$C_6$ alkyl. In some embodiments, $X_1$ is not unsubstituted $C_1$-$C_6$ alkyl. In some embodiments, $X_1$ is not optionally substituted methyl. In some embodiments, $X_1$ is not unsubstituted methyl.

In some embodiments, $R_5$ is selected from H, deuterium, optionally substituted $C_1$-$C_6$ alkyl, optionally substituted $C_2$-$C_6$ alkenyl, optionally substituted $C_2$-$C_6$ alkynyl, and optionally substituted $C_3$-$C_8$ cycloalkyl.

In some embodiments, $R_5$ is selected from H, deuterium, unsubstituted $C_1$-$C_6$ alkyl, unsubstituted $C_2$-$C_6$ alkenyl, unsubstituted $C_2$-$C_6$ alkynyl, and unsubstituted $C_3$-$C_8$ cycloalkyl.

In some embodiments, X is selected from $C(R_5)_2$, $CH(R_5)$, $CH_2$, C=O, and C=S.

In some embodiments, $X_2$ is selected from $(CH_2)_a$, $(CD_2)_a$, $(CF_2)_a$, C=O, NH, N—(an optionally substituted $C_1$-$C_6$ alkyl), and $[(CH_2)_p$—O—$(CH_2)_q]_t$. In some embodiments, $X_2$ is NH or N—(an optionally substituted $C_1$-$C_6$ alkyl). In some embodiments, $X_2$ is NH. In some embodiments, $X_2$ is $(CH_2)_a$. In some embodiments, $X_2$ is $(CD2)_a$. In some embodiments, $X_2$ is C=O. In some embodiments, $X_2$ is NH. In some embodiments, $X_2$ is N—(an optionally substituted $C_1$-$C_6$ alkyl). In some embodiments, $X_2$ is $[(CH_2)_p$—O—$(CH_2)_q]_t$.

In some embodiments, $X_3$ is selected from O, NH, and S. In some embodiments, $X_3$ is O. In some embodiments, $X_3$ is NH. In some embodiments, $X_3$ is S.

In some embodiments, m is 1, 2, 3, 4, or 5. In some embodiments, m is 1. In some embodiments, m is 2. In some embodiments, m is 3. In some embodiments, m is 4. In some embodiments, m is 5. In some embodiments, m is 1 and $X_2$ is NH.

In some embodiments, each Qa and Qb are each independently selected from $C(R_5)_2$, $CH(R_5)$, $CH_2$, C=O, and C=S.

In some embodiments, n is 1, 2, or 3. In some embodiments, n is 1. In some embodiments, n is 2. In some embodiments, n is 3. In some embodiments, when n is 2, then $Q_3$ is —S—, or when n is 2, then $R_1$ is substituted $C_1$-$C_6$ alkyl, optionally substituted $C_3$-$C_8$ cycloalkyl, optionally substituted 3 to 10-membered heterocyclyl, optionally substituted 5 to 10-membered heteroaryl, optionally substituted urea, or L-Y. In some embodiments, when n is 2, then $Q_3$ is —S—. In some embodiments, when n is 2, then $R_1$ is substituted $C_1$-$C_6$ alkyl, optionally substituted $C_3$-$C_8$ cycloalkyl, optionally substituted 3 to 10-membered heterocyclyl, optionally substituted 5 to 10-membered heteroaryl, optionally substituted urea, or L-Y.

In some embodiments, Qa and Qb are each independently selected from $CH_2$ and C=O. In some embodiments, Qa and Qb are each $CH_2$. In some embodiments, Qa and Qb are each C=O. In some embodiments, Qa is $CH_2$ and Qb is C=O. In some embodiments, Qb is $CH_2$ and Qa is C=O.

In some embodiments, $R_5$ is H. In some embodiments, $R_5$ is optionally substituted $C_1$-$C_6$ alkyl.

In some embodiments, L is a linker group. In some embodiments, L is an alkyl linker. In some embodiments, L is a polyethylene glycol (PEG)-based linker. L is connected to Y such that Y maintains binding affinity for its target(s), as discussed herein.

In some embodiments, L is —$Z_1$—$(R_6$—O—$R_6)_t$—$Z_2$—; —$Z_1(R_6$—NH—$R_6)_t$—$Z_2$—; —$Z_1$—$(R_6$—S—$R_6)_t$—$Z_2$—;

—$Z_1$—($R_6$—(C=O)—$R_6$)$_t$—$Z_2$—; —$Z_1$—($R_6$—(CO$_2$)—$R_6$)$_t$—$Z_2$—; —$Z_1$—($R_6$—(NHCO)—$R_6$)$_t$—$Z_2$—; —$Z_1$—($R_6$—(CONH)—$R_6$)$_t$—$Z_2$—; —$Z_1$—($R_6$—(SO)—$R_6$)$_t$—$Z_2$—; —$Z_1$—($R_6$—(SO$_2$)—$R_6$)$_t$—$Z_2$—; —$Z_1$—($R_6$—(NHSO$_2$)—$R_6$)$_t$—$Z_2$—; —$Z_1$—($R_6$—(SO$_2$NH)—$R_6$)$_t$—$Z_2$—; —$Z_1$—($R_6$—NH(C=O)NH—$R_6$)$_t$—$Z_2$—; —$Z_1$—($R_6$—NH(C=NH)NH—$R_6$)$_t$—$Z_2$—; —$Z_1$—($R_6$—NH(C=S)NH—$R_6$)$_t$—$Z_2$—; or —$Z_1$—($R_6$-$R_7$—$R_6$)$_t$—$Z_2$—.

In some embodiments, each t is independently 1, 2, 3, 4, 5, 6, 7, or 8. In some embodiments, t is 0. In some embodiments, t is 1. In some embodiments, t is 2. In some embodiments, t is 3. In some embodiments, t is 4. In some embodiments, t is 5. In some embodiments, t is 6. In some embodiments, t is 7. In some embodiments, t is 8.

In some embodiments, p and q are independently 0, 1, 2, 3, 4, 5, or 6. In some embodiments, p and q are independently 0. In some embodiments, p and q are independently 1. In some embodiments, p and q are independently 2. In some embodiments, p and q are independently 3. In some embodiments, p and q are independently 4. In some embodiments, p and q are independently 5. In some embodiments, p and q are independently 6.

In some embodiments, p is 0. In some embodiments, p is 1. In some embodiments, p is 2. In some embodiments, p is 3. In some embodiments, p is 4. In some embodiments, p is 5. In some embodiments, p is 6. In some embodiments, q is 0. In some embodiments, q is 1. In some embodiments, q is 2. In some embodiments, q is 3. In some embodiments, q is 4. In some embodiments, q is 5. In some embodiments, q is 6. In some embodiments, p and q are each 0, 1, 2, 3, 4, 5, or 6.

In some embodiments, $Z_1$ and $Z_2$ are each independently —CH$_2$—; —O—; —S—; S=O; —SO$_2$—; C=O; —CO$_2$—; —NH—; —NH(CO)—; —(CO)NH—; —NH—SO$_2$—; —SO$_2$—NH—; —$R_6$CH$_2$—; —$R_6$O—; —$R_6$S—; $R_6$—S=O; —$R_6$SO$_2$—; $R_6$—C=O; —$R_6$CO$_2$—; —$R_6$NH—; —$R_6$NH(CO)—; —$R_6$(CO)NH—; —$R_6$NH—SO$_2$—; —$R_6$SO$_2$—NH—; —CH$_2$$R_6$—; —O$R_6$—; —S$R_6$—; S=O—$R_6$; —SO$_2$$R_6$—; C=O—$R_6$; —CO$_2$$R_6$—; —NH$R_6$—; —NH(CO)$R_6$—; —(CO)NH$R_6$—; —NH—SO$_2$$R_6$—; or —SO$_2$—NH$R_6$—.

In some embodiments, each $R_6$ is absent, or independently $C_1$-$C_6$ alkyl, $C_2$-$C_6$ alkenyl, $C_2$-$C_6$ alkynyl, $C_6$-$C_{10}$ aryl, 3 to 10-membered heterocyclyl, or 5 to 10-membered heteroaryl.

In some embodiments, $R_7$ is optionally substituted $C_3$-$C_8$ cycloalkyl, optionally substituted $C_6$-$C_{10}$ aryl, optionally substituted 3 to 10-membered heterocyclyl, or optionally substituted 5 to 10-membered heteroaryl.

In some embodiments, $R_8$ is selected from an optionally substituted $C_3$-$C_{10}$ cycloalkyl, an optionally substituted $C_6$-$C_{10}$ aryl, an optionally substituted 5 to 10-membered heteroaryl, and an optionally substituted 3 to 10-membered heterocyclyl. In some embodiments, the optionally substituted $C_6$-$C_{10}$ aryl is an unsubstituted phenyl group. In some embodiments, the optionally substituted $C_6$-$C_{10}$ aryl is an unsubstituted naphthyl group. In some embodiments, the optionally substituted $C_6$-$C_{10}$ aryl is a phenyl group substituted with halogen. In some embodiments, the optionally substituted $C_6$-$C_{10}$ aryl is a phenyl group substituted with an unsubstituted $C_1$-$C_6$ alkyl. In some embodiments, the optionally substituted $C_6$-$C_{10}$ aryl is a phenyl group substituted with an unsubstituted $C_1$-$C_6$ alkyl and halogen. In some embodiments, the optionally substituted 5 to 10-membered heteroaryl is 5 or 6-membered heteroaryl substituted with halogen. In some embodiments, the optionally substituted 5 to 10-membered heteroaryl is 5 or 6-membered heteroaryl substituted with an unsubstituted $C_1$-$C_6$ alkyl. In some embodiments, the optionally substituted 5 to 10-membered heteroaryl is 5 or 6-membered heteroaryl substituted with an unsubstituted $C_1$-$C_6$ alkyl and halogen.

In some embodiments, the optionally substituted $C_6$-$C_{10}$ aryl is a phenyl group substituted with an optionally substituted 3 to 10-membered heterocyclyl. In some embodiments, the optionally substituted 3 to 10-membered heterocyclyl is an unsubstituted 5 to 7-membered heterocyclyl group. In some embodiments, the unsubstituted 5 to 7-membered heterocyclyl group is pyrrolidinyl, morpholino, piperidinyl, piperazinyl, or azepanyl. In some embodiments, the optionally substituted 5 to 10-membered heteroaryl is 5 or 6-membered heteroaryl substituted with an optionally substituted 3 to 10-membered heterocyclyl. In some embodiments, the optionally substituted 3 to 10-membered heterocyclyl is an unsubstituted 5 to 7-membered heterocyclyl group. In some embodiments, the unsubstituted 5 to 7-membered heterocyclyl group is pyrrolidinyl, morpholino, piperidinyl, piperazinyl, or azepanyl.

In some embodiments, $R_8$ is selected from:

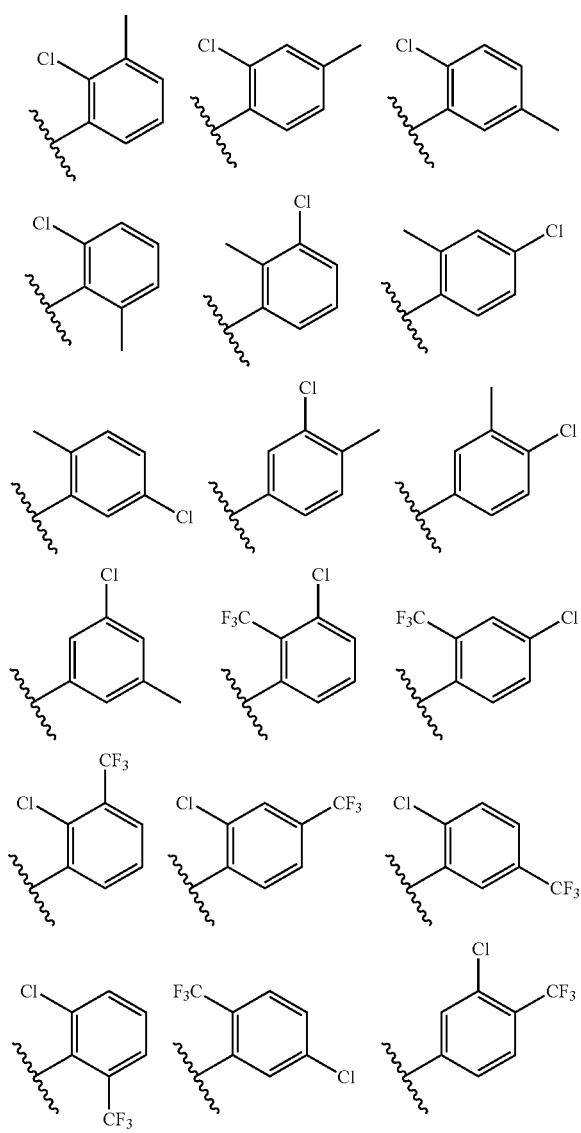

-continued

In some embodiments, $R_8$ is selected from:

-continued
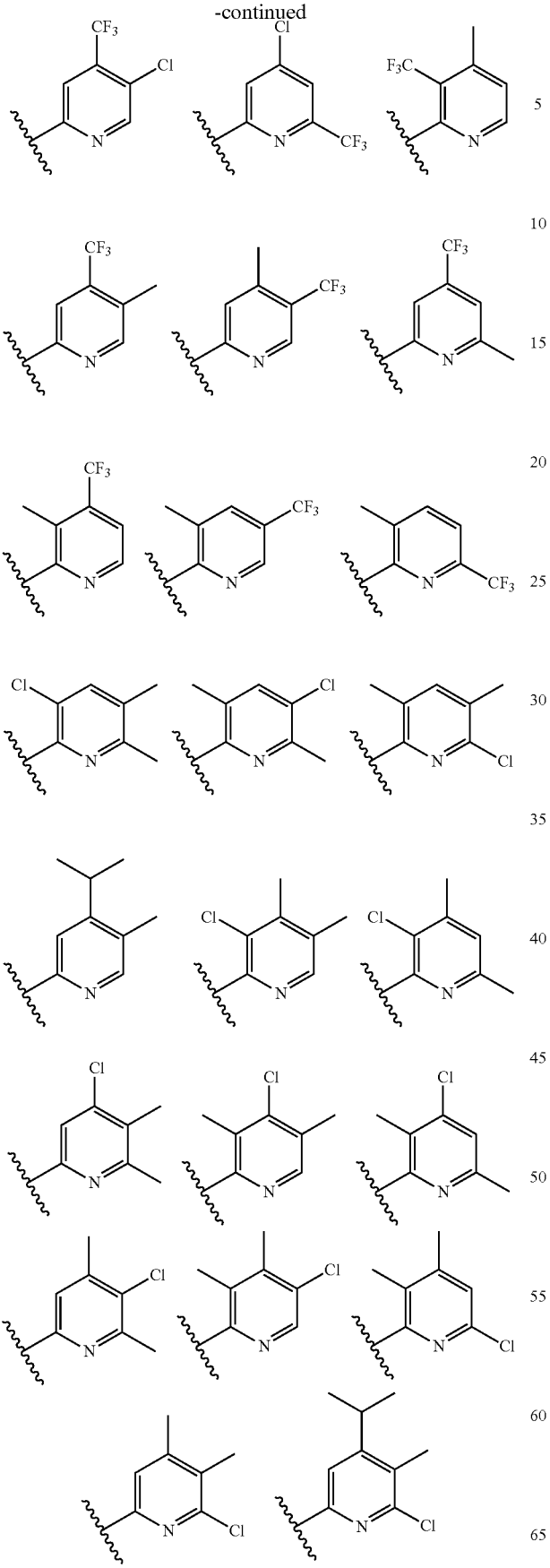
In some embodiments, $R_8$ is selected from:
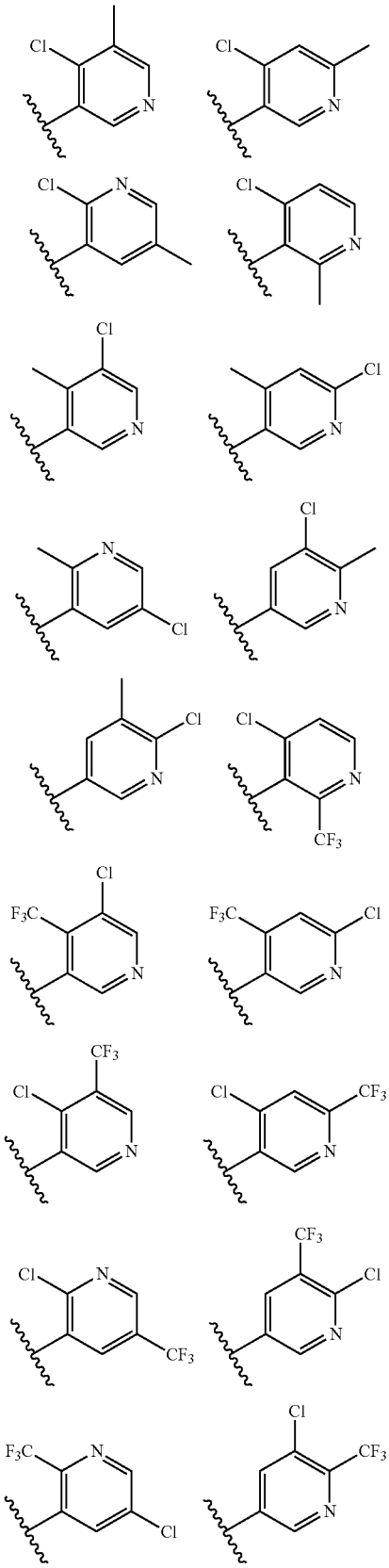

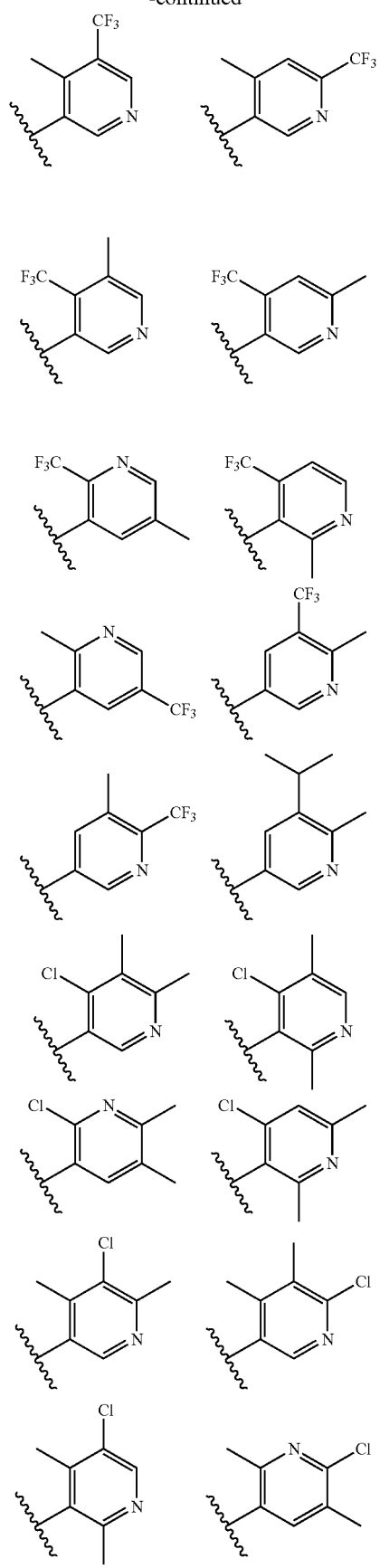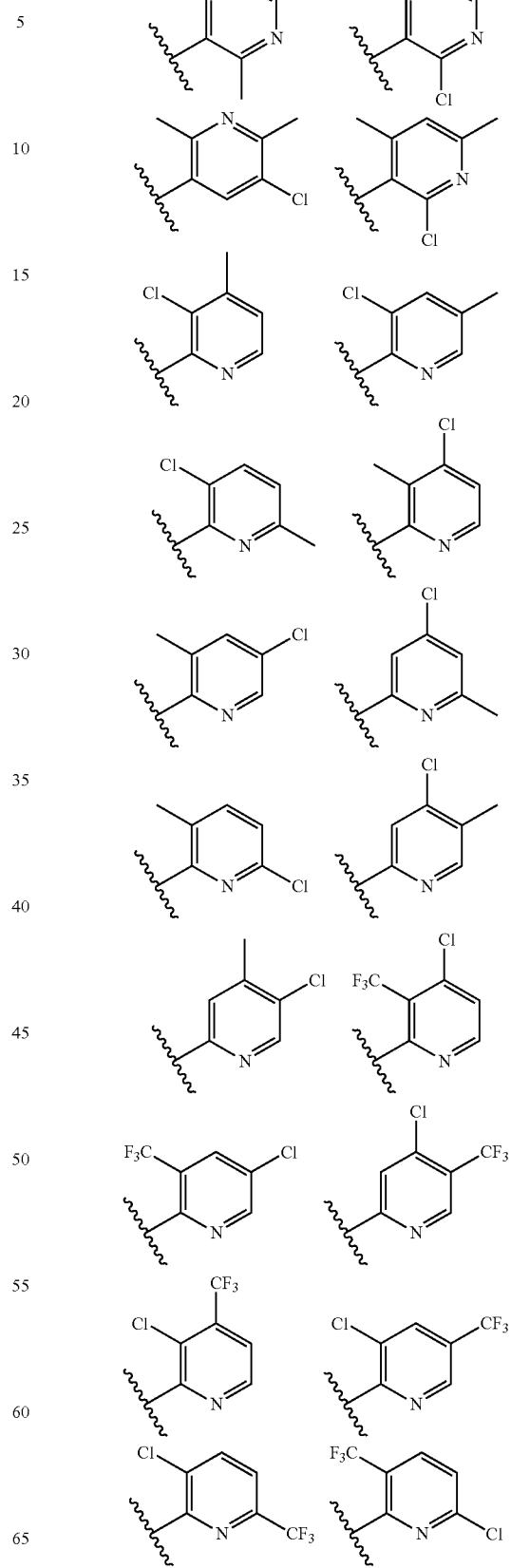

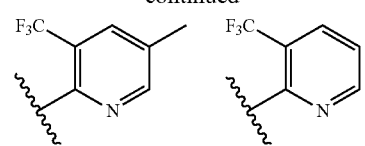
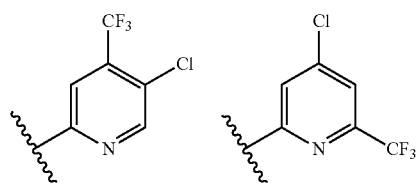
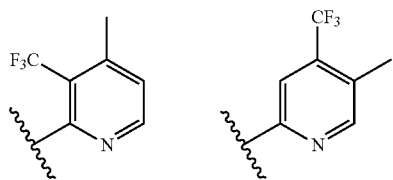
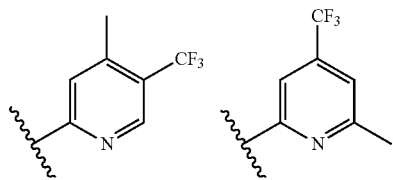
In some embodiments, R$_8$ is selected from:
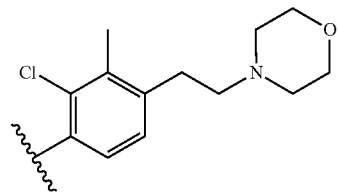
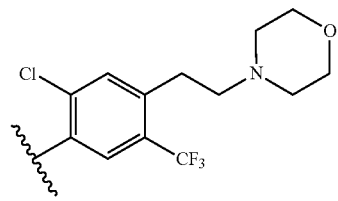
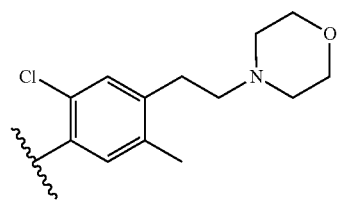
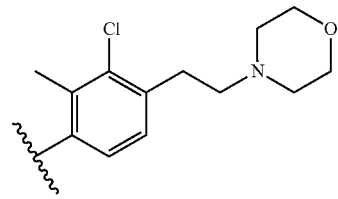
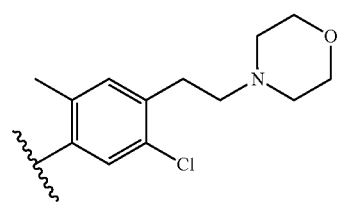
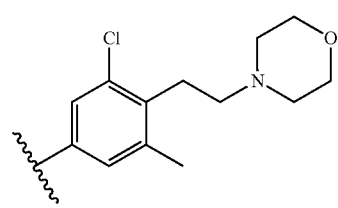
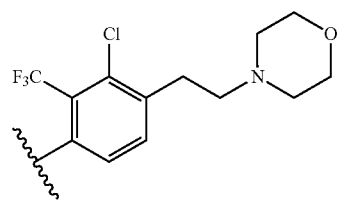
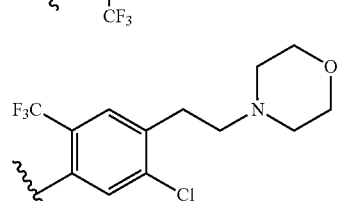
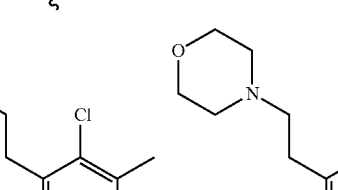
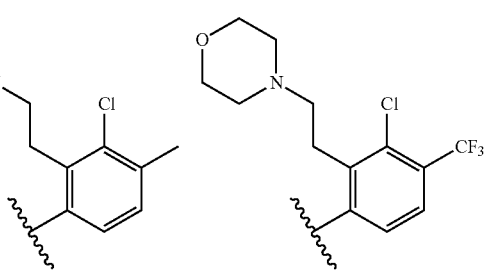

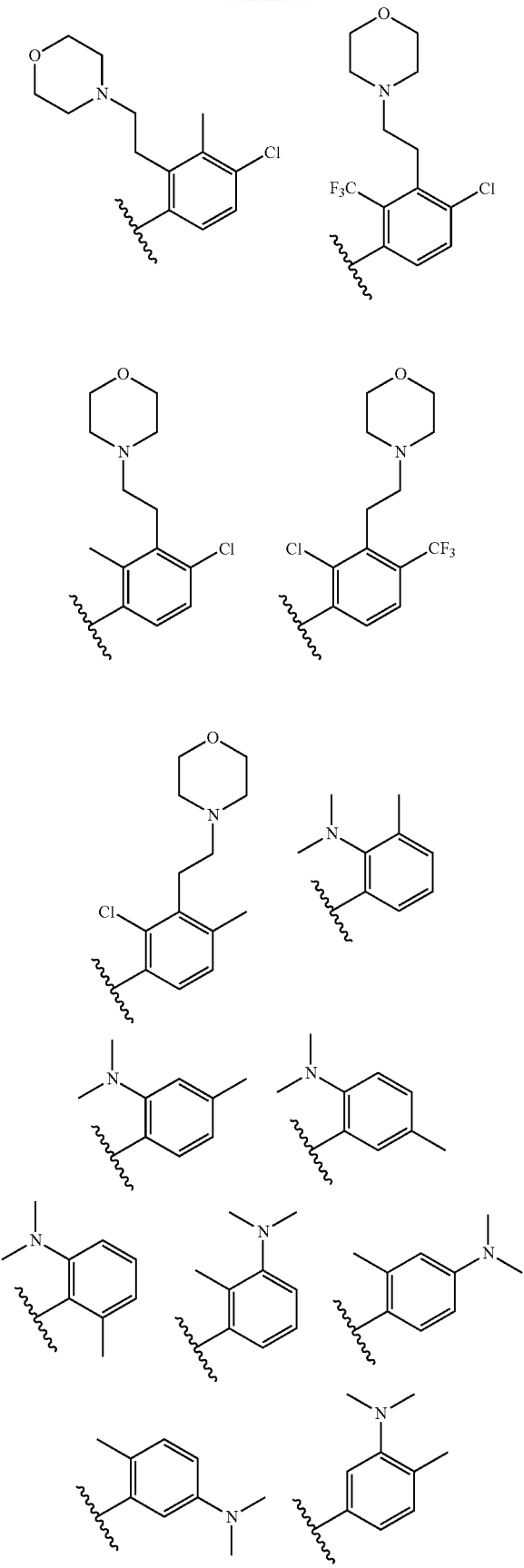

In some embodiments, $R_8$ is $R_{8A}$ and $R_{8A}$ is selected from optionally substituted $C_3$-$C_{10}$ cycloalkyl($C_1$-$C_6$ alkyl), optionally substituted $C_6$-$C_{10}$ aryl($C_1$-$C_6$ alkyl), optionally substituted 5 to 10 membered heteroaryl($C_1$-$C_6$ alkyl), and optionally substituted 3 to 10 membered heterocyclyl($C_1$-$C_6$ alkyl).

In some embodiments, $R_{8A}$ is selected from unsubstituted $C_3$-$C_{10}$ cycloalkyl($C_1$-$C_6$ alkyl), unsubstituted $C_6$-$C_{10}$ aryl ($C_1$-$C_6$ alkyl), unsubstituted 5 to 10 membered heteroaryl ($C_1$-$C_6$ alkyl), and unsubstituted 3 to 10 membered heterocyclyl($C_1$-$C_6$ alkyl).

In some embodiments, $R_{8A}$ is selected from substituted $C_3$-$C_{10}$ cycloalkyl($C_1$-$C_6$ alkyl), substituted $C_6$-$C_{10}$ aryl($C_1$-$C_6$ alkyl), substituted 5 to 10 membered heteroaryl($C_1$-$C_6$ alkyl), and substituted 3 to 10 membered heterocyclyl($C_1$-$C_6$ alkyl).

In some embodiments, $R_8$ is $R_{8B}$ and $R_{8B}$ is $Y_1$. In some embodiments, $Y_1$ is

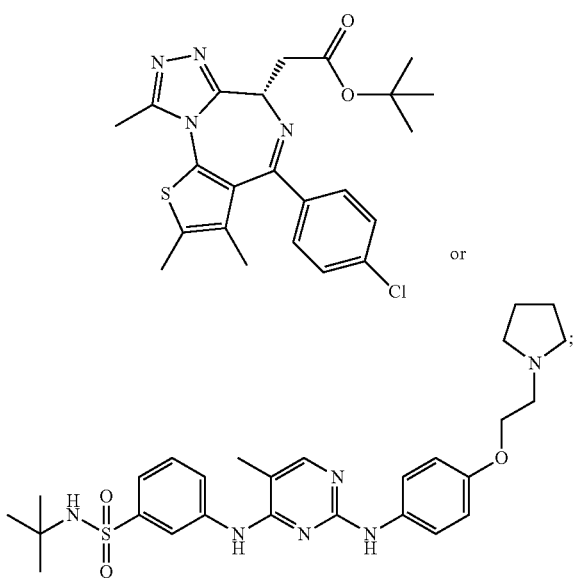

or wherein Y₁ is derivatized to attach to X₂.

In some embodiments, one of $R_1$ and $R_2$ is

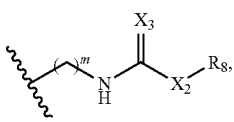

and the other of $R_1$ and $R_2$ is H, deuterium, unsubstituted $C_1$-$C_6$ alkoxy, or unsubstituted $C_1$-$C_6$ alkyl, wherein m is 1, $X_3$ is O, $X_2$ is NH, and $R_8$ is a substituted phenyl or a substituted 5 or 6-membered heteroaryl, wherein the phenyl and 5 or 6-membered heteroaryl are substituted with 1-3 substituents selected from hydroxyl, halogen (e.g., fluoro, chloro, and bromo), cyano, nitro, optionally substituted $C_1$-$C_6$ alkoxy (e.g., methoxy, ethoxy, and isopropoxy), optionally substituted $C_1$-$C_6$ alkyl (e.g., methyl, ethyl, and isopropyl), optionally substituted $C_3$-$C_8$ cycloalkyl (e.g., cyclopropyl, cyclobutyl, and cyclopentyl), and optionally substituted 3 to 10-membered heterocyclyl (e.g., pyrrolidinyl, morpholino, piperidinyl, piperazinyl, and azepanyl).

In some embodiments, one of $R_1$ and $R_2$ is

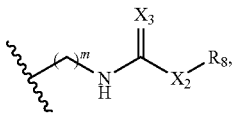

and the other of $R_1$ and $R_2$ is H, deuterium, unsubstituted $C_1$-$C_6$ alkoxy, or unsubstituted $C_1$-$C_6$ alkyl, wherein m is 1, $X_3$ is O, $X_2$ is NH, and $R_8$ is a substituted phenyl or a substituted 5 or 6-membered heteroaryl, wherein the phenyl and 5 or 6-membered heteroaryl are substituted with 1-3 substituents selected from hydroxyl, halogen (e.g., fluoro, chloro, and bromo), cyano, nitro, unsubstituted $C_1$-$C_6$ alkoxy (e.g., methoxy, ethoxy, and isopropoxy), unsubstituted $C_1$-$C_6$ alkyl (e.g., methyl, ethyl, and isopropyl), unsubstituted $C_3$-$C_8$ cycloalkyl (e.g., cyclopropyl, cyclobutyl, and cyclopentyl), and unsubstituted 3 to 10-membered heterocyclyl (e.g., pyrrolidinyl, morpholino, piperidinyl, piperazinyl, and azepanyl).

In some embodiments, one of $R_1$ and $R_2$ is

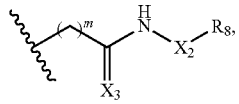

and the other of $R_1$ and $R_2$ is H, deuterium, unsubstituted $C_1$-$C_6$ alkoxy, or unsubstituted $C_1$-$C_6$ alkyl, wherein m is 1, $X_3$ is O, $X_2$ is —CH₂— or —CH₂CH₂—, and $R_8$ is a substituted phenyl or a substituted 5 or 6-membered heteroaryl, wherein the phenyl and 5 or 6-membered heteroaryl are substituted with 1-3 substituents selected from hydroxyl, halogen (e.g., fluoro, chloro, and bromo), cyano, nitro, optionally substituted $C_1$-$C_6$ alkoxy (e.g., methoxy, ethoxy, and isopropoxy), optionally substituted $C_1$-$C_6$ alkyl (e.g., methyl, ethyl, and isopropyl), optionally substituted $C_3$-$C_8$ cycloalkyl (e.g., cyclopropyl, cyclobutyl, and cyclopentyl), and optionally substituted 3 to 10-membered heterocyclyl (e.g., pyrrolidinyl, morpholino, piperidinyl, piperazinyl, and azepanyl).

In some embodiments, one of $R_1$ and $R_2$ is

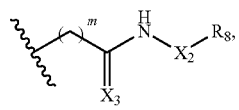

and the other of $R_1$ and $R_2$ is H, deuterium, unsubstituted $C_1$-$C_6$ alkoxy, or unsubstituted $C_1$-$C_6$ alkyl, wherein m is 1, $X_3$ is O, $X_2$ is —CH₂— or —CH₂CH₂—, and $R_8$ is a substituted phenyl or a substituted 5 or 6-membered heteroaryl, wherein the phenyl and 5 or 6-membered heteroaryl are substituted with 1-3 substituents selected from hydroxyl, halogen (e.g., fluoro, chloro, and bromo), cyano, nitro, unsubstituted $C_1$-$C_6$ alkoxy (e.g., methoxy, ethoxy, and isopropoxy), unsubstituted $C_1$-$C_6$ alkyl (e.g., methyl, ethyl, and isopropyl), unsubstituted $C_3$-$C_8$ cycloalkyl (e.g., cyclopropyl, cyclobutyl, and cyclopentyl), and unsubstituted 3 to 10-membered heterocyclyl (e.g., pyrrolidinyl, morpholino, piperidinyl, piperazinyl, and azepanyl).

In some embodiments, one of $R_1$ and $R_2$ is an optionally substituted urea and the other of $R_1$ and $R_2$ is H, deuterium, unsubstituted $C_1$-$C_6$ alkoxy, or unsubstituted $C_1$-$C_6$ alkyl, wherein m is 1, $X_3$ is O, $X_2$ is NH, and $R_8$ is a substituted phenyl or a substituted 5 or 6-membered heteroaryl, wherein the phenyl and 5 or 6-membered heteroaryl are substituted with 1-3 substituents selected from hydroxyl, halogen (e.g., fluoro, chloro, and bromo), cyano, nitro, optionally substituted $C_1$-$C_6$ alkoxy (e.g., methoxy, ethoxy, and isopropoxy), optionally substituted $C_1$-$C_6$ alkyl (e.g., methyl, ethyl, and isopropyl), optionally substituted $C_3$-$C_8$ cycloalkyl (e.g., cyclopropyl, cyclobutyl, and cyclopentyl), and optionally substituted 3 to 10-membered heterocyclyl (e.g., pyrrolidinyl, morpholino, piperidinyl, piperazinyl, and azepanyl).

In some embodiments, one of $R_1$ and $R_2$ is an optionally substituted urea, and the other of $R_1$ and $R_2$ is H, deuterium, unsubstituted $C_1$-$C_6$ alkoxy, or unsubstituted $C_1$-$C_6$ alkyl, wherein m is 1, $X_3$ is O, $X_2$ is NH, and $R_8$ is a substituted phenyl or a substituted 5 or 6-membered heteroaryl, wherein the phenyl and 5 or 6-membered heteroaryl are substituted with 1-3 substituents selected from hydroxyl, halogen (e.g., fluoro, chloro, and bromo), cyano, nitro, unsubstituted $C_1$-$C_6$ alkoxy (e.g., methoxy, ethoxy, and isopropoxy), unsubstituted $C_1$-$C_6$ alkyl (e.g., methyl, ethyl, and isopropyl), unsubstituted $C_3$-$C_8$ cycloalkyl (e.g., cyclopropyl, cyclobutyl, and cyclopentyl), and unsubstituted 3 to 10-membered heterocyclyl (e.g., pyrrolidinyl, morpholino, piperidinyl, piperazinyl, and azepanyl).

In some embodiments, one of $R_1$ and $R_2$ is an optionally substituted urea, and the other of $R_1$ and $R_2$ is H, deuterium, unsubstituted $C_1$-$C_6$ alkoxy, or unsubstituted $C_1$-$C_6$ alkyl, wherein m is 1, $X_3$ is O, $X_2$ is —$CH_2$— or —$CH_2CH_2$—, and $R_8$ is a substituted phenyl or a substituted 5 or 6-membered heteroaryl, wherein the phenyl and 5 or 6-membered heteroaryl are substituted with 1-3 substituents selected from hydroxyl, halogen (e.g., fluoro, chloro, and bromo), cyano, nitro, optionally substituted $C_1$-$C_6$ alkoxy (e.g., methoxy, ethoxy, and isopropoxy), optionally substituted $C_1$-$C_6$ alkyl (e.g., methyl, ethyl, and isopropyl), optionally substituted $C_3$-$C_8$ cycloalkyl (e.g., cyclopropyl, cyclobutyl, and cyclopentyl), and optionally substituted 3 to 10-membered heterocyclyl (e.g., pyrrolidinyl, morpholino, piperidinyl, piperazinyl, and azepanyl).

In some embodiments, one of $R_1$ and $R_2$ is an optionally substituted urea, and the other of $R_1$ and $R_2$ is H, deuterium, unsubstituted $C_1$-$C_6$ alkoxy, or unsubstituted $C_1$-$C_6$ alkyl, wherein m is 1, $X_3$ is O, $X_2$ is —$CH_2$— or —$CH_2CH_2$—, and $R_8$ is a substituted phenyl or a substituted 5 or 6-membered heteroaryl, wherein the phenyl and 5 or 6-membered heteroaryl are substituted with 1-3 substituents selected from hydroxyl, halogen (e.g., fluoro, chloro, and bromo), cyano, nitro, unsubstituted $C_1$-$C_6$ alkoxy (e.g., methoxy, ethoxy, and isopropoxy), unsubstituted $C_1$-$C_6$ alkyl (e.g., methyl, ethyl, and isopropyl), unsubstituted $C_3$-$C_8$ cycloalkyl (e.g., cyclopropyl, cyclobutyl, and cyclopentyl), and unsubstituted 3 to 10-membered heterocyclyl (e.g., pyrrolidinyl, morpholino, piperidinyl, piperazinyl, and azepanyl).

In some embodiments, compounds of Formula (II) are selected from compounds of Formula (IId), Formula (IIe), or Formula (IIf), wherein the definitions of $R_1$ and $R_2$ are as described herein:

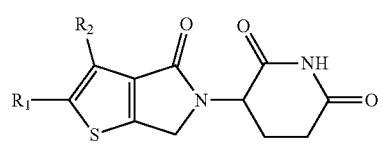
(IId)

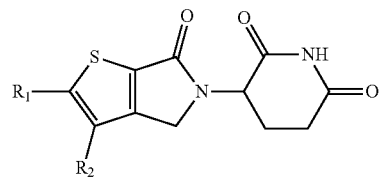
(IIe)

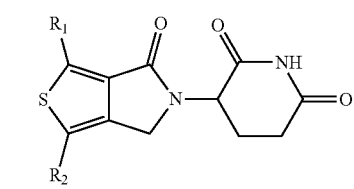
(IIf)

In some embodiments, Y is

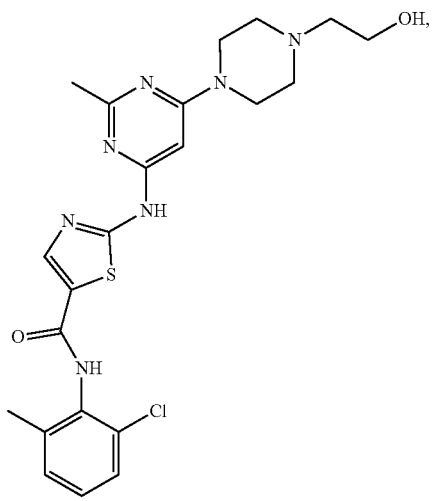

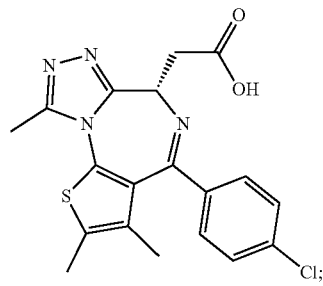

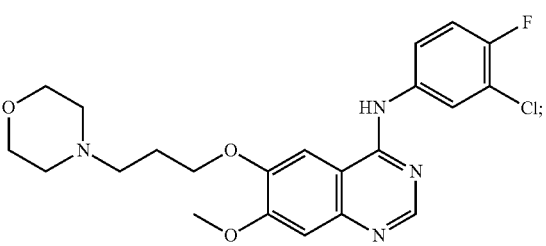

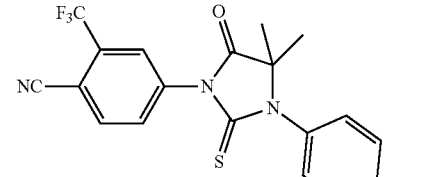

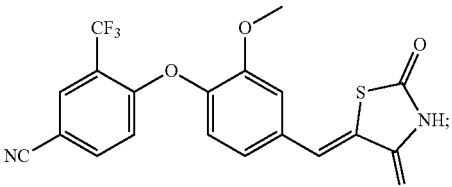

-continued
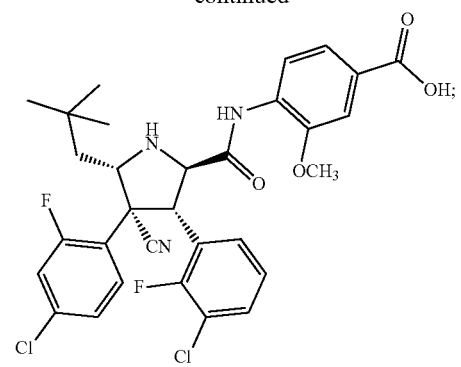
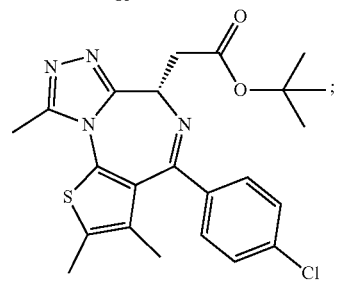
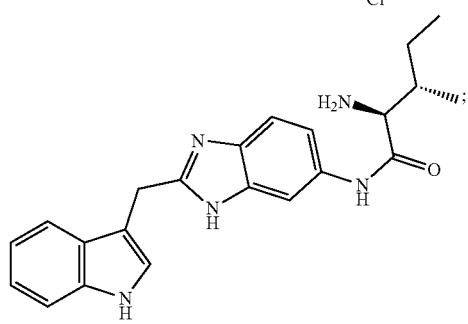
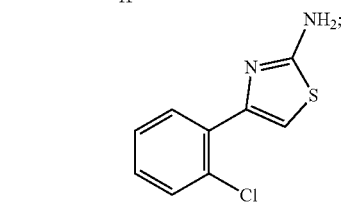
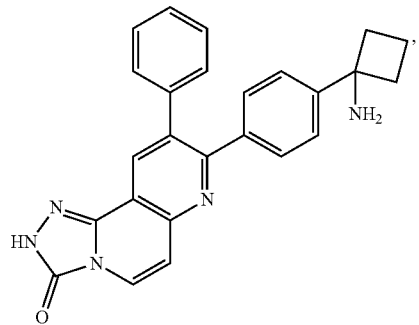
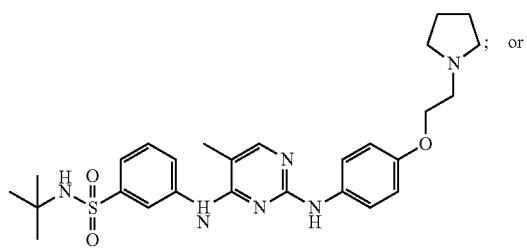
-continued
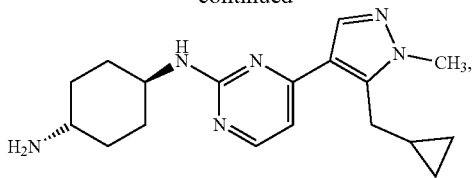
wherein Y is derivatized to attach to L. In some embodiments, Y is
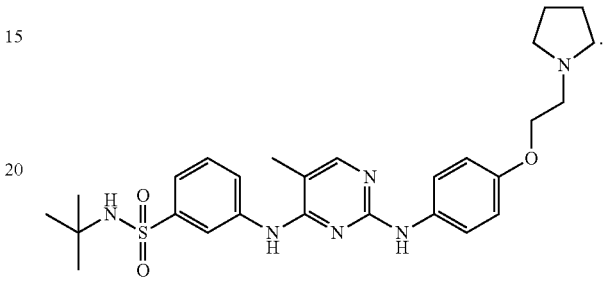
In some embodiments, $Y_1$ is
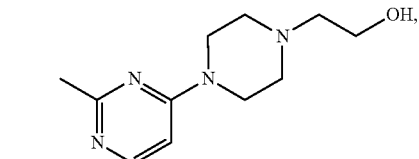
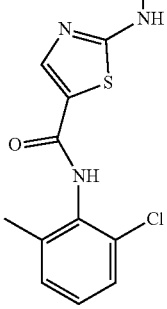
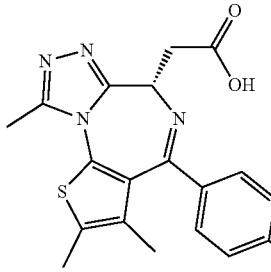
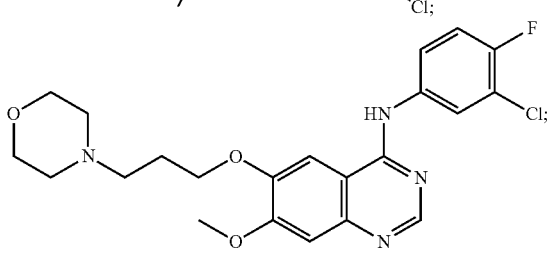

-continued

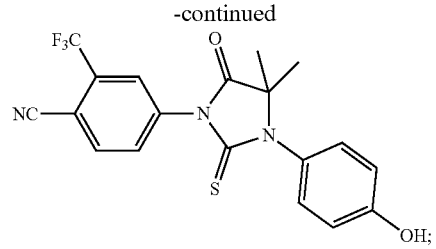

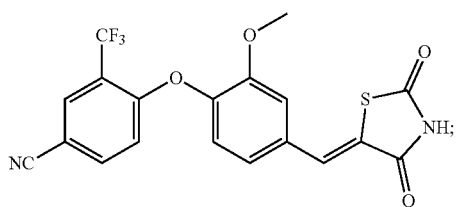

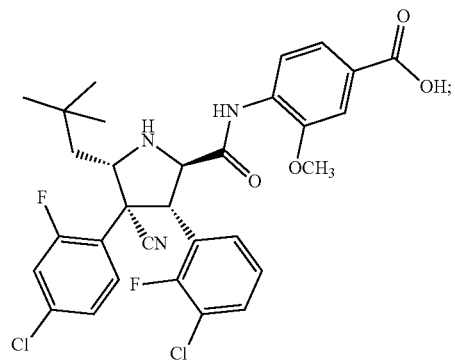

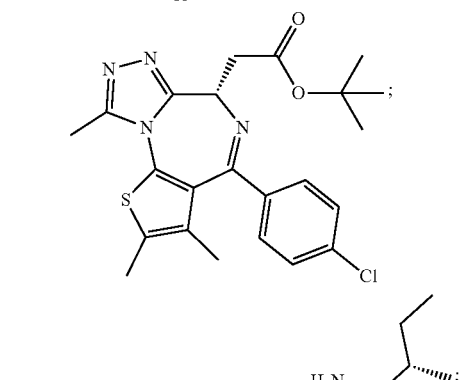

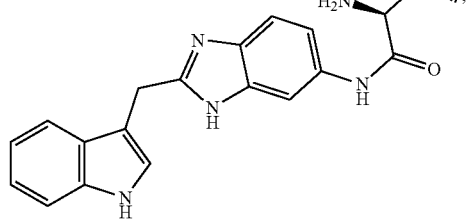

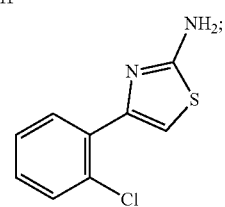

-continued

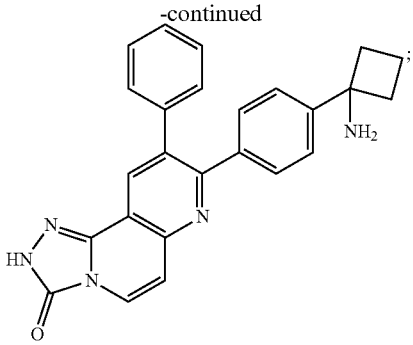

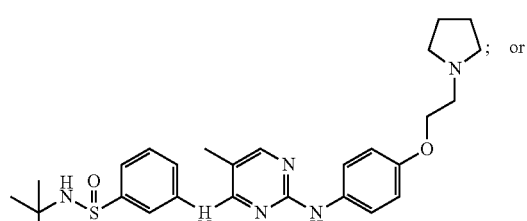

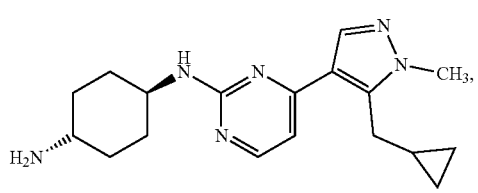

wherein $Y_1$ is derivatized to attach to $X_2$. In some embodiments, $Y_1$ is

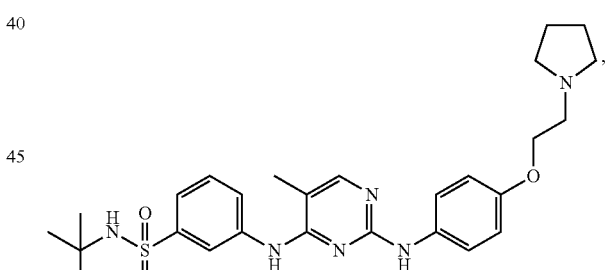

derivatized to attach to $X_2$.

As used herein, the phrases "Y is derivatized to attach to L" and "$Y_1$ is derivatized to attach to $X_2$" are used as would be understood by one having ordinary skill in the art. For example, when Y or $Y_1$ is

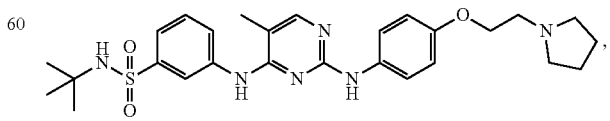

and Y or $Y_1$ is derivatized to attached to L or $X_2$, respectively, Y or $Y_1$ can be:

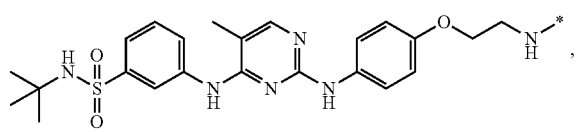
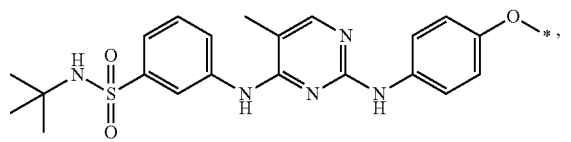
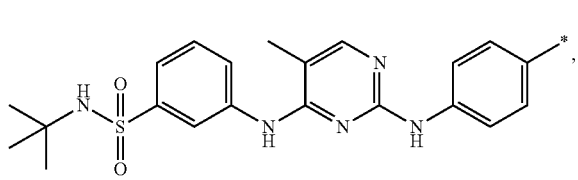
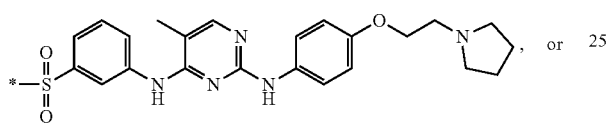
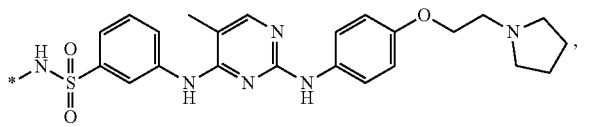
wherein * represents the point of attachment to the L group. Similarly, when Y or Y$_1$ is
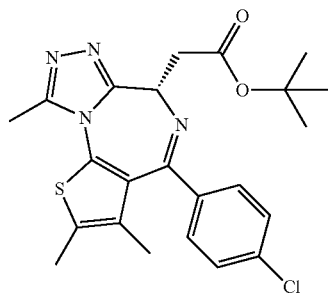 [SMILES: Cc1sc2c(c1C)C(c1ccc(Cl)cc1)=N[C@@H](CC(=O)OC(C)(C)C)c1nnc(C)n1-2]
and Y or Y$_1$ is derivatized to attached to L, Y or Y$_1$ can be, for example:
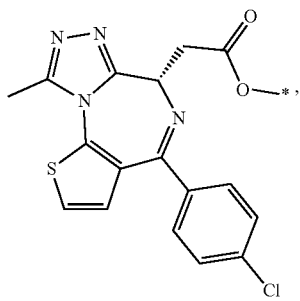
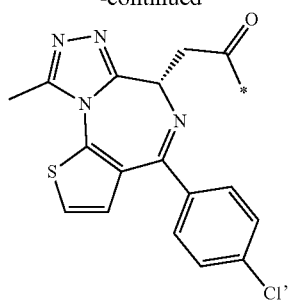
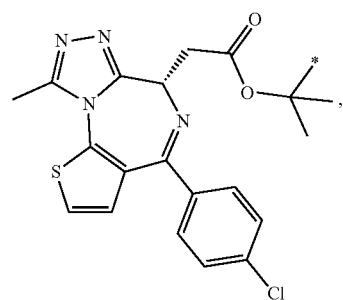
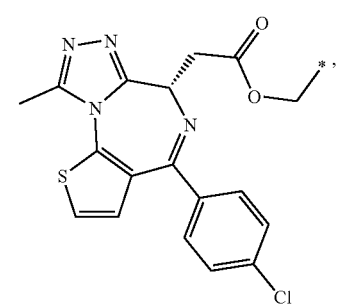
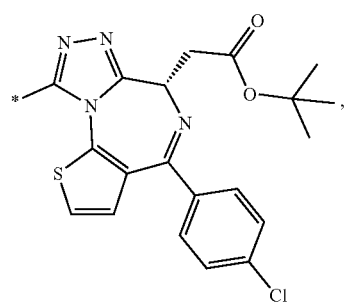
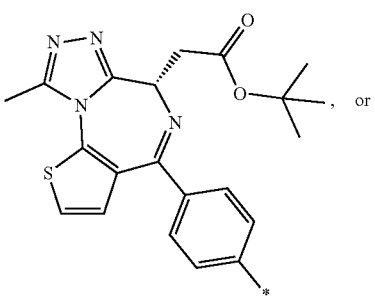

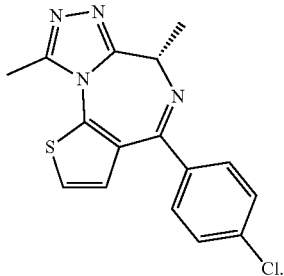 [SMILES: Cc1nnc2n1-c1sccc1C(c1ccc(Cl)cc1)=N[C@H]2C]

In some embodiments, Y and $Y_1$ are selected from: a compound that targets a particular protein, proteins, and/or protein complex, such as an HSP90 inhibitor, a kinase inhibitor, a phosphatase inhibitor, an estrogen receptor agonist, an estrogen receptor antagonist, an androgen receptor agonist, an androgen receptor antagonist, an HDM2/MDM2 inhibitor, an HDAC inhibitor, a lysine methyltransferase inhibitor, or an inhibitor of one or more core-binding factor(s). In some embodiments, and $Y_1$ are selected from a compound targeting: one or more ligase(s), the BET bromodomain, FKBP, acyl-protein thioesterase 1, acyl-protein thioesterase 2, the thyroid hormone receptor, the RAF receptor, the aryl hydrocarbon receptor. In some embodiments, and $Y_1$ are selected from an immunosuppressive compound, an angiogenesis inhibitor, an HIV protease inhibitor, an HIV integrase inhibitor, and an HCV protease inhibitor. In some embodiments, Y and $Y_1$ are derivatized where L is attached.

In some embodiments, Y is a compound disclosed in Vallee, et al., *J. Med. Chem.* 54: 7206 (2011), including, but not limited to (N-[4-(3H-imidazo[4,5-C]Pyridin-2-yl)-9H-Fluoren-9-yl]-succinamide):

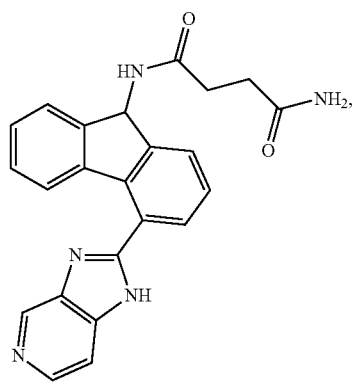 [SMILES: NC(=O)CCC(=O)NC1c2ccccc2-c2c(-c3nc4cnccc4[nH]3)cccc21]

derivatized where a linker group L is attached, for example, via the terminal amide group.

In some embodiments, Y is (8-[(2,4-dimethylphenyl)sulfanyl]-3]pent-4-yn-1-yl-3H-purin-6-amine):

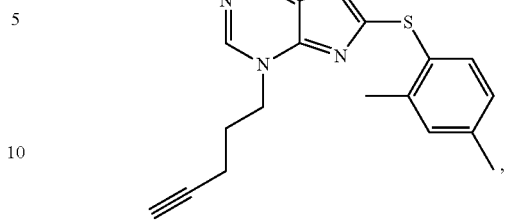

where a linker group L is attached, for example, via the terminal acetylene group.

In some embodiments, Y is a compound disclosed in Brough, et al., "*J. Med. Chem. vol:* 51*, page* 196 (2008), including (5-[2,4-dihydroxy-5-(1-methylethyl)phenyl]-n-ethyl-4-[4-(morpholin-4-ylme-thyl)phenyl]isoxazole-3-carboxamide) having the structure:

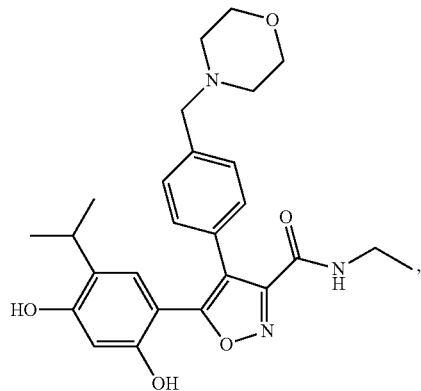 [SMILES: CCNC(=O)c1noc(-c2cc(C(C)C)c(O)cc2O)c1-c1ccc(CN2CCOCC2)cc1]

derivatized, where a linker group L is attached, for example, via the amide group.

In some embodiments, Y is a compound disclosed in Wright, et al., *Chem Biol.*, 11(6):775-85 (2004), including:

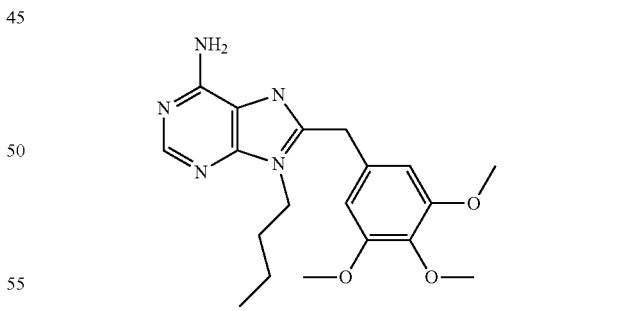

where a linker group L or is attached, for example, via the butyl group.

In some embodiments, Y is geldanamycin ((4E,6Z,8S,9S,10E,12S,13R,14S,16R)-13-hydroxy-8,14,19-trimethoxy-4,10,12,-16-tetramethyl-3,20,22-trioxo-2-azabicyclo[16.3.1], or a derivative thereof (e.g. 17-alkylamino-17-desmethoxygeldanamycin ("17-AAG") or 17-(2-dimethylaminoethyl) amino-17-desmethoxygeldanamycin ("17-DMAG")) (derivatized where a linker group L is attached, for example, via the amide group).

In some embodiments, Y is

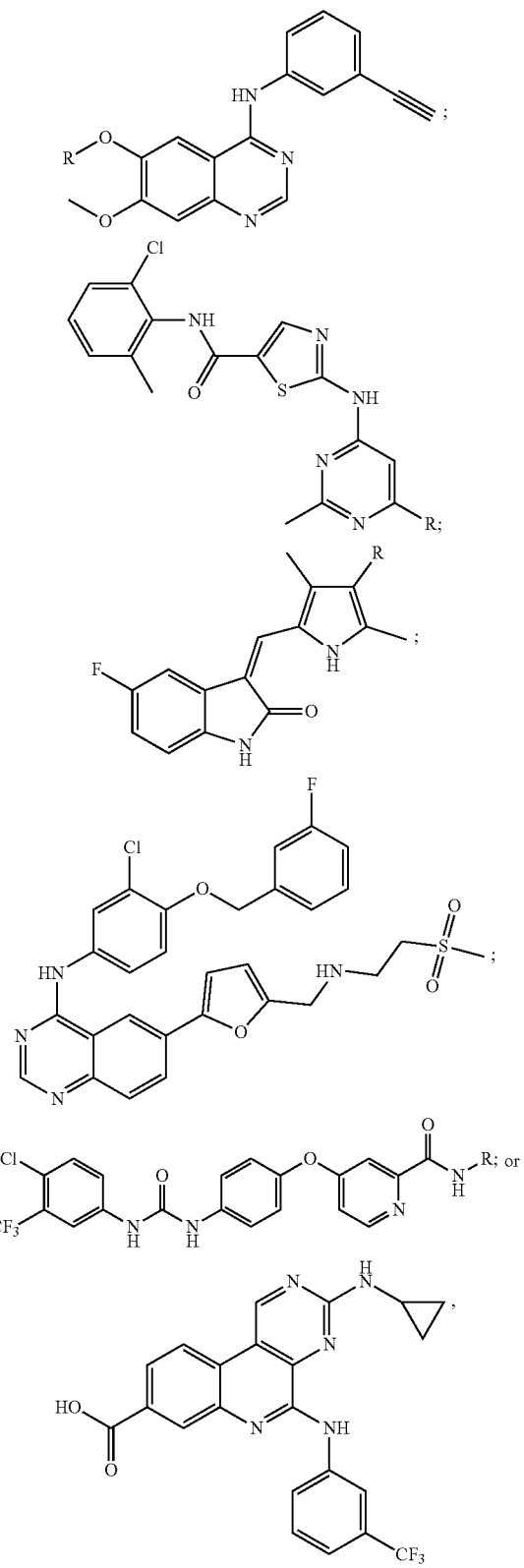

each derivatized either through R (representing a linker group, L), or through another point of attachment.

In some embodiments, Y is a compound disclosed in Millan, et al., *J. Med. Chem.*, vol: 54, pag: 7797 (2011), including:

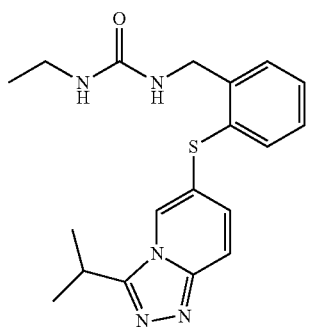 [SMILES: CCNC(=O)NCc1ccccc1Sc1ccc2nnc(C(C)C)n2c1]

(1-ethyl-3-(2-{[3-(1-methylethyl)[1,2,4]triazolo[4,3-a]pyridine-6-yl]sulfanyl}benzyl)urea derivatized where a linker group L is attached, for example, via the isopropyl group;

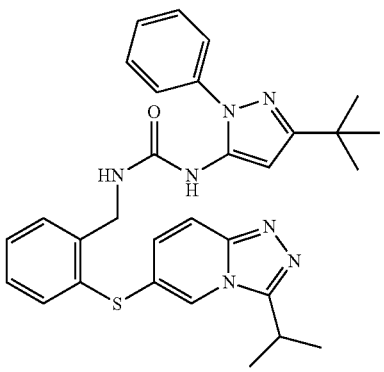 [SMILES: CC(C)c1nnc2ccc(Sc3ccccc3CNC(=O)Nc3cc(C(C)(C)C)nn3-c3ccccc3)cn12]

1-(3-tert-butyl-1-phenyl-1H-pyrazol-5-yl)-3-(2-{[3-(1-methylethyl)[1,2,4]-triazolo[4,3-a]pyridin-6-yl] sulfanyl}benzyl)urea derivatized where a linker group L is attached, for example, via the tert-butyl group.

In some embodiments, Y is a compound disclosed in Schenkel, et al., *J. Med. Chem.*, 54 (24), pp 8440-8450 (2011) including:

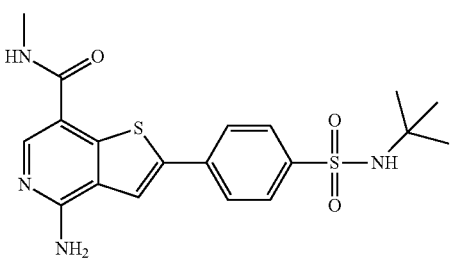 [SMILES: CNC(=O)c1cnc(N)c2cc(-c3ccc(S(=O)(=O)NC(C)(C)C)cc3)sc12]

4-amino-2-[4-(tert-butylsulfamoyl)phenyl]-N-methylthieno[3,2-c]pyridine-7-carboxamide and

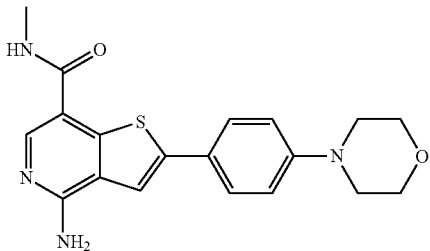 [SMILES: CNC(=O)c1cnc(N)c2cc(-c3ccc(N4CCOCC4)cc3)sc12]

4-amino-N-methyl-2-[4-(morpholin-4-yl)phenyl]thieno[3,2-c]pyridine-7-carboxamide, derivatized where a linker group L is attached, for example, via the terminal amide moiety.

In some embodiments, Y is a compound disclosed in Van Eis, et al., *Biorg. Med. Chem. Lett.* 21(24):7367-72 (2011), including:

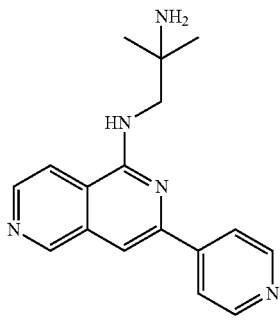 [SMILES: CC(C)(N)CNc1nc(-c2ccncc2)cc2cnccc12]

2-methyl-N–1-[3-(pyridin-4-yl)-2,6-naphthyridin-1-yl]propane-1,2-diamine derivatized where a linker group L is attached, for example, via the terminal amino group.

In some embodiments, Y is a compound disclosed in Lountos, et al., "*J. Struct. Biol.*, vol. 176, page 292 (2011), including:

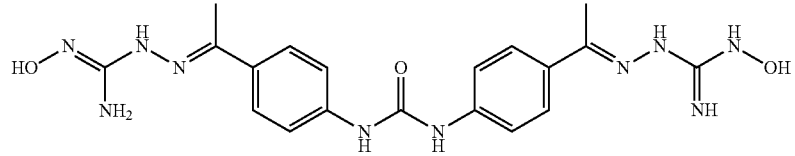 [SMILES: C/C(=N\NC(=N)NO)c1ccc(NC(=O)Nc2ccc(/C(C)=N/N/C(N)=N/O)cc2)cc1]

derivatized where a linker group L is attached, for example, via either of the terminal hydroxyl groups.

In some embodiments, Y is

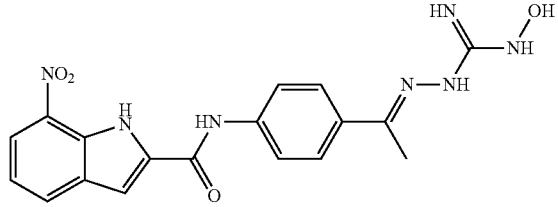 [SMILES: C/C(=N\NC(=N)NO)c1ccc(NC(=O)c2cc3cccc([N+](=O)[O-])c3[nH]2)cc1]

N-{4-[(1E)-N—(N-hydroxycarbamimidoyl)ethanehydrazonoyl]phenyl}-7-nitro-1H-indole-2-carboxamide or

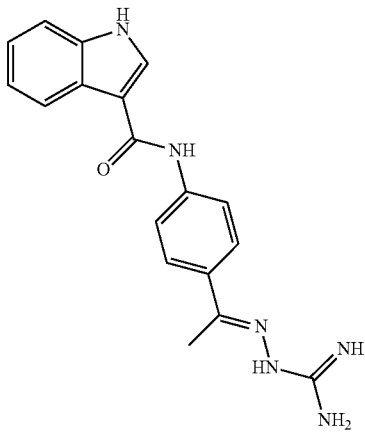 [SMILES: C/C(=N\NC(=N)N)c1ccc(NC(=O)c2c[nH]c3ccccc23)cc1]

N-{4-[(1E)-N-carbamidoylethanehydrazonoyl]phenyl}-1H-indole-3-carboxamide derivatized where a linker group L is attached, for example, via the terminal hydroxyl group or the hydrazone.

In some embodiments, Y is afatinib (derivatized where a linker group L is attached, for example, via the aliphatic amine group); fostamatinib (derivatized where a linker group L is attached, for example, via a methoxy group); gefitinib (derivatized where a linker group L is attached, for example, via a methoxy or ether group); lenvatinib (derivatized where a linker group L is attached, for example, via the cyclopropyl group); vandetanib (derivatized where a linker group L is attached, for example, via the methoxy or hydroxyl group); vemurafenib (derivatized where a linker group L is attached, for example, via the sulfonyl propyl group); Gleevec (derivatized where R as a linker group L is attached, for example, via the amide group or via the aniline amine group); pazopanib (derivatized where R is a linker group L attached, for example, to the phenyl moiety or via the aniline amine group); AT-9283

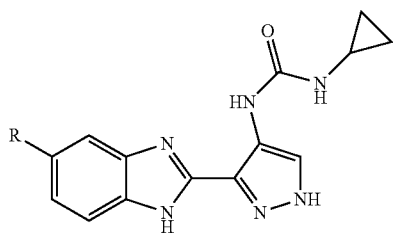

(derivatized where R is a linker group L attached, for example, to the phenyl moiety); TAE684

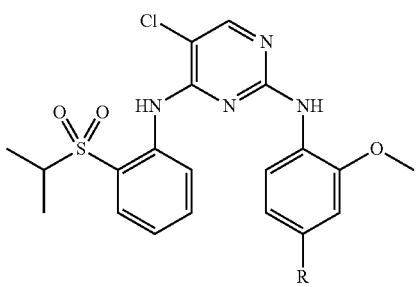

(derivatized where R is a linker group L attached, for example, to the phenyl moiety);

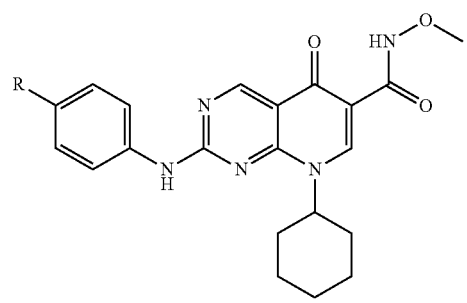

(derivatized where R is a linker group L attached, for example, to the phenyl moiety);

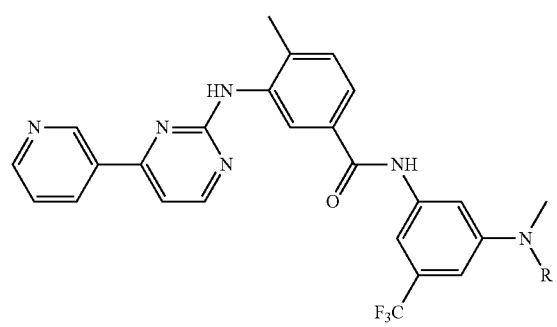

(derivatized where R is a linker group L attached, for example, to the phenyl moiety or the aniline amine group);

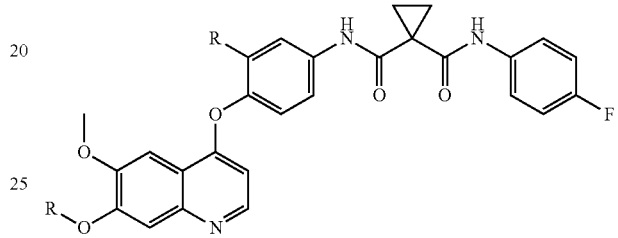

(derivatized where R is a linker group L attached, for example, to the phenyl moiety or a hydroxyl or ether group on the quinoline moiety);

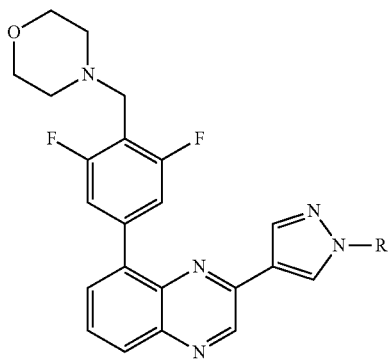

(derivatized where R is a linker group L attached, for example, to the phenyl moiety or the diazole group);

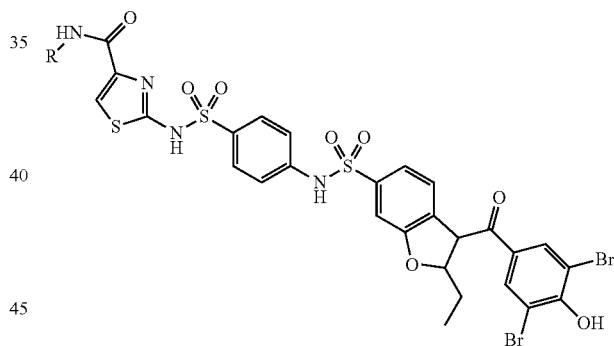

(derivatized where a linker group L is attached, for example, at R);

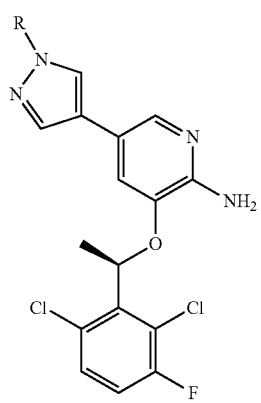

(derivatized where R is a linker group L attached, for example, to the phenyl moiety or the diazole group);

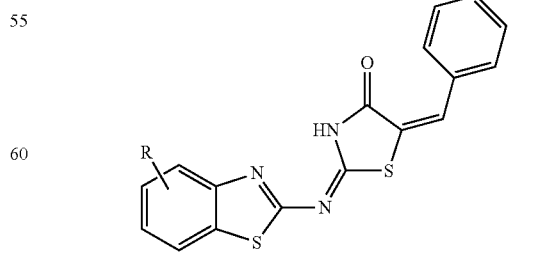

(derivatized where a linker group L is attached, for example, at R);

71

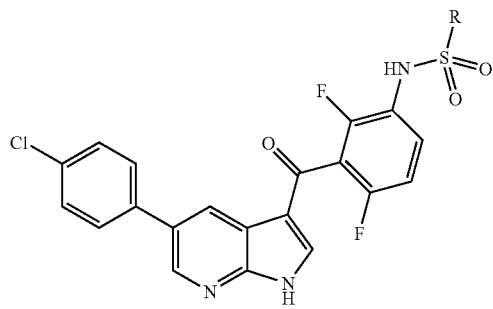

(derivatized where a linker group L is attached, for example, at R);

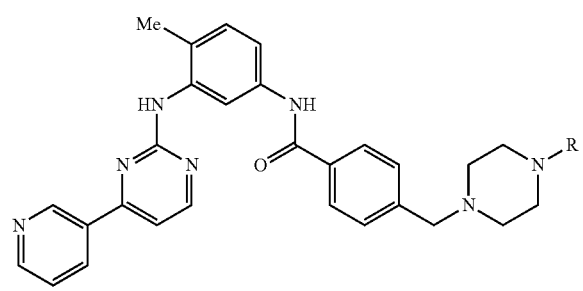

(derivatized where a linker group L is attached, for example, at R);

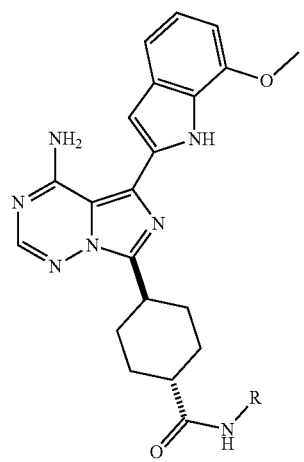

(derivatized where a linker group L is attached, for example, at R);

72

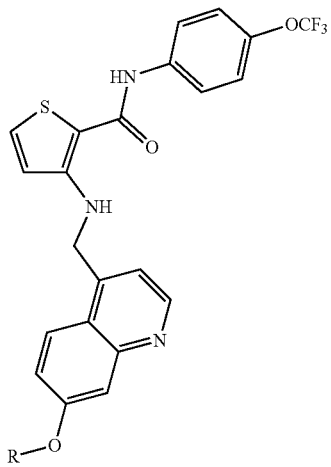

(derivatized where a linker group L is attached, for example, at R); or

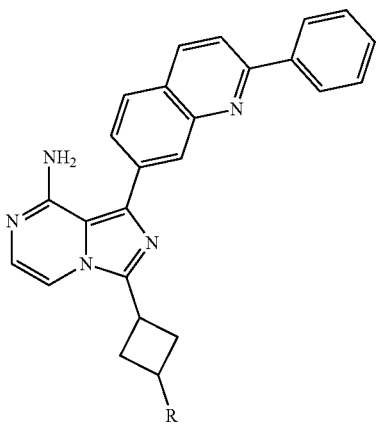

(derivatized where a linker group L is attached, for example, at R).

In some embodiments, Y is a compound disclosed in Vassilev, et al., *Science*, vol. 303, pages 844-848 (2004), and Schneekloth, et al., *Bioorg. Med. Chem. Lett.*, vol. 18, pages 5904-5908 (2008), including nutlin-3, nutlin-2, and nutlin-1 (shown below):

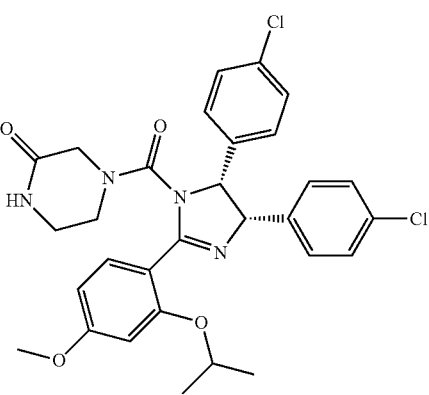 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker group L is attached, for example, at the methoxy group or as a hydroxyl group);

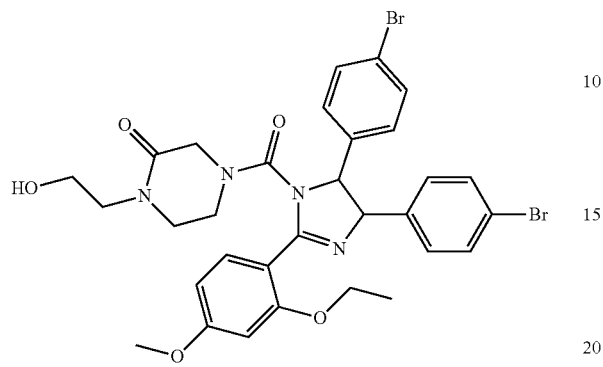

(derivatized where a linker group L is attached, for example, at the methoxy group or hydroxyl group);

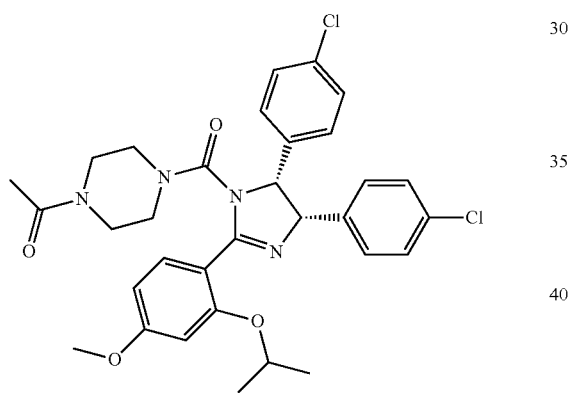

(derivatized where a linker group L is attached, for example, via the methoxy group or as a hydroxyl group); and trans-4-Iodo-4'-Boranyl-Chalcone

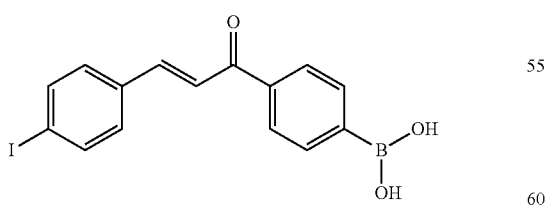

(derivatized where a linker group L or a linker group L is attached, for example, via a hydroxy group).

In some embodiments, Y is one of the compounds shown below, derivatized by the attachment of a linker group L (in some instances denoted by "R," below).

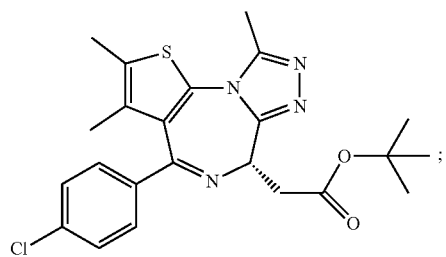

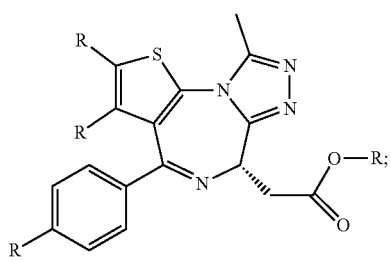

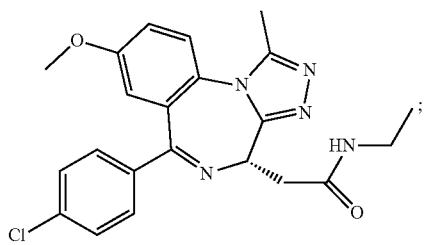

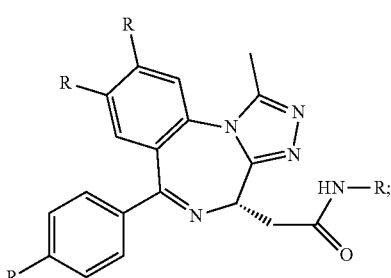

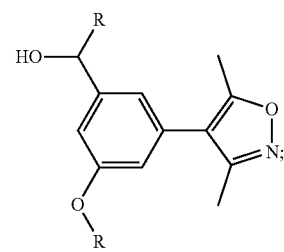

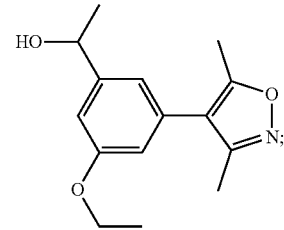

-continued

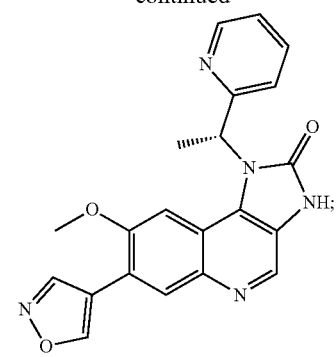

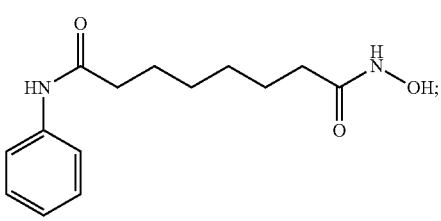

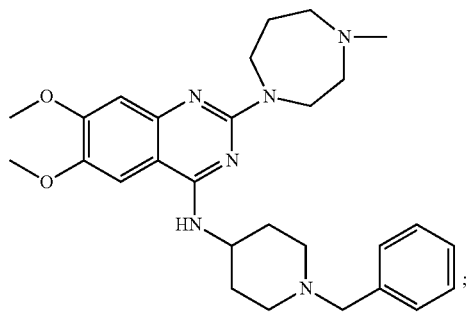

-continued

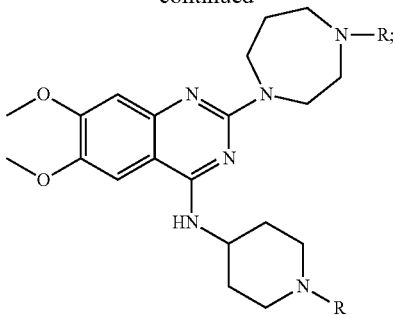

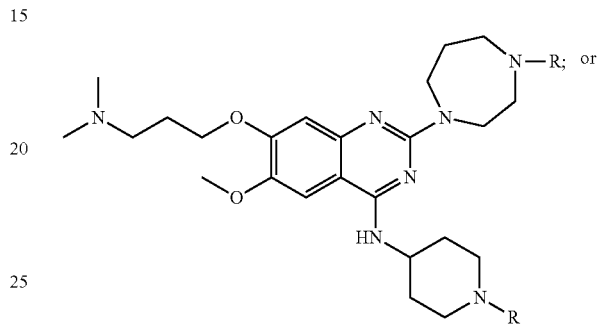

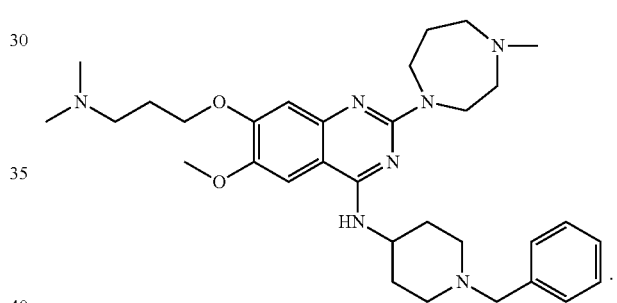

In some embodiments, Y is azacitidine ((derivatized where a linker group L is attached, for example, via the hydroxy or amino groups). In some embodiments, Y is decitabine (derivatized) (4-amino-1-(2-deoxy-b-D-erythro-pentofuranosyl)-1,3,5-triazin-2(1H)-one) (derivatized where a linker group L is attached, for example, via either of the hydroxy groups or at the amino group).

In some embodiments, Y is GA-1 (derivatized) and derivatives and analogs thereof, having the structure(s) and binding to linkers as described in Sakamoto, et al., Development of Protacs to target cancer-promoting proteins for ubiquitination and degradation, *Mol Cell Proteomics*, 2(12): 1350-58 (2003).

In some embodiments, Y is estradiol or testosterone, and related derivatives (including, but not limited to, DHT) which may be bound to a linker group L as is generally described in Rodriguez-Gonzalez, et al., *Oncogene*, 27, 7201-7211 (2008) and/or Sakamoto, et al., *Mol Cell Proteomics*, 2(12):1350-58 (2003).

In some embodiments, Y is ovalicin, fumagillin, a glucocorticoid (including, but not limited to hydrocortisone, prednisone, prednisolone, and methylprednisolone), methotrexate, cyclosporine, tacrolimus (FK-506), rapamycin, apigenin, or an actinomycin, each derivatized where a linker group L is bound.

In some embodiments, Y is
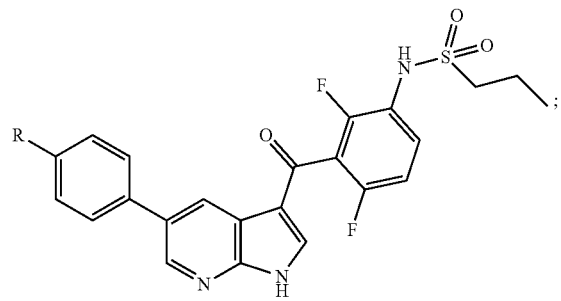
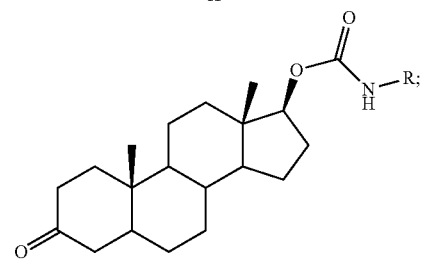
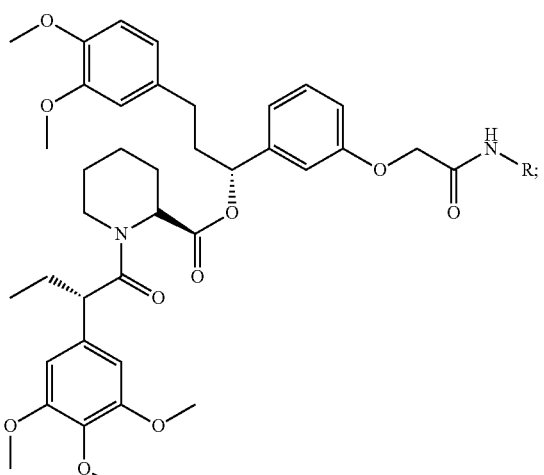
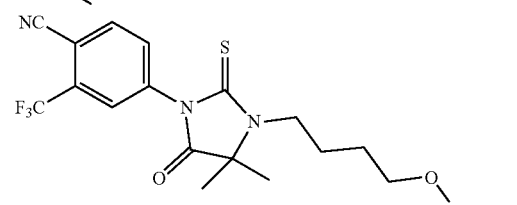
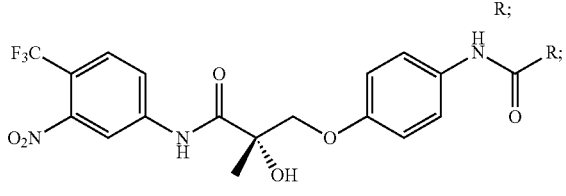
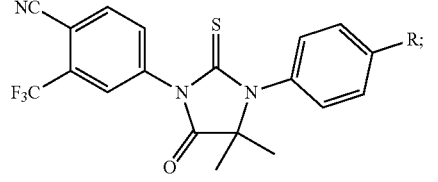
-continued
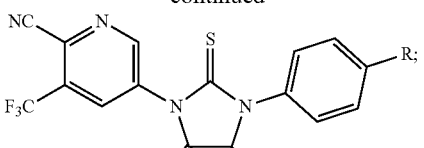
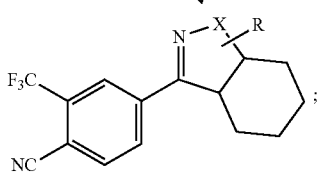
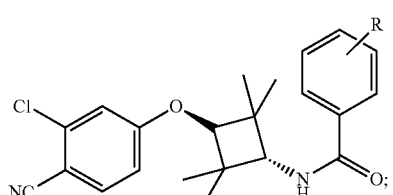
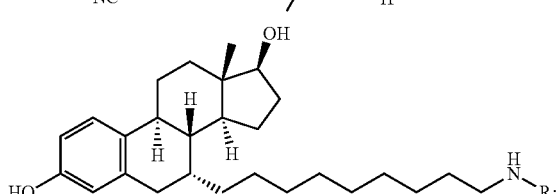
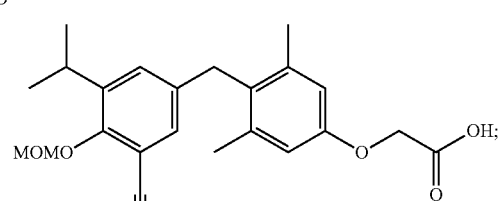
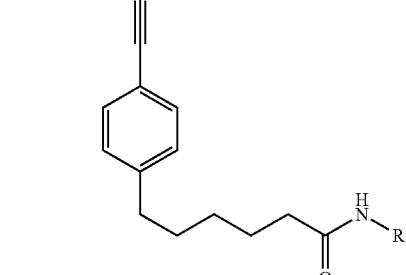
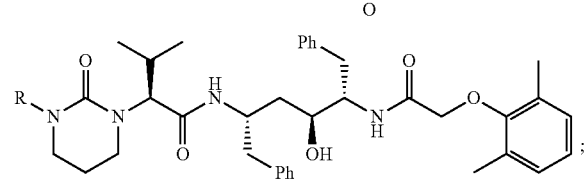
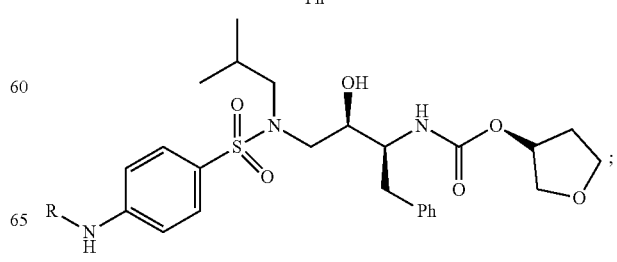

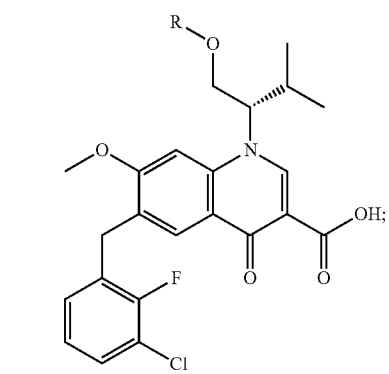

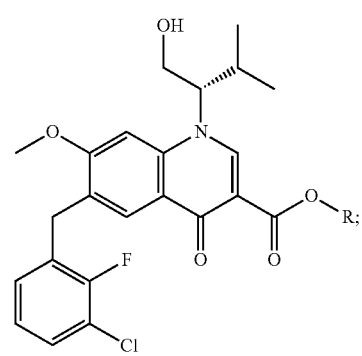

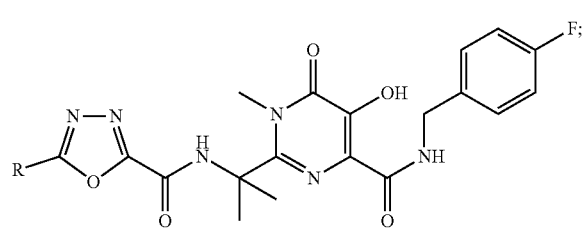

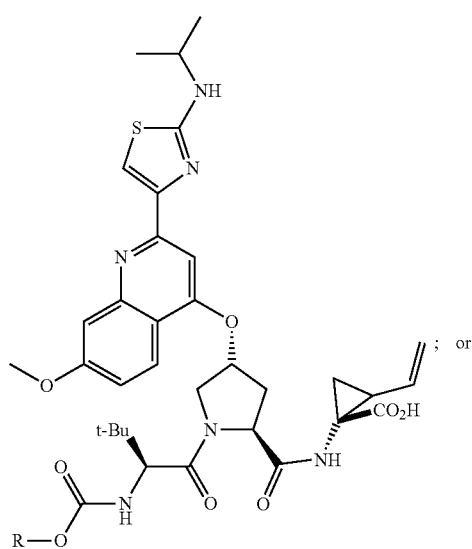

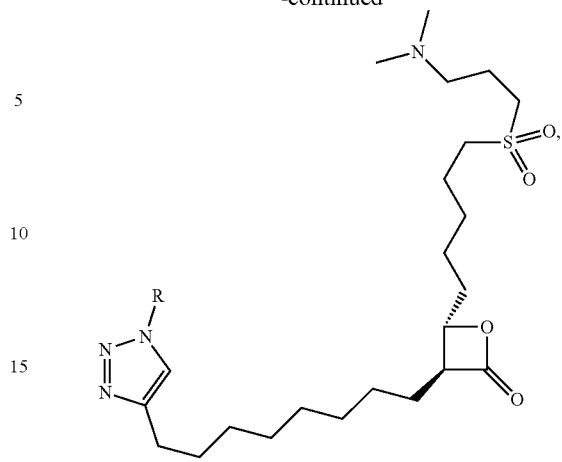

where "R" designates a site for linker group L or group attachment, for example.

In some embodiments, Y is a compound disclosed in *Cancer Research* (2006), 66(11), 5790-5797, including but not limited to the Bcr-Abl tyrosine-kinase inhibitor dasatinib, derivatized where R is a linker group L attached, for example, via an ether or other functional group.

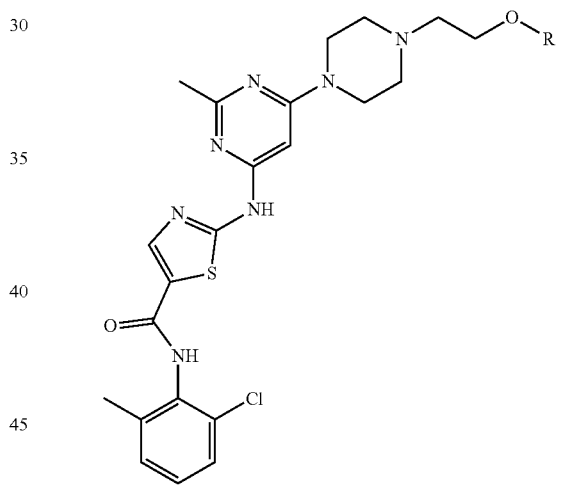

In some embodiments, Y is a compound disclosed in *Cancer Cell* (2007), 11(3), 209-11, including but not limited to the epidermal growth factor receptor (EGFR) tyrosine kinase inhibitor shown below, derivatized where R is a linker group L attached, for example, via an ether or other functional group.

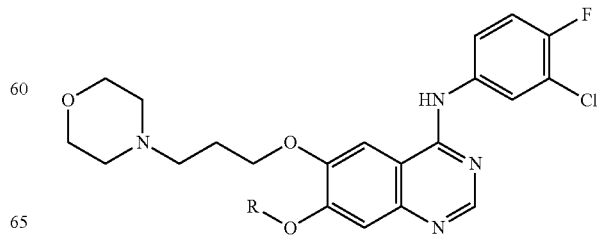

This compound below is replacing [0419] In some embodiments, Y is a compound disclosed in *PLoS One* (2014), 9(10), e109705/1-e109705/12, including but not limited to the AKT kinase inhibitor shown below, derivatized where R is a linker group L attached, for example, via an amide or other functional group.

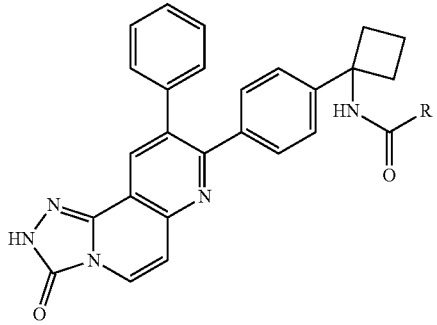

In some embodiments, Y is a compound disclosed in *Scientific Reports* (2015), 5, 14538, including but not limited to the Janus kinase 2 (JAK2) kinase inhibitor shown below, derivatized where R is a linker group L attached, for example, via an ether or other functional group.

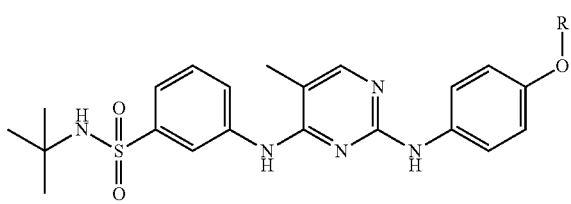

In some embodiments, Y is a CK1α kinase inhibitor including but not limited to the compound shown below, derivatized where R is a linker group L attached, for example, via an amide or other functional group.

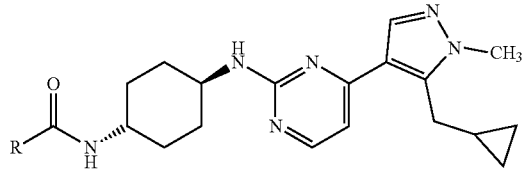

In some embodiments, Y is a compound disclosed in *Journal of Medicinal Chemistry* (2013), 56(14), 5979-5983, including but not limited to the MDM2 inhibitor shown below, derivatized where R is a linker group L attached, for example, via an amide or other functional group.

In some embodiments, Y is a compound disclosed in *Proceedings of the National Academy of Sciences of the United States of America* (2015), 112(51), 15713-15718, including but not limited to the bromodomain-containing protein 4 (BRD4) inhibitor shown below, derivatized where R is a linker group L attached, for example, via an amide or other functional group.

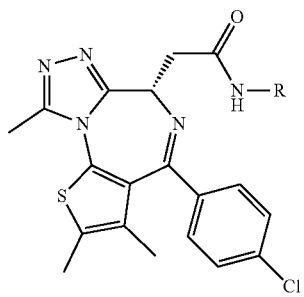

In some embodiments, Y is a compound disclosed in *Journal of Medicinal Chemistry* (2010), 53(7), 2779-2796, including but not limited to the androgen receptor (AR) modulator shown below, derivatized where R is a linker group L attached, for example, via an ether or other functional group.

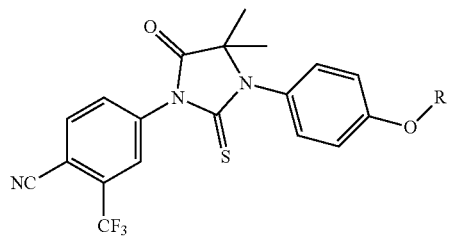

In some embodiments, Y is a compound disclosed in *Journal of Medicinal Chemistry* (2011), 54(3), 788-808, including but not limited to the estrogen receptor alpha (ERα) modulator shown below, derivatized where R is a linker group L attached, for example, to the nitrogen of the thiazolidinedione.

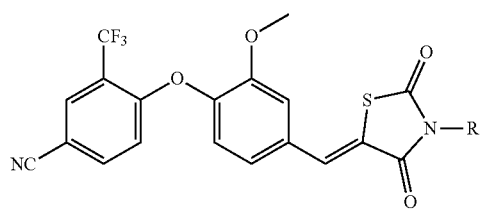

In some embodiments, Y is a compound disclosed in *Chemistry & Biology* (Cambridge, Mass., United States) (2007), 14(10), 1186-1197, including but not limited to the core-binding factor beta (CBFβ) inhibitor shown below, derivatized where R is a linker group L attached, for example, via an amide or other functional group.

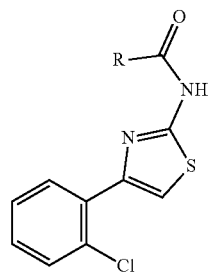

Some embodiments provide a compound of Formula (II):

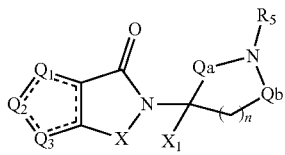

(II)

or a pharmaceutically acceptable salt or solvate thereof, wherein: $Q_1$, $Q_2$, and $Q_3$, are each independently $CR_1$, $CR_2$, or —S—, and at least one of $Q_1$, $Q_2$, and $Q_3$, is $CR_1$ or $CR_2$; each ≡≡≡ is independently selected from a carbon-carbon double bond, a carbon-carbon single bond, and a carbon-sulfur single bond; $R_1$ and $R_2$ are each independently H, deuterium, hydroxyl, halogen, cyano, nitro, optionally substituted amino, optionally substituted C-amido, optionally substituted N-amido, optionally substituted ester, optionally substituted urea, optionally substituted $C_1$-$C_6$ alkoxy, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_6$-$C_{10}$ aryl, optionally substituted 3 to 10-membered heterocyclyl, optionally substituted 5 to 10-membered heteroaryl,

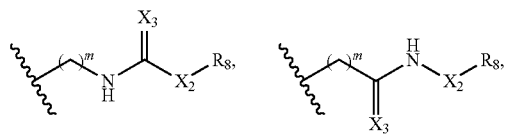

or L-Y; wherein when one of $R_1$ or $R_2$ is H or

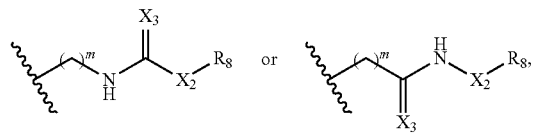

the other of $R_1$ or $R_2$ is not L-Y; $R_5$ is H, deuterium, optionally substituted $C_1$-$C_6$ alkyl, or optionally substituted $C_2$-$C_6$ alkenyl; X is $C(R_5)_2$, $CH(R_5)$, $CH_2$, C=O, or C=S; $X_1$ is selected from H, deuterium, halogen, and optionally substituted $C_1$-$C_6$ alkyl; $X_2$ is selected from $(CH_2)_a$, $(CD_2)_a$, $(CF_2)_a$, C=O, NH, N—(optionally substituted $C_1$-$C_6$ alkyl), and $[(CH_2)_p$—O—$(CH_2)_q]_r$; $X_3$ is selected from O, NH, and S; a is 0, 1, 2, 3, 4, 5, 6, 7, 8, 9, or 10; n is 1, 2, or 3; m is 1, 2, 3, 4, or 5; p and q are independently 0, 1, 2, 3, 4, 5, or 6; r is 0, 1, 2, 3, or 4; Qa and Qb are each independently C=O or C=S; wherein when n is 2, then $Q_3$ is —S—, or when n is 2, then $R_1$ is substituted $C_1$-$C_6$ alkyl,

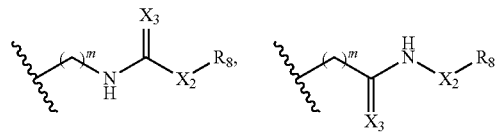

optionally substituted $C_3$-$C_8$ cycloalkyl, optionally substituted 3 to 10-membered heterocyclyl, optionally substituted 5 to 10-membered heteroaryl, optionally substituted urea, or L-Y; L is —$Z_1$—$(R_6$—O—$R_6)_t$—$Z_2$—; —$Z_1$($R_6$—NH—$R_6)_t$—$Z_2$—; —$Z_1$—$(R_6$—S—$R_6)_t$—$Z_2$—; —$Z_1$—$(R_6$—(C=O)—$R_6)_t$—$Z_2$—; —$Z_1$—$(R_6$—$(CO_2)$—$R_6)_t$—$Z_2$—; —$Z_1$—$(R_6$—(NHCO)—$R_6)_t$—$Z_2$—; —$Z_1$—$(R_6$—(CONH)—$R_6)_t$—$Z_2$—$(R_6$—(SO)—$R_6)_t$—$Z_2$—; —$Z_1$—$(R_6$—$(SO_2)$—$R_6)_t$—$Z_2$—; —$Z_1$—$(R_6$—NH(C=NH)NH—$R_6)_t$—$Z_2$—; —$Z_1$—$(R_6$—$(NHSO_2)$—$R_6)_t$—$Z_2$—; —$Z_1$—$(R_6$—$(SO_2NH)$—$R_6)_t$—$Z_2$—; —$Z_1$—$(R_6$—NH(C=O)NH—$R_6)_t$—$Z_2$—; —$Z_1$—$(R_6$—NH(C=S)NH—$R_6)_t$—$Z_2$—; or —$Z_1$—$(R_6$-$R_7$—$R_6)_t$—$Z_2$—; each t is independently 1, 2, 3, 4, 5, 6, 7, or 8; $Z_1$ and $Z_2$ are each independently —$CH_2$—; —O—; —S—; S=O; —$SO_2$—; C=O; —$CO_2$—; —NH—; —NH(CO)—; —(CO)NH—; —NH—$SO_2$—; —$SO_2$—NH—; —$R_6CH_2$—; —$R_6O$—; —$R_6S$—; —$R_6$—S=O; —$R_6SO_2$—; —$R_6$—C=O; —$R_6CO_2$—; —$R_6NH$—; —$R_6NH(CO)$—; —$R_6(CO)NH$—; —$R_6NH$—$SO_2$—; —$R_6SO_2$—NH—; —$CH_2R_6$—; —$OR_6$—; —$SR_6$—; —S=O—$R_6$; —$SO_2R_6$—; —C=O—$R_6$; —$CO_2R_6$—; —$NHR_6$—; —NH(CO)$R_6$—; —(CO)$NHR_6$—; —NH—$SO_2R_6$—; or —$SO_2$—$NHR_6$—; each $R_6$ is absent, or independently $C_1$-$C_6$alkyl, $C_2$-$C_6$ alkenyl, $C_2$-$C_6$ alkynyl, $C_6$-$C_{10}$ aryl, 3 to 10-membered heterocyclyl, or 5 to 10-membered heteroaryl; $R_7$ is optionally substituted $C_3$-$C_8$ cycloalkyl, optionally substituted $C_6$-$C_{10}$ aryl, optionally substituted 3 to 10-membered heterocyclyl, or optionally substituted 5 to 10-membered heteroaryl; $R_8$ is selected from optionally substituted $C_3$-$C_{10}$ cycloalkyl, optionally substituted $C_6$-$C_{10}$ aryl, optionally substituted 5 to 10-membered heteroaryl, optionally substituted 3 to 10-membered heterocyclyl, optionally substituted $C_1$-$C_{10}$ alkyl, $R_{8A}$ and $R_{8B}$; $R_{8A}$ is selected from hydroxyl, halogen, cyano, nitro, unsubstituted amino, mono-substituted amino, di-substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$-$C_6$ alkoxy, optionally substituted $C_1$-$C_6$ haloalkoxy, optionally substituted $C_3$-$C_{10}$ cycloalkyl($C_1$-$C_6$ alkyl), optionally substituted $C_6$-$C_{10}$ aryl($C_1$-$C_6$ alkyl), optionally substituted 5 to 10 membered heteroaryl($C_1$-$C_6$ alkyl), and optionally substituted 3 to 10 membered heterocyclyl($C_1$-$C_6$ alkyl); $R_{8B}$ is $Y_1$; Y and $Y_1$ are independently selected from

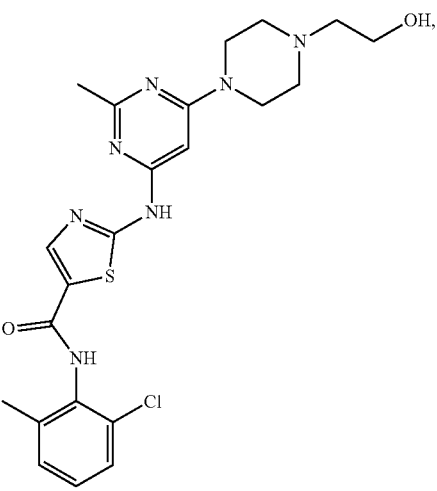

85
-continued
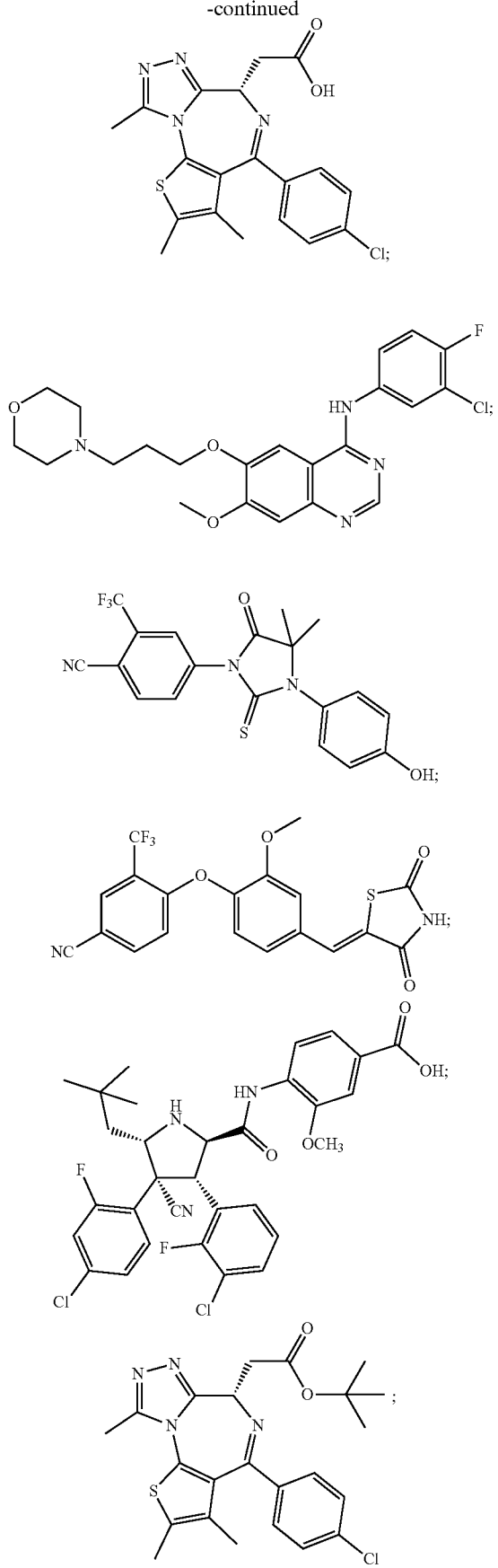
86
-continued
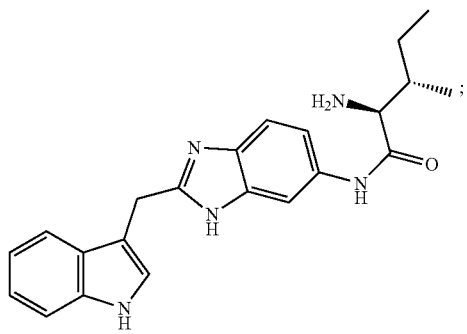
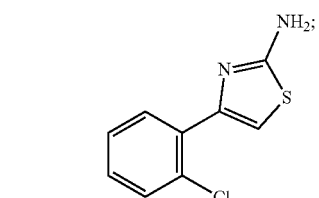
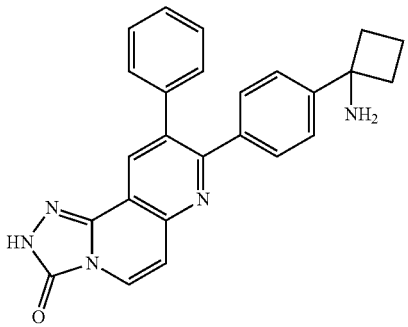
; and
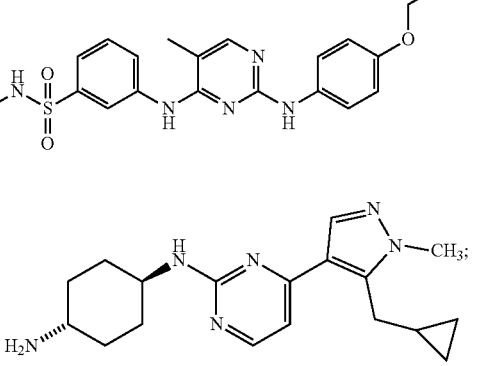
wherein Y is derivatized to attach to L and $Y_1$ is derivatized to attach to $X_2$. In some embodiments, the compound of Formula (II) is selected from compounds of Formula (IIa)
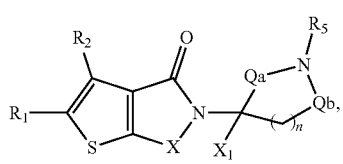

Formula (IIb)

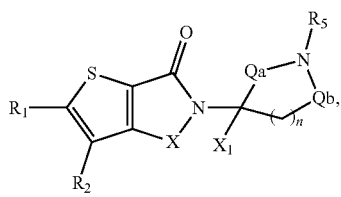

and Formula (IIc)

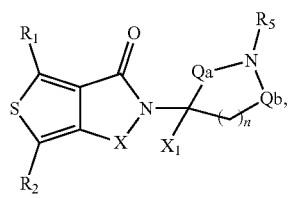

or a pharmaceutically acceptable salt of any of the foregoing. In some embodiments, wherein the compound of Formula (II) is selected from Formulae (IId), (IIe) and (IIf):

(IId)
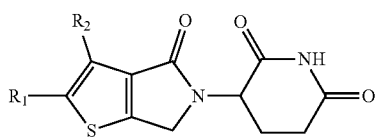

(IIe)
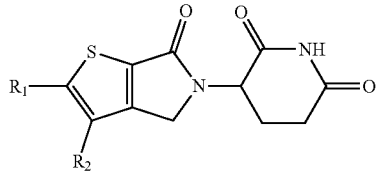

(IIf)
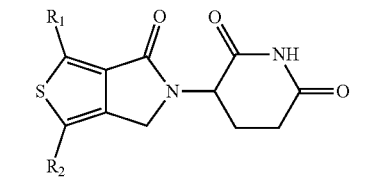

pharmaceutically acceptable salt thereof. In some embodiments, Qa is C=O and Qb is C=O. In some embodiments, n is 2. In some embodiments, n is 3. In some embodiments, $R_5$ is H. In some embodiments, X is $CH_2$. In some embodiments, $X_1$ is selected from H, deuterium, and fluoro. In some embodiments, $R_1$ is optionally substituted $C_3$-$C_6$ cycloalkyl or optionally substituted $C_1$-$C_6$ alkyl; or $R_2$ is optionally substituted $C_3$-$C_6$ cycloalkyl or optionally substituted $C_1$-$C_6$ alkyl. In some embodiments, wherein:
L is —$Z_1$—($R_6$—O—$R_6$)$_t$—$Z_2$—; —$Z_1$($R_6$—NH—$R_6$)$_t$—$Z_2$—; —$Z_1$—($R_6$—(NHCO)—$R_6$)$_t$—$Z_2$—; —$Z_1$—($R_6$—NH(CO)NH—$R_6$)$_t$—$Z_2$—; —Z—($R_6$—NH(C=NH)NH—$R_6$)$_t$—$Z_2$—; —Z—($R_6$—NH(C=S)NH—$R_6$)$_t$—$Z_2$—; or —$Z_1$—($R_6$—(CONH)—$R_6$)$_t$—$Z_2$—; t is 1, 2, 3, or 4; and $Z_1$ and $Z_2$ are each independently —$CH_2$—; —O—; —NH—; —NH(CO)—; or —(CO)NH—. In some embodiments, one of $R_1$ and $R_2$ is an optionally substituted urea, and the other of $R_1$ and $R_2$ is H, fluoro, optionally substituted $C_1$-$C_6$ alkyl or optionally substituted $C_3$-$C_6$ cycloalkyl. In some embodiments, one of $R^1$ and $R^2$ is selected from

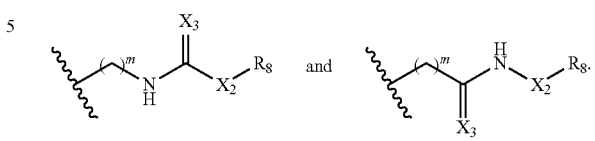

In some embodiments, m is 1, 2, or 3. In some embodiments, m is 1. In some embodiments, $X_3$ is O or S. In some embodiments, $X_2$ is $(CH_2)_a$. In some embodiments, a is 2 or 3. In some embodiments, $X_2$ is NH. In some embodiments, m is 1, 2, or 3; $X_2$ is NH; and $X_3$ is O or S. In some embodiments, $R_8$ is selected from an optionally substituted $C_3$-$C_{10}$ cycloalkyl, an optionally substituted $C_6$-$C_{10}$ aryl, an optionally substituted 5 to 10-membered heteroaryl, and an optionally substituted 3 to 10-membered heterocyclyl. In some embodiments, the optionally substituted $C_6$-$C_{10}$ aryl is a mono-substituted phenyl group, a di-substituted phenyl group, or a tri-substituted phenyl group. In some embodiments, the optionally substituted $C_6$-$C_{10}$ aryl is a phenyl group substituted with halogen, a phenyl group substituted with an unsubstituted $C_1$-$C_6$ alkyl, a phenyl group substituted with an unsubstituted $C_1$-$C_6$ alkyl and halogen, a phenyl group substituted with an unsubstituted $C_1$-$C_6$ alkyl and an unsubstituted $C_1$-$C_3$ alkoxy, a phenyl group substituted with an unsubstituted $C_1$-$C_3$ alkoxy and halogen, a phenyl group substituted with an unsubstituted $C_1$-$C_6$ alkyl and an unsubstituted di($C_1$-$C_3$ alkyl)amino, or a phenyl group substituted with an unsubstituted di($C_1$-$C_3$ alkyl) amino and halogen. In some embodiments, $R_8$ is selected from a 5-6 membered heteroaryl group substituted with halogen, a 5-6 membered heteroaryl group substituted with an unsubstituted $C_1$-$C_6$ alkyl, a 5-6 membered heteroaryl group substituted with an unsubstituted $C_1$-$C_6$ alkyl and halogen, a 5-6 membered heteroaryl group substituted with an unsubstituted $C_1$-$C_6$ alkyl and an unsubstituted $C_1$-$C_3$ alkoxy, a 5-6 membered heteroaryl group substituted with an unsubstituted $C_1$-$C_3$ alkoxy and halogen, a 5-6 membered heteroaryl group substituted with an unsubstituted $C_1$-$C_6$ alkyl and an unsubstituted di($C_1$-$C_3$ alkyl)amino, or a 5-6 membered heteroaryl group substituted with an unsubstituted di($C_1$-$C_3$ alkyl)amino and halogen. In some embodiments, $R_8$ is $R_{8A}$ and $R_{8A}$ is selected from: optionally substituted $C_3$-$C_{10}$ cycloalkyl($C_1$-$C_6$ alkyl), optionally substituted $C_6$-$C_{10}$ aryl($C_1$-$C_6$ alkyl), optionally substituted 5 to 10 membered heteroaryl($C_1$-$C_6$ alkyl), and optionally substituted 3 to 10 membered heterocyclyl($C_1$-$C_6$ alkyl). In some embodiments, $R_8$ is $R_{8B}$; $R_{8B}$ is $Y_1$; and $Y_1$ is

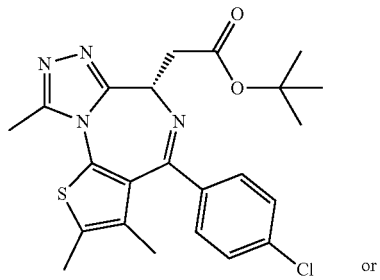

or

89

-continued

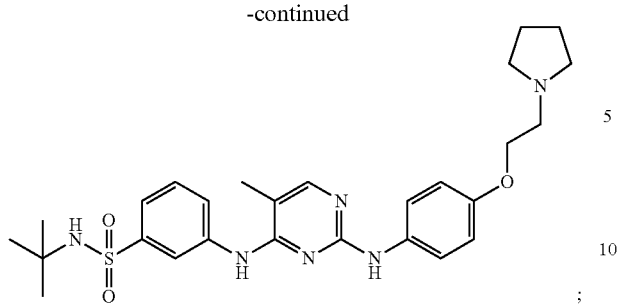

wherein $Y_1$ is derivatized to attach to $X_2$. Some embodiments provide a pharmaceutical composition comprising a compound of Formula (II), or a pharmaceutically acceptable salt thereof, and at least one pharmaceutically acceptable carrier. Some embodiments provide a method of treating, ameliorating, or preventing a disease, disorder, or condition associated with a protein selected from a cytokine, aiolos, ikaros, helios, CK1α, GSPT1, and combinations of any of the foregoing, the method comprising administering a therapeutically effective amount of a compound of Formula (II), or a pharmaceutically acceptable salt thereof; wherein the disease, disorder, or condition is selected from inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer. Some embodiments provide a method of inhibiting protein activity, comprising contacting a cell with a compound of Formula (II), or a pharmaceutically acceptable salt thereof, wherein the protein is aiolos, ikaros, helios, CK1α, GSPT1, a cytokine, or a combination of any of the foregoing.

In some embodiments, the compound of Formula (II) is selected from

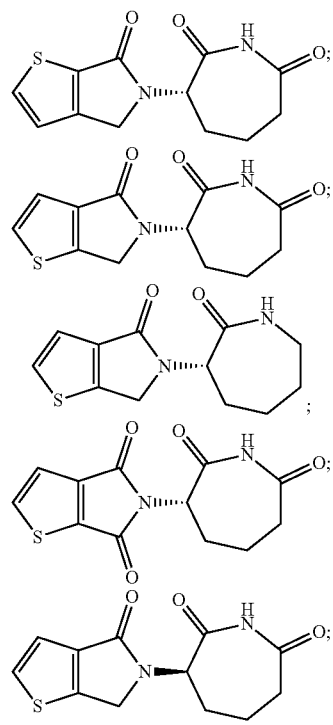

90

-continued

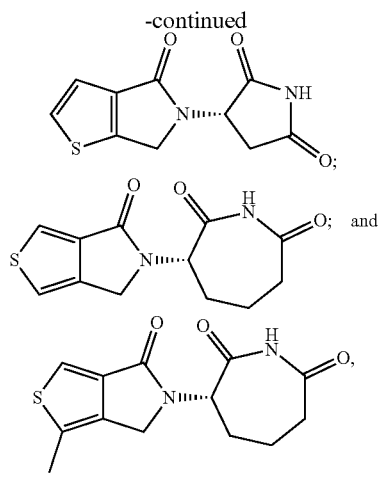

or pharmaceutically acceptable salts or solvates thereof.

In some embodiments, $Q_1$ is —S—, $Q_2$ is $CR_1$, $Q_3$ is $CR_2$, Qa and Qb are each C=O, n is 2, X is $CH_2$, and each of $X_1$, $R_1$, $R_2$, $R_5$, and $R_7$ are independently selected from hydrogen, deuterium, substituted alkyl, and unsubstituted alkyl. In some embodiments, $Q_1$ is $CR_1$, $Q_2$ is —S—, $Q_3$ is $CR_2$, n is 2, X is $CH_2$, and each of $X_1$, $R_1$, $R_2$, $R_5$, and $R_7$ are independently selected from hydrogen, deuterium, substituted alkyl, and unsubstituted alkyl.

In some embodiments, $Q_1$ is —S—, $Q_2$ is $CR_1$, $Q_3$ is $CR_2$, Qa and Qb are each C=O, n is 2, X is $CH_2$, each of $X_1$, $R_5$, and $R_7$ are independently selected from hydrogen, deuterium, substituted alkyl, and unsubstituted alkyl, one of $R_1$ and $R_2$ is

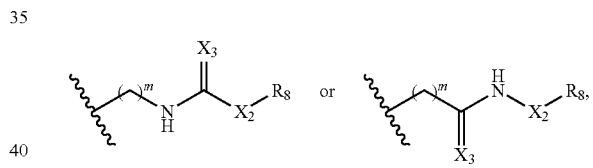

and the other of $R_1$ and $R_2$ is H, substituted alkyl, or unsubstituted alkyl, $X_3$ is O, m is 1, $X_2$ is NH or $CH_2$, and $R_8$ is a substituted $C_6$-$C_{10}$ aryl or a substituted 5 to 10-membered heteroaryl. In some embodiments, $Q_1$ is $CR_1$, $Q_2$ is —S—, $Q_3$ is $CR_2$, n is 2, X is $CH_2$, each of $X_1$, $R_5$, and $R_7$ are independently selected from hydrogen, deuterium, substituted alkyl, and unsubstituted alkyl, one of $R_1$ and $R_2$ is

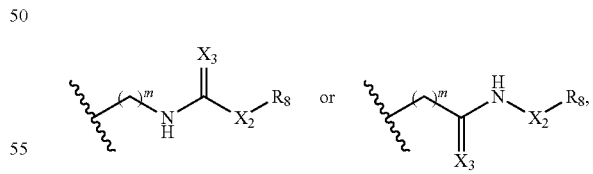

and the other of $R_1$ and $R_2$ is H, substituted alkyl, or unsubstituted alkyl, $X_3$ is O, m is 1, $X_2$ is NH or $CH_2$, and $R_8$ is a substituted $C_6$-$C_{10}$ aryl or a substituted 5 to 10-membered heteroaryl.

In some embodiments, $Q_1$ is —S—, $Q_2$ is $CR_1$, $Q_3$ is $CR_2$, Qa and Qb are each C=O, n is 2, X is C=O, and each of $X_1$, $R_1$, $R_2$, $R_5$, and $R_7$ are independently selected from hydrogen, deuterium, substituted alkyl, and unsubstituted alkyl. In some embodiments, $Q_1$ is $CR_1$, $Q_2$ is —S—, $Q_3$ is $CR_2$, n is 2, X is C=O, and each of $X_1$, $R_1$, $R_2$, $R_5$, and $R_7$ are independently selected from hydrogen, deuterium, substituted alkyl, and unsubstituted alkyl.

In some embodiments, $Q_1$ is —S—, $Q_2$ is $CR_1$, $Q_3$ is $CR_2$, Qa and Qb are each C=O, n is 2, X is C=O, each of $X_1$ and $R_5$ are independently selected from hydrogen, deuterium, substituted alkyl, and unsubstituted alkyl, one of $R_1$ and $R_2$ is

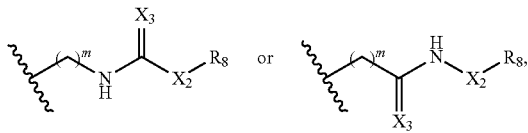

and the other of $R_1$ and $R_2$ is H, substituted alkyl, or unsubstituted alkyl, $X_3$ is O, m is 1, $X_2$ is NH or $CH_2$, and $R_8$ is a substituted $C_6$-$C_{10}$ aryl or a substituted 5 to 10-membered heteroaryl. In some embodiments, $Q_1$ is $CR_1$, $Q_2$ is —S—, $Q_3$ is $CR_2$, n is 2, X is C=O, each of $X_1$ and $R_5$ are independently selected from hydrogen, deuterium, substituted alkyl, and unsubstituted alkyl, one of $R_1$ and $R_2$ is

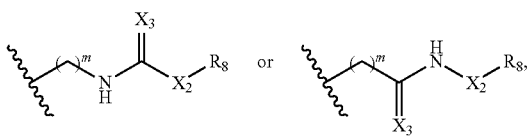

and the other of $R_1$ and $R_2$ is H, substituted alkyl, or unsubstituted alkyl, $X_3$ is O, m is 1, $X_2$ is NH or $CH_2$, and $R_8$ is a substituted $C_6$-$C_{10}$ aryl or a substituted 5 to 10-membered heteroaryl.

In some embodiments, $Q_1$ is $CR_2$, $Q_2$ is $CR_1$, $Q_3$ is —S—, each of $X_1$, $R_1$, $R_2$, $R_5$, and $R_7$ are independently selected from hydrogen, deuterium, substituted alkyl, and unsubstituted alkyl, Qa and Qb are each C=O, n is 1, and X is $CH_2$.

In some embodiments, $Q_1$ is $CR_2$, $Q_2$ is $CR_1$, $Q_3$ is —S—, each of $X_1$ and $R_5$ are independently selected from hydrogen, deuterium, substituted alkyl, and unsubstituted alkyl, Qa and Qb are each C=O, n is 1, X is $CH_2$, one of $R_1$ and $R_2$ is

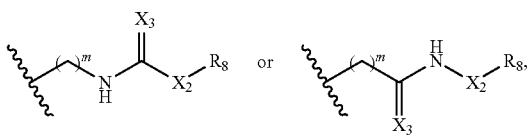

and the other of $R_1$ and $R_2$ is H, substituted alkyl, or unsubstituted alkyl, $X_3$ is O, m is 1, $X_2$ is NH or $CH_2$, and $R_8$ is a substituted $C_6$-$C_{10}$ aryl or a substituted 5 to 10-membered heteroaryl.

In some embodiments, $Q_1$ is $CR_2$, $Q_2$ is $CR_1$, $Q_3$ is —S—, each of $X_1$, $R_1$, $R_2$, $R_5$, and $R_7$ are independently selected from hydrogen, deuterium, substituted alkyl, and unsubstituted alkyl, Qa is C=O and Qb is C=O or $CH_2$, n is 1, and X is $CH_2$.

In some embodiments, $Q_1$ is $CR_2$, $Q_2$ is $CR_1$, $Q_3$ is —S—, each of $X_1$ and $R_5$ are independently selected from hydrogen, deuterium, substituted alkyl, and unsubstituted alkyl, Qa is C=O and Qb is C=O or $CH_2$, n is 1, X is $CH_2$, one of $R_1$ and $R_2$ is

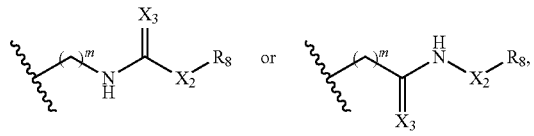

and the other of $R_1$ and $R_2$ is H, substituted alkyl, or unsubstituted alkyl, $X_3$ is O, m is 1, $X_2$ is NH or $CH_2$, and $R_8$ is a substituted $C_6$-$C_{10}$ aryl or a substituted 5 to 10-membered heteroaryl.

In some embodiments, $Q_1$ is $CR_2$, $Q_2$ is $CR_1$, $Q_3$ is —S—, each of $X_1$, $R_1$, $R_2$, $R_5$, and $R_7$ are independently selected from hydrogen, deuterium, substituted alkyl, and unsubstituted alkyl, Qa is C=O and Qb is C=O or $CH_2$, n is 1, and X is C=O.

In some embodiments, $Q_1$ is $CR_2$, $Q_2$ is $CR_1$, $Q_3$ is —S—, each of $X_1$ and $R_5$ are independently selected from hydrogen, deuterium, substituted alkyl, and unsubstituted alkyl, Qa is C=O and Qb is C=O or $CH_2$, n is 1, X is C=O, one of $R_1$ and $R_2$ is

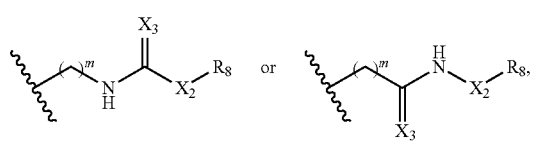

and the other of $R_1$ and $R_2$ is H, substituted alkyl, or unsubstituted alkyl, $X_3$ is O, m is 1, $X_2$ is NH or $CH_2$, and $R_8$ is a substituted $C_6$-$C_{10}$ aryl or a substituted 5 to 10-membered heteroaryl.

In some embodiments, $Q_1$ is $CR_2$, $Q_2$ is $CR_1$, $Q_3$ is —S—, each of $X_1$, $R_1$, $R_2$, $R_5$, and $R_7$ are independently selected from hydrogen, deuterium, substituted alkyl, and unsubstituted alkyl, Qa is C=O and Qb is C=O or $CH_2$, n is 1, and X is C=O.

In some embodiments, $Q_1$ is $CR_2$, $Q_2$ is $CR_1$, $Q_3$ is —S—, each of $X_1$ and $R_5$ are independently selected from hydrogen, deuterium, substituted alkyl, and unsubstituted alkyl, Qa is C=O and Qb is C=O or $CH_2$, n is 1, X is C=O, one of $R_1$ and $R_2$ is

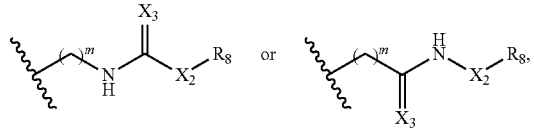

and the other of $R_1$ and $R_2$ is H, substituted alkyl, or unsubstituted alkyl, $X_3$ is O, m is 1, $X_2$ is NH or $CH_2$, and $R_8$ is a substituted $C_6$-$C_{10}$ aryl or a substituted 5 to 10-membered heteroaryl.

In some embodiments, $Q_1$ is $CR_2$, $Q_2$ is $CR_1$, $Q_3$ is —S—, each of $X_1$, $R_1$, $R_2$, $R_5$, and $R_7$ are independently selected from hydrogen, deuterium, substituted alkyl, and unsubstituted alkyl, Qa and Qb are each C=O, n is 2, and X is $CH_2$.

In some embodiments, $Q_1$ is $CR_2$, $Q_2$ is $CR_1$, $Q_3$ is —S—, each of $X_1$ and $R_5$ are independently selected from hydrogen, deuterium, substituted alkyl, and unsubstituted alkyl, Qa and Qb are each C=O, n is 2, X is $CH_2$, one of $R_1$ and $R_2$ is

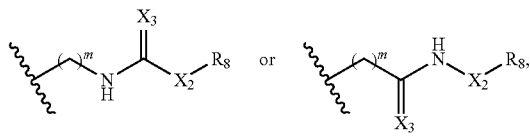

and the other of $R_1$ and $R_2$ is H, substituted alkyl, or unsubstituted alkyl, $X_3$ is O, m is 1, $X_2$ is NH or $CH_2$, and $R_8$ is a substituted $C_6$-$C_{10}$ aryl or a substituted 5 to 10-membered heteroaryl.

In some embodiments, $Q_1$ is $CR_2$, $Q_2$ is $CR_1$, $Q_3$ is —S—, each of $X_1$, $R_1$, $R_2$, $R_5$, and $R_7$ are independently selected from hydrogen, deuterium, substituted alkyl, and unsubstituted alkyl, Qa is C=O and Qb is C=O or $CH_2$, n is 2, and X is $CH_2$.

In some embodiments, $Q_1$ is $CR_2$, $Q_2$ is $CR_1$, $Q_3$ is —S—, each of $X_1$ and $R_5$ are independently selected from hydrogen, deuterium, substituted alkyl, and unsubstituted alkyl, Qa is C=O and Qb is C=O or $CH_2$, n is 2, X is $CH_2$, one of $R_1$ and $R_2$ is

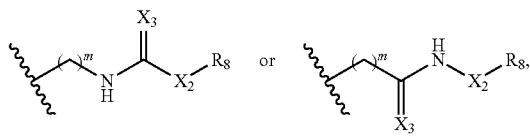

and the other of $R_1$ and $R_2$ is H, substituted alkyl, or unsubstituted alkyl, $X_3$ is O, m is 1, $X_2$ is NH or $CH_2$, and $R_8$ is a substituted $C_6$-$C_{10}$ aryl or a substituted 5 to 10-membered heteroaryl.

In some embodiments, $Q_1$ is $CR_2$, $Q_2$ is $CR_1$, $Q_3$ is —S—, each of $X_1$, $R_1$, $R_2$, $R_5$, and $R_7$ are independently selected from hydrogen, deuterium, substituted alkyl, and unsubstituted alkyl, Qa and Qb are each C=O, n is 2, and X is C=O.

In some embodiments, $Q_1$ is $CR_2$, $Q_2$ is $CR_1$, $Q_3$ is —S—, each of $X_1$ and $R_5$ are independently selected from hydrogen, deuterium, substituted alkyl, and unsubstituted alkyl, Qa and Qb are each C=O, n is 2, X is C=O, one of $R_1$ and $R_2$ is

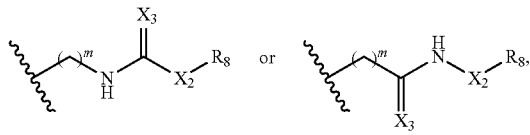

and the other of $R_1$ and $R_2$ is H, substituted alkyl, or unsubstituted alkyl, $X_3$ is O, m is 1, $X_2$ is NH or $CH_2$, and $R_8$ is a substituted $C_6$-$C_{10}$ aryl or a substituted 5 to 10-membered heteroaryl.

In some embodiments, $Q_1$ is $CR_2$, $Q_2$ is $CR_1$, $Q_3$ is —S—, each of $X_1$, $R_1$, $R_2$, $R_5$, and $R_7$ are independently selected from hydrogen, deuterium, substituted alkyl, and unsubstituted alkyl, Qa is C=O and Qb is C=O or $CH_2$, n is 2, and X is C=O.

In some embodiments, $Q_1$ is $CR_2$, $Q_2$ is $CR_1$, $Q_3$ is —S—, each of $X_1$ and $R_5$ are independently selected from hydrogen, deuterium, substituted alkyl, and unsubstituted alkyl, Qa is C=O and Qb is C=O or $CH_2$, n is 2, X is C=O, one of $R_1$ and $R_2$ is

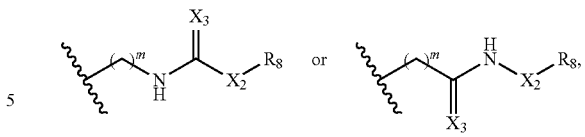

and the other of $R_1$ and $R_2$ is H, substituted alkyl, or unsubstituted alkyl, $X_3$ is O, m is 1, $X_2$ is NH or $CH_2$, and $R_8$ is a substituted $C_6$-$C_{10}$ aryl or a substituted 5 to 10-membered heteroaryl.

Some embodiments provide a pharmaceutical composition comprising a compound of Formula (II) and at least one pharmaceutically acceptable carrier. Some embodiments provide a pharmaceutical composition comprising a pharmaceutically acceptable salt or a solvate of a compound of Formula (II) and at least one pharmaceutically acceptable carrier. The definitions for compounds of Formula (II) are the same as those set forth above.

Some embodiments provide a pharmaceutical composition comprising a compound of Formula (IIa), (IIb), (IIc), (IId), (IIe) or (IIf), and at least one pharmaceutically acceptable carrier. Some embodiments provide a pharmaceutical composition comprising a pharmaceutically acceptable salt or a solvate of a compound of Formula (IIa), (IIb), (IIc), (IId), (IIe) or (IIf), and at least one pharmaceutically acceptable carrier. The definitions for compounds of Formula (II) are the same as those set forth above.

Some embodiments provide methods of treating, ameliorating, or preventing a disease, disorder, or condition associated with cytokines, comprising administering a therapeutically effective amount of a compound of Formula (II). Some embodiments provide methods of treating, ameliorating, or preventing a disease, disorder, or condition associated with cytokines, comprising administering a therapeutically effective amount of a compound of Formula (II), (IIa), (IIb), (IIc), (IId), (IIe) or (IIf). Some embodiments provide methods of treating, ameliorating, or preventing a disease, disorder, or condition associated with cytokines, comprising administering a pharmaceutically acceptable salt of solvate of a compound of Formula (II), (IIa), (IIb), (IIc), (IId), (IIe) or (IIf). The definitions for compounds of Formula (II) are the same as those set forth above.

In some embodiments, the disease, disorder, or condition selected from inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer.

Some embodiments provide methods of inhibiting cytokine activity, comprising contacting a cell with a compound of Formula (II), (IIa), (IIb), (IIc), (IId), (IIe) or (IIf). Some embodiments provide methods of inhibiting cytokine activity, comprising contacting a cell with a pharmaceutically acceptable salt or a solvate of a compound of Formula (II), (IIa), (IIb), (IIc), (IId), (IIe) or (IIf). The definitions for compounds of Formula (II) are the same as those set forth above.

Some embodiments provide methods of treating, ameliorating, or preventing a disease, disorder, or condition associated with GSPT1 function or imbalance, comprising administering a therapeutically effective amount of a compound of Formula (II), (IIa), (IIb), (IIc), (IId), (IIe) or (IIf). Some embodiments provide methods of treating, ameliorating, or preventing a disease, disorder, or condition associated with protein function or imbalance, comprising administering a pharmaceutically acceptable salt of solvate of a compound of Formula (II), (IIa), (IIb), (IIc), (IId), (IIe) or (IIf), to a subject in need thereof. The definitions for compounds of Formula (II), (IIa), (IIb), (IIc), (IId), (IIe) or (IIf) are the same as those set forth above.

In some embodiments of the method for treating, ameliorating, or preventing a disease, disorder, or condition associated with GSPT1 function or imbalance, the disease, disorder, or condition is selected from cancer (for example, breast cancer, hepatocellular carcinoma, gastric cancer, and prostate cancer) and astrogliosis. In some embodiments, the cancer is breast cancer. In some embodiments, the cancer is hepatocellular carcinoma. In some embodiments, the cancer is gastric cancer. In some embodiments, the cancer is prostate cancer. In some embodiments, the disease, disorder, or condition is astrogliosis.

Some embodiments provide methods of inhibiting GSPT1 activity, comprising contacting a cell with a compound of Formula (II), (IIa), (IIb), (IIc), (IId), (IIe) or (IIf). Some embodiments provide methods of inhibiting GSPT1 activity, comprising contacting a cell with a pharmaceutically acceptable salt of a compound of Formula (II), (IIa), (IIb), (IIc), (IId), (IIe) or (IIf). The definitions for compounds of Formula (I) are the same as those set forth above.

Some embodiments provide methods of treating, ameliorating, or preventing a disease, disorder, or condition associated with GSPT1 malfunction, comprising administering a therapeutically effective amount of a compound of Formula (II), (IIa), (IIb), (IIc), (IId), (IIe) or (IIf), or a pharmaceutically acceptable salt thereof, to a subject in need thereof.

In some embodiments, the disease, disorder, or condition is cancer. In some embodiments the cancer is selected from breast cancer, hepatocellular carcinoma, gastric cancer, and prostate cancer. In some embodiments, the disease, disorder, or condition is astrogliosis.

Some embodiments provide methods of treating, ameliorating, or preventing a disease, disorder, or condition associated with a protein selected from a cytokine, aiolos, ikaros, helios, CK1α, and combinations of any of the foregoing, the method comprising administering a therapeutically effective amount of a compound Formula (II), (IIa), (IIb), (IIc), (IId), (IIe) or (IIf), or a pharmaceutically acceptable salt thereof.

In some embodiments, the disease, disorder, or condition is selected from inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer.

Some embodiments provide methods of inhibiting protein activity, comprising contacting a cell with a compound of Formula (II), (IIa), (IIb), (IIc), (IId), (IIe) or (IIf), or a pharmaceutically acceptable salt thereof, wherein the protein is aiolos, ikaros, helios, CK1α, a cytokine, or a combination of any of the foregoing.

Some embodiments provide methods of decreasing the risk of skin cancer in a subject in need thereof, comprising administering an effective amount of a compound of Formula (II), (IIa), (IIb), (IIc), (IId), (IIe) or (IIf), or a pharmaceutically acceptable salt thereof.

Some embodiments provide methods for treating, ameliorating, or preventing a skin disorder, disease, or condition in a subject, comprising administering to the subject a therapeutically effective amount of a compound of Formula (II), (IIa), (IIb), (IIc), (IId), (IIe) or (IIf), or a pharmaceutically acceptable salt thereof. In some embodiments, the skin disorder, disease, or condition is sunburn or skin hypopigmentation.

Some embodiments provide methods for treating, ameliorating, or preventing a skin disorder, disease, or condition in a subject, comprising administering to the subject a therapeutically effective amount of a compound of Formula (II), (IIa), (IIb), (IIc), (IId), (IIe) or (IIf), or a pharmaceutically acceptable salt thereof.

Some embodiments provide methods for increasing skin pigmentation in a subject in need thereof, comprising administering a therapeutically effective amount of a compound of Formula (II), (IIa), (IIb), (IIc), (IId), (IIe) or (IIf), or a pharmaceutically acceptable salt thereof. In some embodiments, the administering comprises contacting the skin with a therapeutically effective amount of Formula (II), (IIa), (IIb), (IIc), (IId), (IIe) or (IIf), or a pharmaceutically acceptable salt thereof.

Some embodiments provide methods for increasing eumelanin level in a subject in need thereof, comprising administering a therapeutically effective amount of a compound of Formula (II), (IIa), (IIb), (IIc), (IId), (IIe) or (IIf), or a pharmaceutically acceptable salt thereof. In some embodiments, administering comprises contacting the skin with a therapeutically effective amount of a compound of Formula (II), (IIa), (IIb), (IIc), (IId), (IIe) or (IIf), or a pharmaceutically acceptable salt thereof.

Some embodiments provide methods for increasing p53 activity, comprising contacting a cell with a compound of Formula (II), (IIa), (IIb), (IIc), (IId), (IIe) or (IIf), or a pharmaceutically acceptable salt thereof. Some embodiments provide methods for decreasing MDM2 activity, comprising contacting a cell with a compound of Formula (II), (IIa), (IIb), (IIc), (IId), (IIe) or (IIf), or a pharmaceutically acceptable salt thereof.

In some embodiments the subject in need thereof is known to possess one or more of wild-type GSPT1, p53, MDM2, CK1α, aiolos, helios, or ikaros. In some embodiments the subject in need thereof is known to possess one or more of aberrant GSPT1, p53, MDM2, CK1α, aiolos, helios, or ikaros.

In some embodiments, the compound of Formula (II), (IIa), (IIb), (IIc), (IId), (IIe) or (IIf) is administered in combination with a second therapeutic agent. In some embodiments the second therapeutic agent is selected from anti-inflammatory agents, anti-cancer agents, immunostimulatory agents, and immunosuppressive agents. In some embodiments the second therapeutic agent is anti-cancer agent.

One or more of the compounds of preferred embodiments can be provided in the form of pharmaceutically acceptable salts, solvates, active metabolites, tautomers, or prodrugs thereof. Some embodiments can be provided in pharmaceutical compositions comprising a therapeutically effective amount of the compound. In some embodiments, the pharmaceutical composition also contains at least one pharmaceutically acceptable inactive ingredient. The pharmaceutical composition can be formulated for intravenous injection, subcutaneous injection, oral administration, buccal administration, inhalation, nasal administration, topical administration, transdermal administration, ophthalmic administration, or otic administration. The pharmaceutical composition can be in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

In some embodiments, the pharmaceutical composition is formulated as a gel, salve, ointment, cream, emulsion, or paste for topical application to the skin.

The pharmaceutical compositions of preferred embodiments can further comprise one or more additional therapeutically active agents other than a compound of the preferred embodiments. Such agents can include, but are not limited to, anti-inflammatory agents, anti-cancer agents, immunostimulatory agents, and immunosuppressive agents.

Other objects, features, and advantages of the compounds, methods, and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description Definitions Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, common organic abbreviations are defined as follows:
° C. Temperature in degrees Centigrade
DCM Dichloromethane (Methylene chloride)
DMSO Dimethylsulfoxide
EDCI 1-Ethyl-3-(3-dimethylaminopropyl)carbodiimide
EA Ethyl acetate
g Gram(s)
h or hr H(s)
HCl Hydrochloric acid
HOBt Hydroxybenzotriazole
IL Interleukin
LPS Lipopolysaccharide
M-CSF Macrophage colony-stimulating factor
MeOH Methanol
MS Mass spectrometry
mg Milligram(s)
mL Milliliter(s)
NaCl Sodium chloride
NaOH Sodium hydroxide
NBS N-Bromosuccinimide
PBMC Peripheral blood mononuclear cell
PG Protecting group
ppt Precipitate
psi Pounds per square inch
RPMI Roswell Park Memorial Institute medium
rt Room temperature
TNF Tumor necrosis factor
µL Microliter(s)
µM Micromolar
wt. weight The terms "co-administration" and similar terms as used herein are broad terms, and are to be given their ordinary and customary meaning to a person of ordinary skill in the art (and are not to be limited to a special or customized meaning), and refer without limitation to administration of the selected therapeutic agents to a single patient, and are intended to include treatment regimens in which the agents are administered by the same or different route of administration or at the same or different time.

The terms "effective amount" and "therapeutically effective amount" are broad terms, and are to be given their ordinary and customary meaning to a person of ordinary skill in the art (and are not to be limited to a special or customized meaning), and refer without limitation to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. Where a drug has been approved by the U.S. Food and Drug Administration (FDA) or a counterpart foreign medicines agency, a "therapeutically effective amount" optionally refers to the dosage approved by the FDA or its counterpart foreign agency for treatment of the identified disease or condition.

The term "pharmaceutical combination" as used herein is a broad term, and is to be given its ordinary and customary meaning to a person of ordinary skill in the art (and is not to be limited to a special or customized meaning), and refers without limitation to a product that results from the mixing or combining of more than one active ingredient and includes both fixed and non-fixed combinations of the active ingredients. The term "fixed combination" means that the active ingredients, e.g., a compound of a preferred embodiment and a co-agent, are both administered to a patient simultaneously in the form of a single entity or dosage. The term "non-fixed combination" means that the active ingredients, e.g., a compound of a preferred embodiment and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

As used herein, any "R" group(s) such as, without limitation, $R_2$, $R_3$, $R_4$, $R_5$, $R_6$, $R_9$, and $R_{10}$ represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^2$ and $R^3$, or $R^2$, $R^3$, or $R^4$, and the atom to which it is attached, are indicated to be "taken together" or "joined together" it means that they are covalently bonded to one another to form a ring:

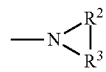

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be individually and independently substituted with one or more group(s) individually and independently selected from alkyl (for example, methyl, ethyl, n-propyl, isopropyl, n-butyl, isobutyl, tert-butyl, pentyl (branched and straight-chained), and hexyl (branched and straight-chained)), alkenyl (for example, vinyl, allyl, isopropenyl, n-butenyl, isobutenyl, pentenyl (branched and straight-chained), and hexenyl (branched and straight-chained)), alkynyl (for example, ethynyl, propynyl, butynyl, pentynyl (branched and straight-chained), and hexynyl (branched and straight-chained)), cycloalkyl (for example, $C_3$-$C_{10}$ cycloalkyl groups such as cyclopropyl, cyclobutyl, cyclopentyl, cyclohexyl, cycloheptyl, and cyclooctyl, as well as bicyclic $C_3$-$C_{10}$ cycloalkyl groups such as bridged, fused, and spiro $C_3$-$C_{10}$ cycloalkyl groups), cycloalkenyl, (for example, rings including a single carbon-carbon double bond, such as cyclopropenyl, cyclobutenyl, cyclohexenyl, cycloheptenyl, and cyclooctenyl, and rings with two or more carbon-carbon double bonds, such as cyclohexa-1,3-diene and cyclohepta-1,3-diene), cycloalkynyl (for example, cyclohexynyl, cycloheptynyl, and cyclooctynyl), aryl (for example, phenyl and naphthyl), heteroaryl (for example, monocyclic and bicyclic 3-10 membered heteroaryl groups with one nitrogen atom, two nitrogen atoms, three nitrogen atoms, four nitrogen atoms, one oxygen atom, one sulfur atom, one oxygen atom and one or two nitrogen atoms, and one sulfur atom and one or two nitrogen atoms), heterocyclyl (for example, monocyclic and bicyclic (including fused, bridged, and spiro) 3-10 membered heterocyclyl groups with one nitrogen atom, two nitrogen atoms, three nitrogen atoms, four nitrogen atoms, one oxygen atom, one sulfur atom, one oxygen atom and one or two nitrogen atoms, and one sulfur atom and one or two nitrogen atoms), aralkyl (for example, phenyl($C_1$-$C_6$ alkyl) and naphthyl($C_1$-$C_6$ alkyl)), heteroaralkyl (for example, monocyclic and bicyclic 3-10 membered heteroaryl($C_1$-$C_6$ alkyl) groups with one nitrogen atom, two nitrogen atoms, three nitrogen atoms, four nitrogen atoms, one oxygen atom, one sulfur atom, one oxygen atom and one or two nitrogen atoms, and one sulfur atom and one or two nitrogen atoms), (heterocyclyl)alkyl, (for example, monocyclic and bicyclic (including fused, bridged, and spiro) 3-10 membered heterocyclyl($C_1$-$C_6$ alkyl) groups with one nitrogen atom, two nitrogen atoms, three nitrogen atoms, four nitrogen atoms, one oxygen atom, one sulfur atom, one oxygen atom and one or two nitrogen atoms, and one sulfur atom and one or two nitrogen atoms), (cycloalkyl) alkyl (for example, $C_3$-$C_{10}$ cycloalkyl($C_1$-$C_6$ alkyl) groups such as cyclopropyl($C_1$-$C_6$ alkyl), cyclobutyl($C_1$-$C_6$ alkyl), cyclohexyl($C_1$-$C_6$ alkyl), cycloheptyl($C_1$-$C_6$ alkyl), and cyclooctyl($C_1$-$C_6$ alkyl), as well as bicyclic $C_3$-$C_{10}$ cycloalkyl($C_1$-$C_6$ alkyl) groups such as bridged, fused, and spiro $C_3$-$C_{10}$ cycloalkyl($C_1$-$C_6$ alkyl) groups), hydroxy, protected hydroxyl (for example, methoxymethyl ether, tetrahydropyranyl ether, t-butyl ether, allyl ether, benzyl ether, silyl ether, acetic acid ester, benzoic acid ester, or pivalic acid ester), alkoxy (for example, methoxy, ethoxy, n-propoxy, isopropoxy, n-butoxy, isobutoxy, tert-butoxy, pentoxy (branched and straight-chained), and hexoxy (branched and straight-chained)), aryloxy (for example, phenoxy or naphtyloxy), acyl (for example, formyl or acetyl), cyano, halogen (for example fluoro, chloro, bromo, or iodo), thiocarbonyl, heterocyclyl(alkoxy) (for example, a 3-10 membered heterocyclyl($C_1$-$C_6$ alkoxy), including monocyclic and bicyclic (fused, bridged, and spiro) 3-10 membered heterocyclyl($C_1$-$C_6$ alkoxy) groups with the heterocyclyl group having one nitrogen atom, two nitrogen atoms, three nitrogen atoms, four nitrogen atoms, one oxygen atom, one sulfur atom, one oxygen atom and one or two nitrogen atoms, and one sulfur atom or one or two nitrogen atoms, such as morpholino (ethoxy), morpholino(n-propoxy), morpholino(n-butoxy), piperidinyl(ethoxy), piperidinyl(n-propoxy), piperidinyl(n-butoxy), piperazinyl(ethoxy), piperazinyl(n-propoxy), and piperazinyl(n-butoxy)), C-amido (for example, carboxamide, N,N-dimethylcarboxamide, N,N-dimethylcarboxamide, and N-methyl-N-phenylcarboxamide), N-amido (for example, formamide, acetamide, and phenylacetamide), C-carboxy (for example, a $C_1$-$C_6$ alkyl ester, an aralkyl ester, and a $C_6$-$C_{10}$ aryl ester), protected C-carboxy (for example, a S-t-butyl ester or a 1,3-oxazoline), O-carboxy (for example, a $C_1$-$C_6$ alkyl carboxylate, an aralkyl carboxylate, and a $C_6$-$C_{10}$ aryl carboxylate), nitro, silyl (for example, tri-methylsilyl, tri-ethylsilyl, tri-isopropyl silyl, and t-butyldimethylsilyl), haloalkyl (for example, a $C_1$-$C_6$ haloalkyl, a $C_1$-$C_6$ fluoroalkyl, a $C_1$-$C_6$ chloroalkyl, a $C_1$-$C_6$ chlorofluoroalkyl, including $C_1$-$C_6$ haloalkyl groups with one fluorine atom, two fluorine atoms, three fluorine, atoms, four fluorine atoms, five fluorine atoms, one chlorine atom, two chlorine atoms, three chlorine atoms, or any combination thereof, such as —$CH_2F$, —$CHF_2$, —$CF_3$, —$CCl_3$, —$CH_2CHF_2$, —$CH_2CF_3$, and —$CF_2CF_3$), haloalkoxy (for example, a $C_1$-$C_6$ haloalkoxy, a $C_1$-$C_6$ fluoroalkoxy, a $C_1$-$C_6$ chloroalkoxy, a $C_1$-$C_6$ chlorofluoroalkoxy, including $C_1$-$C_6$ haloalkoxy groups with one fluorine atom, two fluorine atoms, three fluorine, atoms, four fluorine atoms, five fluorine atoms, one chlorine atom, two chlorine atoms, three chlorine atoms, or any combination thereof, such as —$OCH_2F$, —$OCHF_2$, —$OCF_3$, —$OCH_2CHF_2$, —$OCH_2CF_3$, and —$OCF_2CF_3$), trihalomethanesulfonyl (for example, trifluoromethanesulfonyl), trihalomethanesulfonamido (for example, trifluoromethanesulfonamido), amino, dialkylamino(alkyl) (for example, dimethylamino($C_1$-$C_6$ alkyl), diethylamino($C_1$-$C_6$ alkyl), diisopropylamino($C_1$-$C_6$ alkyl), methylethylmino($C_1$-$C_6$ alkyl), dimethylamino (ethyl), diethylamino(ethyl), diisopropylamino(ethyl), and methylethylmino(ethyl)), mono-substituted amino group (for example, an amino group substituted with alkyl, alkenyl, alkynyl, cycloalkyl, cycloalkenyl, aryl, heteroaryl, heterocyclyl, cycloalkyl(alkyl), aralkyl or heteroaralkyl heterocyclyl(alkyl)), di-substituted amino group (for example, an amino group substituted with two groups independently selected from alkyl, alkenyl, alkynyl, cycloalkyl, cycloalkenyl, aryl, heteroaryl, heterocyclyl, cycloalkyl(alkyl), aralkyl and heteroaralkyl heterocyclyl(alkyl)), and protected derivatives thereof (for example, 9-fluorenylmethyl carbamate, t-butyl carbamate, benzyl carbamate, acetamide, trifluoroacetamide, phthalimide, benzylamine, triphenylamine, benzylidene amine, and p-toluenesulfonamide).

As used herein, "$C_a$—$C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heterocyclyl group. That is, the alkyl, alkenyl, alkynyl, ring of the cycloalkyl, ring of the cycloalkenyl, ring of the cycloalkynyl, ring of the aryl, ring of the heteroaryl or ring of the heterocyclyl can contain from "a" to "b", inclusive, carbon atoms. Thus, for example, a "$C_1$-$C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. Likewise, for example, a heterocyclyl group may contain from "a" to "b", inclusive, total atoms, such as a 3 to 10-membered heterocyclyl group, which includes 3 to ten total atoms (carbon and heteroatoms). If no "a" and "b" are designated with regard to an alkyl, alkenyl, alkynyl, cycloalkyl cycloalkenyl, cycloalkynyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, and hexyls. The alkyl group may be substituted or unsubstituted.

As used herein, "alkenyl" refers to an alkyl group, as defined herein, that contains in the straight or branched hydrocarbon chain one or more double bonds. An alkenyl group may be unsubstituted or substituted.

As used herein, "alkynyl" refers to an alkyl group as defined herein, that contains in the straight or branched hydrocarbon chain one or more triple bonds. An alkynyl group may be unsubstituted or substituted.

As used herein, "cycloalkyl" and "carbocyclyl" refer to a completely saturated (no double or triple bonds) mono- or multi-cyclic (such as bicyclic) hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl, and cyclooctyl.

As used herein, "cycloalkenyl" refers to a mono- or multi-cyclic (such as bicyclic) hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic (such as bicyclic) hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "aryl" refers to a carbocyclic (all carbon) monocyclic or multicyclic (such as bicyclic) aromatic ring system (including, e.g., fused, bridged, or spiro ring systems where two carbocyclic rings share a chemical bond, e.g., one or more aryl rings with one or more aryl or non-aryl rings) that has a fully delocalized pi-electron system throughout at least one of the rings. The number of carbon atoms in an aryl group can vary. For example, the aryl group can be a $C_6$-$C_{14}$ aryl group, a $C_6$-$C_{10}$ aryl group, or a phenyl group. Examples of aryl groups include, but are not limited to, benzene, naphthalene, and azulene. An aryl group may be substituted or unsubstituted.

As used herein, "cycloalkyl(alkyl)" and "cycloalkyl(alkyl)" refer to a cycloalkyl group connected, as a substituent, via a lower alkylene group. The lower alkylene and cycloalkyl of the cycloalkyl(alkyl) group can be substituted or unsubstituted. Examples include but are not limited to cyclopropylalkyl, cyclobutylalkyl, cyclopentylalkyl, cyclohexylalkyl, cycloheptylalkyl, and cyclooctylalkyl. When a cycloalkyl(alkyl) group is substituted, the substitution can be on the cycloalkyl portion of the cycloalkyl(alkyl) group, the alkyl portion of the cycloalkyl(alkyl) group, or on both the cycloalkyl and alkyl portions of the cycloalkyl(alkyl) group.

As used herein, "aralkyl" and "aryl(alkyl)" refer to an aryl group connected, as a substituent, via a lower alkylene group. The lower alkylene and aryl group of aralkyl may be substituted or unsubstituted. Examples include but are not limited to phenyllalkyl (such as benzyl) and naphthylalkyl. An aryl(alkyl) group can be substituted or unsubstituted. When an aryl(alkyl) group is substituted, the substitution can be on the aryl portion of the aryl(alkyl) group, the alkyl portion of the aryl(alkyl) group, or on both the aryl and alkyl portions of the aryl(alkyl) group.

As used herein, "heteroaryl" refers to a monocyclic or multicyclic (such as bicyclic) aromatic ring system (a ring system having a least one ring with a fully delocalized pi-electron system) that contain(s) one or more heteroatoms, that is, an element other than carbon, including but not limited to, nitrogen, oxygen, and sulfur, and at least one aromatic ring. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2, 4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heterocyclic" or "heterocyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. Heterocyclyl groups may be substituted or unsubstituted. A heterocycle may optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, and cyclic carbamates. When composed of two or more rings, the rings may be joined together in a fused fashion. Additionally, any nitrogens in a heterocycle may be quaternized. Examples of such "heterocyclic" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs. A heteroaryl(alkyl) group can be substituted or unsubstituted. When a heteroaryl(alkyl) group is substituted, the substitution can be on the heteroaryl portion of the heteroaryl(alkyl) group, the alkyl portion of the heteroaryl(alkyl) group, or on both the heteroaryl and alkyl portions of the heteroaryl(alkyl) group.

As used herein, "heteroalicyclyl(alkyl)" and "heterocyclyl(alkyl)" refer to a heterocyclic or a heteroalicyclic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl). A heterocyclyl(alkyl) group can be substituted or unsubstituted. When a heterocyclyl(alkyl) group is substituted, the substitution can be on the heterocyclyl portion of the heterocyclyl (alkyl) group, the alkyl portion of the heterocyclyl(alkyl) group, or on both the heterocyclyl and alkyl portions of the heterocyclyl(alkyl) group.

As used herein, "heteroalicyclyl(alkoxy)" and "heterocyclyl(alkoxy)" refer to a heterocyclic or a heteroalicyclic group connected, as a substituent, via a $C_1$-$C_6$ alkoxy group, wherein the heterocyclic or a heteroalicyclic group is connected to a carbon atom of the alkoxy group via a carbon atom or a heteroatom of the heterocyclic or a heteroalicyclic group. The $C_1$-$C_6$ alkoxy and heterocyclyl of a (heteroalicyclyl)alkoxy may be substituted or unsubstituted. Examples include but are not limited to morpholino(ethoxy), morpholino(n-propoxy), morpholino(n-butoxy), piperidinyl (ethoxy), piperidinyl(n-propoxy), piperidinyl(n-butoxy), piperazinyl(ethoxy), piperazinyl(n-propoxy), and piperazinyl(n-butoxy).

"Lower alkylene groups" are straight-chained —$CH_2$— tethering groups, forming bonds to connect molecular fragments via their terminal carbon atoms. Lower alkylene groups contain from 1 to 6 carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl or a cycloalkynyl, as defined above. A non-limiting list of alkoxys is methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "acyl" refers to a hydrogen, alkyl, alkenyl, alkynyl, or aryl, as defined above, connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "aryloxy" and "arylthio" refers to RO— and RS—, in which R is an aryl, as defined above, such as but not limited to phenyl. Both an aryloxy and arylthio may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heterocyclyl, or aralkyl, as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein X is a halogen.

A "trihalomethanesulfonamido" group refers to an "$X_3CS(O)_2N(R_A)$—" group wherein X is a halogen and $R_A$ hydrogen, alkyl, alkenyl, alkynyl, cycloalkyl, cycloalkenyl, cycloalkynyl, aryl, heteroaryl, heterocyclyl, aralkyl, or (heterocyclyl)alkyl.

The term "amino" as used herein refers to a —$NH_2$ group.

A "mono-substituted amine" group refers to a "—$NHR_A$" group in which $R_A$ can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. The $R_A$ may be substituted or unsubstituted. A mono-substituted amine group may also be referred to as, for example, a mono-alkylamine group, a mono-$C_1$-$C_6$ alkylamine group, a mono-arylamine group, a mono-$C_6$-$C_{10}$ arylamine group and the like. Examples of mono-substituted amino groups include, but are not limited to, —NH(methyl), —NH(phenyl) and the like.

A "di-substituted amine" group refers to a "—$NR_AR_B$" group in which $R_A$ and $R_B$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. $R_A$ and $R_B$ can independently be substituted or unsubstituted. A di-substituted amine group may also be referred to as, for example, a di-alkylamine group, a di-$C_1$-$C_6$ alkylamine group, a di-arylamine group, a di-$C_6$-$C_{10}$ arylamine group and the like. Examples of di-substituted amino groups include, but are not limited to, —$N(methyl)_2$, —N(phenyl)(methyl), —N(ethyl)(methyl) and the like.

A "dialkylamino(alkyl)" group refers to a "—($C_1$-$C_6$ alkyl)$NR_AR_B$" group in which $R_A$ and $R_B$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. $R_A$ and $R_B$ can independently be substituted or unsubstituted. A dialkylamino(alkyl) group may also be referred to as, for example, an alkyl(dialkylamino) group. Examples of dialkylamino(alkyl) groups include, but are not limited to, -ethyl[$N(methyl)_2$], -ethyl[N(phenyl)(methyl)], -ethyl[N(ethyl)(methyl)], -methyl[$N(methyl)_2$], -methyl[N(phenyl)(methyl)], -methyl[N(ethyl)(methyl)], -propyl[$N(methyl)_2$], -propyl[N(phenyl)(methyl)], -propyl[N(ethyl)(methyl)], and the like.

As used herein, the term "hydroxy" refers to a —OH group.

A "cyano" group refers to a "—CN" group.

The term "azido" as used herein refers to a —$N_3$ group.

A "carbonyl" group refers to a C=O group.

A "C-amido" group refers to a "—C(=O)$N(R_AR_B)$" group in which $R_A$ and $R_B$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. A C-amido may be substituted or unsubstituted.

An "N-amido" group refers to a "RC(=O)$N(R_A)$—" group in which R and $R_A$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. An N-amido may be substituted or unsubstituted.

A "urea" group refers to a "$N(R_AR_B)C(=O)N(R_C)$—" group in which $R_A$, $R_B$, and $R_C$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. A urea may be substituted or unsubstituted.

A "thiourea" group refers to a "$N(R_AR_B)C(=S)N(R_C)$—" group in which $R_A$, $R_B$, and $R_C$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. A thiourea may be substituted or unsubstituted.

A "guanidino" group refers to a $N(R_AR_B)C(=N)N(R_C)$—" group in which $R_A$, $R_B$, and $R_C$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. A guanidino may be substituted or unsubstituted.

The term "halogen atom" or "halogen" as used herein, means any one of the radio-stable atoms of column 7 of the Periodic Table of the Elements, such as, fluorine, chlorine, bromine, and iodine.

In all of the definitions described herein, the terms used to define a new term are as previously defined herein.

Where the numbers of substituents is not specified (e.g., haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two, or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls (e.g., t-butoxycarbonyl (BOC), acetyl, or isobutyryl); arylalkylcarbonyls (e.g., benzyloxycarbonyl or benzoyl); substituted methyl ether (e.g., methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4''-trimethoxytrityl (TMTr)).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

Some embodiments provide pharmaceutically acceptable salts of Formula (II). In some embodiments, the salt is selected from hydrochloride, sulfate, hemisulfate, acetate, fumarate, malate, and citrate.

The term "solvate" as used herein is a broad term, and is to be given its ordinary and customary meaning to a person of ordinary skill in the art (and is not to be limited to a special or customized meaning), and refers without limitation to mean that the solvent is complexed with a compound in a reproducible molar ratio, including, but not limited to, 0.5:1, 1:1, or 2:1. Thus, the term "pharmaceutically acceptable solvate," refers to a solvate wherein the solvent is one that does not cause significant irritation to an organism to which it is administered and does not abrogate the biological activity and properties of the compound.

Some embodiments provide solvates of Formula (II). In some embodiments, the solvent in the solvate is selected from water, ethanol, and acetone, or combinations thereof.

The term "prodrug" as used herein is a broad term, and is to be given its ordinary and customary meaning to a person of ordinary skill in the art (and is not to be limited to a special or customized meaning), and refers without limitation to a compound or a pharmaceutical composition that can be administered to a patient in a less active or inactive form, which can then be metabolized in vivo into a more active metabolite. In certain embodiments, upon in vivo administration, a prodrug is chemically converted to the biologically, pharmaceutically, or therapeutically active form of the compound. In certain embodiments, a prodrug is enzymatically metabolized by one or more steps or processes to the biologically, pharmaceutically, or therapeutically active form of the compound.

The term "sunburn" as used herein refers to an acute cutaneous inflammatory reaction following skin exposure to UV radiation. In humans, a sunburn may be characterized by red skin that is hot to the touch, skin pain, general fatigue or malaise, and mild dizziness.

The term "skin hypopigmentation," as used herein refers to lack or loss of skin color. Hypopigmentation may be caused by depletion of melanocytes or melanin, or decreased melanin synthesis. Certain disorders associated with skin hypopigmentation include, but are not limited to albinism, idiopathic guttate hypomelanosis, lleucism, phenylketonuria, pityriasis alba, vitiligo, Angelman syndrome, tinea versicolor, and as a side effect of imatinib (Gleeveco) therapy.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns.

Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

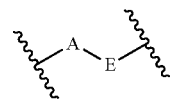

includes the substituent being oriented such that the A is attached at the leftmost attachment point of the molecule as well as the case in which A is attached at the rightmost attachment point of the molecule.

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of preferred embodiments can be provided include amorphous forms, milled forms and nano-particulate forms.

Likewise, it is understood that the compounds described herein, such as compounds of preferred embodiments, include the compound in any of the forms described herein (e.g., pharmaceutically acceptable salts, prodrugs, crystalline forms, amorphous form, solvated forms, enantiomeric forms, tautomeric forms, and the like).

Additional Therapeutic Agents

Suitable additional (or second) therapeutic agents described herein include, for example, anti-inflammatory agents, anti-cancer agents, immunostimulatory agents, and immunosuppressive agents. In some embodiments, the second therapeutic agent is an anti-inflammatory agent. In some embodiments, the second therapeutic agent is a non-steroidal anti-inflammatory agent. In some embodiments, the second therapeutic agent is an anti-cancer agent. In some embodiments, the second therapeutic agent is an immunostimulatory agent. In some embodiments, the second therapeutic agent is an immunosuppressive agent. In some embodiments, the second therapeutic agent is an antibody.

In some embodiments, the second therapeutic agent is selected from aspirin; diflunisal; salsalate; acetaminophen; ibuprofen; dexibuprofen; naproxen; fenoprofen; ketoprofen; dexketoprofen; flurbiprofen; oxaprozin; loxoprofen; indomethacin; tolmetin; sulindac; etodolac; ketorolac; diclofenac; aceclofenac; nabumetone; enolic acid; piroxicam; meloxicam; tenoxicam; droxicam; lornoxicam; isoxicam; mefenamic acid; meclofenamic acid; flufenamic acid; tolfenamic acid; sulfonanilides; clonixin; licofelone; dexamethasone; and prednisone.

In some embodiments, the second therapeutic agent is selected from mechlorethamine; cyclophosphamide; melphalan; chlorambucil; ifosfamide; busulfan; N-nitroso-N-methylurea (MNU); carmustine (BCNU); lomustine (CCNU); semustine (MeCCNU); fotemustine; streptozotocin; dacarbazine; mitozolomide; temozolomide; thiotepa; mytomycin; diaziquone (AZQ); cisplatin; carboplatin; and oxaliplatin.

In some embodiments, the second therapeutic agent is selected from vincristine; vinblastine; vinorelbine; vindesine; vinflunine; paclitaxel; docetaxel; etoposide; teniposide; tofacitinib; ixabepilone; irinotecan; topotecan; camptothecin; doxorubicin; mitoxantrone; and teniposide.

In some embodiments, the second therapeutic agent is selected from actinomycin; bleomycin; plicamycin; mitomycin; daunorubicin; epirubicin; idarubicin; pirarubicin; aclarubicin; mitoxantrone; cyclophosphamide; methotrexate; 5-fluorouracil; prednisolone; folinic acid; methotrexate; melphalan; capecitabine; mechlorethamine; uramustine; melphalan; chlorambucil; ifosfamide; bendamustine; 6-mercaptopurine; and procarbazine.

In some embodiments, the second therapeutic agent is selected from cladribine; pemetrexed; fludarabine; gemcitabine; hydroxyurea; nelarabine; cladribine; clofarabine; ytarabine; decitabine; cytarabine; cytarabine liposomal; pralatrexate; floxuridine; fludarabine; colchicine; thioguanine; cabazitaxel; larotaxel; ortataxel; tesetaxel; aminopterin; pemetrexed; pralatrexate; raltitrexed; pemetrexed; carmofur; and floxuridine.

In some embodiments, the second therapeutic agent is selected from azacitidine; decitabine; hydroxycarbamide; topotecan; irinotecan; belotecan; teniposide; aclarubicin; epirubicin; idarubicin; amrubicin; pirarubicin; valrubicin; zorubicin; mitoxantrone; pixantrone; mechlorethamine; chlorambucil; prednimustine; uramustine; estramustine; carmustine; lomustine; fotemustine; nimustine; ranimustine; carboquone; thioTEPA; triaziquone; and triethylenemelamine.

In some embodiments, the second therapeutic agent is selected from nedaplatin; satraplatin; procarbazine; dacarbazine; temozolomide; altretamine; mitobronitol; pipobroman; actinomycin; bleomycin; plicamycin; aminolevulinic acid; methyl aminolevulinate; efaproxiral; talaporfin; temoporfin; verteporfin; alvocidib; seliciclib; palbociclib; bortezomib; carfilzomib; anagrelide; masoprocol; olaparib; belinostat; panobinostat; romidepsin; vorinosta; idelalisib; atrasentan; bexarotene; testolactone; amsacrine; trabectedin; alitretinoin; tretinoin; demecolcine; elsamitrucin; etoglucid; lonidamine; lucanthone; mitoguazone; mitotane; oblimersen; omacetaxine mepesuccinate; and eribulin.

In some embodiments, the second therapeutic agent is selected from azathioprine; Mycophenolic acid; leflunomide; teriflunomide; tacrolimus; cyclosporin; pimecrolimus; abetimus; gusperimus; lenalidomide; pomalidomide; thalidomide; anakinra; sirolimus; everolimus; ridaforolimus; temsirolimus; umirolimus; zotarolimus; eculizumab; adalimumab; afelimomab; certolizumab pegol; golimumab; infliximab; nerelimomab; mepolizumab; omalizumab; faralimomab; elsilimomab; lebrikizumab; ustekinumab; etanercept; otelixizumab; teplizumab; visilizumab; clenoliximab; keliximab; zanolimumab; efalizumab; erlizumab; obinutuzumab; rituximab; and ocrelizumab.

In some embodiments, the second therapeutic agent is selected from pascolizumab; gomiliximab; lumiliximab; teneliximab; toralizumab; aselizumab; galiximab; gavilimomab; ruplizumab; belimumab; blisibimod; ipilimumab; tremelimumab; bertilimumab; lerdelimumab; metelimumab; natalizumab; tocilizumab; odulimomab; basiliximab; daclizumab; inolimomab; zolimoma; atorolimumab; cedelizumab; fontolizumab; maslimomab; morolimumab; pexelizumab; reslizumab; roveliximab; siplizumab; talizumab; telimomab; vapaliximab; vepalimomab; abatacept; belatacept; pegsunercept; aflibercept; alefacept; and rilonacept.

Dosing Regimes

The definitions for compounds of Formula (II) are the same as those set forth above. In some embodiments, the compound of Formula (II) is a compound of Formula (IIa), (IIb), (IIc), (IId), (IIe) or (IIf), or a pharmaceutically acceptable salt thereof.

In some embodiments, about 1 mg to about 5 grams of a compound of Formula (II) is administered each day. In some embodiments, about 2 mg to about 2 grams of a compound of Formula (II) is administered each day. In some embodiments, the amount of a compound of Formula (II) administered each day is, or is about, 5 mg to 1 gram; 10 mg to 800 mg; 20 mg to 600 mg; 30 mg to 400 mg; 40 mg to 200 mg; 50 mg to 100 mg; or any amount in between.

In some embodiments, about 1 mg to about 5 grams of a compound of Formula (II) is administered each week. In some embodiments, about 2 mg to about 2 grams of a compound of Formula (II) is administered each week. In some embodiments, the amount of a compound of Formula (II) administered each week is, or is about, 5 mg to 1 gram; 10 mg to 800 mg; 20 mg to 600 mg; 30 mg to 400 mg; 40 mg to 200 mg; 50 mg to 100 mg; or any amount in between.

In some embodiments, about 1 mg to about 5 grams of a compound of Formula (II) is administered each cycle of treatment. In some embodiments, about 2 mg to about 2 grams of a compound of Formula (II) is administered each cycle of treatment. In some embodiments, the amount of a compound of Formula (II) administered each cycle of treatment is, or is about, 5 mg to 1 gram; 10 mg to 800 mg; 20 mg to 600 mg; 30 mg to 400 mg; 40 mg to 200 mg; 50 mg to 100 mg; or any amount in between.

In some embodiments, a compound of Formula (II) is administered at least once per day; twice per day; three times per day; or four times per day. In some embodiments, a compound of Formula (II) is administered at least once per week; twice per week; three times per week; or four times per week. In some embodiments, each cycle of treatment lasts 1 day; 2 days; 3 days; 4 days; 5 days; 6 days; 7 days; 8 days; 9 days; 10 days; 11 days; 12 days; 13 days; 14 days, or any time in between. In some embodiments, each cycle of treatment has at least 1 day; 2 days; 3 days; 4 days; 5 days; 6 days; 7 days; 8 days; 9 days; 10 days; 11 days; 12 days; 13 days; or 14 days, between administrations of a compound of Formula (II).

In some embodiments, a compound of Formula (II) is provided intravenously over about 10 minutes; about 20 minutes; about 30 minutes; about 1 h; about 1.5 h; about 2 h; about 2.5 h; about 3 h; about 3.5 h; about 4 h, or any time in between. In some embodiments, the compound of Formula (II) is a compound of Formula (IIa), (IIb), (IIc), (IId), (IIe) or (IIf), or a pharmaceutically acceptable salt thereof.

EXAMPLES

Additional embodiments are disclosed in further detail in the following examples, which are not in any way intended to limit the scope of the claims.

Characterization of the compounds disclosed herein was performed with Bruker AV-500 and DRX-500 NMR spectrometers and a Perkin Elmer PE-SCIEX API-150 mass spectrometer.

Synthesis

Generic Scheme 1

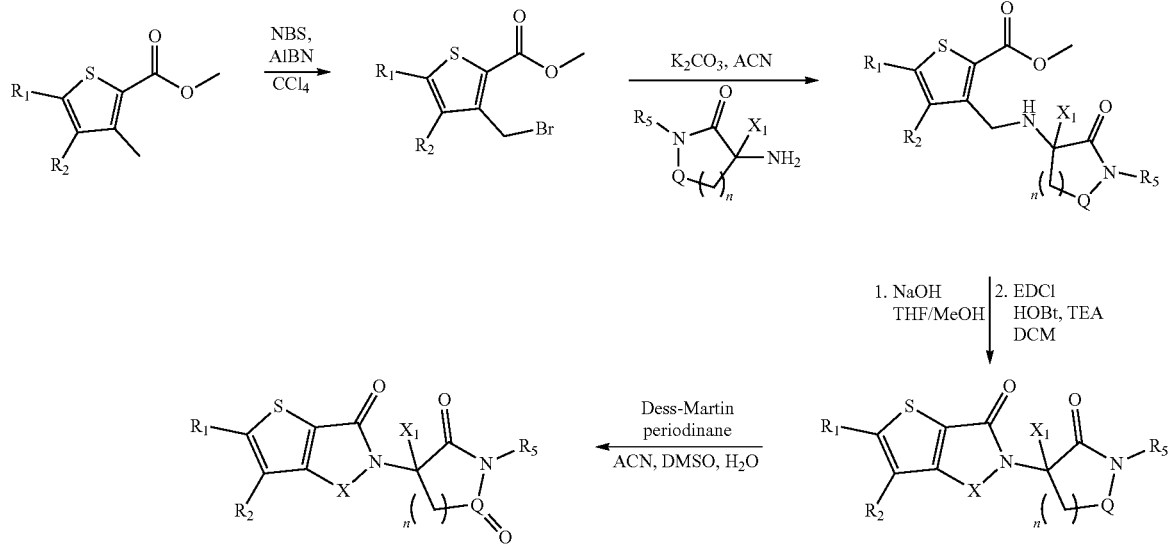

Generic Scheme 2

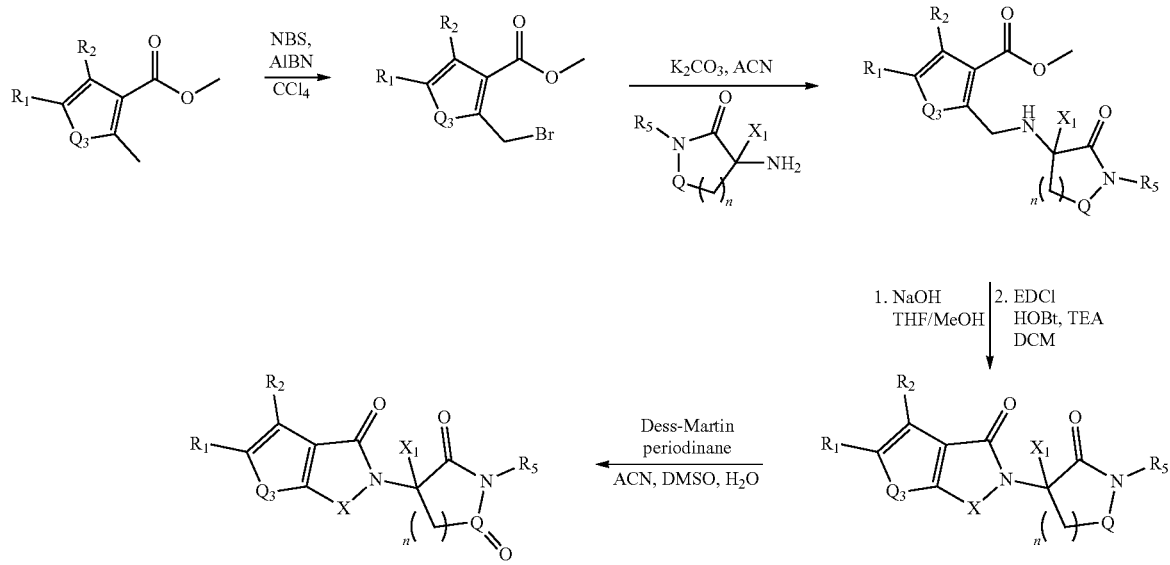

Generic Scheme 3

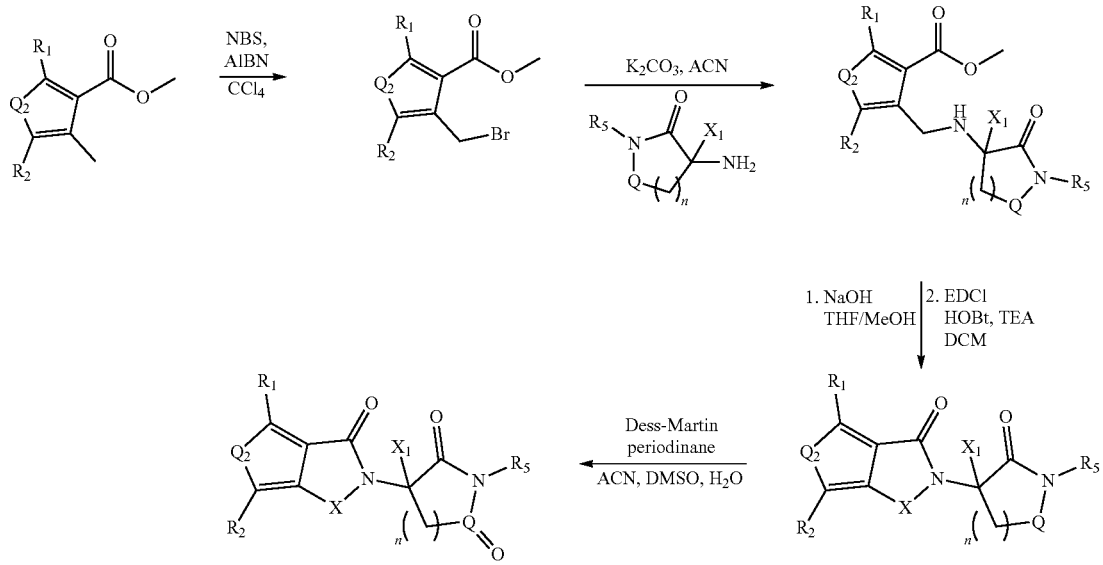

Compound 1: (S)-3-(6-oxo-4,6-dihydro-5H-thieno[2,3-c]pyrrol-5-yl)azepane-2,7-dione

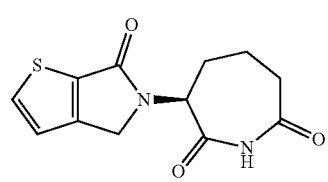 [SMILES: O=C1CCC[C@H](N2Cc3ccsc3C2=O)C(=O)N1]

Methyl 3-methylthiophene-2-carboxylate (1.5 g, 9.60 mmol) was dissolved in CCl₄ (45 mL). NBS (1.7 g, 9.55 mmol) was added followed by AIBN (0.5 mL, 12% in acetone). The mixture was heated at 80° C. for 18 h, followed by workup to provide methyl 3-(bromomethyl)thiophene-2-carboxylate (2.15 g, 97%). MS (M+Na) 258.1

Methyl 3-(bromomethyl)thiophene-2-carboxylate (1.0 g, 4.25 mmol) was dissolved in ACN (12 mL) followed by (S)-3-aminoazepan-2-one hydrochloride (0.700 g, 4.25 mmol) and K₂CO₃ (2.0 g, 14.8 mmol). The reaction was stirred at rt for 20 h. Following workup, the reaction was purified on silica gel (EA/MeOH; 90:10) to give methyl (S)-3-(((2-oxoazepan-3-yl)amino)methyl)thiophene-2-carboxylate (0.300 g, 25%). (M+1) 283.3.

Methyl (S)-3-(((2-oxoazepan-3-yl)amino)methyl)thiophene-2-carboxylate (0.300 g, 1.06 mmol) was dissolved in THF and MeOH. A 1 M solution of NaOH was added and the reaction was stirred at rt for 18 h, followed by acidification with 1 N HCl and evaporation to a solid. DCM (15 mL) was added followed by HOBt (0.244 g, 1.59 mmol), EDCI (0.303 g, 1.59 mmol) and trimethylamine (0.321 g, 3.18 mmol). The mixture was stirred at rt for 18 h, followed by workup to provide (S)-5-(2-oxoazepan-3-yl)-4,5-dihydro-6H-thieno[2,3-c]pyrrol-6-one (0.180 g, 35%). (M+1) 251.3.

(S)-5-(2-oxoazepan-3-yl)-4,5-dihydro-6H-thieno[2,3-c]pyrrol-6-one (0.078 g, 0.312 mmol) was slurried in ACN with wet DMSO. Dess-Martin reagent (0.27 g, 0.636 mmol, 2.1 eq.) was added and the mixture was stirred at 80° C. for 18 h, cooled to rt and worked up. The resulting oil was purified on silica gel (EA/Hexanes; 1:1 to 100% EA) to provide (S)-3-(6-oxo-4,6-dihydro-5H-thieno[2,3-c]pyrrol-5-yl)azepane-2,7-dione (0.020 g, 20%). (M+1) 265.3. 1H NMR (DMSO-d6) δ 10.6 (s, 1H), 8.02 (d, 1H), 7.25 (d, 1H), 5.13 (q, 1H), 4.46 (d, 2H), 3.08 (m, 1H), 2.59 (m, 1H), 2.23 (m, 1H), 2.12 (m, 1H), 2.09 (m, 1H), 1.82 (m, 1H).

Compound 2: (S)-3-(4-oxo-4,6-dihydro-5H-thieno[2,3-c]pyrrol-5-yl)azepane-2,7-dione

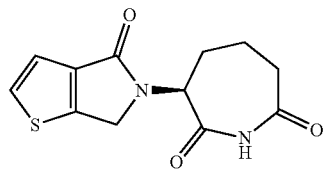 [SMILES: O=C1CCC[C@H](N2Cc3sccc3C2=O)C(=O)N1]

Methyl 2-methylthiophene-3-carboxylate (0.915 g, 5.86 mmol) was dissolved in CCl$_4$ (30 mL). NBS (1.04 g, 5.86 mmol) was added followed by AIBN (0.4 mL, 12% in acetone). The mixture was heated at 80° C. for 18 h, followed by workup to provide methyl 2-(bromomethyl)thiophene-3-carboxylate (1.35 g, 98%). MS (M+1) 236.1.

Methyl 2-(bromomethyl)thiophene-3-carboxylate (1.32 g, 5.62 mmol) was dissolved in ACN (15 mL) followed by (S)-3-aminoazepan-2-one hydrochloride (0.870 g, 5.62 mmol) and K$_2$CO$_3$ (2.6 g, 18.8 mmol). The mixture was stirred at rt for 20 h, followed by workup. The mixture was purified on silica gel (EA/MeOH; 90:10) to provide methyl (S)-2-(((2-oxoazepan-3-yl)amino)methyl)thiophene-3-carboxylate (0.557 g, 37%). (M+1) 283.3.

Methyl (S)-2-(((2-oxoazepan-3-yl)amino)methyl)thiophene-3-carboxylate (0.557 g, 1.97 mmol) was dissolved in THF and MeOH, followed by addition of 1 M NaOH (6 mL) and the reaction was stirred at rt for 18 h. The reaction was acidified with 1 N HCl (6 mL) then evaporated to a solid. DCM (35 mL) was added followed by HOBt (0.452 g, 2.96 mmol), EDCI (0.564 g, 2.96 mmol) and trimethylamine (0.795 g, 7.88 mmol) and at rt for 18 h. The reaction was then worked up with DCM and saturated NaHCO$_3$ to give (S)-5-(2-oxoazepan-3-yl)-5,6-dihydro-4H-thieno[2,3-c]pyrrol-4-one (0.465 g, 94%). (M+1) 251.3

(S)-5-(2-oxoazepan-3-yl)-5,6-dihydro-4H-thieno[2,3-c]pyrrol-4-one (0.300 g, 1.20 mmol) was slurried in ACN (12 mL) with 20 drops of wet DMSO (prepared by adding 2 drops water in 10 mL DMSO). The Dess-Martin periodinane reagent (1.07 g, 2.52 mmol, 2.1 eq) was added and the mixture was stirred at 80° C. for 18 h. Cooled to rt and 10 mL of a saturated sodium thiosulfate solution was added followed by stirring for 5 min. The mixture was poured into DCM and washed with 10% aq. sodium thiosulfate/NaHCO$_3$ (1:1 mixture) and brine. The compound was purified on silica gel (EA/Hexanes; 1:1 to EA 100%) to give (S)-3-(4-oxo-4,6-dihydro-5H-thieno[2,3-c]pyrrol-5-yl)azepane-2,7-dione (0.068 g, 22%) as a white solid. (M+1) 265.3. $^1$H NMR (DMSO-d$_6$) δ 10.6 (s, 1H), 7.67 (d, 1H), 7.22 (d, 1H), 5.15 (dd, 1H), 4.59 (m, 2H), 3.05 (m, 1H), 2.58 (m, 1H), 2.22 (m, 1H), 2.10 (m, 1H), 2.01 (m, 1H), 1.82 (m, 1H).

Compound 3: (S)-5-(2,7-dioxoazepan-3-yl)-4H-thieno[2,3-c]pyrrole-4,6(5H)-dione

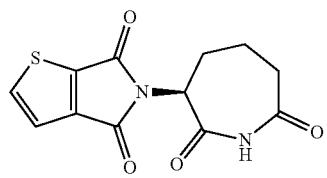 [SMILES: O=C1CCC[C@H](N2C(=O)c3ccsc3C2=O)C(=O)N1]

Thieno[2,3-c]furan-4,6-dione (0.305 g, 1.98 mmol) was dissolved in acetic acid (7 mL), NaOAc (0.163 g, 1.98 mmol) and (S)-3-aminoazepan-2-one hydrochloride (0.325 g, 1.98 mmol) were added, and the mixture was heated at 110° C. for 18 h. The solvent was removed under reduced pressure to afford a crude solid followed by stirring in water for 3 h. Filtration and drying provided (S)-2-((2-oxoazepan-3-yl)carbamoyl)thiophene-3-carboxylic acid (0.140 g, 25%). MS (M+1) 283.3.

(S)-2-((2-oxoazepan-3-yl)carbamoyl)thiophene-3-carboxylic acid (0.140 g, 0.496 mmol) was slurried in ACN (1 mL) with carbonyldiimidazole (0.170 g, 1.04 mmol), and stirred for 72 h. The residue was slurried in ACN with wet DMSO. Dess-Martin reagent (0.54 g, 1.27 mmol) was added and the mixture was stirred at 80° C. for 18 h, cooled to rt and worked up. The crude compound was triturated with EA to give (S)-5-(2,7-dioxoazepan-3-yl)-4H-thieno[2,3-c]pyrrole-4,6(5H)-dione (0.020 g, 15%) as a tan solid. (M+Na) 301.2. $^1$H NMR (DMSO-d$_6$) δ 10.8 (s, 1H), 8.29 (d, 1H), 7.53 (d, 1H), 5.13 (dd, 1H), 3.10 (m, 1H), 2.57 (m, 1H), 2.52 (m, 1H), 2.12 (m, 1H), 1.96 (m, 1H), 1.85 (m, 1H).

Compound 4: (S)-5-(2-oxoazepan-3-yl)-5,6-dihydro-4H-thieno[2,3-c]pyrrol-4-one

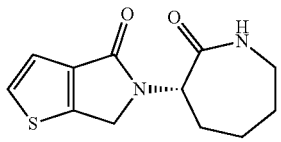 [SMILES: O=C1NCCCC[C@@H]1N1Cc2sccc2C1=O]

Methyl 2-methylthiophene-3-carboxylate (0.915 g, 5.86 mmol) was dissolved in CCl$_4$ (30 mL), and NBS (1.04 g, 5.86 mmol) and AIBN (0.4 mL, 12% in acetone) were added. The mixture was heated at 80° C. for 18 h and then worked up to provide methyl 2-(bromomethyl)thiophene-3-carboxylate (1.35 g, 98%). MS (M+1) 236.1.

Methyl 2-(bromomethyl)thiophene-3-carboxylate (1.32 g, 5.62 mmol) was dissolved in ACN (15 mL) followed by (S)-3-aminoazepan-2-one hydrochloride (0.870 g, 5.62 mmol) and K$_2$CO$_3$ (2.6 g, 18.8 mmol). The mixture was stirred at rt for 20 h, worked up, and purified on silica gel (EA/MeOH; 90:10) to give methyl (S)-2-(((2-oxoazepan-3-yl)amino)methyl)thiophene-3-carboxylate (0.557 g, 37%). (M+1) 283.3.

Methyl (S)-2-(((2-oxoazepan-3-yl)amino)methyl)thiophene-3-carboxylate (0.557 g, 1.97 mmol) was dissolved in THF and MeOH, 1 M solution of NaOH was added (6 mL), and the reaction was stirred at rt for 18 h. The reaction was acidified with 1 N HCl (6 mL) and evaporated to a solid. DCM (35 mL) was added followed by HOBt (0.452 g, 2.96 mmol), EDCI (0.564 g, 2.96 mmol) and trimethylamine (0.795 g, 7.88 mmol). The mixture was stirred at rt for 18 h, followed by workup to provide (S)-5-(2-oxoazepan-3-yl)-5,6-dihydro-4H-thieno[2,3-c]pyrrol-4-one (0.465 g, 94%). (M+1) 251.3

Compound 5: (R)-3-(4-oxo-4,6-dihydro-5H-thieno[2,3-c]pyrrol-5-yl)azepane-2,7-dione

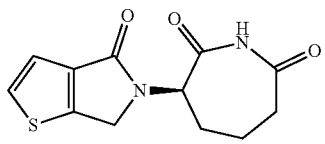 [SMILES: O=C1CCC[C@@H](N2Cc3sccc3C2=O)C(=O)N1]

Methyl 2-methylthiophene-3-carboxylate (0.915 g, 5.86 mmol) was dissolved in CCl$_4$ (30 mL), NBS (1.04 g, 5.86 mmol) and AIBN (0.4 mL, 12% in acetone) were added, and the mixture was heated at 80° C. for 18 h. Workup provided methyl 2-(bromomethyl)thiophene-3-carboxylate (1.35 g, 98%). MS (M+1) 236.1.

Methyl 2-(bromomethyl)thiophene-3-carboxylate (1.32 g, 5.62 mmol) was dissolved in ACN (15 mL) and (R)-3-aminoazepan-2-one hydrochloride (0.870 g, 5.62 mmol) and K$_2$CO$_3$ (2.6 g, 18.8 mmol) were added. The mixture was stirred at rt for 20 h, followed by workup and purification on silica gel (EA/MeOH; 90:10), providing methyl (R)-2-(((2-oxoazepan-3-yl)amino)methyl)thiophene-3-carboxylate (0.557 g, 37%). (M+1) 283.3.

Methyl (R)-2-(((2-oxoazepan-3-yl)amino)methyl)thiophene-3-carboxylate (0.557 g, 1.97 mmol) was dissolved in THF and MeOH, and 1 M NaOH was added (6 mL). The reaction was stirred at rt for 18 h, followed by acidification with 1 N HCl (6 mL) and removal of solvent under reduced pressure. DCM (35 mL) was added followed by HOBt (0.452 g, 2.96 mmol), EDCI (0.564 g, 2.96 mmol) and trimethylamine (0.795 g, 7.88 mmol). The mixture was stirred at rt for 18 h. The reaction was then worked up with DCM and saturated NaHCO$_3$ to give (R)-5-(2-oxoazepan-3-yl)-5,6-dihydro-4H-thieno[2,3-c]pyrrol-4-one (0.465 g, 94%). (M+1) 251.3

(R)-5-(2-oxoazepan-3-yl)-5,6-dihydro-4H-thieno[2,3-c]pyrrol-4-one (0.300 g, 1.20 mmol) was slurried in ACN (12 mL) with 20 drops of wet DMSO (prepared by adding 2 drops water in 10 mL DMSO). The Dess-Martin periodinane reagent (1.07 g, 2.52 mmol, 2.1 eq) was added and the mixture was stirred at 80° C. for 18 h. Cooled to rt and 10 mL of a saturated aq. sodium thiosulfate was added. The mixture was poured into DCM and washed with 10% aq. sodium thiosulfate/NaHCO$_3$ (1:1 mixture) and brine. The compound was purified on silica gel (EA/Hexanes; 1:1 to EA 100%) to give (R)-3-(4-oxo-4,6-dihydro-5H-thieno[2,3-c]pyrrol-5-yl)azepane-2,7-dione (0.068 g, 22%) as a white solid. (M+1) 265.3. 1H NMR (DMSO-d6) δ 10.6 (s, 1H), 7.67 (d, 1H), 7.22 (d, 1H), 5.15 (dd, 1H), 4.59 (m, 2H), 3.05 (m, 1H), 2.58 (m, 1H), 2.22 (m, 1H), 2.10 (m, 1H), 2.01 (m, 1H), 1.82 (m, 1H).

Compound 6: (S)-3-(4-oxo-4,6-dihydro-5H-thieno[2,3-c]pyrrol-5-yl)pyrrolidine-2,5-dione

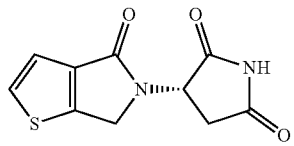 [SMILES: O=C1C[C@H](N2Cc3sccc3C2=O)C(=O)N1]

Methyl 2-(bromomethyl)thiophene-3-carboxylate (1.30 g, 5.62 mmol) was dissolved in ACN (15 mL) followed by (S)-3-aminopyrrolidin-2-one (0.760 g, 5.62 mmol) and K$_2$CO$_3$ (2.6 g, 18.8 mmol). The mixture was stirred at rt for 20 h. The reaction was worked up with DCM and saturated Na$_2$CO$_3$ and purified on silica gel (EA/MeOH; 90:10) to give methyl (S)-2-(((2-oxopyrrolidin-3-yl)amino)methyl)thiophene-3-carboxylate (0.281 g, 20%). (M+1) 254.3

Methyl (S)-2-(((2-oxopyrrolidin-3-yl)amino)methyl)thiophene-3-carboxylate (0.281 g, 1.10 mmol) was dissolved in THF and MeOH and a 1 M solution of NaOH was added (3.5 mL). The reaction was stirred at rt for 18 h followed by acidification with 1 N HCl (6 mL) and removal of solvent under reduced pressure. DCM (20 mL) was added followed by HOBt (0.253 g, 1.63 mmol), EDCI (0.315 g, 1.63 mmol) and trimethylamine (0.8 mL). The mixture was stirred at rt for 18 h, and worked up to provide (S)-5-(2-oxopyrrolidin-3-yl)-5,6-dihydro-4H-thieno[2,3-c]pyrrol-4-one (0.079 g, 32%). (M+1) 222.2.

(S)-5-(2-oxopyrrolidin-3-yl)-5,6-dihydro-4H-thieno[2,3-c]pyrrol-4-one (0.078 g, 0.351 mmol) was slurried in ACN (4 mL) and wet DMSO. Dess-Martin reagent (0.313 g, 2.1 eq) was added and the mixture was stirred at 80° C. for 18 h, cooled to rt, and worked up. The crude mixture was purified on silica gel (EA/Hexanes; 1:1 to EA 100%) to give (S)-3-(4-oxo-4,6-dihydro-5H-thieno[2,3-c]pyrrol-5-yl)pyrrolidine-2,5-dione (0.006 g, 7%) as a white solid. (M+1) 236.3. $^1$H NMR (DMSO-d$_6$) δ 11.4 (s, 1H), 7.69 (d, 1H), 7.21 (d, 1H), 5.12 (dd, 1H), 4.56 (q, 2H), 2.93 (m, 3H).

Compound 7: (S)-3-(4-oxo-4H-thieno[3,4-c]pyrrol-5(6H)-yl)azepane-2,7-dione

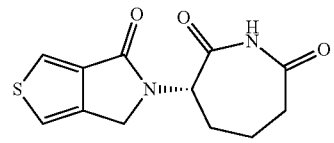 [SMILES: O=C1CCC[C@H](N2Cc3cscc3C2=O)C(=O)N1]

Methyl 4-methylthiophene-3-carboxylate (1.50 g, 9.60 mmol) was dissolved in CCl$_4$ (40 mL) and NBS (1.79 g, 10.1 mmol) and dibenzoylperoxide (0.232 g, 0.1 eq) were added. The mixture was heated at 80° C. for 4 h and worked up to provide methyl 4-(bromomethyl)thiophene-3-carboxylate (2.2 g, 100%). MS (M+1) 236.1.

Methyl 2-(bromomethyl)thiophene-3-carboxylate (2.2 g, 9.36 mmol) was dissolved in ACN (100 mL) and (S)-3-aminoazepan-2-one hydrochloride (1.53 g, 9.36 mmol) and K₂CO₃ (3.86 g, 27.9 mmol) were added. The mixture was stirred at rt for 18 h, followed by workup and purification on silica gel (EA/MeOH; 90:10) to give methyl (S)-4-(((2-oxoazepan-3-yl)amino)methyl)thiophene-3-carboxylate (0.308 g, 11%). (M+1) 283.3.

Methyl (S)-2-(((2-oxoazepan-3-yl)amino)methyl)thiophene-3-carboxylate (0.310 g, 1.09 mmol) was dissolved in MeOH (10 mL) and a 1 M solution of NaOH was added (3 mL). The reaction was stirred at rt for 18 h, followed by acidification with 1 N HCl (6 mL) and removal of solvent under reduced pressure. DCM (20 mL) was added followed by HOBt (0.253 g, 1.65 mmol), EDCI (0.317 g, 1.65 mmol) and trimethylamine (0.7 mL). The mixture was stirred at rt for 18 h, followed by workup to provide (S)-5-(2-oxoazepan-3-yl)-5,6-dihydro-4H-thieno[3,4-c]pyrrol-4-one (0.230 g, 84%). (M+1) 251.3.

(S)-5-(2-oxoazepan-3-yl)-5,6-dihydro-4H-thieno[3,4-c]pyrrol-4-one (0.230 g, 0.920 mmol) was slurried in ACN (10 mL) with wet DMSO. Dess-Martin reagent (0.819 g, 2.1 eq) was added and the mixture was stirred at 80° C. for 18 h, cooled to rt and worked up. The crude mixture was purified on silica gel (EA/Hexanes; 1:1 to EA 100%) to give (S)-3-(4-oxo-4H-thieno[3,4-c]pyrrol-5(6H)-yl)azepane-2,7-dione (0.028 g, 12%) as a white solid. (M+1) 265.3. ¹H NMR (DMSO-d₆) δ 10.7 (s, 1H), 8.03 (d, 1H), 7.50 (d, 1H), 5.14 (dd, 1H), 4.40 (m, 2H), 3.05 (m, 1H), 2.54 (m, 1H), 2.21 (m, 1H), 2.08 (m, 1H), 1.96 (m, 1H), 1.80 (m, 1H).

Compound 8: (S)-3-(1-methyl-4-oxo-4H-thieno[3,4-c]pyrrol-5(6H)-yl)azepane-2,7-dione

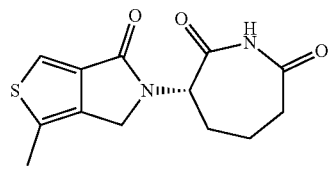 [SMILES: Cc1scc2c1CN([C@H]1CCCC(=O)NC1=O)C2=O]

Methyl 4-methylthiophene-3-carboxylate (3.62 g, 23.2 mmol) was dissolved in N,N-dimethylformamide (60 mL), NBS (4.33 g, 24.3 mmol) was added, and the reaction was stirred at rt for 18 h. The mixture was then worked up, filtered, and dried to give methyl 5-bromo-4-methylthiophene-3-carboxylate (4.45 g, 82%). MS (M+Na) 258.1.

Methyl 5-bromo-4-methylthiophene-3-carboxylate (2.16 g, 9.19 mmol) was dissolved in CCl₄ (60 mL) and NBS (1.72 g, 9.66 mmol) and dibenzoylperoxide (0.1 eq) were added. The mixture was heated at 80° C. for 4 h and worked up to provide methyl 5-bromo-4-(bromomethyl)thiophene-3-carboxylate (2.55 g, 89%). MS (M+Na) 337.1.

(S)-3-Aminoazepan-2-one (1.1 g, 8.59 mmol) was stirred in ACN (40 mL) and K₂CO₃ (1.35 g, 9.76 mmol) was added, followed up dropwise addition of methyl 5-bromo-4-(bromomethyl)thiophene-3-carboxylate (2.55 g, 8.12 mmol) dissolved in 40 mL of ACN, and the mixture was stirred at rt for 20 h. Following workup, the crude mixture was purified on silica gel (EA/MeOH; 90:10) to give methyl (S)-5-bromo-4-(((2-oxoazepan-3-yl)amino)methyl)thiophene-3-carboxylate (0.84 g, 30%). (M+1) 362.3.

Methyl (S)-5-bromo-4-(((2-oxoazepan-3-yl)amino)methyl)thiophene-3-carboxylate (0.84 g, 1.06 mmol) was dissolved in methanol (25 mL), and a 1 M solution of NaOH was added (8 mL). The reaction was stirred at rt for 18 h, followed by acidification with 1 N HCl (8 mL) and removal of solvent under reduced pressure. DCM (40 mL) was added followed by HOBt (0.531 g, 3.47 mmol), EDCI (0.667 g, 3.47 mmol) and trimethylamine (0.98 g, 9.70 mmol). The mixture was stirred at rt for 48 h, and then worked up to provide (S)-1-bromo-5-(2-oxoazepan-3-yl)-5,6-dihydro-4H-thieno[3,4-c]pyrrol-4-one (0.740 g, 97%). (M+1) 330.3.

(S)-1-bromo-5-(2-oxoazepan-3-yl)-5,6-dihydro-4H-thieno[3,4-c]pyrrol-4-one (0.320 g, 0.973 mmol) was slurried in dioxane (9 mL) and water (3 mL) and methylboronic acid (0.160 g, 2.67 mmol), tetrakis(triphenylphosphine)palladium (0.112 g, 0.097 mmol) and cesium carbonate (0.96 g, 2.94 mmol) were added. The reaction was flushed with nitrogen and heated at 90° C. for 18 h. Workup and silica gel purification provided (S)-1-methyl-5-(2-oxoazepan-3-yl)-5,6-dihydro-4H-thieno[3,4-c]pyrrol-4-one (0.103 g, 40%). (M+Na) 352.2.

(S)-1-methyl-5-(2-oxoazepan-3-yl)-5,6-dihydro-4H-thieno[3,4-c]pyrrol-4-one (0.13 g, 0.492 mmol) was slurried in ACN (6 mL) with wet and Dess-Martin reagent (0.438 g, 1.032 mmol, 2.1 eq) was added. The mixture was stirred at 80° C. for 18 h, cooled to rt, and worked up. The crude mixture was purified on silica gel (EA/Hexanes; 1:1 to EA 100%) to give (S)-3-(1-methyl-4-oxo-4H-thieno[3,4-c]pyrrol-5(6H)-yl)azepane-2,7-dione (0.033 g, 24%) as a yellow solid. (M+23) 301.2. ¹H NMR (DMSO-d₆) δ 10.6 (s, 1H), 7.76 (s, 1H), 5.13 (q, 1H), 4.31 (s, 2H), 3.05 (m, 1H), 2.57 (m, 1H), 2.41 (s, 3H), 2.20 (m, 1H), 1.99-2.03 (m, 2H), 1.82 (m, 1H).

Compound 9: 1-(3-chloro-4-methylphenyl)-3-((5-(2,6-dioxopiperidin-3-yl)-4-oxo-5,6-dihydro-4H-thieno[3,4-c]pyrrol-1-yl)methyl)urea

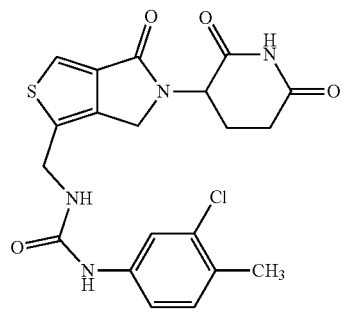 [SMILES: Cc1ccc(NC(=O)NCc2scc3c2CN(C2CCC(=O)NC2=O)C3=O)cc1Cl]

To a solution of 3-aminopiperidine-2,6-dione (1.26 g, 7.67 mmol) in DMF (60 mL) at 0° C. was added triethylamine (1.62 g, 15.98 mmol) followed by methyl 5-bromo-4-(bromomethyl)thiophene-3-carboxylate (2.0 g, 6.39 mmol). The mixture was warmed to rt and stirred overnight. The mixture was then concentrated to afford a residue, which was purified on silica gel eluting with EA in petroleum (10% to 100%) to give methyl 5-bromo-4-(((2,6-dioxopiperidin-3-yl)amino)methyl)thiophene-3-carboxylate as a purple solid (977 mg, 42.5%). MS (ESI) m/z=361 [M+H]⁺.

To a solution of methyl 5-bromo-4-(((2,6-dioxopiperidin-3-yl) amino)methyl) thiophene-3-carboxylate (892 mg, 2.48 mmol) in THF (20 mL) at 0° C. was added NaOH (1N, 6 mL). The mixture was warmed to rt and stirred overnight. HCl (1N) was then added until a pH of 3-4 was reached. The mixture was concentrated to give a mixture of 5-bromo-4-(((2,6-dioxopiperidin-3-yl)amino)methyl)thiophene-3-carboxylic acid and NaCl as a white solid (858 mg). DMF (20 mL) was added to the mixture and cooled 0° C. To this was added HATU (1.41 g, 3.72 mmol) and pyridine (588.5 mg, 7.44 mmol). The mixture was heated to 40° C. and stirred overnight. Additional HATU (1.41 g, 3.72 mmol) and pyridine (588.5 mg, 7.44 mmol) were added to the mixture and stirred at 40° C. for two days. The mixture was then concentrated and the residue was purified on silica gel eluting with EA in petroleum (10% to 90%) to give 3-(1-bromo-4-oxo-4H-thieno[3,4-c]pyrrol-5(6H)-yl)piperidine-2,6-dione as a white solid (415 mg, 55.0%). MS (ESI) m/z=329 [M+H]+.

To a solution of 3-(1-bromo-4-oxo-4H-thieno[3,4-c]pyrrol-5(6H)-yl)piperidine-2,6-dione (370 mg, 1.128 mmol) in anhydrous DMF (11 mL) was added Pd$_2$(dba)$_3$ (107.2 mg, 0.1128 mmol), 1,1'-bis(diphenylphosphino)ferrocene (dppf) (133.6 mg, 0.2482 mmol) and Zn(CN)$_2$ (145.7 mg, 1.241 mmol). The mixture was heated to 150° C. for 1 h with microwave. The mixture was concentrated and the residue was purified on silica gel eluting with EA in petroleum (20% to 100%) to give 5-(2,6-dioxopiperidin-3-yl)-4-oxo-5,6-dihydro-4H-thieno[3,4-c]pyrrole-1-carbonitrile as a tan solid (88 mg, 45.9%). MS (ESI) m/z=276 [M+H]+.

To a solution of 5-(2,6-dioxopiperidin-3-yl)-4-oxo-5,6-dihydro-4H-thieno[3,4-c]pyrrole-1-carbonitrile (88 mg, 0.32 mmol) in tetrahydrofuran (6 mL) was added Raney-Ni (50 mg) and Boc$_2$O (83.7 mg, 0.384 mmol). The suspension was degassed under vacuum and purged twice with hydrogen. The mixture was stirred at rt overnight. The mixture was then filtered and concentrated. The residue was purified on silica gel eluting with EA in petroleum (10% to 100%) to give tert-butyl ((5-(2,6-dioxopiperidin-3-yl)-4-oxo-5,6-dihydro-4H-thieno[3,4-c]pyrrol-1-yl)methyl)carbamate as a tan solid (32 mg, 26.4%). MS (ESI) m/z=380 [M+H]+.

To a solution of tert-butyl ((5-(2,6-dioxopiperidin-3-yl)-4-oxo-5,6-dihydro-4H-thieno[3,4-c]pyrrol-1-yl)methyl)carbamate (32 mg, 0.08443 mmol) in dichloromethane (2 mL) at 0° C. was added TFA (0.5 mL). The mixture was stirred at rt for 2 h. The mixture was then concentrated, diluted with water, and extracted with DCM. The aqueous phase was concentrated to give 3-(1-(aminomethyl)-4-oxo-4H-thieno[3,4-c]pyrrol-5(6H)-yl)piperidine-2,6-dione TFA salt as a yellow solid (23.5 mg, 100%). MS (ESI) m/z=280 [M+H]+.

3-(1-(aminomethyl)-4-oxo-4H-thieno[3,4-c]pyrrol-5(6H)-yl)piperidine-2,6-dione TFA salt (8) (23.5 mg, 0.084 mmol) in THF (3 mL) at rt was added TEA (21.4 mg, 0.211 mmol) followed 2-chloro-4-isocyanato-1-methylbenzene (9) (17 mg, 0.1013 mmol). The mixture was stirred at rt for 1.5 h. The mixture was concentrated and the residue was purified on silica gel eluting with MeOH in DCM (0% to 10%) to give 1-(3-chloro-4-methylphenyl)-3-((5-(2,6-dioxopiperidin-3-yl)-4-oxo-5,6-dihydro-4H-thieno[3,4-c]pyrrol-1-yl)methyl)urea as a white solid (19.3 mg, yield: 51.3%). $^1$H NMR (400 MHz, DMSO-d$_6$) δ 10.99 (s, 1H), 8.77 (s, 1H), 7.88 (s, 1H), 7.63 (s, 1H), 7.20-7.13 (m, 2H), 6.84 (t, J=6.0, 1H), 5.04-5.0 (m, 1H), 4.43 (d, J=5.6, 2H), 4.28 (dd, J=15.2, 42.8, 2H), 2.94-2.85 (m, 1H), 2.61 (s, 1H), 2.35-2.29 (m, 1H), 2.24 (s, 3H), 2.02-1.99 (m, 1H). MS (ESI) m/z=447 [M+H]+.

Compound 10: (S)-3-(1-Cyclopentyl-4-oxo-4H-thieno[3,4-c]pyrrol-5(6H)-yl)azepane-2,7-dione

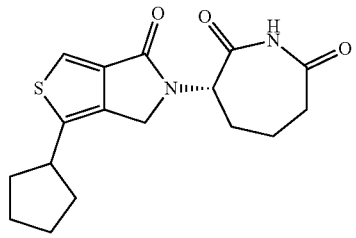 [SMILES: O=C1CCC[C@H](N2Cc3c(csc3C3CCCC3)C2=O)C(=O)N1]

To a solution of (S)-1-bromo-5-(2-oxoazepan-3-yl)-5,6-dihydro-4H-thieno[3,4-c]pyrrol-4-one (250 mg, 0.7622 mmol) in toluene/water (10 mL/1 mL) was added cyclopent-1-en-1-ylboronic acid (128 mg, 1.143 mmol) and K$_2$CO$_3$ (263 mg, 1.906 mmol). Following an N$_2$ purge, [1,1'-bis(diphenylphosphino)ferrocene]dichloropalladium(II) [Pd(dppf)Cl$_2$] (112 mg, 0.152 mmol) was added. The suspension was heated to 100° C., stirred overnight then cooled to RT and concentrated under vacuum. The residue was diluted in water and extracted with DCM (×2). The organic layers were concentrated and the residue purified on silica gel eluting with EA in petroleum (0% to 10%) to give (S)-1-(cyclopent-1-en-1-yl)-5-(2-oxoazepan-3-yl)-5,6-dihydro-4H-thieno[3,4-c]pyrrol-4-one (145 mg, 60.2%) as a white solid. MS (ESI) m/z=317 [M+H]+.

To a solution of (S)-1-(cyclopent-1-en-1-yl)-5-(2-oxoazepan-3-yl)-5,6-dihydro-4H-thieno[3,4-c]pyrrol-4-one (145 mg, 0.4589 mmol) in THF (5 mL) at RT was added Pd/C (80 mg). The suspension was stirred at RT overnight then filtered, and the filtrate was concentrated to give (S)-1-cyclopentyl-5-(2-oxoazepan-3-yl)-5,6-dihydro-4H-thieno[3,4-c]pyrrol-4-one (136 mg, 93.2%) as a yellow solid. MS (ESI) m/z=319 [M+H]+.

To a solution of (S)-1-cyclopentyl-5-(2-oxoazepan-3-yl)-5,6-dihydro-4H-thieno[3,4-c]pyrrol-4-one (136 mg, 0.4277 mmol) in fluorobenzene (4 mL) with 0.4 mL wet dimethyl sulfoxate at 0° C. was added Dess-Martin (544.2 mg, 1.283 mmol). The suspension was heated to 80° C. and stirred overnight. The mixture was cooled to RT and 5 mL of sat. sodium thiosulfate was added followed by stirring for 5 min. The mixture was extracted with DCM (15 mL×2) and the combined extracts were washed with 10% aq. sodium thiosulfate/aq. NaHCO$_3$ (1:1 mixture) (20 mL) and brine. The organic layer was dried over Na$_2$SO$_4$, filtered, and concentrated to afford the crude product, which was purified by prep-TLC (EA) to give (S)-3-(1-cyclopentyl-4-oxo-4H-thieno[3,4-c]pyrrol-5(6H)-yl)azepane-2,7-dione (5.2 mg, 3.7%) as a white solid. $^1$H NMR (400 MHz, DMSO-d$_6$) δ 10.74 (s, 1H), 7.80 (s, 1H), 5.14 (d, J=12.8 Hz, 1H), 4.42-4.34 (m, 2H), 3.28-3.26 (m, 2H), 2.60 (s, 1H), 2.23-2.00 (m, 5H), 1.77 (s, 2H), 1.64-1.62 (m, 5H). MS (ESI) m/z 333 [M+H]+.

Compound 11: (S)-3-(2-Methyl-4-oxo-4,6-dihydro-5H-thieno[2,3-c]pyrrol-5-yl)azepane-2,7-dione

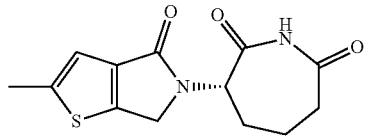 [SMILES: Cc1cc2c(s1)CN([C@H]1CCCC(=O)NC1=O)C2=O]

Methyl 2-methylthiophene-3-carboxylate (4.62 g, 29.6 mmol) was dissolved in DMF (23 mL) and AcOH (15 mL). N-Bromosuccinimide (5.54 g, 29.6 mmol) was added and the reaction was stirred at RT for 18 h. The mixture was evaporated to dryness then dissolved in EA and washed with sat. aq. NaHCO$_3$ to give methyl 5-bromo-2-methylthiophene-3-carboxylate (4.90 g, 70%) as an orange oil. MS (M+1) 236.1.

5-Bromo-2-methylthiophene-3-carboxylate (4.90 g, 20.8 mmol) was dissolved in carbon tetrachloride (75 mL). N-Bromosuccinimide (3.90 g, 20.9 mmol) was added followed by the addition of dibenzoylperoxide (0.1 eq). The mixture was heated at 80° C. for 18 h then cooled to RT. DCM was added and the solution was washed with sat. aq. NaHCO$_3$ The organic layer was concentrated to give methyl 5-bromo-2-(bromomethyl)thiophene-3-carboxylate (5.49 g, 84%). MS (M+1) 315.1.

(S)-3-Aminoazepan-2-one hydrochloride (2.9 g, 17.7 mmol) was stirred in ACN (75 mL) and followed by K$_2$CO$_3$ (8.00 g, 57.9 mmol). Methyl 5-bromo-2-(bromomethyl)thiophene-3-carboxylate (5.49 g, 17.5 mmol) dissolved in 75 mL of ACN was added dropwise and the mixture was stirred at RT for 20 h. The reaction was concentrated under vacuum and EA was added. The solution was washed with sat. aq. NaHCO$_3$. The organic layer was dried under vacuum then triturated with EA to give methyl (S)-5-bromo-2-(((2-oxoazepan-3-yl)amino)methyl)thiophene-3-carboxylate (2.97 g, 47%). MS (M+1) 362.3.

Methyl (S)-5-bromo-2-(((2-oxoazepan-3-yl)amino)methyl)thiophene-3-carboxylate (2.97 g, 8.22 mmol) was dissolved in MeOH (90 mL). A 1 M solution of NaOH was added (28 mL) and the reaction was stirred at RT for 18 h. The reaction was acidified with 1 N HCl (28 mL) then evaporated to a solid. DCM (140 mL) was added followed by HOBt (1.67 g, 12.4 mmol), EDCI (2.37 g, 12.4 mmol) and trimethylamine (5 mL). The mixture was stirred at RT for 48 h. The reaction was then worked up with DCM and sat. aq. NaHCO$_3$ to give (S)-2-bromo-5-(2-oxoazepan-3-yl)-5,6-dihydro-4H-thieno[2,3-c]pyrrol-4-one (2.70 g, 100%). MS (M+1) 330.3.

(S)-2-Bromo-5-(2-oxoazepan-3-yl)-5,6-dihydro-4H-thieno[2,3-c]pyrrol-4-one (0.600 g, 1.82 mmol) was slurried in dioxane (17 mL) and water (6 mL) followed by the addition of methylboronic acid (0.300 g, 5.00 mmol), tetrakis(triphenylphosphine)palladium (0.210 g, 0.182 mmol) and cesium carbonate (1.80 g, 5.51 mmol). The reaction was flushed with nitrogen then heated at 90° C. for 18 h. The reaction was worked up with EA and water followed on silica gel to give (S)-2-methyl-5-(2-oxoazepan-3-yl)-5,6-dihydro-4H-thieno[2,3-c]pyrrol-4-one (0.180 g, 37%). MS (M+1) 265.3.

(S)-2-Methyl-5-(2-oxoazepan-3-yl)-5,6-dihydro-4H-thieno[2,3-c]pyrrol-4-one (0.18 g, 0.682 mmol) was slurried in ACN (9 mL) with 12 drops of wet DMSO (prepared by adding 2 drops water in 10 ml DMSO). The Dess-Martin periodinane reagent (0.607 g, 1.43 mmol, 2.1 eq) was added and the mixture was stirred at 80° C. for 18 h. After cooling to RT, 5 mL of a saturated sodium thiosulfate solution was added followed by stirring for 5 min. The mixture was poured into DCM and washed with 10% aq. sodium thiosulfate/aq. NaHCO$_3$ (1:1 mixture) then brine. The compound was purified on silica gel (EA) to give (S)-3-(2-methyl-4-oxo-4,6-dihydro-5H-thieno[2,3-c]pyrrol-5-yl)azepane-2,7-dione (0.050 g, 40%) as an off white solid. MS (M+23) 301.2. 1H NMR (DMSO-d6) δ 10.6 (s, 1H), 6.92 (s, 1H), 5.12 (q, 1H), 4.53 (s, 2H), 3.04 (m, 1H), 2.57 (m, 1H), 2.49 (s, 3H), 2.19 (m, 1H), 1.99-2.03 (m, 2H), 1.80 (m, 1H).

Compound 12: (S)-3-(1-Isopropyl-4-oxo-4H-thieno[3,4-c]pyrrol-5(6H)-yl)azepane-2,7-dione

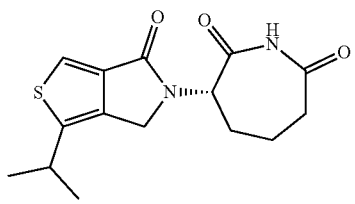 [SMILES: CC(C)c1scc2c1CN([C@H]1CCCC(=O)NC1=O)C2=O]

(S)-1-Bromo-5-(2-oxoazepan-3-yl)-5,6-dihydro-4H-thieno[3,4-c]pyrrol-4-one (0.430 g, 1.31 mmol) was slurried in dioxane (12 mL) and water (4 mL) followed by the addition of isopropenyl boronic pinacol ester (0.550 g, 2.62 mmol), tetrakis(triphenylphosphine)palladium (0.150 g, 0.130 mmol) and cesium carbonate (1.29 g, 3.95 mmol). The reaction was flushed with nitrogen then heated at 90° C. for 18 h. The reaction was cooled to RT then EA and water was added. The organic phase was concentrated and purified on silica gel to give (S)-5-(2-oxoazepan-3-yl)-1-(prop-1-en-2-yl)-5,6-dihydro-4H-thieno[3,4-c]pyrrol-4-one (0.236 g, 62%). MS (M+1) 291.3.

(S)-5-(2-Oxoazepan-3-yl)-1-(prop-1-en-2-yl)-5,6-dihydro-4H-thieno[3,4-c]pyrrol-4-one (0.227 g, 0.783 mmol) was dissolved in MeOH (20 mL) followed by the addition of a catalytic amount of Pd—C. The reaction was stirred under hydrogen gas for 18 h. The reaction was filtered through celite then concentrated to give (S)-1-isopropyl-5-(2-oxoazepan-3-yl)-5,6-dihydro-4H-thieno[3,4-c]pyrrol-4-one (0.215 g, 94%).

(S)-1-Isopropyl-5-(2-oxoazepan-3-yl)-5,6-dihydro-4H-thieno[3,4-c]pyrrol-4-one (0.214 g, 0.732 mmol) was slurried in ACN (11 mL) with 14 drops of wet DMSO (prepared by adding 2 drops water in 10 ml DMSO). The Dess-Martin periodinane reagent (0.653 g, 1.53 mmol, 2.1 eq) was added and the mixture was stirred at 80° C. for 18 h. After cooling to RT, 5 mL of a saturated sodium thiosulfate solution was added followed by stirring for 5 min. The mixture was poured into DCM and washed with 10% aq. sodium thiosulfate/aq. NaHCO$_3$ (1:1 mixture) then brine. The compound was purified on silica gel (EA) to give (S)-3-(1-isopropyl-4-oxo-4H-thieno[3,4-c]pyrrol-5(6H)-yl)azepane-2,7-dione (0.023 g, 10%) as an off white solid. MS (M+23) 329.3.

Compound 13: (S)-3-(1-Bromo-4-oxo-4H-thieno[3,4-c]pyrrol-5(6H)-yl)azepane-2,7-dione

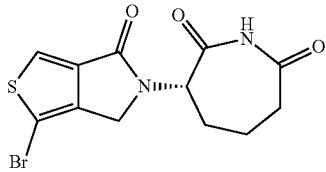 [SMILES: O=C1CCC[C@H](N2Cc3c(csc3Br)C2=O)C(=O)N1]

(S)-1-Bromo-5-(2-oxoazepan-3-yl)-5,6-dihydro-4H-thieno[3,4-c]pyrrol-4-one (0.15 g, 0.456 mmol) was slurried in ACN (6 mL) with 8 drops of wet DMSO (prepared by adding 2 drops water in 10 ml DMSO). The Dess-Martin periodinane reagent (0.406 g, 0.957 mmol, 2.1 eq) was added and the mixture was stirred at 80° C. for 18 h. After cooling to RT, 5 mL of a saturated sodium thiosulfate solution was added followed by stirring for 5 min. The mixture was poured into DCM and washed with 10% aq. sodium thiosulfate/aq. NaHCO₃ (1:1 mixture) then brine. The compound was purified on silica gel (EA) to give (S)-3-(i-bromo-4-oxo-4H-thieno[3,4-c]pyrrol-5(6H)-yl)azepane-2,7-dione (0.013 g, 8%) as an off white solid. MS (M+1) 344.2. ¹H NMR (DMSO-d6) δ 10.7 (s, 1H), 8.10 (s, 1H), 5.15 (d, 1H), 4.32 (q, 2H), 3.05 (m, 1H), 2.55 (m, 1H), 2.24 (m, 1H), 1.99-2.08 (m, 2H), 1.80 (m, 1H).

Compound 14: (S)-3-(2-Bromo-4-oxo-4,6-dihydro-5H-thieno[2,3-c]pyrrol-5-yl)azepane-2,7-dione

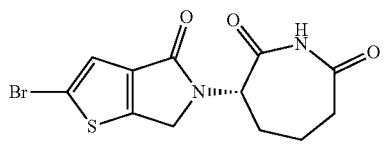 [SMILES: O=C1CCC[C@H](N2Cc3sc(Br)cc3C2=O)C(=O)N1]

(S)-2-Bromo-5-(2-oxoazepan-3-yl)-5,6-dihydro-4H-thieno[2,3-c]pyrrol-4-one (0.30 g, 0.912 mmol) was slurried in ACN (12 mL) with 16 drops of wet DMSO (prepared by adding 2 drops water in 10 ml DMSO). The Dess-Martin periodinane reagent (0.812 g, 1.91 mmol, 2.1 eq) was added and the mixture was stirred at 80° C. for 18 h. After cooling to RT, 5 mL of a saturated sodium thiosulfate solution was added followed by stirring for 5 min. The mixture was poured into DCM and washed with 10% aq. sodium thiosulfate/aq. NaHCO₃ (1:1 mixture) then brine. The compound was purified on silica gel (EA) to give (S)-3-(2-bromo-4-oxo-4,6-dihydro-5H-thieno[2,3-c]pyrrol-5-yl)azepane-2,7-dione (0.035 g, 12%) as an off white solid. MS (M+1) 344.2. ¹H NMR (DMSO-d6) δ 10.7 (s, 1H), 7.29 (s, 1H), 5.15 (d, 1H), 4.32 (q, 2H), 3.05 (m, 1H), 2.55 (m, 1H), 2.24 (m, 1H), 1.99-2.08 (m, 2H), 1.80 (m, 1H).

Compound 15: (S)-5-(2,7-Dioxoazepan-3-yl)-1-nitro-4H-thieno[3,4-c]pyrrole-4,6(5H)-dione

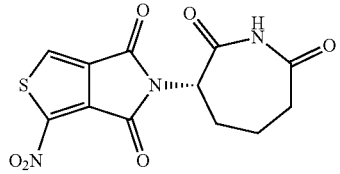 [SMILES: O=C1CCC[C@H](N2C(=O)c3csc([N+](=O)[O-])c3C2=O)C(=O)N1]

1H,3H-Thieno[3,4-c]furan-1,3-dione (2.48 g, 16.1 mmol) was dissolved in THF (150 mL) followed by the addition of (S)-3-aminoazepan-2-one HCl (2.64 g, 16.1 mmol) and trimethylamine (3 mL). The mixture was stirred at RT for 18 h. Carbonyldiimidazole (3.13 g, 19.3 mmol) was added and the reaction was heated at 64° C. for 2 h. Standard workup with DCM and water gave (S)-5-(2-oxoazepan-3-yl)-4H-thieno[3,4-c]pyrrole-4,6(5H)-dione (3.78 g, 89%). MS (M+1) 265.3.

(S)-5-(2-Oxoazepan-3-yl)-4H-thieno[3,4-c]pyrrole-4,6(5H)-dione (1.38 g, 5.22 mmol) was dissolved in 6 mL of sulfuric acid. The reaction was cooled to 0° C. followed by the addition of fuming nitric acid (3 mL) dissolved in sulfuric acid (2 mL). The mixture was stirred for 1 h at 0° C. then poured into 200 mL of an ice-water mixture. The resultant solid was filtered and washed with water to give (S)-1-nitro-5-(2-oxoazepan-3-yl)-4H-thieno[3,4-c]pyrrole-4,6(5H)-dione (0.485 g, 30%). MS (M+1) 310.2.

(S)-1-Nitro-5-(2-oxoazepan-3-yl)-4H-thieno[3,4-c]pyrrole-4,6(5H)-dione (0.485 g, 1.57 mmol) was slurried in ACN (25 mL) with 31 drops of wet DMSO (prepared by adding 2 drops water in 10 ml DMSO). The Dess-Martin periodinane reagent (1.40 g, 3.30 mmol, 2.1 eq) was added and the mixture was stirred at 80° C. for 18 h. After cooling to RT, 5 mL of a saturated sodium thiosulfate solution was added followed by stirring for 5 min. The mixture was poured into DCM and washed with 10% aq. sodium thiosulfate/aq. NaHCO₃ (1:1 mixture) then brine. The compound was triturated with EA to give (S)-5-(2,7-dioxoazepan-3-yl)-1-nitro-4H-thieno[3,4-c]pyrrole-4,6(5H)-dione (0.150 g, 30%). MS (M+1) 324.3.

Compound 16: (S)-1-Amino-5-(2,7-dioxoazepan-3-yl)-4H-thieno[3,4-c]pyrrole-4,6(5H)-dione

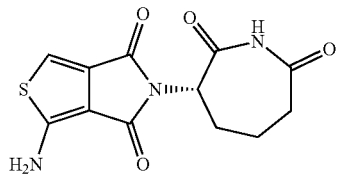

(S)-5-(2,7-Dioxoazepan-3-yl)-1-nitro-4H-thieno[3,4-c]pyrrole-4,6(5H)-dione (0.018 g, 0.056 mmol) was dissolved in MeOH (10 mL) followed by the addition of a catalytic amount of platinum 1% and vanadium 2%, on activated carbon (50-70% wetted powder). The reaction was stirred under hydrogen gas for 3 h then filtered through celite. The solvent was evaporated to give (S)-1-amino-5-(2,7-dioxoazepan-3-yl)-4H-thieno[3,4-c]pyrrole-4,6(5H)-dione (0.010 g, 70% purity). MS (M+1) 294.3.

Compound 17: (S)-5-(2,7-Dioxoazepan-3-yl)-4-oxo-5,6-dihydro-4H-thieno[3,4-c]pyrrole-1-carbonitrile

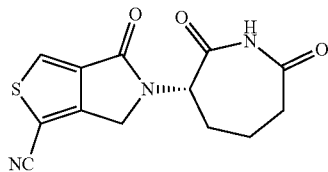

To a solution of methyl 4-methylthiophene-3-carboxylate (20.0 g, 128.1 mmol) in DMF (250 mL) at 0° C. was added N-bromosuccinimide (NBS) (23.9 g, 134.2 mmol). The mixture was warmed to RT and stirred overnight. The mixture was diluted in ice-water and stirred for 15 minutes. It was then filtered, and the cake was washed with water and dried under vacuum to give methyl 5-bromo-4-methylthiophene-3-carboxylate (28.1 g, 93.6%) as a yellow solid.

To a solution of methyl 5-bromo-4-methylthiophene-3-carboxylate (28.1 g, 120.1 mmol) in carbon tetrachloride (80 mL) at RT was added N-bromosuccinimide (NBS) (25.6 g, 143.8 mmol) and dibenzoyl peroxide (BPO) (2.9 g, 11.9 mmol). The mixture was heated to 85° C. for 5 h. It was filtered and the filtrate was purified on silica gel eluting with EA in petroleum (0% to 6%) to give methyl 5-bromo-4-(bromomethyl)thiophene-3-carboxylate (26.3 g, 70.1%) as a white solid.

To a solution of (S)-3-aminoazepan-2-one (5.75 g, 44.94 mmol) in DMF (200 mL) at 0° C. was added TEA (7.61 g, 74.91 mmol) and methyl 5-bromo-4-(bromomethyl)thiophene-3-carboxylate (11.68 g, 37.45 mmol). The mixture was warmed to RT for 2 h. The mixture was concentrated and the residue was purified on silica gel eluting with EA in petroleum (0% to 100%) to give methyl (S)-5-bromo-4-(((2-oxoazepan-3-yl)amino)methyl)thiophene-3-carboxylate (9.21 g, 68%) as white solid. MS (ESI) m/z=361 [M+H]⁺.

To a solution of methyl (S)-5-bromo-4-(((2-oxoazepan-3-yl)amino)methyl)thiophene-3-carboxylate (9.2 g, 25.5 mmol) in ACN (300 mL) was added trimethylaluminium (153 mL, 1 M in toluene) at 0° C. A saturated solution of ammonium chloride (20 mL) was added dropwise into the mixture at 0° C., then the mixture was extracted with DCM (200 mL×2). The combined organic layers were washed with water, dried over Na₂SO₄, filtered, and concentrated to give the crude product, which was purified on silica gel eluting with EA in petroleum (1:1) to give (S)-1-bromo-5-(2-oxoazepan-3-yl)-5,6-dihydro-4H-thieno[3,4-c]pyrrol-4-one (7.04 g, 85%) as white solid. MS (ESI) m/z=329, 331 [M+H]⁺.

To a solution of (S)-1-bromo-5-(2-oxoazepan-3-yl)-5,6-dihydro-4H-thieno[3,4-c]pyrrol-4-one (1.1 g, 3.35 mmol) in DMF (12 mL) was added zinc cyanide (394 mg, 3.69 mmol), tris(dibenzylideneacetone)dipalladium(0) [Pd₂(dba)₃] (323 mg, 0.34 mmol) and 1,1'-bisdiphenylphosphinoferrocene [dppf] (396 mg, 0.74 mmol). The mixture was heated to 150° C. for 1 h by microwave. The solvent was removed under vacuum. The residue was purified on silica gel eluting with EA:MeOH (from 0% to 10%) to afford (S)-4-oxo-5-(2-oxoazepan-3-yl)-5,6-dihydro-4H-thieno[3,4-c]pyrrole-1-carbonitrile (700 mg, 84%) as yellow solid. MS (ESI) m/z=276 [M+H]⁺.

To a solution of (S)-4-oxo-5-(2-oxoazepan-3-yl)-5,6-dihydro-4H-thieno[3,4-c]pyrrole-1-carbonitrile (5.2 g, 18.9 mmol) in ACN (120 mL) and wet dimethyl sulfoxide (20 mL) was added Dess-Martin (19.9 g, 47.3 mmol). The mixture was heated to 80° C. and stirred for 6 h. After cooling to RT, a saturated sodium thiosulfate solution was added followed by stirring for 5 min. The mixture was extracted with DCM (150 mL×2) and the combined solution was washed with 10% aq. sodium thiosulfate/aq. NaHCO₃ (1:1 mixture) (200 mL) then brine. The organic layer was dried over Na₂SO₄, filtered, and concentrated to afford the crude product. It was purified on silica gel eluting with DCM/MeOH (30:1) to give (S)-5-(2,7-dioxoazepan-3-yl)-4-oxo-5,6-dihydro-4H-thieno[3,4-c]pyrrole-1-carbonitrile (3.3 g, 61.1%) as yellow solid. MS (ESI) m/z=290 [M+H]⁺. ¹H NMR (400 MHz, DMSO-d₆) δ 10.77 (s, 1H), 8.55 (s, 1H), 5.18-5.15 (m, 1H), 4.64 (dd, J=18.8, 38.8, 2H), 3.07-3.02 (m, 1H), 2.58 (s, 1H), 2.45 (s, 1H), 2.10-2.01 (m, 2H), 1.82 (s, 1H).

Compound 18: (S)-3-(1-(Aminomethyl)-4-oxo-4H-thieno[3,4-c]pyrrol-5(6H)-yl)azepane-2,7-dione 2,2,2-trifluoroacetic acid salt

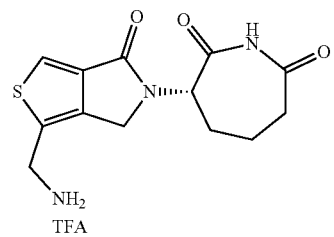 [SMILES: NCc1scc2c1CN([C@H]1CCCC(=O)NC1=O)C2=O]

To a solution of the(S)-5-(2,7-dioxoazepan-3-yl)-4-oxo-5,6-dihydro-4H-thieno[3,4-c]pyrrole-1-carbonitrile (3.3 g, 11.42 mmol) in THF (100 mL) was added di-t-butyl-dicarbonate (Boc)₂O (4.78 g, 22.84 mmol), Raney-Ni (1 g). Then the suspension was stirred under hydrogen atmosphere for 10 h at RT. It was filtered and the filtrated was concentrated to give the crude product. The residue was purified on silica gel eluting with EA in petroleum (20% to 100%) to give tert-butyl (S)—((5-(2,7-dioxoazepan-3-yl)-4-oxo-5,6-dihydro-4H-thieno[3,4-c]pyrrol-1-yl)methyl)carbamate (2.57 g, 57.2%) as a yellow solid. MS (ESI) m/z=394 [M+H]⁺.

To a solution of tert-butyl (S)—((5-(2,7-dioxoazepan-3-yl)-4-oxo-5,6-dihydro-4H-thieno[3,4-c]pyrrol-1-yl)methyl)carbamate (35 mg, 0.08906 mmol) in DCM (2 mL) at 0° C. was added 2,2,2-trifluoroacetic acid (0.5 mL). The mixture was warmed to RT and stirred for 1.5 h. The reaction was concentrated to remove the solvent and the residue was diluted in water. It was extracted with DCM. The aqueous phase was lyophilized to afford (S)-3-(1-(aminomethyl)-4-oxo-4H-thieno[3,4-c]pyrrol-5(6H)-yl)azepane-2,7-dione 2,2,2-trifluoroacetic acid salt (10.8 mg) as a tan solid. ¹H NMR (400 MHz, DMSO-d₆) δ 10.77 (s, 1H), 8.26 (s, 3H), 8.11 (s, 1H), 5.20-5.16 (m, 1H), 4.48 (dd, J=14.0, 18.8, 2H), 4.27 (s, 2H), 3.11-3.04 (m, 1H), 2.59 (s, 1H), 2.18-1.99 (m, 3H), 1.85-1.81 (m, 1H). MS (ESI) m/z 294 [M+H]⁺.

Compound 19: (S)-3-(1-(Difluoromethyl)-4-oxo-4H-thieno[3,4-c]pyrrol-5(6H)-yl)azepane-2,7-dione

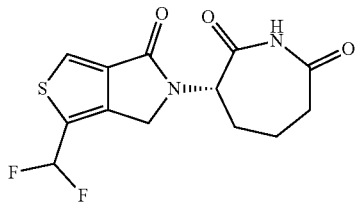 [SMILES: O=C1CCC[C@H](N2Cc3c(csc3C(F)F)C2=O)C(=O)N1]

To a solution of methyl 5-bromo-4-methylthiophene-3-carboxylate (3.0 g, 12.8 mmol) in DMF (30 mL) was added zinc cyanide (4.51 g, 38.4 mmol), tris(dibenzylideneacetone)dipalladium(0) [Pd$_2$(dba)$_3$] (580 mg, 0.60 mmol), 1,1'-bisdiphenylphosphinoferrocene [dppf] (760 mg, 0.14 mmol) at RT. The mixture was stirred at 150° C. for 1 h in a microwave under N$_2$. The suspension was filtered and concentrated in vacuo to get the crude product, which was purified on silica gel eluting with (petroleum ether/EA=50/1 to 20/1) to afford methyl 5-cyano-4-methylthiophene-3-carboxylate (1.20 g, 52%) as a yellow solid. $^1$H NMR (300 MHz, CDCl$_3$) δ 8.28 (s, 1H), 3.90 (s, 3H), 2.67 (s, 3H). MS (ESI) m/z 182.0 [M+H]$^+$.

To a solution of methyl 5-cyano-4-methylthiophene-3-carboxylate (900 mg, 4.97 mmol) and sodium hypophosphite in water/pyridine/AcOH=1/2/1 (5 mL/10 mL/5 mL) was added Raney-Ni (100 mg). The mixture was stirred at RT overnight. After the reaction was complete, the solvent was removed under vacuum and water was added, the mixture was extracted with DCM (100 mL×2), washed with brine, dried over Na$_2$SO$_4$, filtered, and concentrated in vacuo to afford the crude product, which was purified on silica gel eluting with petroleum ether/EA=100/1 to 80/1 to 60/1 to afford methyl 5-formyl-4-methylthiophene-3-carboxylate (410 mg, 44%) as a yellow solid. $^1$H NMR (300 MHz, CDCl$_3$) δ 10.13 (s, 1H), 8.43 (s, 1H), 3.90 (s, 3H), 2.82 (s, 3H). MS (ESI) m/z 185.0 [M+H]$^+$.

Methyl 5-formyl-4-methylthiophene-3-carboxylate (410 mg, 2.23 mmol) in DCM (10 mL) was cooled to 0° C., diethylaminosulfur trifluoride (DAST) (1.8 g, 11.14 mmol) was added dropwise. The mixture was stirred at RT overnight under nitrogen atmosphere. The reaction was quenched with NaHCO$_3$ (aq) at 0° C., then the mixture was extracted with DCM, washed with brine (120 mL), dried over Na$_2$SO$_4$, filtered and concentrated in vacuo to afford the crude product, which was purified on silica gel eluting with petroleum ether/EA=100/1 to 80/1 to 70/1 to get methyl 5-(difluoromethyl)-4-methylthiophene-3-carboxylate (340 mg, 74%) as a red oil. $^1$H NMR (300 MHz, CDCl$_3$) δ 8.19 (s, 1H), 6.91 (t, J=55.5 Hz, 1H), 3.88 (s, 3H), 2.53 (s, 3H).

To a solution of methyl 5-(difluoromethyl)-4-methylthiophene-3-carboxylate (340 mg, 1.65 mmol) in carbon tetrachloride (6 mL) at RT was added N-bromosuccinimide (NBS) (440 mg, 2.47 mmol) and 2,2'-azobis(2-methylpropionitrile) (AIBN) (172 mg, 0.66 mmol). The suspension was stirred at 90° C. overnight. After the reaction was complete, the solvent was removed under vacuum to get the crude methyl 4-(bromomethyl)-5-(difluoromethyl)thiophene-3-carboxylate (540 mg) as a yellow oil, which was used in the next step without purification. $^1$H NMR (300 MHz, CDCl$_3$) δ 8.23 (s, 1H), 6.91 (t, J=55.5 Hz, 1H), 4.92 (s, 2H), 3.93 (s, 3H).

To a solution of methyl 4-(bromomethyl)-5-(difluoromethyl)thiophene-3-carboxylate (540 mg, 1.65 mmol) in DMF (5 mL) was added TEA (333 mg, 3.3 mmol) and (S)-3-aminoazepan-2-one (253 mg, 1.98 mmol). The mixture was stirred at 50° C. for 2 h. After the reaction was complete, the solvent was removed under vacuum to get the crude product, which was purified on silica gel eluting with petroleum ether/EA=2/1 to DCM/MeOH=50/1 to get methyl (S)-5-(difluoromethyl)-4-(((2-oxoazepan-3-yl)amino)methyl) thiophene-3-carboxylate (310 mg, 56%) as a yellow solid. MS (ESI) m/z 333.0 [M+H]$^+$.

Trimethylaluminium (4.8 mL, 9.6 mmol) was added into a solution of (S)-5-(difluoromethyl)-4-(((2-oxoazepan-3-yl)amino)methyl)thiophene-3-carboxylate (310 mg, 0.96 mmol) in ACN (10 mL) at 0° C. The mixture was stirred at RT for 5 h under nitrogen atmosphere. The mixture was quenched with ammonium chloride (aq) at 0° C., then the mixture was extracted with DCM (80 mL×2), washed with brine (70 mL), over Na$_2$SO$_4$, and concentrated in vacuo to get the crude product, which was purified on silica gel (DCM/MeOH=100/1 to 50/1) to get (S)-1-(difluoromethyl)-5-(2-oxoazepan-3-yl)-5,6-dihydro-4H-thieno[3,4-c]pyrrol-4-one (160 mg, 55%) as a yellow solid. $^1$H NMR (300 MHz, CDCl$_3$) δ 7.83 (s, 1H), 7.03 (t, J=71.4 Hz, 1H), 5.93 (s, 1H), 5.31-5.12 (m, 1H), 4.95 (d, J=6.3 Hz, 1H), 4.37 (d, J=16.2 Hz, 1H), 3.45-3.40 (m, 1H), 3.30-3.27 (m, 1H), 2.17-2.11 (m, 1H), 1.98-1.82 (m, 3H), 1.74-1.61 (m, 1H), 1.52-1.47 (m, 1H). MS (ESI) m/z 301.0 [M+H]$^+$.

To a solution of (S)-1-(difluoromethyl)-5-(2-oxoazepan-3-yl)-5,6-dihydro-4H-thieno[3,4-c]pyrrol-4-one (160 mg, 0.53 mmol) in fluorobenzene/dimethyl sulfoxide (6 mL/0.6 mL) at RT was added Dess-Martin periodinane (564 mg, 1.33 mmol). The mixture was stirred at 80° C. overnight. The mixture was cooled to RT and 20 mL of sat. aq. sodium thiosulfate was added followed by stirring for 5 min. The mixture was extracted with DCM (30 mL×2) and the combined solution was washed with 10% aq. sodium thiosulfate/aq. NaHCO$_3$ (1:1 mixture) (50 mL) then brine (50 mL). The organic layer was dried over Na$_2$SO$_4$, filtered and concentrated to afford the crude product. The crude product was purified by reverse-LC to afford (S)-3-(1-(difluoromethyl)-4-oxo-4H-thieno[3,4-c]pyrrol-5(6H)-yl)azepane-2,7-dione (74 mg, 44%) as a white solid. $^1$H NMR (400 MHz, DMSO-d6) δ 10.59 (s, 1H), 8.22 (s, 1H), 7.32 (t, J=55.6 Hz, 1H), 5.11-5.07 (m, 1H), 4.47 (s, 2H), 2.99 (t, J=13.2 Hz, 1H), 2.42 (s, 1H), 2.13 (s, 1H), 2.04-1.93 (m, 2H), 1.73 (s, 1H). MS (ESI) m/z 315.0 [M+H]$^+$.

Compound 20: (S)-3-(1-Methyl-4-oxo-4H-thieno[3,4-c]pyrrol-5(6H)-yl) pyrrolidine-2,5-dione

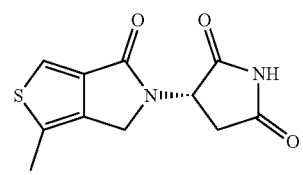 [SMILES: Cc1scc2c1CN([C@H]1CC(=O)NC1=O)C2=O]

To a solution of (tert-butoxycarbonyl)-L-asparagine (2.0 g, 8.61 mmol) in DMF (20 mL) was added 1-hydroxypyrrolidine-2,5-dione (HOSU) (988 mg, 8.61 mmol) and dicyclohexylcarbodiimide (DCC) (886 mg, 8.61 mmol). The mixture was stirred at 80° C. for 10 h. The solvent was removed and the residue was diluted with EA (40 mL). The solid was filtered and the filtrate was washed with water, dried over Na$_2$SO$_4$, filtered, and concentrated to give the crude product, which was purified on silica gel eluting with EA in petroleum (10% to 60%) to give tert-butyl (S)—(2,5-dioxopyrrolidin-3-yl)carbamate (775 mg, 42.1%) as a white solid. $^1$H NMR (CDCl$_3$, 400 MHz) δ: 11.18 (s, 1H), 7.44 (d, J=8.4 Hz, 1H), 4.32-4.26 (m, 1H), 2.87-2.82 (m, 1H), 2.47-2.41 (m, 1H), 1.37 (s, 9H).

To a solution of tert-butyl (S)—(2,5-dioxopyrrolidin-3-yl)carbamate (675 mg, 3.153 mmol) in DCM (26 mL) at 0° C. was added TFA (8 mL). The mixture was stirred at RT for 3.5 h. The solvent was removed and the residue was dried in vacuo to give the crude (S)-3-aminopyrrolidine-2,5-dione (359.7 mg, 100%) as a yellow oil. MS (ESI) m/z=115.1 [M+H]$^+$.

To a solution of (S)-3-aminopyrrolidine-2,5-dione (3) (359.7 mg, 3.153 mmol) in DMF (26 mL) at 0° C. was added methyl 5-bromo-4-(bromomethyl)thiophene-3-carboxylate (820 mg, 2.63 mmol) and TEA (664.6 mg, 6.568 mmol). The mixture was stirred at RT for 16 h. The solvent was removed and the residue was purified on silica gel eluting with EA in petroleum (10% to 100%) to give methyl (S)-5-bromo-4-(((2,5-dioxopyrrolidin-3-yl)amino)methyl)thiophene-3-carboxylate (584 mg, 64.2%) as a yellow solid.

To a solution of methyl (S)-5-bromo-4-(((2,5-dioxopyrrolidin-3-yl)amino)methyl)thiophene-3-carboxylate (450 mg, 1.3 mmol) in THF (10 mL) was added NaOH (1M, 3.2 mL). The mixture was stirred at RT overnight. The mixture was adjusted to pH=5 with 2 N HCl then the solvent was removed and the residue was dried in vacuo to give the crude (S)-5-bromo-4-(((2,5-dioxopyrrolidin-3-yl)amino)methyl)thiophene-3-carboxylic acid (432 mg, 100%), which was used directly for the next step.

To a solution of (S)-5-bromo-4-(((2,5-dioxopyrrolidin-3-yl)amino)methyl)thiophene-3-carboxylic acid (431 mg, 1.3 mmol) in DMF (15 mL) at 0° C. was added 1-[bis(dimethylamino)methylene]-1H-1,2,3-triazolo[4,5-b]pyridinium 3-oxid hexafluorophosphate (HATU) (988 mg, 2.6 mmol) and N,N-diisopropylethylamine (419.3 mg, 3.25 mmol). The mixture was stirred at RT for 16 h. The reaction was diluted with water (10 mL) and extracted with EA (30 mL×3). The combined organic layers were washed with water (30 mL), dried over Na$_2$SO$_4$, filtered, and concentrated to give crude product, which was purified on silica gel eluting with EA in petroleum (30% to 50%) to give (S)-3-(1-bromo-4-oxo-4H-thieno[3,4-c]pyrrol-5(6H)-yl)pyrrolidine-2,5-dione (238 mg, 58.3%) as a light-yellow solid.

To a solution of (S)-3-(1-bromo-4-oxo-4H-thieno[3,4-c]pyrrol-5(6H)-yl)pyrrolidine-2,5-dione (226 mg, 0.719 mmol) in DMF (10 mL) was added K$_2$CO$_3$ (166 mg, 0.144 mmol). It was degassed and purged with NITROGEN twice. Then tetrakis(triphenylphosphine)palladium (Pd(PPh$_3$)$_4$) (297.6 mg, 2.16 mmol) and 2,4,6-trimethyl-1,3,5,2,4,6-trioxatriborinane (906.3 mg, 3.59 mmol) were added. The suspension was heated to 130° C. and stirred for 16 h. The solvent was removed and the residue was purified by prep-TLC (petroleum ether: EA=1:2) to afford crude product (45 mg), which was further purified by prep-HPLC with 5% to 95% ACN in 0.02% NH$_4$Ac on a C18, 4.6×50 mm column to give (S)-3-(1-methyl-4-oxo-4H-thieno[3,4-c]pyrrol-5(6H)-yl) pyrrolidine-2,5-dione (5.1 mg, 2.8%) as a white solid. $^1$H NMR (DMSO-d$_6$, 400 MHz) δ: 11.23 (s, 1H), 7.78 (s, 1H), 5.12 (dd, J=6.4, 9.6 Hz, 1H), 4.27 (dd, J=15.2, 108.8 Hz, 2H), 2.98-2.82 (m, 2H), 2.39 (s, 3H). MS (ESI) m/z=250.9 [M+H]$^+$.

Compound 21: 3-(4-Oxo-4H-thieno[2,3-c]pyrrol-5(6H)-yl)piperidine-2,6-dione

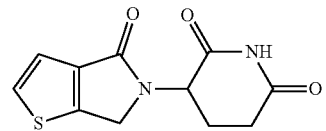 [SMILES: O=C1CCC(N2Cc3sccc3C2=O)C(=O)N1]

To a solution of methyl 2-methylthiophene-3-carboxylate (1.9 g, 12.16 mmol) in carbon tetrachloride (50 mL) at RT was added N-bromosuccinimide (NBS) (2.6 g, 14.6 mmol). The mixture was heated to 85° C. for 5 minutes and azodiisobutyronitrile (AIBN) (1.05 g, 6.08 mmol) was added in the mixture. The mixture was stirred at 85° C. overnight. It was filtered and the filtrate was concentrated. The residue was purified on silica gel eluting with EA in petroleum (0% to 10%) to give methyl 2-(bromomethyl)thiophene-3-carboxylate (660 mg, 23.5%) as a yellow oil.

To a solution of 3-aminopiperidine-2,6-dione hydrochloride acid salt (696.3 mg, 4.23 mmol) in DMF (15 mL) at 0° C. was added TEA (713.4 mg, 7.05 mmol) and methyl 2—(bromomethyl)thiophene-3-carboxylate (660 mg, 2.82 mmol). The mixture was stirred at RT overnight. The mixture was concentrated to remove the solvent and the residue was purified on silica gel eluting with MeOH in DCM (0% to 10%) to give methyl 2-(((2,6-dioxopiperidin-3-yl)amino)methyl)thiophene-3-carboxylate (195 mg, 24.5%) as a green solid. MS (ESI) m/z=283 [M+H]$^+$.

To a solution of methyl 2-(((2,6-dioxopiperidin-3-yl)amino)methyl)thiophene-3-carboxylate (195 mg, 0.6914 mmol) in THF (10 mL) at 0° C. was added NaOH (1 M, 1.7 mL). The mixture was stirred at RT for 2 h. The mixture was adjusted by HCl (2 N) to pH 3-4. It was then concentrated to afford crude 2-(((2,6-dioxopiperidin-3-yl)amino)methyl)thiophene-3-carboxylic acid (185.3 mg, 100%) as a yellow solid.

To a solution of 2-(((2,6-dioxopiperidin-3-yl)amino)methyl)thiophene-3-carboxylic acid (185.3 mg, 0.6914 mmol) in DMF (10 mL) at 0° C. was added 1-hydroxybenzotriazole (HOBt) (143.1 mg, 1.037 mmol), 3-(ethyliminomethylideneamino)—N,N-dimethylpropan-1-amine, hydrochloride (EDCI) (199.1 mg, 1.037 mmol) and TEA (175 mg, 1.729 mmol). The mixture was stirred at RT overnight. After removing the solvent under vacuum, the residue was diluted with water, and extracted with EA (×2), dried over Na$_2$SO$_4$, filtered, concentrated, and purified by prep-HPLC with 5% to 95% ACN in 0.02% NH$_4$Ac on a C18, 4.6×50 mm column to give 3-(4-oxo-4H-thieno[2,3-c]pyrrol-5(6H)-yl)piperidine-2,6-dione (7.5 mg, 4.3%) as a tan solid. $^1$H NMR (400 MHz, DMSO-d$_6$) δ 10.97 (s, 1H), 7.69 (d, J=4.4, 1H), 7.24 (d, J=4.8, 1H), 5.04-4.99 (m, 1H), 4.56-4.43 (m, 2H), 2.90-2.86 (m, 1H), 2.62 (s, 1H), 2.38-2.34 (m, 1H), 2.03-1.99 (m, 1H). MS (ESI) m/z=251 [M+H]$^+$.

Compound 22: 3-Cyclopentyl-5-(2,6-dioxopiperidin-3-yl)-4H-thieno[2,3-c]pyrrole-4,6(5H)-dione

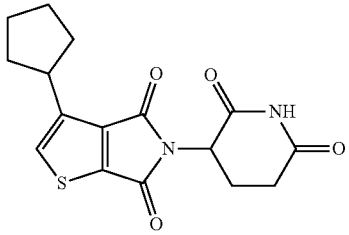 [SMILES: O=C1CCC(N2C(=O)c3scc(C4CCCC4)c3C2=O)C(=O)N1]

A solution of 4-bromo-3-methylthiophene-2-carboxylic acid (5.0 g, 18.25 mmol) and aq. NaOH (3.75 N, 77.4 mL, 0.29 mol) was heated to 80° C. Then potassium permanganate (10.6 g, 66.5 mmol) was added in 4.21 g portions to the warm solution over 2 h. The resultant suspension was heated to reflux temperature for 3 h then cooled to RT. The solid was filtered and washed twice with 1 N NaOH and twice with water. The solution was acidified to pH<3 with concentrated HCl, washed twice with DCM, and concentrated to a solid residue. The crude product was recrystallized from water to afford 4-bromothiophene-2,3-dicarboxylic acid (1.7 g, 30%) as a s white solid.

To a solution of 4-bromothiophene-2,3-dicarboxylic acid (1.7 g, 6.77 mmol) in dry MeOH (10 mL) at 0° C. was added thionyl chloride (681 mg, 5.72 mmol). Then the reaction was heated to 80° C. for 16 h. The reaction was cooled to RT and the solvent was removed. The residue was diluted with water (20 mL) and extracted with EA (40 mL) twice. The combined organic layers were washed with sat. aq. NaHCO$_3$ (30 mL), brine, dried over Na$_2$SO$_4$, filtered, and concentrated and the residue purified on silica gel eluting with petroleum ether:EA (from 0% to 8%) to give dimethyl 4-bromothiophene-2,3-dicarboxylate (1.15 g, 61%) as a colorless oil.

To a solution of dimethyl 4-bromothiophene-2,3-dicarboxylate (1.15 g, 4.12 mmol) in toluene/water (40 mL/4 mL) was added 2-(cyclopent-1-en-1-yl)-4,4,5,5-tetramethyl-1,3,2-dioxaborolane (1.65 g, 9.81 mmol), followed by K$_2$CO$_3$ (2.26 g, 16.35 mmol). The suspension was purged with nitrogen twice. Then tetrakis(triphenylphosphine)palladium [Pd(PPh$_3$)$_4$] (957 mg, 1.31 mmol) was added and the mixture was heated at 90° C. for 16 h. The reaction was cooled to RT and filtered. The filtrate was concentrated to give the crude product, which was purified on silica gel eluting with EA/petroleum ether (from 0% to 3%) to give dimethyl 4-(cyclopent-1-en-1-yl)thiophene-2,3-dicarboxylate (619 mg, 56.6%) as a white solid.

To a solution of dimethyl 4-(cyclopent-1-en-1-yl)thiophene-2,3-dicarboxylate (619 mg, 2.33 mmol) in THF (15 mL) at RT was added Pd/C (619 mg), the suspension was stirred at RT for 16 h under hydrogen (1 atm). The suspension was filtered and the filtrate was concentrated to give dimethyl 4-cyclopentylthiophene-2,3-dicarboxylate (573 mg, 92%) as a white solid.

To a solution of dimethyl 4-cyclopentylthiophene-2,3-dicarboxylate (573 mg, 2.14 mmol) in MeOH (10 mL) at RT was added lithium hydroxide (154.1 mg, 4.28 mmol), and the suspension was stirred at RT for 2 h. The reaction was adjusted to pH=3 with 1 M HCl. The suspension was concentrated to give 4-cyclopentylthiophene-2,3-dicarboxylic acid (480 mg, 94%) as a white solid.

The solution of 4-cyclopentylthiophene-2,3-dicarboxylic acid (100 mg, 0.42 mmol) in acetic anhydride (5 mL) was heated to 140° C. for 2 h. The solvent was removed and the residue was dried in vacuo to give 3-cyclopentylthieno[2,3-c]furan-4,6-dione (90 mg, crude) as an oil, which was used for the next step without purification.

The suspension of 3-cyclopentylthieno[2,3-c]furan-4,6-dione (90 mg, 0.41 mmol) and 3-aminopiperidine-2,6-dione hydrochloride acid salt (333 mg, 2.03 mmol) in THF (10 mL) was stirred at RT for 4 h. Then N,N'-carbonyldiimidazole (CDI) (66 mg, 0.41 mmol) and 4-dimethylaminopyridine (10 mg, 0.08 mmol) was added to the mixture, then the mixture was heated to 85° C. for 18 h. The mixture was purified on silica gel eluting with EA/petroleum ether from 20% to 60% to give 3-cyclopentyl-5-(2,6-dioxopiperidin-3-yl)-4H-thieno[2,3-c]pyrrole-4,6(5H)-dione (17.0 mg, 12%) as a white solid. $^1$H NMR (400 MHz, DMSO-d$_6$) δ 11.08 (s, 1H), 7.36 (s, 1H), 5.05-5.00 (m, 1H), 3.44-3.40 (m, 1H), 2.88-2.82 (m, 1H), 2.60-2.55 (m, 1H), 2.47-2.42 (m, 1H), 2.20-2.12 (m, 2H), 2.07-2.01 (m, 1H), 1.77-1.60 (m, 6H). MS (ESI) m/z 332.8 [M+H]$^+$.

Compound 23: 3-(1-(Difluoromethyl)-4-oxo-4H-thieno[3,4-c]pyrrol-5(6H)-yl)piperidine-2,6-dione

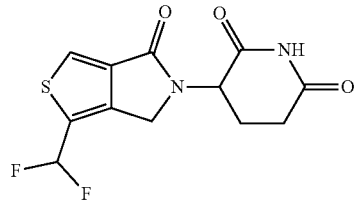 [SMILES: O=C1CCC(N2Cc3c(csc3C(F)F)C2=O)C(=O)N1]

To a solution of methyl 4-(bromomethyl)-5-(difluoromethyl)thiophene-3-carboxylate (420 mg, 1.47 mmol) in DMF (10 mL) were added 3-aminopiperidine-2,6-dione hydrochloride acid salt (242 mg, 1.47 mmol) and TEA (447 mg, 4.42 mmol). The mixture was stirred at RT for 2 h. After the reaction was complete, the mixture was diluted with water and extracted with EA (30 mL×3). The combined organic layers were washed with brine, filtered, and concentrated to afford residue, which was purified on silica gel eluting with 10% MeOH in DCM to afford methyl 5-(difluoromethyl)-4-(((2,6-dioxopiperidin-3-yl)amino)methyl)thiophene-3-carboxylate (300 mg, 61%) as a brown solid. $^1$H NMR (400 MHz, DMSO-d$_6$) δ 10.73 (s, 1H), 8.52 (s, 1H), 7.5 (t, J=54.4 Hz, 1H), 4.07-4.06 (m, 2H), 3.29-3.24 (m, 1H), 2.95-2.82 (m, 1H), 2.53-2.52 (m, 1H), 2.14-2.07 (m, 1H), 1.74-1.64 (m, 1H). MS (ESI) m/z 333.0 [M+H]$^+$.

To a solution of 5-(difluoromethyl)-4-(((2,6-dioxopiperidin-3-yl)amino)methyl)thiophene-3-carboxylate (200 mg, 0.6024 mmol) in ACN (10 mL) at 0° C. was added trimethylaluminium (4.8 mL, 1 M in toluene). The mixture was warmed to RT and continued stirring for 6 h. The reaction was quenched with ammonium hydrochloride (aq.) and extracted with DCM (×2). The organic layer was purified by prep-TLC to give 3-(1-(difluoromethyl)-4-oxo-4H-thieno[3,4-c]pyrrol-5(6H)-yl)piperidine-2,6-dione (5.6 mg, 3.1%) as a white solid. $^1$H NMR (400 MHz, DMSO-d$_6$) δ 10.99 (s, 1H), 8.28 (s, 1H), 7.37 (t, J=55.6, 1H), 5.05-5.00 (m, 1H), 4.48-4.33 (m, 2H), 2.92-2.83 (m, 1H), 2.64 (d, J=25.2, 1H), 2.37-2.33 (m, 1H), 2.02-1.97 (m, 1H). MS (ESI) m/z=301 [M+H]$^+$.

Compound 24: (S)-3-(3-Cyclopentyl-6-oxo-4H-thieno[2,3-c]pyrrol-5(6H)-yl)azepane-2,7-dione

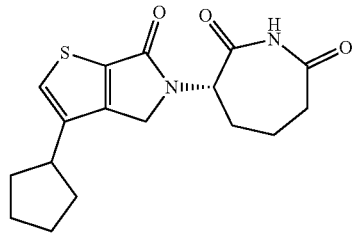 [SMILES: O=C1CCC[C@H](N2Cc3c(C4CCCC4)csc3C2=O)C(=O)N1]

To a stirred solution of methyl 3-methylthiophene-2-carboxylate (10 g, 0.064 mol) and NaOH (6.15 g, 0.15 mol) in AcOH glacial (38 mL) was heated to 60° C. Bromine (7.5 mL, 0.15 mol) was added dropwise and stirred at 85° C. for 12 h. The solution was allowed to cool to 50° C. and zinc (7.7 g, 0.12 mol) was added in portions, then the mixture was stirred at 85° C. for 1 h. After 1 h, the reaction was cooled to RT and filtered, then water and EA were added. The organic layer was washed with water and concentrated to dryness to give methyl 4-bromo-3-methylthiophene-2-carboxylate (12 g, 80%) as a white solid. $^1$H NMR (400 MHz, CDCl$_3$) δ 7.42 (s, 1H), 3.85 (s, 3H), 2.54 (s, 3H).

To a stirred solution of methyl 4-bromo-3-methylthiophene-2-carboxylate (0.5 g, 2.14 mmol) in carbon tetrachloride (8 mL) was added N-bromosuccinimide (0.392 g, 2.2 mmol) and benzoyl peroxide (0.254 g, 1.05 mmol). The mixture was stirred at 90° C. for 10 h. The mixture was then filtered, evaporated and purified on silica gel (petroleum) to give methyl 4-bromo-3-(bromomethyl)thiophene-2-carboxylate (0.25 g, 37%) as a white solid. $^1$H NMR (300 MHz, CDCl$_3$) δ 7.47 (s, 1H), 4.89 (s, 2H), 3.92 (s, 3H).

To a stirred solution of methyl 4-bromo-3-(bromomethyl)thiophene-2-carboxylate (200 mg, 0.64 mmol) and (S)-3-aminoazepan-2-one (100 mg, 0.78 mmol) in DMF (4 mL) was added TEA (130 mg, 1.28 mmol). The mixture was stirred at RT for 2 h. After 2 h, water was added, and the crude mixture was extracted with EA. The organic layers were washed with brine, dried over Na$_2$SO$_4$, evaporated, and purified on silica gel (EA) to give (S)-methyl 4-bromo-3-(((2-oxoazepan-3-yl)amino)methyl)thiophene-2-carboxylate (160 mg, 69%) as a colorless oil. $^1$H NMR (300 MHz, CDCl$_3$) δ 7.42 (s, 1H), 5.88 (s, 1H), 4.15 (q, J=7.5 Hz, 2H), 3.89 (s, 3H), 3.32 (d, J=7.5 Hz, 1H), 3.18-3.14 (m, 2H), 1.87-1.38 (m, 6H).

To a stirred solution of (S)-methyl 4-bromo-3-(((2-oxoazepan-3-yl)amino)methyl)thiophene-2-carboxylate (160 mg, 0.44 mmol) in ACN (3 mL) was added trimethylaluminium (1 M solution in hexane) (3 mL) slowly at 0° C. under nitrogen. The mixture was stirred at RT overnight then quenched with saturated ammonium chloride and extracted with EA. The organic layer was washed with water, brine, dried over Na$_2$SO$_4$, and evaporated to give (S)-3-bromo-5-(2-oxoazepan-3-yl)-4H-thieno[2,3-c]pyrrol-6(5H)-one (150 mg, 100%) as a yellow solid. MS (ESI) m/z=330.9 [M+H]$^+$.

To a suspension of (S)-3-bromo-5-(2-oxoazepan-3-yl)-4H-thieno[2,3-c]pyrrol-6(5H)-one (150 mg, 0.46 mmol), 2-(cyclopent-1-en-1-yl)-4,4,5,5-tetramethyl-1,3,2-dioxaborolane (106 mg, 0.55 mmol) and K$_2$CO$_3$ (190 mg, 1.38 mmol) in toluene (5 mL) and water (0.5 mL) was added [1,1'-bis(diphenylphosphino)ferrocene]dichloropalladium (II) (30 mg, 0.04 mmol). The mixture was stirred at 100° C. overnight under nitrogen. After cooling to RT, water was added and the mixture was extracted with EA. The organic layers were washed with brine, dried over Na$_2$SO$_4$, evaporated, and purified by prep-TLC (EA) to give (S)-3-(cyclopent-1-en-1-yl)-5-(2-oxoazepan-3-yl)-4H-thieno[2,3-c]pyrrol-6(5H)-one (70 mg, 48%) as white solid. MS (ESI) m/z=317.0 [M+H]$^+$.

To a stirred solution of (S)-3-(cyclopent-1-en-1-yl)-5-(2-oxoazepan-3-yl)-4H-thieno[2,3-c]pyrrol-6(5H)-one (70 mg, 0.22 mmol) in THF (2 mL) was added 10% Pd/C (70 mg). The mixture was stirred at RT overnight under hydrogen then filtered and evaporated to give (S)-3-cyclopentyl-5-(2-oxoazepan-3-yl)-4H-thieno[2,3-c]pyrrol-6(5H)-one (60 mg, 85%) as a white solid. MS (ESI) m/z=319.0 [M+H]$^+$.

To a stirred solution (S)-3-cyclopentyl-5-(2-oxoazepan-3-yl)-4H-thieno[2,3-c]pyrrol-6(5H)-one (60 mg, 0.19 mmol) in fluorobenzene (5 mL) and dimethyl sulfoxide (0.5 mL) was added Dess-Martin reagent (200 mg, 0.47 mmol) at 0° C. The mixture was stirred at 80° C. overnight. After cooling to RT, the reaction was filtered. The filtrate was washed with aq. sodium thiosulfate, aq. NaHCO$_3$, and brine, then dried over Na$_2$SO$_4$, evaporated, and purified by prep-TLC (petroleum/EA=1/1) to give (S)-3-(3-cyclopentyl-6-oxo-4H-thieno[2,3-c]pyrrol-5(6H)-yl)azepane-2,7-dione (12 mg, 19%) as a white solid. $^1$H NMR (400 MHz, DMSO-d$_6$) δ 10.68 (s, 1H), 7.64 (s, 1H), 5.13 (dd, J=5.6, 8.4 Hz, 1H), 4.46 (s, 2H), 3.10-3.02 (m, 2H), 2.58-2.54 (m, 1H), 2.28-2.23 (m, 1H), 2.10-1.99 (m, 4H), 1.80-1.72 (m, 3H), 1.65-1.53 (m, 4H). MS (ESI) m/z=333.1 [M+H]$^+$.

Compound 25: (S)-3-(3-Chloro-1-methyl-4-oxo-4H-thieno[3,4-c]pyrrol-5(6H)-yl)azepane-2,7-dione

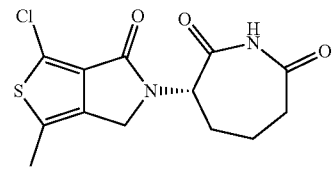 [SMILES: Cc1sc(Cl)c2c1CN([C@H]1CCCC(=O)NC1=O)C2=O]

To a solution of (S)-3-(1-methyl-4-oxo-4H-thieno[3,4-c]pyrrol-5(6H)-yl)azepane-2,7-dione (50 mg, 0.179 mmol) in DMF (0.5 mL) at RT was added N-chlorosuccinimide (23 mg, 0.173 mmol). The mixture was stirred for 2 h followed by work up with EA and sa.t aq. NaHCO$_3$ to give a solid after filtration and concentration of the organic phase. Trituration with EA and hexanes gave (S)-3-(3-chloro-1-methyl-4-oxo-4H-thieno[3,4-c]pyrrol-5(6H)-yl)azepane-2,7-dione (35 mg, 63%) as a white solid. MS (ESI) m/z 313.8 [M+H]$^+$. $^1$H NMR (DMSO-d$_6$, 400 MHz) δ: 10.7 (s, 1H), 5.11 (d, 1H), 4.26 (d, 2H), 3.04 (m, 1H), 2.56 (m, 1H), 2.17 (m, 1H), 2.02 (m, 2H), 1.81 (m, 1H).

Compound 26: 2-Cyclopentyl-5-(2,6-dioxopiperidin-3-yl)-4H-thieno[2,3-c]pyrrole-4,6(5H)-dione

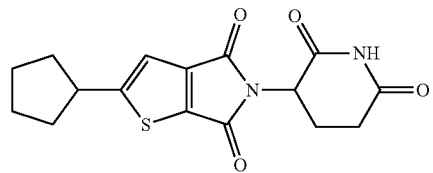 [SMILES: O=C1CCC(N2C(=O)c3cc(C4CCCC4)sc3C2=O)C(=O)N1]

A solution of 5-bromo-3-methylthiophene-2-carboxylic acid (5.0 g, 22.62 mmol) and aq. NaOH (5.1 N, 100 mL, 0.51 mol) was heated to 80° C. then potassium permanganate (18.0 g, 113.9 mmol) was added in 3.0 g portions to the warm solution over 1 h. The resultant suspension was heated to reflux temperature for 3 h then cooled to RT. The solid was filtered and washed twice with 1 N NaOH and twice with water. The solution was acidified to pH<3 with concentrated HCl, washed twice with water, and concentrated to a solid residue. The crude product was recrystallized from water to afford 5-bromothiophene-2,3-dicarboxylic acid (2.7 g, 47%) as a white solid.

To a solution of 5-bromothiophene-2,3-dicarboxylic acid (2.9 g, 11.55 mmol) in dry MeOH (50 mL) at 0° C. was added thionyl chloride (2.74 g, 23.10 mmol). Then the reaction was heated to 70° C. for 16 h. The reaction was cooled to RT and the solvent was removed under vacuum. The residue was diluted with water (20 mL) and extracted with EA (40 mL) twice. The combined organic layers were washed with sat. aq. NaHCO$_3$ (30 mL) and brine, then dried over Na$_2$SO$_4$, filtered, and concentrated to give crude product, which was purified on silica gel eluting with petroleum ether: EA (from 0% to 8%) to give dimethyl 5-bromothiophene-2,3-dicarboxylate (2.0 g, 62%) as a colorless oil.

To a solution of dimethyl 5-bromothiophene-2,3-dicarboxylate (500 mg, 1.79 mmol) in dioxane/water (10 mL/1 mL) was added 2-(cyclopent-1-en-1-yl)-4,4,5,5-tetramethyl-1,3,2-dioxaborolane (695 mg, 3.58 mmol), followed by cesium carbonate (1.46 g, 4.48 mmol) was added. The suspension was purged with nitrogen for twice. Then tetrakis (triphenylphosphine)palladium [Pd(PPh$_3$)$_4$] (414 mg, 0.36 mmol) was added and the mixture was heated at 90° C. for 16 h. The reaction was cooled to RT and filtered. The filtrate was concentrated to give the crude product, which was purified on silica gel eluting with EA/petroleum ether (from 0% to 5%) to give dimethyl 5-(cyclopent-1-en-1-yl)thiophene-2,3-dicarboxylate (410 mg, 86%) as a white solid.

To a solution of dimethyl 5-(cyclopent-1-en-1-yl)thiophene-2,3-dicarboxylate (410 mg, 1.54 mmol) in THF (10 mL) at RT was added Pd/C (200 mg), the suspension was stirred at RT for 6 h under hydrogen (1 atm). The suspension was filtered, the filtrate was concatenated to give dimethyl 5-cyclopentylthiophene-2,3-dicarboxylate (390 mg, 94%) as a white solid.

To a solution of dimethyl 5-cyclopentylthiophene-2,3-dicarboxylate (390 mg, 1.45 mmol) in MeOH (10 mL) at RT was added lithium hydroxide (305 mg, 7.27 mmol), the suspension was stirred at RT for 2 h. The reaction was adjusted to pH=3 with 1 M HCl. The suspension was concentrated to give 5-cyclopentylthiophene-2,3-dicarboxylic acid (330 mg, 94%) as a white solid.

To a solution of 5-cyclopentylthiophene-2,3-dicarboxylic acid (280 mg, 1.17 mmol) in acetic anhydride (7 mL). The reaction was heated to 140° C. for 2 h. The solvent was removed and the residue was dried in vacuo to give 2-cyclopentylthieno[2,3-c]furan-4,6-dione (300 mg, crude) as a white oil, which was used for the next step without purification.

The suspension of 2-cyclopentylthieno[2,3-c]furan-4,6-dione (300 mg, 1.35 mmol) and 3-aminopiperidine-2,6-dione hydrochloride acid salt (1.02 g, 6.75 mmol) in THF (8 mL) was stirred at RT for 4 h. Then N,N'-carbonyldiimidazole (CDI) (215 mg, 1.35 mmol) and 4-dimethylaminopyridine (32 mg, 0.27 mmol) was added to the mixture, then heated to 85° C. for 18 h. The mixture was purified on silica gel eluting with EA/petroleum ether from 20% to 60% to give 2-cyclopentyl-5-(2,6-dioxopiperidin-3-yl)-4H-thieno[2,3-c]pyrrole-4,6(5H)-dione (180 mg, 46%) as a yellow solid. $^1$H NMR (400 MHz, DMSO-d$_6$) δ 11.08 (s, 1H), 7.36 (s, 1H), 5.05-5.00 (m, 1H), 3.44-3.40 (m, 1H), 2.91-2.82 (m, 1H), 2.60-2.55 (m, 1H), 2.50-2.42 (m, 1H), 2.18-2.12 (m, 2H), 2.07-2.02 (m, 1H), 1.80-1.61 (m, 6H). MS (ESI) m/z 331.1 [M−H]$^+$.

Compound 27: 1-Cyclopentyl-5-(2,6-dioxopiperidin-3-yl)-4H-thieno[3,4-c]pyrrole-4,6(5H)-dione

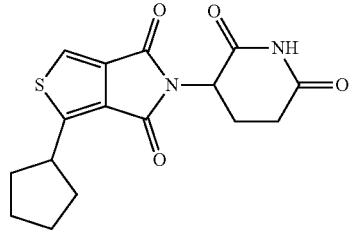 [SMILES: O=C1CCC(N2C(=O)c3csc(C4CCCC4)c3C2=O)C(=O)N1]

To a solution of methyl 2-oxopropanoate (20 g, 176.3 mmol) in DMF (200 mL) was added ethyl 2-cyanoacetate (20 g, 195.9 mmol) and sulfur (7.54 g, 235.1 mmol). The mixture was stirred at RT, then TEA (46 mL, 331.8 mmol) was added slowly over 10 min. The reaction was heated to 50° C. and stirred overnight. The reaction was cooled to RT and poured into water (300 mL) and brine (30 mL) mixture, extracted with EA (3×200 mL). The organic phase was washed with water (2×200 mL), followed by brine (200 mL), then dried over Na$_2$SO$_4$, filtered and concentrated to afford crude product, which was purified on silica gel to afford 3-ethyl 4-methyl 2-aminothiophene-3,4-dicarboxylate (24.79 g, 61.34%) as a yellow solid. $^1$H NMR (300 MHz, DMSO-d$_6$) δ 7.26 (s, 2H), 6.70 (s, 1H), 4.10 (m, 2H), 3.68 (s, 3H), 1.17 (m, 3H). MS (ESI) m/z 230.1 [M+H]$^+$.

3-Ethyl 4-methyl 2-aminothiophene-3,4-dicarboxylate (24.79 g, 108.1 mmol) in HCl (500 mL, 2N) was cooled to 0° C. and sodium nitrite (11.2 g, 162.2 mmol) was added. The mixture was stirred at 0° C. for 30 min. Then potassium iodide (44.83 g, 270.4 mmol) was added in small portions. The mixture was warmed up to RT and stirred for 45 min. The mixture was poured into water (250 mL) and extracted with EA (3×200 mL). The combined organic phase was dried over Na$_2$SO$_4$, filtered and concentrated to afford crude product, which was purified on silica gel to afford 3-ethyl 4-methyl 2-iodothiophene-3,4-dicarboxylate (18.19 g, 49.46%) as a yellow oil. $^1$H NMR (400 MHz, DMSO-d$_6$) δ 8.45 (s, 1H), 4.30-4.32 (m, 2H), 4.10-4.15 (m, 2H), 3.77 (s, 3H), 1.26-12.9 (m, 3H). MS (ESI) m/z 341.0 [M+H]$^+$.

To a solution of 3-ethyl 4-methyl 2-iodothiophene-3,4-dicarboxylate (3.0 g, 8.82 mmol), 2-(cyclopent-1-en-1-yl)-4,4,5,5-tetramethyl-1,3,2-dioxaborolane (1.48 g, 8.82 mmol) and K$_2$CO$_3$ (3.04 g, 22.05 mmol) in toluene/water (50 mL/5 mL) was added [1,1'-Bis(diphenylphosphino)ferrocene]dichloropalladium(II) [Pd(dppf)$_2$Cl$_2$] (1.29 g, 1.76 mmol) under nitrogen. The suspension was heated to reflux and stirred for 16 h. Then the mixture was poured into water (100 mL) and extracted with EA (3×50 mL). The combined organic phase was dried over Na$_2$SO$_4$, filtered and concentrated to afford crude product, which was purified on silica gel to afford 3-ethyl 4-methyl 2-(cyclopent-1-en-1-yl)thiophene-3,4-dicarboxylate (1.395 g, 56.43%). as white solid. $^1$H NMR (300 MHz, DMSO-d$_6$) δ 8.21 (s, 1H), 6.10 (s, 1H), 4.24-4.27 (m, 2H), 3.75 (s, 3H), 2.57-2.62 (m, 2H), 2.42-2.46 (m, 2H), 1.91-1.95 (m, 2H), 1.21-1.25 (m, 3H). MS (ESI) m/z 281.0 [M+H]$^+$.

To a solution of 3-ethyl 4-methyl 2-(cyclopent-1-en-1-yl) thiophene-3,4-dicarboxylate (1.342 g, 4.79 mmol) in MeOH (25 mL) was added Pt—C(10% of content, 0.3 g). The suspension was degassed under vacuum and purged with hydrogen twice. The mixture was stirred under hydrogen atmosphere for 2 h. The suspension was filtered and the filtrate was concentrated to give 3-ethyl 4-methyl 2-cyclopentylthiophene-3,4-dicarboxylate (1.304 g, 96.48%) as a colorless oil. $^1$H NMR (300 MHz, DMSO-d$_6$) δ 8.04 (s, 1H), 4.23-4.25 (m, 2H), 3.75 (s, 3H), 2.40 (s, 1H), 2.06-2.12 (m, 2H), 1.65-1.70 (m, 6H), 1.25-1.28 (m, 3H). MS (ESI) m/z 283.1 [M+H]$^+$.

A solution of 3-ethyl 4-methyl 2-cyclopentylthiophene-3,4-dicarboxylate (1.303 g, 4.615 mmol) in HCl (25 mL, 2N) was refluxed and stirred for 16 h. Then the mixture was cooled to RT and the solvent was removed under vacuum. The crude product was purified on silica gel to afford 2-cyclopentylthiophene-3,4-dicarboxylic acid (0.962 g, 86.7%) as yellow solid. $^1$H NMR (300 MHz, DMSO-d$_6$) δ 13.05 (br, 2H), 7.92 (s, 1H), 3.15 (s, 1H), 1.98-2.01 (m, 2H), 1.73-1.75 (m, 6H). MS (ESI) m/z 240.1 [M+H]$^+$.

To a solution of 2-cyclopentylthiophene-3,4-dicarboxylic acid (120 mg, 0.5 mmol) in acetic anhydride (10 mL) at RT. The mixture was refluxed at 135° C. overnight. The solvent was removed to give the crude 4-cyclopentylthieno[3,4-c]furan-1,3-dione (100 mg, crude) as a yellow oil, which was used directly for next step.

To a solution of 4-cyclopentylthieno[3,4-c]furan-1,3-dione (50 mg, 0.22 mmol) in THF (4 mL) was added 3-aminopiperidine-2,6-dione hydrochloride acid salt (181.5 mg, 1.1 mmol), N,N'-carbonyldiimidazole (35.6 mg, 0.22 mmol) and 4-dimethylaminopyridine (5.4 mg, 0.44 mmol). The suspension was heated at 70° C. overnight. After the reaction was completed, the solvent was removed to give the crude product, which was purified by prep-TLC with petroleum ether in EA from 10% to 20% to give 1-cyclopentyl-5-(2,6-dioxopiperidin-3-yl)-4H-thieno[3,4-c]pyrrole-4,6(5H)-dione (20 mg, 27.0%) as a white solid. $^1$H NMR (400 MHz, DMSO-d$_6$) δ 11.07 (d, J=6.4 Hz, 1H), 8.19 (s, 1H), 5.05-5.00 (m, 1H), 3.62-3.35 (m, 1H), 2.91-2.82 (m, 1H), 2.59-2.50 (m, 1H), 2.46-2.42 (m, 1H), 2.19-2.18 (m, 2H), 2.05-1.97 (m, 1H), 1.81 (s, 2H), 1.67 (s, 4H). MS (ESI) m/z 333.1 [M+H]$^+$.

Compound 28: (S)-1-Methyl-5-(2-oxoazepan-3-yl)-5,6-dihydro-4H-thieno[3,4-c]pyrrol-4-one

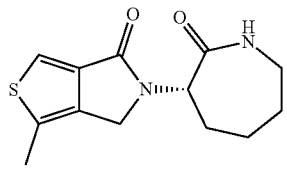 [SMILES: Cc1scc2c1CN([C@H]1CCCCNC1=O)C2=O]

To a solution of (S)-1-bromo-5-(2-oxoazepan-3-yl)-5,6-dihydro-4H-thieno[3,4-c]pyrrol-4-one (300 mg, 0.9146 mmol) in dioxane/water (12 mL/4 mL) at RT was added cesium carbonate (891.8 mg, 2.744 mmol). The atmosphere was exchanged with nitrogen twice. Then 2,4,6-trimethyl-1,3,5,2,4,6-trioxatriborinane (1.2 mL) and tetrakis(triphenylphosphine)palladium [Pd(PPh$_3$)$_4$] (105.7 mg, 0.09146 mmol) were added. The resulting suspension was stirred at 90° C. overnight. The mixture was cooled to RT and concentrated under vacuum. The resulting residue was diluted with water and extracted with DCM (×2). The combined organic layer was dried over Na$_2$SO$_4$, filtered, and concentrated to give the crude product, which was purified on silica gel eluting with petroleum ether/EA from 0% to 6% to give (S)-1-methyl-5-(2-oxoazepan-3-yl)-5,6-dihydro-4H-thieno[3,4-c]pyrrol-4-one (59.4 mg, 24.6%) as a yellow solid. $^1$H NMR (DMSO-d$_6$, 400 MHz) δ: 7.81 (t, J=5.2 Hz, 1H), 7.71 (s, 1H), 4.81 (d, J=10.4 Hz, 1H), 4.36 (dd, J=14.8 Hz, 2H), 3.27-3.19 (m, 1H), 3.12-3.07 (m, 1H), 2.41 (s, 3H), 1.98 (t, J=10.0 Hz, 2H), 1.84-1.66 (m, 3H), 1.32-1.24 (m, 1H). MS (ESI) m/z 265 [M+H]$^+$.

Compound 29: 3-(4-Oxo-1-(trifluoromethyl)-4H-thieno[3,4-c]pyrrol-5(6H)-yl)piperidine-2,6-dione

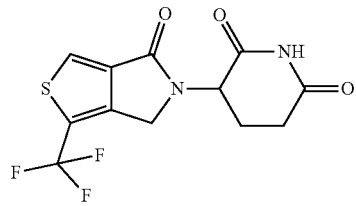 [SMILES: O=C1CCC(N2Cc3c(csc3C(F)(F)F)C2=O)C(=O)N1]

To a stirred solution of 3-(1-bromo-4-oxo-4H-thieno[3,4-c]pyrrol-5(6H)-yl)piperidine-2,6-dione (230 mg, 0.7 mmol) in DMF (5 mL) was added methyl 2,2-difluoro-2-(fluorosulfonyl)acetate (400 mg, 2.1 mmol), cuprous iodide (110 mg, 0.58 mmol) and 2 drops of hexamethylphosphoramide under nitrogen. The mixture was stirred at 80° C. for 2 days. Then the mixture was diluted with water and extracted with EA. The organic layer was washed with sat. aq. NaHCO$_3$ and brine, dried over Na$_2$SO$_4$, evaporated and purified by prep-HPLC with 5% to 95% ACN in 0.02% NH$_4$Ac on a C18, 4.6×50 mm column to give (20 mg, 9%) as a yellow solid. MS (ESI) m/z 318.8 [M+H]$^+$. $^1$H NMR (400 MHz, DMSO-d6) δ 11.00 (s, 1H), 8.47 (s, 1H), 5.04 (dd, J=5.2, 13.6 Hz, 1H), 4.45 (q, J=16.8 Hz, 2H), 2.89-2.85 (m, 1H), 2.60-2.56 (m, 1H), 2.41-2.36 (m, 1H), 2.00-1.97 (m, 1H).

Compound 30: (S)-1-(3-Chloro-4-methylphenyl)-3-((5-(2,7-dioxoazepan-3-yl)-4-oxo-5,6-dihydro-4H-thieno[3,4-c]pyrrol-1-yl)methyl)urea

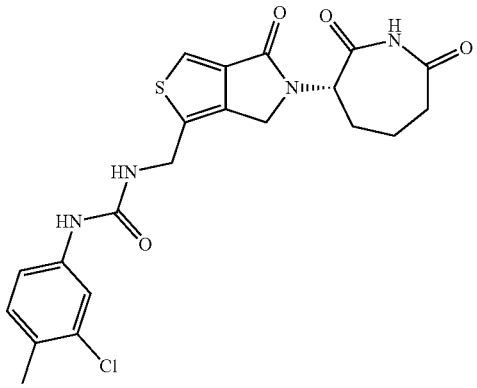 [SMILES: Cc1ccc(NC(=O)NCc2scc3c2CN([C@H]2CCCC(=O)NC2=O)C3=O)cc1Cl]

To a solution of (S)-tert-butyl ((5-(2,7-dioxoazepan-3-yl)-4-oxo-5,6-dihydro-4H-thieno[3,4-c]pyrrol-1-yl)methyl)carbamate (60 mg, 0.1526 mmol) in DCM (4 mL) at 0° C. was added 2,2,2-trifluoroacetic acid (1 mL). The mixture was warmed to RT and stirred for 1.5 h. It was concentrated to remove the solvent and the residue was diluted in water and washed with DCM. The aqueous layer was dried in vacuo to give (S)-3-(1-(aminomethyl)-4-oxo-4H-thieno[3,4-c]pyrrol-5(6H)-yl)azepane-2,7-dione 2,2,2-trifluoroacetic acid salt (44.7 mg, 100%) as a white solid. MS (ESI) m/z 294 [M+H]$^+$.

To a solution of (S)-3-(1-(aminomethyl)-4-oxo-4H-thieno[3,4-c]pyrrol-5(6H)-yl)azepane-2,7-dione 2,2,2-trifluoroacetic acid salt (44.7 mg, 0.1526 mmol) in THF (3 mL) at 0° C. was added 2-chloro-4-isocyanato-1-methylbenzene (30.7 mg, 0.1832 mmol) and TEA (38.6 mg, 0.3815 mmol). The mixture was warmed to RT and stirred for 2 h. It was concentrated and purified on silica gel eluting with DCM/MeOH from 0% to 10% to give (S)-1-(3-chloro-4-methylphenyl)-3-((5-(2,7-dioxoazepan-3-yl)-4-oxo-5,6-dihydro-4H-thieno[3,4-c]pyrrol-1-yl)methyl)urea (29.4 mg, 41.9%) as a white solid. $^1$H NMR (400 MHz, DMSO-d$_6$) δ 10.71 (s, 1H), 8.78 (s, 1H), 7.88 (s, 1H), 7.64 (s, 1H), 7.21-7.14 (m, 2H), 6.85 (t, J=6.0, 1H), 5.15 (dd, J=4.8, 12.0, 1H), 4.42 (dd, J=4.8, 17.6, 4H), 3.10-3.03 (m, 1H), 2.57 (d, J=17.2, 1H), 2.24 (s, 3H), 2.18-2.15 (m, 1H), 2.10-2.00 (m, 2H), 1.84-1.79 (m, 1H). MS (ESI) m/z 461 [M+H]$^+$.

Compound 31: (S)-2-(3-Chloro-4-methylphenyl)-N-((5-(2,7-dioxoazepan-3-yl)-4-oxo-5,6-dihydro-4H-thieno[3,4-c]pyrrol-1-yl)methyl)acetamide

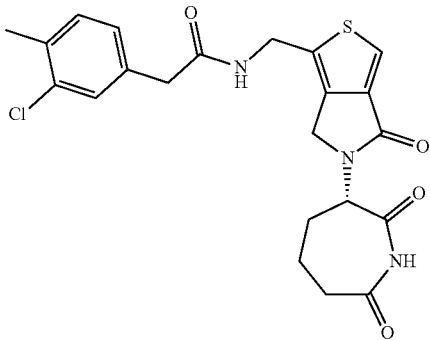 [SMILES: Cc1ccc(CC(=O)NCc2scc3c2CN([C@H]2CCCC(=O)NC2=O)C3=O)cc1Cl]

To a solution of 2-(3-chloro-4-methylphenyl)acetic acid (70 mg, 0.38 mmol) in DMF (5 mL) was added 1-hydroxybenzotriazole (HOBt) (78 mg, 0.57 mmol) and 3-(ethyliminomethylideneamino)—N,N-dimethylpropan-1-amine,hydrochloride (EDCI) (109 mg, 0.57 mmol), followed by diethylisopropylamine (98 mg, 0.76 mmol). Then to the reaction was added (S)-3-(1-(aminomethyl)-4-oxo-4H-thieno[3,4-c]pyrrol-5(6H)-yl)azepane-2,7-dione 2,2,2-trifluoroacetic acid salt. The resulting solution was stirred at RT for 16 h. The reaction was diluted with water (10 mL), extracted with EA (20 mL×2). The combined organic layers were concentrated to give the crude product, which was purified by prep-HPLC with 5% to 95% ACN in 0.02% NH$_4$Ac on a C18, 4.6×50 mm column to give (S)-2-(3-chloro-4-methylphenyl)-N-((5-(2,7-dioxoazepan-3-yl)-4-oxo-5,6-dihydro-4H-thieno[3,4-c]pyrrol-1-yl)methyl)acetamide (39 mg, 22.0%) as a white solid. $^1$H NMR (400 MHz, DMSO-d$_6$) δ 10.67 (s, 1H), 8.71 (t, J=6.0 Hz, 1H), 7.87 (s, 1H), 7.33 (s, 1H), 7.26 (d, J=7.6 Hz, 1H), 7.13 (d, J=6.4 Hz, 1H), 5.11 (dd, J=6.4, 12.0 Hz, 1H), 4.42 (d, J=5.6 Hz, 2H), 4.23 (q, J=13.6 Hz, 2H), 3.44 (s, 2H), 3.08-3.00 (m, 1H), 2.56 (d, J=15.6 Hz, 1H), 2.28 (s, 3H), 2.08-1.94 (m, 3H), 1.82-1.75 (m, 1H). MS (ESI) m/z=460.0, 462.0 [M+H]$^+$.

Compound 32: (S)-1-(3-Chloro-4-(trifluoromethyl)phenyl)-3-((5-(2,7-dioxoazepan-3-yl)-4-oxo-5,6-dihydro-4H-thieno[3,4-c]pyrrol-1-yl)methyl)urea

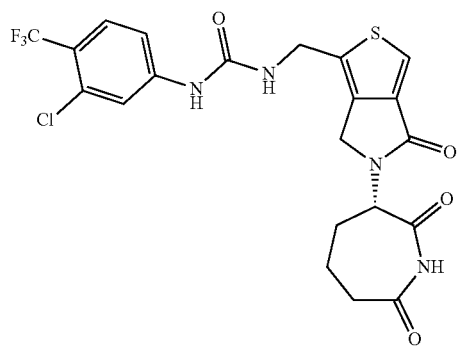 [SMILES: O=C1CCC[C@H](N2Cc3c(csc3CNC(=O)Nc3ccc(C(F)(F)F)c(Cl)c3)C2=O)C(=O)N1]

To a solution of triphosgene (609 mg, 2.14 mmol) in toluene (5 mL) was added dropwise a solution of 3-chloro-4-(trifluoromethyl)aniline (100 mg, 0.51 mmol) and refluxed at 80° C. for 0.5 h. Then the mixture was concentrated to give 2-chloro-4-isocyanato-1-(trifluoromethyl)benzene. To the solution of 2-chloro-4-isocyanato-1-(trifluoromethyl)benzene in THF was added (S)-3-(1-(aminomethyl)-4-oxo-4H-thieno[3,4-c]pyrrol-5(6H)-yl)azepane-2, 7-dione 2,2,2-trifluoroacetic acid salt (52.2 mg, 0.18 mmol), followed by TEA (34 mg, 0.34 mmol). The mixture was stirred at RT for 2 h. The mixture was concentrated to give crude product, which was purified by prep-HPLC with 5% to 95% ACN in 0.02% NH$_4$Ac on a C18, 4.6×50 mm column to give (S)-1-(3-chloro-4-(trifluoromethyl)phenyl)-3-((5-(2,7-dioxoazepan-3-yl)-4-oxo-5,6-dihydro-4H-thieno[3,4-c]pyrrol-1-yl)methyl)urea (6.5 mg, 7.1%) as a white solid. $^1$H NMR (400 MHz, DMSO-d$_6$) δ 10.70 (s, 1H), 9.34 (s, 1H), 7.88 (s, 2H), 7.69 (d, J=8.4 Hz, 1H), 7.43 (d, J=8.8 Hz, 1H), 7.11 (t, J=6.0 Hz, 1H), 5.14 (dd, J=7.6, 12.4 Hz, 1H), 4.46 (d, J=5.2 Hz, 2H), 4.40 (d, J=4.8 Hz, 2H), 3.07-3.01 (m, 1H), 2.57-2.49 (m, 1H), 2.19-1.96 (m, 3H), 1.88-1.76 (m, 1H). MS (ESI) m/z 515.0, 517.0 [M+H]$^+$ Compound 33: 1-(3-Chloro-4-methylbenzyl)-3-((5-(2,6-dioxopiperidin-3-yl)-4-oxo-5,6-dihydro-4H-thieno[3,4-c]pyrrol-1-yl)methyl)urea

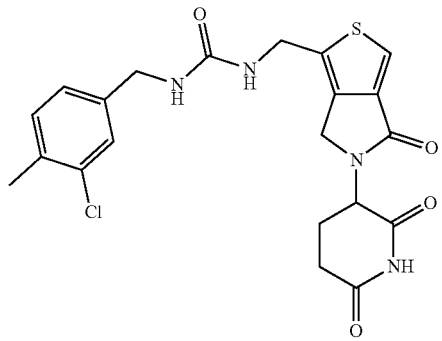 [SMILES: Cc1ccc(CNC(=O)NCc2scc3c2CN(C2CCC(=O)NC2=O)C3=O)cc1Cl]

To a solution of 3-(1-(aminomethyl)-4-oxo-4H-thieno[3,4-c]pyrrol-5(6H)-yl)piperidine-2,6-dione 2,2,2-trifluoroacetic acid salt (61.8 mg, 0.2216 mmol) in THF (3 mL) at 0° C. was added TEA (56.1 mg, 0.554 mmol) and 2-chloro-4-(isocyanatomethyl)-1-methylbenzene (80.5 mg, 0.4432 mmol). The mixture was warmed to RT for 4 h. The compound was consumed completely and a new spot was present. The mixture was concentrated to afford residue, which was purified on silica gel eluting with MeOH in DCM from 0% to 10% to give 1-(3-chloro-4-methylbenzyl)-3-((5-(2,6-dioxopiperidin-3-yl)-4-oxo-5,6-dihydro-4H-thieno[3,4-c]pyrrol-1-yl)methyl)urea (31.8 mg, 31.2%) as a white solid. $^1$H NMR (400 MHz, DMSO-d$_6$) δ 10.99 (s, 1H), 7.84 (s, 1H), 7.27-7.10 (m, 3H), 6.64 (d, J=17.6, 2H), 5.00 (d, J=13.2, 1H), 4.36-4.14 (m, 6H), 2.92-2.85 (m, 1H), 2.57 (d, J=18.4, 1H), 2.28 (s, 3H), 2.22-2.19 (m, 1H), 1.97-1.94 (m, 1H). MS (ESI) m/z=461 [M+H]$^+$.

Compound 34: (S)-1-(3-Chloro-4-methylbenzyl)-3-((5-(2,7-dioxoazepan-3-yl)-4-oxo-5,6-dihydro-4H-thieno[3,4-c]pyrrol-1-yl)methyl)urea

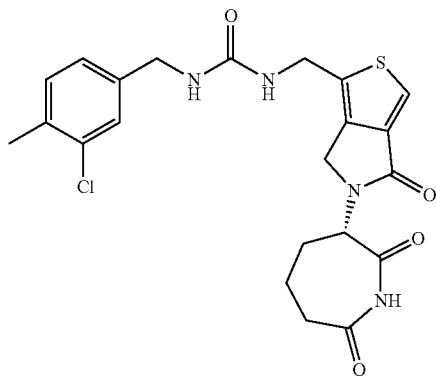 [SMILES: Cc1ccc(CNC(=O)NCc2scc3c2CN([C@H]2CCCC(=O)NC2=O)C3=O)cc1Cl]

To the solution of (S)-3-(1-(aminomethyl)-4-oxo-4H-thieno[3,4-c]pyrrol-5(6H)-yl)azepane-2,7-dione 2,2,2-trifluoroacetic acid salt (101.5 mg, 0.26 mmol) in THF (4 mL) was added 2-chloro-4-(isocyanatomethyl)-1-methylbenzene (56 mg, 0.31 mmol), followed by TEA (52 mg, 0.52 mmol). The mixture was stirred at RT for 2 h. The reaction was concentrated to give the crude product, which was purified by prep-HPLC with 5% to 95% ACN in 0.02% NH$_4$Ac on a C18, 4.6×50 mm column to give (S)-1-(3-chloro-4-methylbenzyl)-3-((5-(2,7-dioxoazepan-3-yl)-4-oxo-5,6-dihydro-4H-thieno[3,4-c]pyrrol-1-yl)methyl)urea (43.3 mg, 45.0%) as a white solid. $^1$H NMR (400 MHz, DMSO-d$_6$) δ 10.71 (s, 1H), 7.85 (s, 1H), 7.27-7.25 (m, 2H), 7.11 (dd, J=6.0, 7.6 Hz, 1H), 6.69-6.61 (m, 2H), 5.13 (dd, J=6.4, 12.0 Hz, 1H), 4.38-4.27 (m, 4H), 4.19 (d, J=6.0 Hz, 2H), 3.09-3.02 (m, 1H), 2.56 (d, J=18.0 Hz, 1H), 2.28 (s, 3H), 2.09-1.96 (m, 3H), 1.79-1.76 (m, 1H). MS (ESI) m/z=475.1, 477.1[M+H]$^+$.

Compound 35: (S)-1-(3-Chloro-4-methylphenyl)-3-((5-(2,7-dioxoazepan-3-yl)-6-oxo-5,6-dihydro-4H-thieno[2,3-c]pyrrol-2-yl)methyl)urea

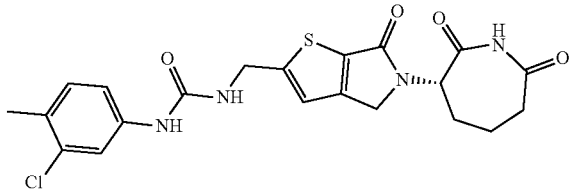 [SMILES: Cc1ccc(NC(=O)NCc2cc3c(s2)C(=O)N([C@H]2CCCC(=O)NC2=O)C3)cc1Cl]

To a solution of methyl 5-bromo-3-methylthiophene-2-carboxylate (2.3 g, 9.79 mmol) in carbon tetrachloride (50 mL) was added N-bromosuccinimide (NBS) (1.83 g, 10.3 mmol) and benzoyl peroxide (BPO) (240 mg, 0.98 mmol), the suspension was heated at 80° C. for 16 h. The reaction was cooled to RT and filtered the solid. The filtrate was concentrated to give the crude product, which was purified on silica gel eluting with petroleum ether/EA from 0% to 5% to give methyl 5-bromo-3-(bromomethyl)thiophene-2-carboxylate (2.7 g, crude) as a white solid.

To a solution of methyl 5-bromo-3-(bromomethyl)thiophene-2-carboxylate (2.7 g, 8.6 mmol) in DMF (25 mL) was added (S)-3-aminoazepan-2-one (1.1 g, 8.6 mmol), followed by TEA (1.74 g, 17.2 mmol). The suspension was stirred at RT for 1 h. The solvent was removed and purified on silica gel eluting with petroleum ether/EA from 50% to 100% to give (S)-methyl 5-bromo-3-(((2-oxoazepan-3-yl)amino)methyl)thiophene-2-carboxylate (1.42 g, 45%) as a white solid. MS (ESI) m/z 360.9 [M+H]$^+$.

To a solution of (S)-methyl 5-bromo-3-(((2-oxoazepan-3-yl)amino)methyl)thiophene-2-carboxylate (1.67 g, 4.63 mmol) in ACN (50 mL) at 0° C. was added Trimethylaluminium (37 mL, 37 mmol, 1M in toluene). The suspension was stirred at RT for 4 h. The mixture was quenched with NH$_4$Cl at 0° C., then the mixture was extracted with DCM (80 mL×2), washed with brine (70 mL), dried over Na$_2$SO$_4$, and concentrated in vacuo to get the crude product, which was purified on silica gel eluting with petroleum ether/EA from 50% to 100% to give (S)-2-bromo-5-(2-oxoazepan-3-yl)-4H-thieno[2,3-c]pyrrol-6(5H)-one (1.0 g, 65%) as a white solid. MS (ESI) m/z 328.9 [M+H]$^+$ To a solution of (S)-2-bromo-5-(2-oxoazepan-3-yl)-4H-thieno[2,3-c]pyrrol-6(5H)-one (1.2 g, 3.68 mmol) in DMF was added tris(dibenzylideneacetone)dipalladium(0) [Pd$_2$(dba)$_3$] (205 mg, 0.22 mmol), 1,1'-bisdiphenylphosphinoferrocene [dppf] (233 mg, 0.43 mmol) and zinc cyanide (278 mg, 2.38 mmol). The mixture was stirred at 150° C. for 1 h in a microwave under nitrogen atmosphere. The mixture was concentrated to give crude product, which was purified on silica gel eluting with petroleum ether/EA from 50% to 100% to give (S)-6-oxo-5-(2-oxoazepan-3-yl)-5,6-dihydro-4H-thieno[2,3-c]pyrrole-2-carbonitrile (460 mg, 46%) as a red solid. MS (ESI) m/z 276.0 [M+H]$^+$.

To a solution of (S)-6-oxo-5-(2-oxoazepan-3-yl)-5,6-dihydro-4H-thieno[2,3-c]pyrrole-2-carbonitrile (360 mg, 1.31 mmol) in ACN/DMSO (21 mL/3.5 mL, 1 drop water in DMSO) was added Dess-Martin periodinane (1.38 g, 3.27 mmol). The suspension was heated at 80° C. for 16 h. The mixture was cooled to RT and 20 mL of a saturated sodium thiosulfate solution was added followed by stirring for 5 min. The mixture was extracted with DCM (30 mL×2) and the combined solution was washed with 10% aq. sodium thiosulfate/aq. NaHCO$_3$ (1:1 mixture) (50 mL) and brine (50 mL). The organic layer was dried over Na$_2$SO$_4$, filtered, and concentrated to afford the crude product, which was purified on silica gel eluting with petroleum ether/EA from 50% to 100% to give (S)-5-(2,7-dioxoazepan-3-yl)-6-oxo-5,6-dihydro-4H-thieno[2,3-c]pyrrole-2-carbonitrile (300 mg, 62%) as a white solid. MS (ESI) m/z 289.9 [M+H]$^+$.

To a solution of (S)-5-(2,7-dioxoazepan-3-yl)-6-oxo-5,6-dihydro-4H-thieno[2,3-c]pyrrole-2-carbonitrile (250 mg, 0.86 mmol) in THF (15 mL) was added Raney Ni (200 mg), followed by Di-tert-butyl dicarbonate [(Boc)$_2$O] (377 g, 1.73 mmol). The suspension was stirred at RT under hydrogen for 16 h. The suspension was filtered and the filter cake was washed with DCM (10 mL). The combined filtrate was concentrated to give the crude product, which was purified on silica gel eluting with DCM/MeOH from 0% to 4% to give (S)-tert-butyl ((5-(2,7-dioxoazepan-3-yl)-6-oxo-5,6-dihydro-4H-thieno[2,3-c]pyrrol-2-yl)methyl) carbamate (180 mg, 44%) as a white solid. MS (ESI) m/z 392.0 [M−H]$^+$.

To a solution of (S)-tert-butyl ((5-(2,7-dioxoazepan-3-yl)-6-oxo-5,6-dihydro-4H-thieno[2,3-c]pyrrol-2-yl)methyl) carbamate (80.0 mg, 0.20 mmol) in DCM (4 mL) was added 2,2,2-trifluoactic acid (1.5 mL) at 0° C., and the solution was stirred at RT for 2 h. The suspension was concentrated to give crude product (60.0 mg), which was used directly for next step without further purification.

To a solution of (S)-3-(2-(aminomethyl)-6-oxo-4H-thieno[2,3-c]pyrrol-5(6H)-yl)azepane-2,7-dione (60.0 mg, 0.20 mmol) dissolved in DMF (4 mL) was added TEA (42 mg, 0.41 mmol) and the suspension was stirred at RT, then 2-chloro-4-isocyanato-1-methylbenzene (69.0 mg, 0.41 mmol) was added to the mixture and stirred at RT for 2 h. The mixture was purified on silica gel eluting with DCM/MeOH from 0% to 10% to give (S)-1-(3-chloro-4-methylphenyl)-3-((5-(2,7-dioxoazepan-3-yl)-6-oxo-5,6-dihydro-4H-thieno[2,3-c]pyrrol-2-yl)methyl)urea (53.0 mg, 56%) a white solid. $^1$H NMR (400 MHz, DMSO-d$_6$) δ 10.68 (s, 1H), 8.77 (s, 1H), 7.65 (d, J=2.4 Hz, 1H), 7.20-7.13 (m, 2H), 6.89-6.86 (m, 1H), 5.14-5.10 (m, 1H), 5.20 (d, J=6 Hz, 2H), 4.51 (d, J=2.4 Hz, 2H), 3.08-3.04 (m, 1H), 2.59-2.53 (m, 1H), 2.25-2.16 (m, 4H), 2.10-1.98 (m, 2H), 1.81-1.75 (m, 1H). MS (ESI) m/z 461.1 [M+H]$^+$.

Compound 36: (S)-1-(5-Chloro-2,4-dimethylphenyl)-3-((5-(2,7-dioxoazepan-3-yl)-4-oxo-5,6-dihydro-4H-thieno[3,4-c]pyrrol-1-yl)methyl)urea

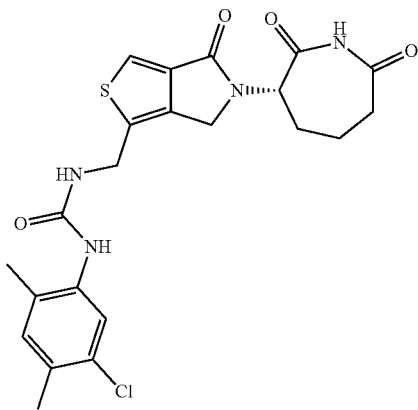 [SMILES: Cc1cc(C)c(NC(=O)NCc2scc3c2CN([C@H]2CCCC(=O)NC2=O)C3=O)cc1Cl]

To a solution of 5-chloro-2,4-dimethylaniline (27.5 mg, 0.18 mmol) in DCM (4 mL) was added 4-nitrophenyl chloroformate (35.7 mg, 0.18 mmol) at RT and stirred for 1 h. Then (S)-3-(1-(aminomethyl)-4-oxo-4H-thieno[3,4-c]pyrrol-5(6H)-yl)azepane-2,7-dione 2,2,2-trifluroacetic acid salt (51.9 mg, 0.18 mmol) was added, followed by TEA (36 mg, 0.36 mmol). The resulting solution was stirred at RT for 2 h. The reaction was concentrated to give the crude product, which was purified by prep-HPLC to give (S)-1-(5-chloro-2,4-dimethylphenyl)-3-((5-(2,7-dioxoazepan-3-yl)-4-oxo-5,6-dihydro-4H-thieno[3,4-c]pyrrol-1-yl)methyl)urea (26.1 mg, 31.1%) as a white solid. MS (ESI) m/z 474.8 [M+H]$^+$. $^1$H NMR (400 MHz, DMSO-d$_6$) δ 10.69 (s, 1H), 7.87 (d, J=6.4 Hz, 3H), 7.18 (t, J=5.6 Hz, 1H), 7.10 (s, 1H), 5.14 (dd, J=7.2, 12.0 Hz, 1H), 4.46 (d, J=4.8 Hz, 2H), 4.39 (d, J=4.0 Hz, 2H), 3.09-3.01 (m, 1H), 2.56 (d, J=16.4 Hz, 1H), 2.22 (s, 3H), 2.16-1.96 (m, 6H), 1.84-1.77 (m, 1H).

Compound 37: (S)-1-((5-(2,7-Dioxoazepan-3-yl)-4-oxo-5,6-dihydro-4H-thieno[3,4-c]pyrrol-1-yl)methyl)-3-(6-methylpyridin-3-yl)urea

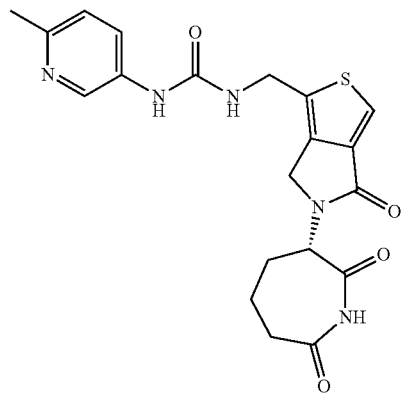 [SMILES: Cc1ccc(NC(=O)NCc2scc3c2CN([C@H]2CCCC(=O)NC2=O)C3=O)cn1]

To a solution of 6-methylpyridin-3-amine (27.4 mg, 0.25 mmol) in DCM (4 mL) was added 4-nitrophenyl chloroformate (50.3 mg, 0.25 mmol) at RT and stirred for 1 h. Then (S)-3-(1-(aminomethyl)-4-oxo-4H-thieno[3,4-c]pyrrol-5(6H)-yl)azepane-2, 7-dione 2,2,2-trifluoroacetic acid salt (74.5 mg, 0.25 mmol) was added, followed by TEA (36 mg, 0.36 mmol). The mixture was stirred at RT for 2 h. The mixture was concentrated to give the crude product, which was purified by prep-HPLC to give (S)-1-((5-(2,7-dioxoazepan-3-yl)-4-oxo-5,6-dihydro-4H-thieno[3,4-c]pyrrol-1-yl)methyl)-3-(6-methylpyridin-3-yl)urea (13.2 mg, 12.0%) as a white solid. $^1$H NMR (400 MHz, DMSO-d$_6$) δ 10.70 (s, 1H), 8.74 (s, 1H), 8.41 (d, J=2.8 Hz, 1H), 7.87 (s, 1H), 7.75 (dd, J=5.6, 8.4 Hz, 1H), 7.11 (d, J=8.0 Hz, 1H), 6.88 (t, J=6.0 Hz, 1H), 5.14 (dd, J=6.8, 12.0 Hz, 1H), 4.44 (d, J=4.4 Hz, 2H), 4.39 (d, J=5.2 Hz, 2H), 3.08-3.01 (m, 1H), 2.54 (d, J=21.2 Hz, 1H), 2.37 (s, 3H), 2.17-1.96 (m, 3H), 1.82-1.77 (m, 1H). MS (ESI) m/z 427.8[M+H]$^+$.

Compound 38: (S)-1-((5-(2,7-Dioxoazepan-3-yl)-4-oxo-5,6-dihydro-4H-thieno[3,4-c]pyrrol-1-yl)methyl)-3-(4-methyl-3-(trifluoromethyl)phenyl)urea

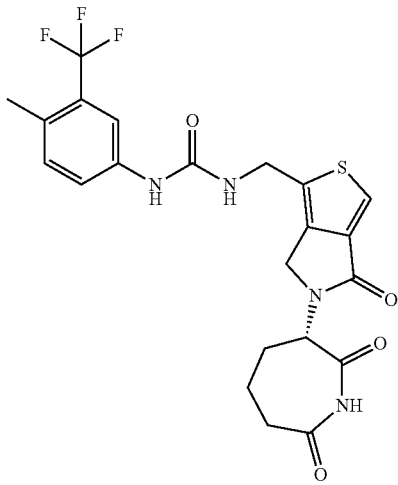 [SMILES: Cc1ccc(NC(=O)NCc2scc3c2CN([C@H]2CCCC(=O)NC2=O)C3=O)cc1C(F)(F)F]

To a solution of triphosgene (609 mg, 2.14 mmol) in toluene (5 mL) was added dropwise a solution of 4-methyl-3-(trifluoromethyl)aniline (100 mg, 0.51 mmol) and refluxed at 80° C. for 0.5 h. Then the mixture was concentrated to give crude 4-isocyanato-1-methyl-2-(trifluoromethyl)benzene. To the solution of crude 4-isocyanato-1-methyl-2-(trifluoromethyl)benzene in THF (4 ml) was added (S)-3-(1-(aminomethyl)-4-oxo-4H-thieno[3,4-c]pyrrol-5(6H)-yl)azepane-2, 7-dione 2,2,2-trifluoroacetic acid salt (52.2 mg, 0.18 mmol), followed by TEA (34 mg, 0.34 mmol). The mixture was stirred at RT for 2 h. The mixture was concentrated to give crude product, which was purified by prep-HPLC to give (S)-1-((5-(2,7-dioxoazepan-3-yl)-4-oxo-5,6-dihydro-4H-thieno[3,4-c]pyrrol-1-yl)methyl)-3-(4-methyl-3-(trifluoromethyl)phenyl)urea (25.7 mg, 29.0%) as a white solid. $^1$H NMR (400 MHz, DMSO-$d_6$) δ 10.69 (s, 1H), 8.94 (s, 1H), 7.89 (s, 1H), 7.85 (d, J=2.4 Hz, 1H), 7.48 (dd, J=6.4, 8.4 Hz, 1H), 7.28 (d, J=8.4 Hz, 1H), 6.89 (t, J=6.0 Hz, 1H), 5.14 (dd, J=6.8, 12.0 Hz, 1H), 4.45 (d, J=6.0 Hz, 2H), 4.39 (d, J=4.8 Hz, 2H), 3.09-3.01 (m, 1H), 2.57-2.55 (m, 1H), 2.34 (s, 3H), 2.16-1.95 (m, 3H), 1.82-1.76 (m, 1H). MS (ESI) m/z 495.1 [M+H]$^+$.

Compound 39: (S)-1-(3-Chloro-4-methylbenzyl)-3-((5-(2,7-dioxoazepan-3-yl)-6-oxo-5,6-dihydro-4H-thieno[2,3-c]pyrrol-2-yl)methyl)urea

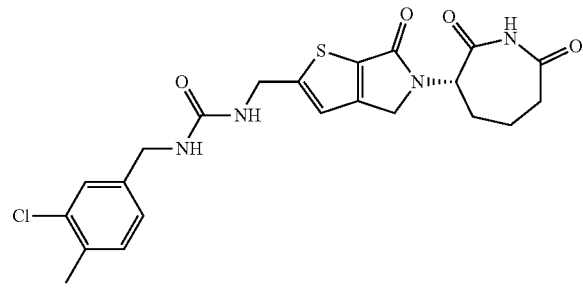 [SMILES: Cc1ccc(CNC(=O)NCc2cc3c(s2)C(=O)N([C@H]2CCCC(=O)NC2=O)C3)cc1Cl]

To a solution of (S)-3-(2-(aminomethyl)-6-oxo-4H-thieno[2,3-c]pyrrol-5(6H)-yl)azepane-2,7-dione (75.0 mg, 0.25 mmol) dissolved in DMF (5 mL) was added TEA (52.0 mg, 0.51 mmol) and the suspension was stirred at RT, then 2-chloro-4-(isocyanatomethyl)-1-methylbenzene (93.0 mg, 0.51 mmol) was added to the mixture and stirred at RT for 2 h. The mixture was purified on silica gel eluting with DCM/MeOH from 0% to 10% to give (S)-1-(3-chloro-4-methylbenzyl)-3-((5-(2,7-dioxoazepan-3-yl)-6-oxo-5,6-dihydro-4H-thieno[2,3-c]pyrrol-2-yl)methyl)urea (22.9 mg, 18%) as a white solid. $^1$H NMR (400 MHz, DMSO-$d_6$) δ 10.68 (s, 1H), 7.28-7.07 (m, 4H), 6.77-6.63 (m, 2H), 5.14-5.10 (m, 1H), 4.46-4.35 (m, 4H), 4.19 (d, J=5.6 Hz, 2H), 3.08-3.01 (m, 1H), 2.58-2.50 (m, 1H), 2.28-2.17 (m, 4H), 2.12-1.99 (m, 2H), 1.82-1.77 (m, 1H). MS (ESI) m/z 475.1 [M+H]$^+$.

Compound 40: 1-(3-Chloro-4-methylphenyl)-3-((5-(2,6-dioxopiperidin-3-yl)-6-oxo-5,6-dihydro-4H-thieno[2,3-c]pyrrol-2-yl)methyl)urea

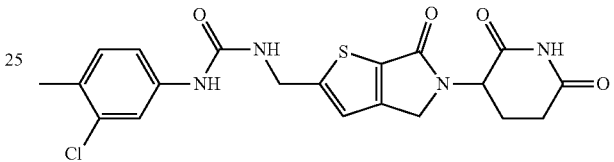

To a solution of 5-bromo-3-methylthiophene-2-carboxylic acid (5 g, 22.6 mmol) in a mixture of DCM (80 mL) and DMF (1 mL) was added oxalyl chloride (5.7 g, 45.2 mmol) dropwise at 0° C. The mixture was stirred at RT for 4 h. Then the solvent was removed under vacuum and residue was dissolved with DCM (50 mL). Potassium tert-butoxide (7.6 g, 67.8 mmol) was added portion wise to the solution at 0° C., and the mixture was stirred at RT for 30 min. Solvent was removed under vacuum and residue was purified on silica gel eluting with petroleum ether to give tert-butyl 5-bromo-3-methylthiophene-2-carboxylate as a pale yellow oil (3 g, 48%).

To a solution of tert-butyl 5-bromo-3-methylthiophene-2-carboxylate (3.0 g, 10.8 mmol) in carbon tetrachloride (30 mL) were added N-bromosuccinimide (NBS) (1.92 g, 10.8 mmol) and Benzoyl peroxide (0.52 g, 2.16 mmol). The mixture was stirred at 80° C. overnight. After the reaction was completion, the solvent was removed and residue was purified on silica gel eluting with petroleum ether to give tert-butyl 5-bromo-3-(bromomethyl)thiophene-2-carboxylate as a colorless oil (2.6 g, 67%).

To a solution of tert-butyl 5-bromo-3-(bromomethyl)thiophene-2-carboxylate (2.4 g, 6.72 mmol) in DMF (30 mL) was added 3-aminopiperidine-2,6-dione (1.1 g, 6.72 mmol) and TEA (1.36 g, 13.44 mmol). The mixture was stirred at 80° C. overnight. After concentration under vacuum, the residue was diluted with water (20 mL) and extracted with EA. The organic layers were combined, dried over $Na_2SO_4$ and concentrated to give the crude product, which was purified on silica gel eluting with EA/petroleum ether (0% to 45%) to give tert-butyl 5-bromo-3-(((2,6-dioxopiperidin-3-yl)amino)methyl)thiophene-2-carboxylate as a green solid. (500 mg, 18.5%). MS (ESI) m/z 402.9 [M+1$^+$].

To a solution of tert-butyl 5-bromo-3-(((2,6-dioxopiperidin-3-yl)amino)methyl)thiophene-2-carboxylate (500 mg, 1.24 mmol) in DCM (20 mL) was added 2,2,2-trifluoroacetic acid (5 mL). The mixture was stirred at RT overnight. Then the solvent was removed to afford 5-bromo-3-(((2,6-dioxopiperidin-3-yl)amino)methyl)thiophene-2-carboxylic acid (440 mg, 100%), which was directly used in the next step without further purification. MS (ESI) m/z 346.8 [M+1]⁺.

To a solution of 5-bromo-3-(((2,6-dioxopiperidin-3-yl)amino)methyl)thiophene-2-carboxylic acid (430 mg, 1.24 mmol) in DMF (30 mL) was added 2-(7-aza-1H-benzotriazole-1-yl)-1,1,3,3-tetramethyluronium hexafluorophosphate (HATU) (590 mg, 1.55 mmol) and DIEA (400 mg, 3.1 mmol). The mixture was stirred at RT for 3 h. After the reaction was completion, the solvent was removed under vacuum to afford residue, which was diluted with water (10 mL), extracted with DCM. The organic layers were dried over Na₂SO₄, concentrated and triturated with EA to give 3-(2-bromo-6-oxo-4H-thieno[2,3-c]pyrrol-5(6H)-yl)piperidine-2,6-dione (360 mg, 88%) as white solid. MS (ESI) m/z 328.9 [M+1]⁺.

To a solution of 3-(2-bromo-6-oxo-4H-thieno[2,3-c]pyrrol-5(6H)-yl)piperidine-2,6-dione (310 mg, 0.95 mmol) in DMF (5 mL) was added tris(dibenzylideneacetone)dipalladium(0) [Pd₂(dba)₃] (90 mg, 0.095 mmol), 1,1'-bisdiphenylphosphinoferrocene [dppf] (128 mg, 0.23 mmol) and Zinc cyanide (122 mg, 1.04 mmol). The mixture was stirred at 150° C. under microwave for 1 h. After the reaction was completion, the solvent was removed to afford residue, which was purified on silica gel eluting with EA/petroleum ether (20% to 100%) to give 5-(2,6-dioxopiperidin-3-yl)-6-oxo-5,6-dihydro-4H-thieno[2,3-c]pyrrole-2-carbonitrile (138 mg, 53%) as a pale brown solid. MS (ESI) m/z 276.0 [M+1]⁺.

To a suspension of 5-(2,6-dioxopiperidin-3-yl)-6-oxo-5,6-dihydro-4H-thieno[2,3-c]pyrrole-2-carbonitrile (50 mg, 0.18 mmol) and Raney nickel (50 mg) in THF (5 mL) was added 2-chloro-4-isocyanato-1-methylbenzene (66 mg, 0.36 mmol). The mixture was purged with hydrogen and stirred at RT for 7 h. After the reaction was completion, Raney nickel was filtered, the resulting solution was concentrated and purified by prep-HPLC to give 1-(3-chloro-4-methylphenyl)-3-((5-(2,6-dioxopiperidin-3-yl)-6-oxo-5,6-dihydro-4H-thieno[2,3-c]pyrrol-2-yl)methyl)urea (9.9 mg, 12.3%) as a white solid. ¹H NMR (400 MHz, DMSO-d₆) δ 10.95 (s, 1H), 8.80 (s, 1H), 7.65 (s, 1H), 7.19-6.89 (m, 3H) 6.89-6.88 (app.t, J=6 Hz, 1H), 4.98-4.95 (dd, J=4.4, 13.2 Hz, 1H), 4.52-4.51 (d, J=4.4 Hz, 2H), 4.36-4.18 (q, J=13.2 Hz, 2H), 2.81-2.83 (m, 1H), 2.59-2.55 (m, 1H), 2.35-2.31 (m, 1H), 2.23 (s, 3H), 1.99-1.98 (m, 1H). MS (ESI) m/z 447.0 [M+1]⁺.

Compound 41: (S)-1-(3-Chloro-4-methylbenzyl)-3-((5-(2,7-dioxoazepan-3-yl)-4-oxo-5,6-dihydro-4H-thieno[3,4-c]pyrrol-1-yl)methyl)thiourea

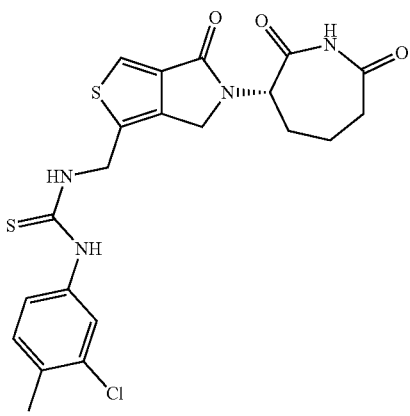 [SMILES: Cc1ccc(NC(=S)NCc2scc3c2CN([C@H]2CCCC(=O)NC2=O)C3=O)cc1Cl]

To the solution of (S)-3-(1-(aminomethyl)-4-oxo-4H-thieno[3,4-c]pyrrol-5(6H)-yl)azepane-2,7-dione 2,2,2-trifluoroacetic acid salt (70.3 mg, 0.18 mmol) in THF (4 mL) was added 2-chloro-4-(isothiocyanatomethyl)-1-methylbenzene (33 mg, 0.18 mmol), followed by TEA (36 mg, 0.36 mmol). The mixture was stirred at RT for 2 h. The reaction was concentrated to give the crude product, which was purified by prep-HPLC to give (S)-1-(3-chloro-4-methylbenzyl)-3-((5-(2,7-dioxoazepan-3-yl)-4-oxo-5,6-dihydro-4H-thieno[3,4-c]pyrrol-1-yl)methyl)thiourea (43.3 mg, 45.0%) as a white solid. ¹H NMR (400 MHz, DMSO-d₆) δ 10.70 (s, 1H), 9.75 (s, 1H), 8.37 (s, 1H), 7.88 (s, 1H), 7.30 (d, J=8.0 Hz, 1H), 7.18 (dd, J=6.4, 8.4 Hz, 1H), 5.15 (dd, J=7.2, 11.6 Hz, 1H), 4.88 (d, J=6.0 Hz, 2H), 4.41 (q, J=7.2 Hz, 2H), 3.09-3.02 (m, 1H), 2.56 (d, J=18.0 Hz, 1H), 2.29 (s, 3H), 2.17-1.99 (m, 3H), 1.84-1.79 (m, 1H). MS (ESI) m/z=477.0, 479.0[M+H]⁺.

Compound 42: (S)-1-((5-(2,7-Dioxoazepan-3-yl)-4-oxo-5,6-dihydro-4H-thieno[3,4-c]pyrrol-1-yl)methyl)-3-(3-isopropyl-4-methylphenyl)urea

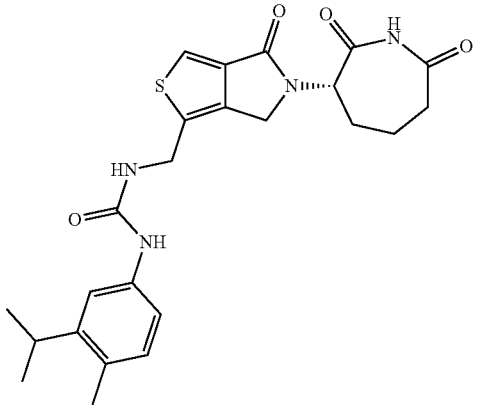 [SMILES: Cc1ccc(NC(=O)NCc2scc3c2CN([C@H]2CCCC(=O)NC2=O)C3=O)cc1C(C)C]

To a solution of 3-isopropyl-4-methylaniline (26.5 mg, 0.18 mmol) in DCM (4 mL) was added 4-nitrophenyl chloroformate (35.8 mg, 0.18 mmol) at RT and stirred for 1 h. Then (S)-3-(1-(aminomethyl)-4-oxo-4H-thieno[3,4-c]pyrrol-5(6H)-yl)azepane-2,7-dione 2,2,2-trifluoroacetic acid salt (52.2 mg, 0.18 mmol) was added, followed by TEA (36 mg, 0.36 mmol). The mixture was stirred at RT for 2 h. The reaction was concentrated to give the crude product, which was purified by prep-HPLC to give (S)-1-((5-(2,7-dioxoazepan-3-yl)-4-oxo-5,6-dihydro-4H-thieno[3,4-c]pyrrol-1-yl)methyl)-3-(3-isopropyl-4-methylphenyl)urea (25.1 mg, 30.3%) as a white solid. ¹H NMR (400 MHz, DMSO-d₆) δ 10.69 (s, 1H), 8.50 (s, 1H), 7.86 (s, 1H), 7.21 (d, J=2.0 Hz, 1H), 7.14 (dd, J=6.0, 8.4 Hz, 1H), 6.96 (d, J=8.0 Hz, 1H), 6.67 (t, J=6.8 Hz, 1H), 5.14 (dd, J=6.8, 11.6 Hz, 1H), 4.43 (d, J=5.6 Hz, 2H), 4.39 (d, J=4.4 Hz, 2H), 3.05-3.01 (m, 2H), 2.56 (d, J=16.8 Hz, 1H), 2.20 (s, 3H), 2.17-1.96 (m, 3H), 1.82-1.77 (m, 1H), 1.13 (d, J=6.8 Hz, 6H). MS (ESI) m/z=469.2[M+H]⁺.

Compound 43: (S)-1-(3-Chloro-5-isopropyl-4-methylphenyl)-3-((5-(2,7-dioxoazepan-3-yl)-4-oxo-5,6-dihydro-4H-thieno[3,4-c]pyrrol-1-yl)methyl)urea

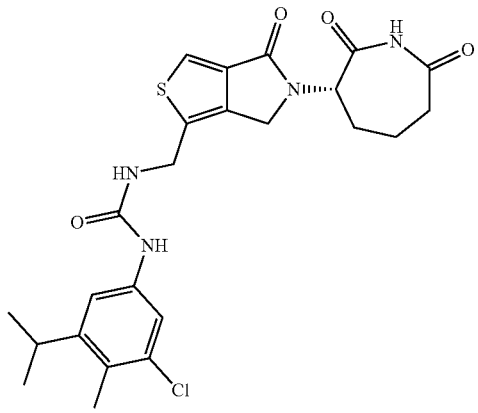 [SMILES: Cc1c(Cl)cc(NC(=O)NCc2scc3c2CN([C@H]2CCCC(=O)NC2=O)C3=O)cc1C(C)C]

To a solution of 3-chloro-5-isopropyl-4-methylaniline (32.6 mg, 0.18 mmol) in DCM (4 mL) was added 4-nitrophenyl chloroformate (35.8 mg, 0.18 mmol) at RT and stirred for 1 h. Then (S)-3-(1-(aminomethyl)-4-oxo-4H-thieno[3,4-c]pyrrol-5(6H)-yl)azepane-2,7-dione 2,2,2-trifluoroacetic acid salt (52.2 mg, 0.18 mmol) was added, followed by TEA (36 mg, 0.36 mmol). The mixture was stirred at RT for 2 h. The reaction was concentrated to give the crude product, which was purified by prep-HPLC to give (S)-1-(3-chloro-5-isopropyl-4-methylphenyl)-3-((5-(2,7-dioxoazepan-3-yl)-4-oxo-5,6-dihydro-4H-thieno[3,4-c]pyrrol-1-yl)methyl)urea (23.8 mg, 26.7%) as a white solid. $^1$H NMR (400 MHz, DMSO-d$_6$) δ 10.71 (s, 1H), 8.76 (s, 1H), 7.87 (s, 1H), 7.53 (d, J=2.0 Hz, 1H), 7.09 (d, J=1.6 Hz, 1H), 6.80 (t, J=5.6 Hz, 1H), 5.14 (dd, J=4.0, 11.6 Hz, 1H), 4.43 (d, J=4.8 Hz, 2H), 4.39 (d, J=4.8 Hz, 2H), 3.14-3.01 (m, 2H), 2.59-2.56 (m, 1H), 2.24 (s, 3H), 2.16-1.97 (m, 3H), 1.82-1.76 (m, 1H), 1.14 (d, J=11.2 Hz, 6H). MS (ESI) m/z 503.1, 505.1[M+H]$^+$.

Compound 44: 1-(3-Chloro-4-methylbenzyl)-3-((5-(2,6-dioxopiperidin-3-yl)-6-oxo-5,6-dihydro-4H-thieno[2,3-c]pyrrol-2-yl)methyl)urea

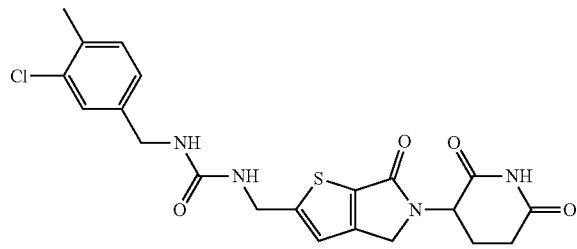 [SMILES: Cc1ccc(CNC(=O)NCc2cc3c(s2)C(=O)N(C2CCC(=O)NC2=O)C3)cc1Cl]

To a suspension of 5-(2,6-dioxopiperidin-3-yl)-6-oxo-5,6-dihydro-4H-thieno[2,3-c]pyrrole-2-carbonitrile (40 mg, 0.14 mmol) and Raney nickel (50 mg) in THF (3 mL) was added 2-chloro-4-(isocyanatomethyl)-1-methylbenzene (136 mg, 0.7 mmol). The mixture was purged with hydrogen and stirred at RT for 7 h. After the reaction was completion, Raney nickel was filtered, the resulting solution was concentrated and purified by prep-HPLC to give 1-(3-chloro-4-methylbenzyl)-3-((5-(2,6-dioxopiperidin-3-yl)-6-oxo-5,6-dihydro-4H-thieno[2,3-c]pyrrol-2-yl)methyl)urea (10.0 mg, 18%) as a white solid. $^1$H NMR (400 MHz, DMSO-d$_6$) δ 10.95 (s, 1H), 7.28-7.26 (m, 2H), 7.11-7.09 (d, J=7.6 Hz, 1H), 7.05 (s, 1H) 6.74-6.72 (t, J=11.6 Hz, 1H), 6.64-6.61 (t, J=11.6 Hz, 1H), 5.00-4.95 (q, J=13.2 Hz, 1H), 4.46-4.44 (d, J=6 Hz, 2H), 4.30 (s, 1H), 4.22-4.19 (m, 3H), 2.92-2.88 (m, 1H), 2.50-2.49 (m, 1H), 2.36-2.33 (m, 1H), 2.28 (s, 3H), 2.00-1.97 (m, 1H). MS (ESI) m/z 460.7 [M+1]$^+$.

Compound 45: (S)-1-(3-Chloro-4-methylphenyl)-3-((5-(2,7-dioxoazepan-3-yl)-6-oxo-5,6-dihydro-4H-thieno[2,3-c]pyrrol-3-yl)methyl)urea

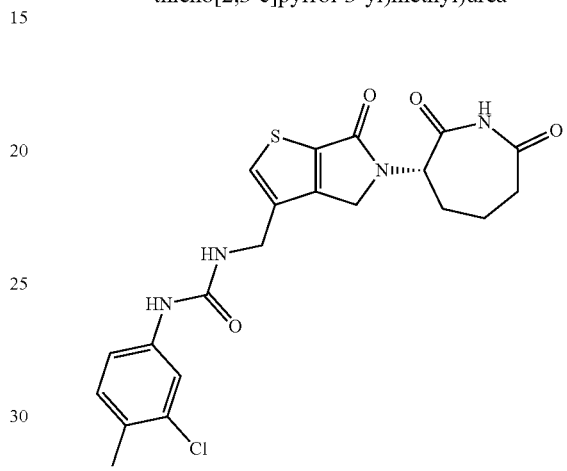

To a solution of methyl 4-bromo-3-methylthiophene-2-carboxylate (5.0 g, 21.37 mmol) in carbon tetrachloride (90 mL) was added N-bromosuccinimide (NBS) (4 g, 22.44 mmol) and Benzoyl peroxide (518 mg, 2.14 mmol). The mixture was stirred at 80° C. overnight. The solid was filtered and the filtrate was diluted with sat. aq. NaHCO$_3$, then extracted with DCM. The combined organic layers were concentrated and purified on silica gel to give methyl 4-bromo-3-(bromomethyl)thiophene-2-carboxylate (5.03 g, 75.4%) as a white solid. $^1$H NMR (CDCl$_3$, 400 MHz) δ: 7.49 (s, 1H), 4.91 (s, 2H), 3.94 (s, 3H).

To a solution of methyl 4-bromo-3-(bromomethyl)thiophene-2-carboxylate (5.0 g, 16.026 mmol) and (S)-3-aminoazepan-2-one (2.46 g, 19.231 mmol) in DMF (80 mL) was added TEA (3.24 g, 32.052 mmol). The mixture was stirred at RT for 2 h then diluted with water and extracted with EA. After removing the solvent under vacuum, the residue was purified on silica gel to give (S)-methyl 4-bromo-3-(((2-oxoazepan-3-yl)amino)methyl)thiophene-2-carboxylate (3.20 g, 55.5%) as a white solid. MS (ESI) m/z 361.4 [M+H]$^+$.

To a solution of (S)-methyl 4-bromo-3-(((2-oxoazepan-3-yl)amino)methyl)thiophene-2-carboxylate (3.16 g, 8.778 mmol) in ACN (50 mL) was added Trimethylaluminium (1 M in toluene) (52.7 mL) slowly at 0° C. under nitrogen. The mixture was stirred at RT overnight. It was quenched with saturated ammonium chloride, then extracted with EA. The organic layers were washed with water, brine, dried over Na$_2$SO$_4$, evaporated to give (S)-3-bromo-5-(2-oxoazepan-3-yl)-4H-thieno[2,3-c]pyrrol-6(5H)-one (2.05 g, 71.1%) as a yellow solid. MS (ESI) m/z 328.9 [M+H]$^+$.

To a solution of (S)-3-bromo-5-(2-oxoazepan-3-yl)-4H-thieno[2,3-c]pyrrol-6(5H)-one (1.2 g, 3.658 mmol) in DMF (36 mL) was added tris(dibenzylideneacetone)dipalladium (0) [Pd$_2$(dba)$_3$] (520 mg, 0.548 mmol), zinc cyanide (516 mg, 4.390 mmol) and 1,1'-bisdiphenylphosphinoferrocene [dppf] (650 mg, 1.208 mmol). The mixture was stirred at 150° C. for 1 h in a microwave under nitrogen atmosphere. It was concentrated to afford a residue, which was purified on silica gel to give (S)-6-oxo-5-(2-oxoazepan-3-yl)-5,6-dihydro-4H-thieno[2,3-c]pyrrole-3-carbonitrile (630 mg, 59.6%) as a grey solid.

To a solution of (S)-6-oxo-5-(2-oxoazepan-3-yl)-5,6-dihydro-4H-thieno[2,3-c]pyrrole-3-carbonitrile (580 mg, 2.109 mmol) in fluorobenzene/DMSO (30 mL/5 mL) was added Dess-Martin reagent (2.68 g, 6.327 mmol). The mixture was stirred to 80° C. overnight. The mixture was cooled to RT and 20 mL of a saturated sodium thiosulfate solution was added followed by stirring for 5 min. The mixture was extracted with DCM (30 mL×2) and the combined solution was washed with 10% aq. sodium thiosulfate/aq. NaHCO$_3$ (1:1 mixture) (50 mL) and brine (50 mL). The organic layer was dried over Na$_2$SO$_4$, filtered, and concentrated to afford the crude product which was purified on silica gel to give (S)-5-(2,7-dioxoazepan-3-yl)-6-oxo-5,6-dihydro-4H-thieno[2,3-c]pyrrole-3-carbonitrile (221 mg, 33.4%) as a yellow solid. MS (ESI) m/z 290.0 [M+H]$^+$.

To a solution of (S)-5-(2,7-dioxoazepan-3-yl)-6-oxo-5,6-dihydro-4H-thieno[2,3-c]pyrrole-3-carbonitrile (100 mg, 0.346 mmol) in THF (4 mL) was added Raney nickel (10 mg) and Di-tert-butyl dicarbonate (150 mg, 0.692 mmol). The suspension was stirred at RT under hydrogen atmosphere for 3 h. LC-MS showed the starting material was consumed and the desired product was detected. The mixture was filtered and the filtrate was concentrated to give crude product, which was purified by prep-TLC in EA to give (S)-tert-butyl((5-(2,7-dioxoazepan-3-yl)-6-oxo-5,6-dihydro-4H-thieno[2,3-c]pyrrol-3-yl)methyl)carbamate (78.5 mg, 57.7%) as a yellow solid. MS (ESI) m/z 395.0 [M+H]$^+$.

To a solution of (S)-tert-butyl ((5-(2,7-dioxoazepan-3-yl)-6-oxo-5,6-dihydro-4H-thieno[2,3-c]pyrrol-3-yl)methyl)carbamate (38 mg, 0.097 mmol) in DCM (2.4 mL) at 0° C. was added 2,2,2-trifluoroacetic acid (0.6 mL). The mixture was stirred at RT for 1 h. The solvent was removed to give the crude product (28.3 mg, 100%) as a yellow oil.

To a solution of crude product (28.3 mg, 0.097 mmol) in THF (4 mL) was added TEA (24.4 mg, 0.242 mmol) and 2-chloro-4-isocyanato-1-methylbenzene (19.4 mg, 0.116 mmol). The mixture was stirred at RT for 2 h. LC-MS showed the starting material was consumed and the desired product was detected. The solvent was removed to give the crude product, which was purified by prep-TLC in EA to give (S)-1-(3-chloro-4-methylphenyl)-3-((5-(2,7-dioxoazepan-3-yl)-6-oxo-5,6-dihydro-4H-thieno[2,3-c]pyrrol-3-yl)methyl)urea (30.0 mg, 67.4%) as a white solid. MS (ESI) m/z 460.7 [M+H]$^+$. $^1$H NMR (DMSO-d$_6$, 400 MHz) δ: 10.70 (s, 1H), 8.69 (s, 1H), 7.77 (s, 1H), 7.64 (d, J=2.0 Hz, 1H), 7.18 (d, J=8.4 Hz, 1H), 7.12 (dd, J=8.0, 2.0 Hz, 1H), 6.83 (t, J=5.6 Hz, 1H), 5.14 (dd, J=11.2, 5.6 Hz, 1H), 4.45 (d, J=8.4 Hz, 2H), 4.32 (d, J=5.6 Hz, 2H), 3.10-3.01 (m, 1H), 2.56 (d, J=18.8 Hz, 1H), 2.23 (s, 3H), 2.20-1.97 (m, 3H), 1.80-1.76 (m, 1H).

Compound 46: 1-(6-Chloro-5-methylpyridin-2-yl)-3-((5-(2,6-dioxopiperidin-3-yl)-4-oxo-5,6-dihydro-4H-thieno[3,4-c]pyrrol-1-yl)methyl)urea

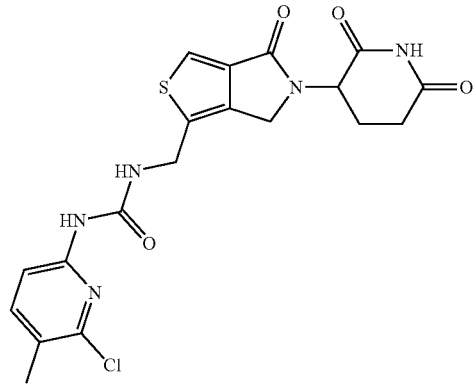

To a solution of 6-chloro-5-methylpyridin-2-amine (25.6 mg, 0.18 mmol) in DCM (4 mL) was added sodium hydride (4.3 mg, 0.18 mmol) at 0° C., the resulting solution was warmed to RT and stirred for 0.5 h, then the 4-Nitrophenyl chloroformate (36.2 mg, 0.18 mmol) was added into the mixture, and the mixture was stirred at RT for 1 h. TLC showed 4-nitrophenyl (6-chloro-5-methylpyridin-2-yl)carbamate had formed, which was used directly to next step.

The crude 4-nitrophenyl (6-chloro-5-methylpyridin-2-yl) carbamate in DCM (4 mL) was added 3-(1-(aminomethyl)-4-oxo-4H-thieno[3,4-c]pyrrol-5(6H)-yl)piperidine-2,6-dione 2,2,2-trifluoroactic acid salt (51.5 mg, 0.18 mmol), followed by TEA (36 mg, 0.36 mmol). The resulting solution was stirred at RT for 2 h. The reaction was concentrated to give the crude product, which was purified by prep-HPLC to give 1-(6-chloro-5-methylpyridin-2-yl)-3-((5-(2,6-dioxopiperidin-3-yl)-4-oxo-5,6-dihydro-4H-thieno[3,4-c]pyrrol-1-yl)methyl)urea (66.7 mg, 80.6%) as a white solid. MS (ESI) m/z 448.1 [M+H]$^+$. $^1$H NMR (400 MHz, DMSO-d$_6$) δ 10.99 (s, 1H), 9.49 (s, 1H), 7.88 (s, 1H), 7.68 (d, J=8.4 Hz, 1H), 7.58 (d, J=8.4 Hz, 1H), 7.47 (t, J=5.2 Hz, 1H), 5.01 (dd, J=8.8, 14.0 Hz, 1H), 4.50 (d, J=6.0 Hz, 2H), 4.27 (q, J=46.4 Hz, 2H), 2.92-2.83 (m, 1H), 2.60-2.56 (m, 1H), 2.33-2.27 (m, 1H), 2.23 (s, 3H), 2.02-1.96 (m, 1H).

Compound 47: 1-((5-(2,6-Dioxopiperidin-3-yl)-4-oxo-5,6-dihydro-4H-thieno[3,4-c]pyrrol-1-yl)methyl)-3-(3-isopropyl-4-methylphenyl)urea

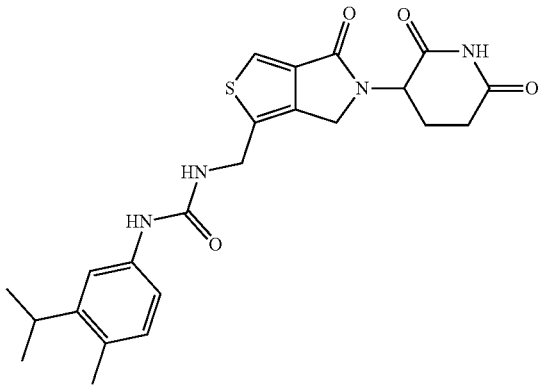 [SMILES: Cc1ccc(NC(=O)NCc2scc3c2CN(C2CCC(=O)NC2=O)C3=O)cc1C(C)C]

To a solution of 3-isopropyl-4-methylaniline (27.5 mg, 0.18 mmol) in DCM (4 mL) was added 4-Nitrophenyl chloroformate (36.2 mg, 0.18 mmol) at RT and stirred for 1 h. Then 3-(1-(aminomethyl)-4-oxo-4H-thieno[3,4-c]pyrrol-5(6H)-yl)piperidine-2,6-dione 2,2,2-trifluoroactic acid salt (50.2 mg, 0.18 mmol) was added, followed by TEA (36 mg, 0.36 mmol). The resulting solution was stirred at RT for 2 h. The reaction was concentrated to give the crude product, which was purified by prep-HPLC to give 1-((5-(2,6-dioxopiperidin-3-yl)-4-oxo-5,6-dihydro-4H-thieno[3,4-c]pyrrol-1-yl)methyl)-3-(3-isopropyl-4-methylphenyl)urea (25.1 mg, 29.9%) as a white solid. MS (ESI) m/z 455.1[M+H]$^+$. $^1$H NMR (400 MHz, DMSO-d$_6$) δ 10.98 (s, 1H), 8.51 (s, 1H), 7.86 (s, 1H), 7.20 (d, J=2.0 Hz, 1H), 7.14 (dd, J=6.0, 8.4 Hz, 1H), 6.96 (d, J=8.4 Hz, 1H), 6.67 (t, J=6.0 Hz, 1H), 5.01 (dd, J=8.4, 13.6 Hz, 1H), 4.42 (d, J=5.6 Hz, 2H), 4.39 (q, J=43.2 Hz, 2H), 3.06-2.99 (m, 1H), 2.93-2.84 (m, 1H), 2.57 (d, J=17.6 Hz, 1H), 2.32-2.23 (m, 1H), 2.19 (s, 3H), 2.00-1.96 (m, 1H), 1.13 (d, J=6.8 Hz, 6H).

Compound 48: 1-(3-Chloro-5-isopropyl-4-methylphenyl)-3-((5-(2,6-dioxopiperidin-3-yl)-4-oxo-5,6-dihydro-4H-thieno[3,4-c]pyrrol-1-yl)methyl)urea

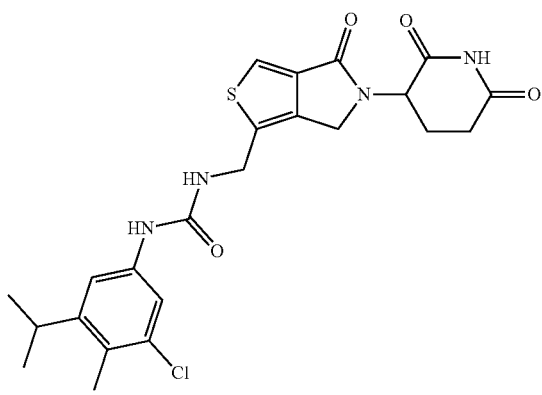 [SMILES: Cc1c(Cl)cc(NC(=O)NCc2scc3c2CN(C2CCC(=O)NC2=O)C3=O)cc1C(C)C]

To a solution of 3-chloro-5-isopropyl-4-methylaniline (32.9 mg, 0.18 mmol) in DCM (4 mL) was added 4-Nitrophenyl chloroformate (36.2 mg, 0.18 mmol) at RT and stirred for 1 h. Then 3-(1-(aminomethyl)-4-oxo-4H-thieno[3,4-c]pyrrol-5(6H)-yl)piperidine-2,6-dione 2,2,2-trifluoroactic acid salt (50.2 mg, 0.18 mmol) was added, followed by TEA (36 mg, 0.36 mmol). The resulting solution was stirred at RT for 2 h. The reaction was concentrated to give the crude product, which was purified by prep-HPLC to give 1-(3-chloro-5-isopropyl-4-methylphenyl)-3-((5-(2,6-dioxopiperidin-3-yl)-4-oxo-5,6-dihydro-4H-thieno[3,4-c]pyrrol-1-yl)methyl)urea (15.9 mg, 17.7%) as a white solid. MS (ESI) m/z 489.1[M+H]$^+$. $^1$H NMR (400 MHz, DMSO-d$_6$) δ 10.99 (s, 1H), 8.76 (s, 1H), 7.87 (s, 1H), 7.54 (d, J=2.0 Hz, 1H), 7.09 (s, 1H), 6.79 (t, J=6.0 Hz, 1H), 5.02 (dd, J=8.4, 13.2 Hz, 1H), 4.42 (d, J=6.0 Hz, 2H), 4.27 (q, J=42.8 Hz, 2H), 3.15-3.06 (m, 1H), 2.94-2.83 (m, 1H), 2.57 (d, J=12.0 Hz, 1H), 2.32-2.27 (m, 1H), 2.25 (s, 3H), 2.03-1.94 (m, 1H), 1.14 (d, J=6.8 Hz, 6H).

Compound 49: 1-(5-Chloro-2,4-dimethylphenyl)-3-((5-(2,6-dioxopiperidin-3-yl)-4-oxo-5,6-dihydro-4H-thieno[3,4-c]pyrrol-1-yl)methyl)urea

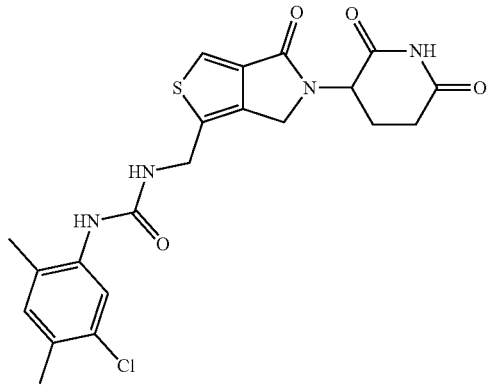 [SMILES: Cc1cc(C)c(NC(=O)NCc2scc3c2CN(C2CCC(=O)NC2=O)C3=O)cc1Cl]

To a solution of 5-chloro-2,4-dimethylaniline (28.6 mg, 0.18 mmol) in DCM (4 mL) was added 4-nitrophenyl chloroformate (36.2 mg, 0.18 mmol) at RT and stirred for 1 h. Then 3-(1-(aminomethyl)-4-oxo-4H-thieno[3,4-c]pyrrol-5(6H)-yl)piperidine-2,6-dione 2,2,2-trifluoroactic acid salt (50.2 mg, 0.18 mmol) was added, followed by TEA (36 mg, 0.36 mmol). The resulting solution was stirred at RT for 2 h. The reaction was concentrated to give the crude product, which was purified by prep-HPLC to give 1-(5-chloro-2,4-dimethylphenyl)-3-((5-(2,6-dioxopiperidin-3-yl)-4-oxo-5,6-dihydro-4H-thieno[3,4-c]pyrrol-1-yl)methyl)urea (27.8 mg, 32.7%) as a white solid. MS (ESI) m/z 461.1 [M+H]$^+$. $^1$H NMR (400 MHz, DMSO-d$_6$) δ 10.99 (s, 1H), 7.89 (s, 1H), 7.86 (d, J=3.2 Hz, 2H), 7.18 (t, J=6.0 Hz, 1H), 7.10 (s, 1H), 5.02 (dd, J=8.4, 13.6 Hz, 1H), 4.45 (d, J=5.2 Hz, 2H), 4.27 (q, J=44.8 Hz, 2H), 2.94-2.85 (m, 1H), 2.58 (d, J=17.2 Hz, 1H), 2.34-2.27 (m, 1H), 2.22 (s, 3H), 2.13 (s, 3H), 2.04-1.97 (m, 1H).

Compound 50: 1-(3-Chloro-4-methylphenyl)-3-(5-(2,6-dioxopiperidin-3-yl)-4-oxo-5,6-dihydro-4H-thieno[3,4-c]pyrrol-1-yl)urea

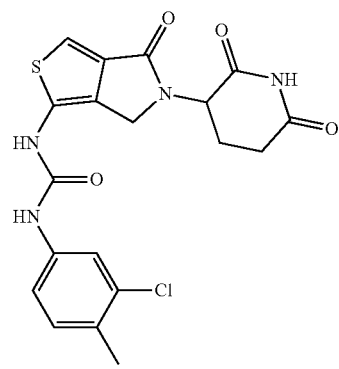 [SMILES: Cc1ccc(NC(=O)Nc2scc3c2CN(C2CCC(=O)NC2=O)C3=O)cc1Cl]

To a stirred solution of tert-butyl 4-methylthiophene-3-carboxylate (3.0 g, 15 mmol) in carbon tetrachloride (30 mL) was added N-bromosuccinimide (NBS) (2.83 g, 16 mmol) and benzoyl peroxide (1.83 g, 7.5 mmol). The mixture was stirred at 90° C. for 4 h then cooled to RT, filtered, evaporated, and purified on silica gel (petroleum ether) to give tert-butyl 4-(bromomethyl)thiophene-3-carboxylate (1.86 g, 44%) as a colorless oil. $^1$H NMR (300 MHz, DMSO-$d_6$) δ 8.22 (d, J=4.0, 1H), 7.73 (d, J=4.0, 1H), 4.84 (s, 2H), 1.50 (s, 9H).

To a stirred solution of tert-butyl 4-(bromomethyl)thiophene-3-carboxylate (1.83 g, 6.74 mmol) in DMF (4 mL) was added 3-aminopiperidine-2,6-dione hydrochloride salt (1.66 g, 10.08 mmol) and TEA (3 mL). The mixture was stirred at 80° C. for 4 h. Then the reaction was cooled to RT, diluted with water, and extracted with EA. The organic layers were washed with brine, dried over Na$_2$SO$_4$, evaporated under vacuum, and purified on silica gel (petroleum/EA=1/1) to give tert-butyl 4-(((2,6-dioxopiperidin-3-yl)amino)methyl)thiophene-3-carboxylate (750 mg, 34%) as a blue oil. MS (ESI) m/z 325.0 [M+H]$^+$.

To a stirred solution of tert-butyl 4-(((2,6-dioxopiperidin-3-yl)amino)methyl) thiophene-3-carboxylate (750 mg, 2.3 mmol) in DCM (10 mL) was added TFA (5 mL). The mixture was stirred at RT overnight then concentrated to give 4-(((2,6-dioxopiperidin-3-yl)amino)methyl)thiophene-3-carboxylic acid, used crude in the next step. MS (ESI) m/z 269.0 [M+H]$^+$.

To a stirred solution of 4-(((2,6-dioxopiperidin-3-yl)amino)methyl)thiophene-3-carboxylic acid (2.3 mmol) in DMF (10 mL) was added DIEA (1.3 mL) and 2-(7-azabenzotriazol-1-yl)-N,N,N',N'-tetramethyluronium hexafluorophosphate (HATU) (1.3 g, 3.45 mmol). The mixture was stirred at RT for 2 h then water and DCM were added. The organic layer was filtered to give 3-(4-oxo-4H-thieno[3,4-c]pyrrol-5(6H)-yl)piperidine-2,6-dione (400 mg, 69%) as a white solid. MS (ESI) m/z 251.0 [M+H]$^+$. $^1$H NMR (300 MHz, DMSO-d6) δ 10.97 (s, 1H), 8.03 (s, 1H), 7.50 (s, 1H), 5.05-4.99 (m, 1H), 4.25 (q, J=15.9 Hz, 2H), 2.61-2.59 (m, 1H), 2.55-2.54 (m, 1H), 2.38-2.33 (m, 1H), 2.00-1.98 (m, 1H).

To a stirred solution of fuming nitric acid (5 mL) was added 3-(4-oxo-4H-thieno[3,4-c]pyrrol-5(6H)-yl)piperidine-2,6-dione (350 mg, 1.4 mmol) at 0° C. The mixture was stirred at 0° C. for 5 h then poured into ice water, and the pH was adjusted to 2 with 1M NaOH solution. The mixture was filtered to give 3-(1-nitro-4-oxo-4H-thieno[3,4-c]pyrrol-5 (6H)-yl)piperidine-2,6-dione (250 mg, 61%) as a pink solid. MS (ESI) m/z 295.9 [M+H]$^+$. $^1$H NMR (400 MHz, DMSO-$d_6$) δ 11.01 (s, 1H), 8.50 (s, 1H), 5.05 (dd, J=5.2, 13.6 Hz, 1H), 4.60 (q, J=18.4 Hz, 2H), 2.91-2.84 (m, 1H), 2.60-2.55 (m, 1H), 2.46-2.42 (m, 1H), 2.00-1.96 (m, 1H).

To a stirred solution of 3-(1-nitro-4-oxo-4H-thieno[3,4-c]pyrrol-5(6H)-yl)piperidine-2,6-dione (100 mg, 0.34 mmol) in THF (8 mL) was added Raney nickel (50 mg). The mixture was stirred at RT overnight under hydrogen then filtered and concentrated under vacuum to give 3-(1-amino-4-oxo-4H-thieno[3,4-c]pyrrol-5(6H)-yl)piperidine-2,6-dione, which was used crude for the next step. MS (ESI) m/z 266.0 [M+H]$^+$.

To a stirred solution of 3-(1-amino-4-oxo-4H-thieno[3,4-c]pyrrol-5(6H)-yl)piperidine-2,6-dione (0.34 mmol) in THF (4 mL) was added 2-chloro-4-isocyanato-1-methylbenzene (86 mg, 0.51 mmol). The mixture was stirred at RT for 4 h then evaporated under vacuum and purified by prep-HPLC to give 1-(3-chloro-4-methylphenyl)-3-(5-(2,6-dioxopiperidin-3-yl)-4-oxo-5,6-dihydro-4H-thieno[3,4-c]pyrrol-1-yl) urea (18 mg, 12%) as a white solid. MS (ESI) m/z 433.0 [M+H]$^+$. $^1$H NMR (400 MHz, DMSO-$d_6$) δ 10.97 (s, 1H), 9.79 (s, 1H), 8.93 (s, 1H), 7.68 (s, 1H), 7.42 (s, 1H), 7.25 (s, 1H), 5.00 (dd, J=4.8, 13.6 Hz, 1H), 4.21 (q, J=15.2 Hz, 2H), 2.91-2.84 (m, 1H), 2.61-2.56 (m, 1H), 2.36-2.32 (m, 1H), 2.26 (s, 1H), 2.00-1.98 (m, 1H).

Compound 51: (S)-1-(3-Chloro-4-methylbenzyl)-3-((5-(2,7-dioxoazepan-3-yl)-6-oxo-5,6-dihydro-4H-thieno[2,3-c]pyrrol-3-yl)methyl)urea

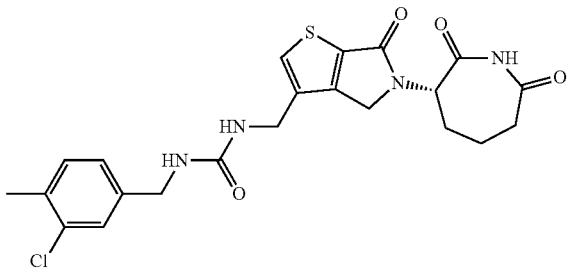 [SMILES: Cc1ccc(CNC(=O)NCc2csc3c2CN([C@H]2CCCC(=O)NC2=O)C3=O)cc1Cl]

To a solution of (S)-tert-butyl ((5-(2,7-dioxoazepan-3-yl)-6-oxo-5,6-dihydro-4H-thieno[2,3-c]pyrrol-3-yl)methyl)carbamate (60 mg, 0.153 mmol) in DCM (3.6 mL) at 0° C. was added 2,2,2-trifluoroacetic acid (0.9 mL). The mixture was stirred at RT for 1 h. The solvent was removed under vacuum to give the crude product (44.7 mg, 100%) as a yellow oil.

To a solution of crude product (44.7 mg, 0.153 mmol) in THF (3 mL) was added TEA (38.6 mg, 0.383 mmol) and 2-chloro-4-(isocyanatomethyl)-1-methylbenzene (41.5 mg, 0.230 mmol). The mixture was stirred at RT for 2 h. The solvent was removed to give the crude product, which was purified on silica gel to give (S)-1-(3-chloro-4-methylbenzyl)-3-((5-(2,7-dioxoazepan-3-yl)-6-oxo-5,6-dihydro-4H-thieno[2,3-c]pyrrol-3-yl)methyl)urea (44.0 mg, 53.7%) as a white solid. MS (ESI) m/z 475.1 [M+H]$^+$. $^1$H NMR (DMSO-$d_6$, 400 MHz) δ: 10.71 (s, 1H), 7.70 (s, 1H), 7.26 (d, J=8.4 Hz, 2H), 7.11 (d, J=7.6 Hz, 1H), 6.55 (t, J=5.2 Hz, 2H), 5.13 (t, J=8.4 Hz, 1H), 4.44-4.18 (m, 6H), 3.06 (t, J=14.0 Hz, 1H), 2.56 (d, J=16.8 Hz, 1H), 2.28 (s, 3H), 2.08-1.98 (m, 3H), 1.79-1.74 (m, 1H).

Compound 52: 1-(3-Chloro-4-methylphenyl)-3-((5-(2,6-dioxopiperidin-3-yl)-4-oxo-5,6-dihydro-4H-thieno[3,4-c]pyrrol-1-yl)methyl)thiourea

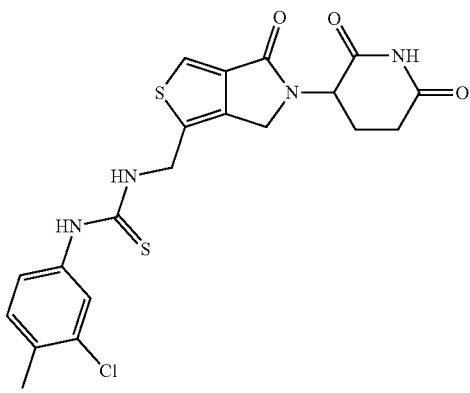 [SMILES: Cc1ccc(NC(=S)NCc2scc3c2CN(C2CCC(=O)NC2=O)C3=O)cc1Cl]

To a solution of tert-butyl ((5-(2,6-dioxopiperidin-3-yl)-4-oxo-5,6-dihydro-4H-thieno[3,4-c]pyrrol-1-yl)methyl)carbamate (80 mg, 89% purity, 0.19 mmol) in DCM (4 mL) at 0° C. was added 2,2,2-trifluoroacetic acid (1 mL). The mixture was warmed to RT and stirred for 2 h then concentrated under vacuum to afford 3-(1-(aminomethyl)-4-oxo-4H-thieno[3,4-c]pyrrol-5(6H)-yl)piperidine-2,6-dione 2,2,2-trifluoro-acetic acid salt (52.4 mg, 100%) as a white solid. MS (ESI) m/z 280 [M+H]+

To a solution of 3-(1-(aminomethyl)-4-oxo-4H-thieno[3,4-c]pyrrol-5(6H)-yl)piperidine-2,6-dione 2,2,2-trifluoroacetic acid salt (52.4 mg, 0.19 mmol) in THF (3 mL) at 0° C. was added TEA (28.5 mg, 0.2818 mmol) and 2-chloro-4-isothiocyanato-1-methylbenzene (37.9 mg, 0.21 mmol). The mixture was warmed to RT and stirred for 4 h then concentrated and purified on silica gel eluting with MeOH in DCM from 0% to 10% to give 1-(3-chloro-4-methylphenyl)-3-((5-(2,6-dioxopiperidin-3-yl)-4-oxo-5,6-dihydro-4H-thieno[3,4-c]pyrrol-1-yl)methyl)thiourea (60.6 mg, 69.8%) as a white solid. MS (ESI) m/z 463 [M+H]+. 1H NMR (400 MHz, DMSO-$d_6$) δ 10.99 (s, 1H), 9.74 (s, 1H), 8.36 (s, 1H), 7.88 (s, 1H), 7.50 (s, 1H), 7.30 (t, J=8.0, 1H), 7.18-7.16 (m, 1H), 5.04-5.00 (m, 1H), 4.86 (d, J=5.6, 2H), 4.28 (q, J=15.6, 41.6, 2H), 2.94-2.90 (m, 1H), 2.61-2.57 (m, 1H), 2.32-2.29 (m, 4H), 2.00-1.97 (m, 1H).

Compound 53: 1-((5-(2,6-Dioxopiperidin-3-yl)-4-oxo-5,6-dihydro-4H-thieno[3,4-c]pyrrol-1-yl)methyl)-3-(6-methylpyridin-3-yl)urea

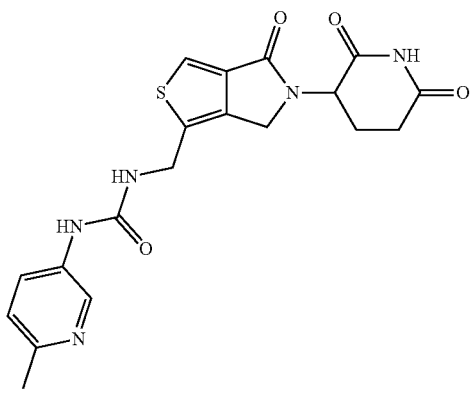 [SMILES: Cc1ccc(NC(=O)NCc2scc3c2CN(C2CCC(=O)NC2=O)C3=O)cn1]

To a solution of 6-methylpyridin-3-amine (19.4 mg, 0.18 mmol) in DCM (4 mL) was added 4-nitrophenyl chloroformate (36.2 mg, 0.18 mmol) at RT and stirred for 1 h. Then 3-(1-(aminomethyl)-4-oxo-4H-thieno[3,4-c]pyrrol-5(6H)-yl)piperidine-2,6-dione 2,2,2-trifluoroactic acid salt (50.2 mg, 0.18 mmol) was added, followed by TEA (36 mg, 0.36 mmol). The resulting solution was stirred at RT for 2 h then concentrated and purified by prep-HPLC to give 1-((5-(2,6-dioxopiperidin-3-yl)-4-oxo-5,6-dihydro-4H-thieno[3,4-c]pyrrol-1-yl)methyl)-3-(6-methylpyridin-3-yl)urea (19.6 mg, 25.7%) as a white solid. MS (ESI) m/z 414.1[M+H]+. 1H NMR (400 MHz, DMSO-$d_6$) δ 10.99 (s, 1H), 8.74 (s, 1H), 8.40 (d, J=2.8 Hz, 1H), 7.87 (s, 1H), 7.75 (dd, J=5.6, 8.4 Hz, 1H), 7.11 (d, J=8.4 Hz, 1H), 6.88 (t, J=6.0 Hz, 1H), 5.01 (dd, J=8.0, 13.2 Hz, 1H), 4.43 (d, J=4.8 Hz, 2H), 4.27 (q, J=42.8 Hz, 2H), 2.93-2.83 (m, 1H), 2.45 (d, J=15.6 Hz, 1H), 2.37 (s, 3H), 2.32-2.24 (m, 1H), 2.00-1.96 (m, 1H).

Compound 54: 1-((5-(2,6-Dioxopiperidin-3-yl)-4-oxo-5,6-dihydro-4H-thieno[3,4-c]pyrrol-1-yl)methyl)-3-(4-methyl-3-(trifluoromethyl)phenyl)urea

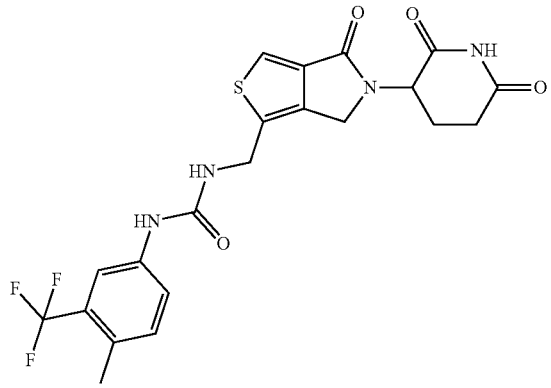 [SMILES: Cc1ccc(NC(=O)NCc2scc3c2CN(C2CCC(=O)NC2=O)C3=O)cc1C(F)(F)F]

To a solution of triphosgene (609 mg, 2.14 mmol) in toluene (5 mL) was added 4-methyl-3-(trifluoromethyl)aniline (100 mg, 0.51 mmol) dropwise, and the mixture was refluxed for 0.5 h. Then the mixture was concentrated, and the crude 4-isocyanato-1-methyl-2-(trifluoromethyl)benzene was dissolved in THF (4 ml) at RT, then 3-(1-(aminomethyl)-4-oxo-4H-thieno[3,4-c]pyrrol-5(6H)-yl)piperidine-2,6-dione 2,2,2-trifluoroacetic acid salt (51.5 mg, 0.18 mmol) was added, followed by TEA (36 mg, 0.36 mmol). The resulting solution was stirred at RT for 2 h then the mixture was concentrated and purified by prep-HPLC to give 1-((5-(2,6-dioxopiperidin-3-yl)-4-oxo-5,6-dihydro-4H-thieno[3,4-c]pyrrol-1-yl)methyl)-3-(4-methyl-3-(trifluoromethyl)phenyl)urea (35.9 mg, 40.5%) as a white solid. MS (ESI) m/z 481.1 [M+H]+. 1H NMR (400 MHz, DMSO-$d_6$) δ 10.98 (s, 1H), 8.93 (s, 1H), 7.87 (s, 1H), 7.85 (d, J=2.0 Hz, 1H), 7.48 (dd, J=6.4, 8.4 Hz, 1H), 7.28 (d, J=8.4 Hz, 1H), 6.88 (t, J=6.4 Hz, 1H), 5.01 (dd, J=8.4, 13.2 Hz, 1H), 4.43 (d, J=6.0 Hz, 2H), 4.39 (q, J=42.8 Hz, 2H), 2.93-2.84 (m, 1H), 2.59-2.55 (m, 1H), 2.34-2.27 (m, 4H), 2.00-1.91 (m, 1H).

Compound 55: 1-(3-chloro-4-(trifluoromethyl)phenyl)-3-((5-(2,6-dioxopiperidin-3-yl)-4-oxo-5,6-dihydro-4H-thieno[3,4-c]pyrrol-1-yl)methyl)urea

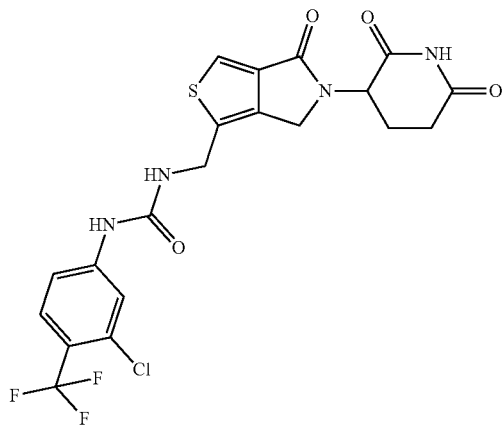 [SMILES: O=C1CCC(N2Cc3c(csc3CNC(=O)Nc3ccc(C(F)(F)F)c(Cl)c3)C2=O)C(=O)N1]

To a solution of triphosgene (609 mg, 2.14 mmol) in toluene (5 mL) was added a solution of 3-chloro-4-(trifluoromethyl)aniline (100 mg, 0.51 mmol) and the mixture was refluxed at 80° C. for 0.5 h. After cooling to RT, the mixture was concentrated under vacuum and dissolved in THF (4 mL), then 3-(1-(aminomethyl)-4-oxo-4H-thieno[3,4-c]pyrrol-5(6H)-yl)piperidine-2,6-dione 2,2,2-trifluoroacetic acid (51.5 mg, 0.18 mmol) was added, followed by TEA (36 mg, 0.36 mmol). The solution was stirred at RT for 2 h then concentrated under vacuum and purified by prep-HPLC to give 1-(3-chloro-4-(trifluoromethyl)phenyl)-3-((5-(2,6-dioxopiperidin-3-yl)-4-oxo-5,6-dihydro-4H-thieno[3,4-c]pyrrol-1-yl)methyl)urea (18.6 mg, yield: 20.7%) as a white solid. MS (ESI) r/z 500.7, 502.6 [M+H]+. 1H NMR (400 MHz, DMSO-d6) δ 10.98 (s, 1H), 9.35 (s, 1H), 7.87 (s, 1H), 7.69 (d, J=9.2 Hz, 1H), 7.43 (dd, J=7.2, 8.4 Hz, 1H), 7.11 (t, J=6.0 Hz, 1H), 5.01 (dd, J=8.0, 13.2 Hz, 1H), 4.40 (d, J=6.0 Hz, 2H), 4.28 (q, J=41.6 Hz, 2H), 2.93-2.84 (m, 1H), 2.73-2.60 (m, 1H), 2.37-2.26 (m, 1H), 2.07-1.97 (m, 1H).

Compound 56: 2-(3-Chloro-4-methylphenyl)-N-(5-(2,6-dioxopiperidin-3-yl)-4-oxo-5,6-dihydro-4H-thieno[3,4-c]pyrrol-1-yl)acetamide

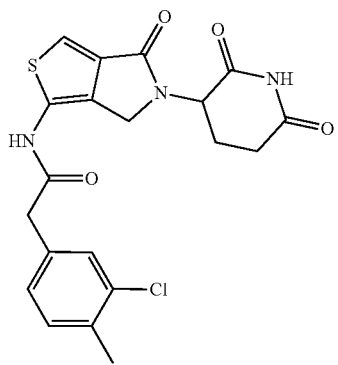 [SMILES: Cc1ccc(CC(=O)Nc2scc3c2CN(C2CCC(=O)NC2=O)C3=O)cc1Cl]

To a stirred solution of 3-(1-nitro-4-oxo-4H-thieno[3,4-c]pyrrol-5(6H)-yl)piperidine-2,6-dione (100 mg, 0.34 mmol) in THF (8 mL) was added Raney nickel (50 mg). The mixture was stirred at RT overnight under hydrogen, then filtered and concentrated to give 3-(1-amino-4-oxo-4H-thieno[3,4-c]pyrrol-5(6H)-yl)piperidine-2,6-dione, which was used in the next step without further purification. MS (ESI) m/z 266.0 [M+H]+.

To a stirred solution of 3-(1-amino-4-oxo-4H-thieno[3,4-c]pyrrol-5(6H)-yl)piperidine-2,6-dione (0.34 mmol) and 2-(3-chloro-4-methylphenyl)acetic acid (60 mg, 0.32 mmol), TEA (0.1 mL) in DCM (4 mL) was dropwise added 2,4,6-tripropyl-1,3,5,2,4,6-trioxatriphosphorinane-2,4,6-trioxide (T3P) (0.1 mL) at −10° C. The mixture was stirred at RT for 5 h then quenched with sat. aq. NaHCO3 and extracted with EA. The organic layer was washed with brine, dried over Na2SO4, evaporated, and purified by prep-HPLC to give 2-(3-chloro-4-methylphenyl)-N-(5-(2,6-dioxopiperidin-3-yl)-4-oxo-5,6-dihydro-4H-thieno[3,4-c]pyrrol-1-yl)acetamide (10 mg, 7%) as a yellow solid. MS (ESI) m/z 432.1 [M+H]+. 1H NMR (400 MHz, DMSO-d6) δ 11.39 (s, 1H), 10.99 (s, 1H), 7.45 (s, 1H), 7.37 (s, 1H), 7.30 (d, J=7.6 Hz, 1H), 7.18 (d, J=7.6 Hz, 1H), 5.01 (dd, J=5.2, 8.8 Hz, 1H), 4.25 (q, J=8.8 Hz, 2H), 3.69 (s, 2H), 2.90-2.85 (m, 1H), 2.61-2.57 (m, 1H), 2.30-2.26 (m, 1H), 2.25 (s, 1H), 2.03-1.98 (m, 1H).

Compound 57: (S)-1-(6-Chloro-5-methylpyridin-2-yl)-3-((5-(2,7-dioxoazepan-3-yl)-4-oxo-5,6-dihydro-4H-thieno[3,4-c]pyrrol-1-yl)methyl)urea

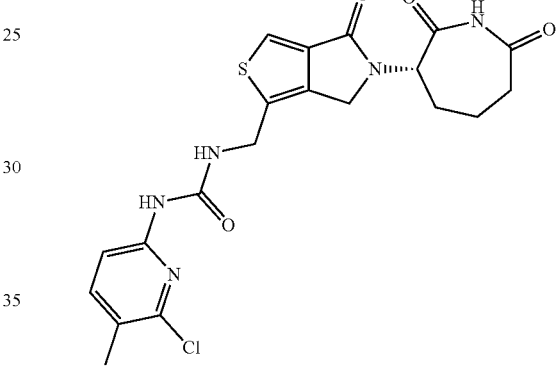

To a solution of 6-chloro-5-methylpyridin-2-amine (25.6 mg, 0.18 mmol) in DCM (4 mL) was added sodium hydride (4.3 mg, 0.18 mmol) at 0° C. The solution was warmed to RT and stirred for 0.5 h. 4-Nitrophenyl chloroformate (36.2 mg, 0.18 mmol) was added, and the mixture was stirred for 1 h then concentrated under vacuum to give crude 4-nitrophenyl (6-chloro-5-methylpyridin-2-yl)carbamate, which was used directly to the next step.

To the solution of crude 4-nitrophenyl (6-chloro-5-methylpyridin-2-yl)carbamate in DCM (4 mL) was added (S)-3-(1-(aminomethyl)-4-oxo-4H-thieno[3,4-c]pyrrol-5(6H)-yl)azepane-2,7-dione 2,2,2-trifluoroacetic acid salt (70.3 mg, 0.18 mmol), followed by TEA (36 mg, 0.36 mmol). The mixture was stirred at RT for 2 h then concentrated and purified by prep-HPLC to give (S)-1-(6-chloro-5-methylpyridin-2-yl)-3-((5-(2,7-dioxoazepan-3-yl)-4-oxo-5,6-dihydro-4H-thieno[3,4-c]pyrrol-1-yl)methyl)urea (26.7 mg, yield: 33.0%) as a white solid. 1H NMR (400 MHz, DMSO-d6) δ 10.71 (s, 1H), 9.49 (s, 1H), 7.88 (s, 1H), 7.68 (d, J=8.4 Hz, 1H), 7.58 (d, J=8.4 Hz, 1H), 7.48 (t, J=5.6 Hz, 1H), 5.14 (dd, J=6.8, 12.0 Hz, 1H), 4.51 (d, J=6.0 Hz, 2H), 4.39 (d, J=2.4 Hz, 2H), 3.09-3.01 (m, 1H), 2.55 (d, J=16.8 Hz, 1H), 2.23 (s, 3H), 2.16-1.97 (m, 3H), 1.82-1.79 (m, 1H). MS (ESI) m/z=461.7, 463.7[M+H]+.

Compound 58: (S)-2-((3-(4-((4-((3-(N-(tert-Butyl)sulfamoyl)phenyl)amino)-5-methylpyrimidin-2-yl)amino)phenoxy)propyl)amino)—N-((5-(2,7-dioxoazepan-3-yl)-4-oxo-5,6-dihydro-4H-thieno[3,4-c]pyrrol-1-yl)methyl)acetamide methyl)acetamide (100 mg, 0.24 mmol). The suspension was heated at 60° C. for 2 h. The solvent was removed and the residue was purified by prep-HPLC to give (S)-2-((3-(4-((4-((3-(N-(tert-butyl)sulfamoyl)phenyl)amino)-5-methylpyrimidin-2-yl)amino)phenoxy)propyl)amino)—N-((5-

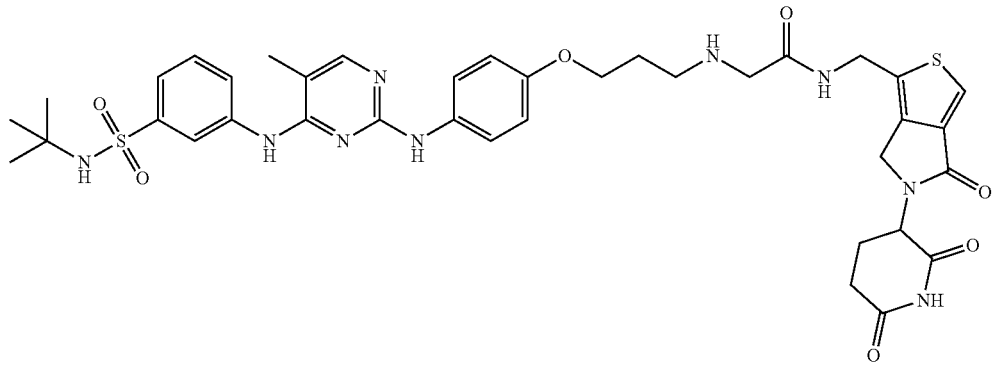 [SMILES: Cc1cnc(Nc2ccc(OCCCNCC(=O)NCc3scc4c3CN(C3CCC(=O)NC3=O)C4=O)cc2)nc1Nc1cccc(S(=O)(=O)NC(C)(C)C)c1]

To a solution of (S)-tert-butyl ((5-(2,7-dioxoazepan-3-yl)-4-oxo-5,6-dihydro-4H-thieno[3,4-c]pyrrol-1-yl)methyl)carbamate (500 mg, 0.254 mmol) in DCM (4 mL) was added 2,2,2-trifluoroacetic acid (2 mL) at RT. The mixture was stirred for 0.5 h. The solvent was removed to give (S)-3-(1-(aminomethyl)-4-oxo-4H-thieno[3,4-c]pyrrol-5(6H)-yl)azepane-2,7-dione 2,2,2-trifluoro-acetic acid salt (372 mg, crude), which was used directly for the next step.

(S)-3-(1-(aminomethyl)-4-oxo-4H-thieno[3,4-c]pyrrol-5(6H)-yl)azepane-2,7-dione 2,2,2-trifluoro-acetic acid salt was dissolved in DCM (15 mL) and TEA (256 mg, 2.54 mmol) was added. The reaction was cooled to 0° C. and bromoacetyl chloride (241 mg, 1.53 mmol) was added. The mixture was stirred at RT for 1 h. The solvent was removed and the residue was purified on silica gel eluting with EA/MeOH from 0% to 8% to give (S)-2-bromo-N-((5-(2,7-dioxoazepan-3-yl)-4-oxo-5,6-dihydro-4H-thieno[3,4-c]pyrrol-1-yl)methyl)acetamide (478 mg, 90.1%) as a yellow oil. MS (ESI) m/z 414.1, 416.1 [M+1, M+3]⁺.

(2,7-dioxoazepan-3-yl)-4-oxo-5,6-dihydro-4H-thieno[3,4-c]pyrrol-1-yl)methyl)acetamide (14.6 mg, 7.3%) as a white solid. ¹H NMR (400 MHz, DMSO-d$_6$) δ 10.71 (s, 1H), 8.76 (s, 1H), 8.53 (s, 1H), 8.50 (t, J=6.4 Hz, 1H), 8.15-8.12 (m, 2H), 7.90 (s, 1H), 7.85 (s, 1H), 7.55-7.47 (m, 6H), 6.77 (d, J=9.2 Hz, 2H), 5.12 (dd, J=6.8, 11.6 Hz, 1H), 4.43 (d, J=6.0 Hz, 2H), 4.35 (d, J=4.4 Hz, 2H), 3.95 (t, J=6.4 Hz, 1H), 3.14 (s, 2H), 3.07-2.99 (m, 1H), 2.62 (t, J=6.8 Hz, 2H), 2.57-2.55 (m, 2H), 2.38-2.34 (m, 1H), 2.12 (s, 3H), 2.02-1.96 (m, 2H), 1.93-1.78 (m, 3H), 1.11 (s, 9H). MS (ESI) m/z 818.2 [M+H]⁺.

Compound 59: 2-((3-(4-((4-((3-(N-(tert-Butyl)sulfamoyl)phenyl)amino)-5-methylpyrimidin-2-yl)amino)phenoxy)propyl)amino)—N-((5-(2,6-dioxopiperidin-3-yl)-4-oxo-5,6-dihydro-4H-thieno[3,4-c]pyrrol-1-yl)methyl)acetamide To a solution of 3-((2-((4-(3-aminopropoxy)phenyl)amino)-5-methylpyrimidin-4-yl)amino)—N-(tert-butyl)benzenesulfinamide 2,2,2-trifluoroacetic acid salt (117.0 mg, 0.24 mmol) in DMF (5 mL) was added DIEA (61.9 mg, 0.48 mmol), followed by (S)-2-bromo-N-((5-(2,7-dioxoazepan-3-yl)-4-oxo-5,6-dihydro-4H-thieno[3,4-c]pyrrol-1-yl)

To a solution of 3-(1-(aminomethyl)-4-oxo-4H-thieno[3,4-c]pyrrol-5(6H)-yl)piperidine-2,6-dione 2,2,2-trifluoroacetic acid salt in DCM (5 mL) was added TEA (26.5 mg, 0.262 mmol). The mixture was cooled to 0° C. then bromoacetyl chloride (25 mg, 0.157 mmol) was added. The mixture was stirred at RT for 2 h. The solvent was removed under vacuum and the residue was purified on silica gel eluting with DCM/MeOH from 0% to 7% to give 2-bromo-N-((5-(2,6-dioxopiperidin-3-yl)-4-oxo-5,6-dihydro-4H-thieno[3,4-c]pyrrol-1-yl)methyl)acetamide (25 mg, 47.7%) as a white solid. MS (ESI) m/z 400.1, 402.1 [M+H, M+3]⁺.

To a solution of 3-((2-((4-(3-aminopropoxy)phenyl)amino)-5-methylpyrimidin-4-yl)amino)—N-(tert-butyl)benzenesulfonamide 2,2,2-trifluoroacetic acid salt (30.3 mg, 0.0625 mmol) in DMF (2 mL) was added K₂CO₃ (17.4 mg, 0.125 mmol), followed by 2-bromo-N-((5-(2,6-dioxopiperidin-3-yl)-4-oxo-5,6-dihydro-4H-thieno[3,4-c]pyrrol-1-yl)methyl)acetamide (25 mg, 0.0625 mmol). The suspension was heated at 50° C. for 3 h. The solvent was removed and the residue was purified by prep-HPLC to give 2-((3-(4-((4-((3-(N-(tert-butyl)sulfamoyl)phenyl)amino)-5-methylpyrimidin-2-yl)amino)phenoxy)propyl)amino)—N-((5-(2,6-dioxopiperidin-3-yl)-4-oxo-5,6-dihydro-4H-thieno[3,4-c]pyrrol-1-yl)methyl)acetamide (14.0 mg, 27.9%) as a white solid. ¹H NMR (400 MHz, DMSO-d₆) δ 10.98 (s, 1H), 8.76 (s, 1H), 8.53 (s, 1H), 8.49 (t, J=5.6 Hz, 1H), 8.13 (s, 2H), 7.90 (s, 1H), 7.85 (s, 1H), 7.55-7.49 (m, 5H), 6.78 (d, J=8.8 Hz, 2H), 4.99 (dd, J=4.8, 13.6 Hz, 1H), 4.41 (d, J=5.6 Hz, 2H), 4.30-4.15 (m, 3H), 3.95 (t, J=6.0 Hz, 2H), 3.15 (s, 2H), 2.91-2.82 (m, 1H), 2.64-2.54 (m, 4H), 2.33-2.26 (m, 1H), 2.12 (s, 3H), 1.97-1.91 (m, 1H), 1.84-1.80 (m, 1H), 1.24 (s, 9H). MS (ESI) m/z 803.7 [M+H]⁺.

Compound 60: 2-((S)-4-(4-Chlorophenyl)-2,3,9-trimethyl-6H-thieno[3,2-f][1,2,4]triazolo[4,3-a][1,4]diazepin-6-yl)-N-(4—((2-(((5-(2,6-dioxopiperidin-3-yl)-4-oxo-5,6-dihydro-4H-thieno[3,4-c]pyrrol-1-yl)methyl)amino)-2-oxoethyl)amino)butyl)acetamide

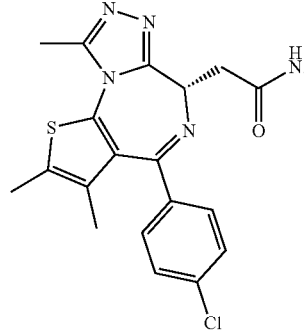

To a solution of (S)-2-(4-(4-chlorophenyl)-2,3,9-trimethyl-6H-thieno[3,2-f][1,2, 4]triazolo[4,3-a][1,4]diazepin-6-yl)acetic acid (40 mg, 0.1 mmol) in DMF (5 mL) at RT was added tert-butyl (4-aminobutyl)carbamate (22.4 mg, 0.12 mmol), followed by 2-(7-aza-1H-benzotriazole-1-yl)-1,1,3,3-tetramethyluronium hexafluorophosphate (HATU) (57 mg, 0.15 mmol) and DIEA (25.8 mg, 0.2 mmol). The mixture was stirred at RT for 10 h. The reaction was diluted with water (5 mL) and extracted with DCM (10 mL×2). The combined organic layers were dried over Na₂SO₄, filtered, and concentrated to give the crude (S)-tert-butyl (4-(2-(4-(4-chlorophenyl)-2,3,9-trimethyl-6H-thieno[3,2-f][1,2,4]triazolo[4,3-a][1,4]diazepin-6-yl)acetamido)butyl)carbamate (62 mg) as a white solid. MS (ESI) m/z 571.3[M+1]⁺.

To a solution of (S)-tert-butyl (4-(2-(4-(4-chlorophenyl)-2,3,9-trimethyl-6H-thieno[3,2-f][1,2,4]triazolo[4,3-a][1,4]diazepin-6-yl)acetamido)butyl)carbamate (62 mg, 0.1 mmol) in DCM (5 mL) was added 2,2,2-trifluoroacetic acid (1 mL) at RT. The mixture was stirred for 2 h. The solvent was removed to give (S)—N-(4-aminobutyl)-2-(4-(4-chlorophenyl)-2,3,9-trimethyl-6H-thieno[3,2-f][1,2,4]triazolo[4,3-a][1,4]diazepin-6-yl)acetamide 2,2,2-trifluoroacetic acid salt (50 mg, crude) which was used directly for the next step. MS (ESI) m/z 471.3 [M+1]⁺.

To a solution of (S)—N-(4-aminobutyl)-2-(4-(4-chlorophenyl)-2,3,9-trimethyl-6H-thieno[3,2-f][1,2,4]triazolo[4,3-a][1,4]diazepin-6-yl)acetamide 2,2,2-trifluoroacetic acid salt (47 mg, 0.1 mmol) in DMF (4 mL) was added K₂CO₃ (27.6 mg, 0.2 mmol), followed by 2-bromo-N-((5-(2,6-dioxopiperidin-3-yl)-4-oxo-5,6-dihydro-4H-thieno[3,4-c]pyrrol-1-yl)methyl)acetamide (60 mg, 0.15 mmol). The mixture was heated at 50° C. for 2 h then concentrated under vacuum and purified by prep-HPLC to give 2-((S)-4-(4-chlorophenyl)-2,3,9-trimethyl-6H-thieno[3,2-f][1,2,4]triazolo[4,3-a][1,4]diazepin-6-yl)-N-(4—((2-(((5-(2,6-dioxopiperidin-3-yl)-4-oxo-5,6-dihydro-4H-thieno[3,4-c]pyrrol-1-yl)methyl)amino)-2-oxoethyl)amino)butyl)acetamide (8.5 mg, 12.7%) as a white solid. ¹H NMR (400 MHz, DMSO-d₆) δ 8.50 (t, J=5.6 Hz, 1H), 8.20 (t, J=5.6 Hz, 1H), 7.84 (s, 1H), 7.49-7.40 (m, 4H), 5.00 (dd, J=4.0, 12.4 Hz, 1H), 4.51 (t, J=7.2 Hz, 1H), 4.41 (d, J=5.6 Hz, 2H), 4.30-4.15 (m, 3H), 3.26-3.21 (m, 4H), 3.11 (s, 3H), 2.92-2.82 (m, 1H), 2.58 (s, 3H), 2.61-2.56 (m, 2H), 2.34-2.25 (m, 1H), 2.00-1.94 (m, 2H), 1.61 (s, 3H), 1.44 (s, 4H). MS (ESI) m/z 789.6 [M+H]⁺.

Compound 61: (S)—N-(tert-Butyl)-3-((2-((4-(3-(3-((5-(2,7-dioxoazepan-3-yl)-4-oxo-5,6-dihydro-4H-thieno[3,4-c]pyrrol-1-yl)methyl)ureido)propoxy)phenyl)amino)-5-methylpyrimidin-4-yl)amino)benzenesulfonamide

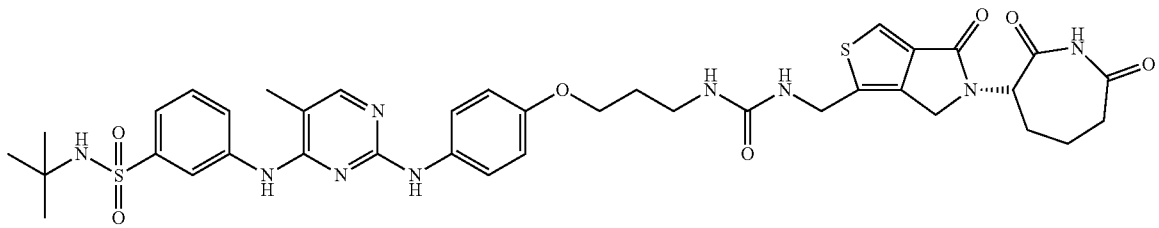

To a solution of (S)-3-(1-(aminomethyl)-4-oxo-4H-thieno[3,4-c]pyrrol-5(6H)-yl)azepane-2, 7-dione 2,2,2-trifluoroacetic acid salt in DCM (5 mL) was added TEA (12.7 mg, 0.127 mmol). The mixture was cooled to 0° C., then 4-nitrophenyl carbonochloridate (26 mg, 0.127 mmol) was added. The mixture was stirred at RT for 2 h and concentrated under vacuum to give (S)-4-nitrophenyl ((5-(2,7-dioxoazepan-3-yl)-4-oxo-5,6-dihydro-4H-thieno[3,4-c]pyrrol-1-yl)methyl)carbamate (70 mg, crude) as a yellow gum. MS (ESI) m/z 459.1[M+1]+.

To a solution of (S)-4-nitrophenyl ((5-(2,7-dioxoazepan-3-yl)-4-oxo-5,6-dihydro-4H-thieno[3,4-c]pyrrol-1-yl)methyl)carbamate (70 mg, crude, 0.127 mmol) in DCM (4 mL) was added TEA (26 mg, 0.254 mmol), then 3-((2-((4-(3-aminopropoxy)phenyl)amino)-5-methylpyrimidin-4-yl)amino)—N-(tert-butyl)benzenesulfonamide (62 mg, 0.127 mmol) was added. The mixture was stirred at RT for 2 h then concentrated and purified on silica gel eluting with DCM/MeOH from 0% to 9% and further purification by prep-HPLC to give (S)—N-(tert-butyl)-3-((2-((4-(3-(3-((5-(2,7-dioxoazepan-3-yl)-4-oxo-5,6-dihydro-4H-thieno[3,4-c]pyrrol-1-yl)methyl)ureido)propoxy)phenyl)amino)-5-methylpyrimidin-4-yl)amino)benzenesulfonamide (15.2 mg, 14.9%) as a white solid. $^1$H NMR (400 MHz, DMSO-d$_6$) δ 10.71 (s, 1H), 8.78 (s, 1H), 8.55 (s, 1H), 8.14 (s, 2H), 7.91 (s, 1H), 7.84 (s, 1H), 7.56-7.49 (m, 5H), 6.80 (d, J=9.2 Hz, 2H), 6.54 (t, J=4.8 Hz, 1H), 6.18 (t, J=5.6 Hz, 1H), 5.14 (dd, J=5.2, 12.4 Hz, 1H), 4.41-4.31 (m, 4H), 3.92 (t, J=5.6 Hz, 2H), 3.20-3.17 (m, 3H), 3.09-3.01 (m, 2H), 2.68-2.58 (m, 1H), 2.17 (s, 3H), 2.09-1.98 (m, 2H), 1.84-1.77 (m, 2H), 1.13 (s, 9H). MS (ESI) m/z 803.7 [M+1]+.

Compound 62: N-(tert-Butyl)-3-((2-((4-(3-(3-((5-(2,6-dioxopiperidin-3-yl)-4-oxo-5,6-dihydro-4H-thieno[3,4-c]pyrrol-1-yl)methyl)ureido)propoxy)phenyl)amino)-5-methylpyrimidin-4-yl)amino)benzenesulfonamide To a solution of tert-butyl (3-(4-((4-((3-(N-(tert-butyl)sulfamoyl)phenyl)amino)-5-methylpyrimidin-2-yl)amino)phenoxy)propyl)carbamate (55 mg, 0.094 mmol) in DCM (5 mL) at RT was added 2,2,2-trifluoroacetic acid (1 mL). The mixture was stirred for 2 h. The solvent was removed to give 3-((2-((4-(3-aminopropoxy)phenyl)amino)-5-methylpyrimidin-4-yl)amino)—N-(tert-butyl)benzenesulfonamide 2,2,2-trifluoroacetic acid salt (60 mg, crude), which was used directly for the next step.

3-((2-((4-(3-aminopropoxy)phenyl)amino)-5-methylpyrimidin-4-yl)amino)—N-(tert-butyl)benzenesulfonamide 2,2,2-trifluoroacetic acid salt (60 mg, crude) was dissolved in DCM (5 mL) and TEA (18.9 mg, 0.188 mmol) was added. The suspension was stirred at RT for 5 min. Then 4-nitrophenyl carbonochloridate (18.9 mg, 0.094 mmol) was added and the mixture was stirred at RT for 3 h. The solvent was removed to give crude 4-nitrophenyl (3-(4-((4-((3-(N-(tert-butyl) sulfamoyl)phenyl)amino)-5-methyl pyrimidin-2-yl)amino)phenoxy)propyl)carbamate (70 mg) as a yellow gum, which was used directly for the next step. MS (ESI) m/z 651.1[M+1]+.

To a solution of tert-butyl ((5-(2,6-dioxopiperidin-3-yl)-4-oxo-5,6-dihydro-4H-thieno[3,4-c]pyrrol-1-yl)methyl)carbamate (40 mg, 0.105 mmol) in DCM (5 mL) was added TFA (1 mL) at RT. The mixture was stirred for 1 h. The solvent was removed to give 3-(1-(aminomethyl)-4-oxo-4H-thieno[3,4-c]pyrrol-5(6H)-yl)piperidine-2,6-dione 2,2,2-trifluoroacetic acid salt (50 mg, crude) which was used directly for the next step.

3-(1-(aminomethyl)-4-oxo-4H-thieno[3,4-c]pyrrol-5(6H)-yl)piperidine-2,6-dione 2,2,2-trifluoroacetic acid salt was dissolved in DCM (5 mL) and TEA (21 mg, 0.21 mmol) was added. 4-nitrophenyl (3-(4-((4-((3-(N-(tert-butyl)sulfamoyl)phenyl)amino)-5-methylpyrimidin-2-yl)amino)phenoxy)propyl)carbamate (70 mg, crude) was added and the mixture was stirred at RT for 3 h. The solvent was removed under vacuum and the residue was purified on silica gel eluting with DCM/MeOH from 0% to 7% to give crude compound. It was purified by prep-TLC (DCM/MeOH=10/1) to give N-(tert-butyl)-3-((2-((4-(3-(3-((5-(2,6-dioxopiperidin-3-yl)-4-oxo-5,6-dihydro-4H-thieno[3,4-c]pyrrol-1-yl)methyl)ureido)propoxy)phenyl)amino)-5-methylpyrimidin-4-yl)amino)benzenesulfonamide (20 mg, 24.2%) as a white solid. MS (ESI) m/z 789.7 [M+1]+. $^1$H

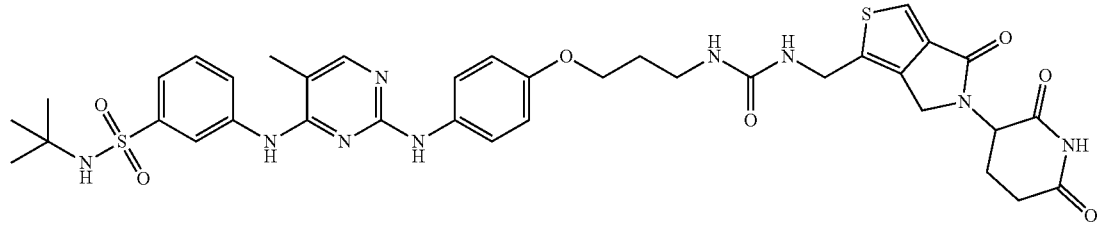 [SMILES: Cc1cnc(Nc2ccc(OCCCNC(=O)NCc3scc4c3CN(C3CCC(=O)NC3=O)C4=O)cc2)nc1Nc1cccc(S(=O)(=O)NC(C)(C)C)c1]

NMR (400 MHz, DMSO-d$_6$) δ 10.99 (s, 1H), 8.78 (s, 1H), 8.54 (s, 1H), 8.14 (s, 1H), 8.12 (s, 1H), 7.91 (s, 1H), 7.83 (s, 1H), 7.57 (s, 1H), 7.53 (d, J=8.4 Hz, 2H), 7.48 (t, J=4.4 Hz, 2H), 6.78 (d, J=8.8 Hz, 2H), 6.52 (t, J=4.8 Hz, 1H), 6.17 (t, J=6.0 Hz, 1H), 5.01 (dd, J=4.4, 13.6 Hz, 1H), 4.33 (d, J=6.0 Hz, 2H), 4.29-4.14 (m, 2H), 3.91 (t, J=6.0 Hz, 2H), 3.18-3.13 (m, 2H), 2.94-2.83 (m, 1H), 2.59-2.55 (m, 1H), 2.34-2.22 (m, 1H), 2.12 (s, 3H), 1.98-1.95 (m, 1H), 1.81-1.77 (m, 2H), 1.12 (s, 9H).

Compound 63: 2-((S)-4-(4-Chlorophenyl)-2,3,9-trimethyl-6H-thieno[3,2-f][1,2,4]triazolo[4,3-a][1,4]diazepin-6-yl)-N-(4—((2-(((5-((S)-2,7-dioxoazepan-3-yl)-4-oxo-5,6-dihydro-4H-thieno[3,4-c]pyrrol-1-yl)methyl)amino)-2-oxoethyl)amino)butyl)acetamide

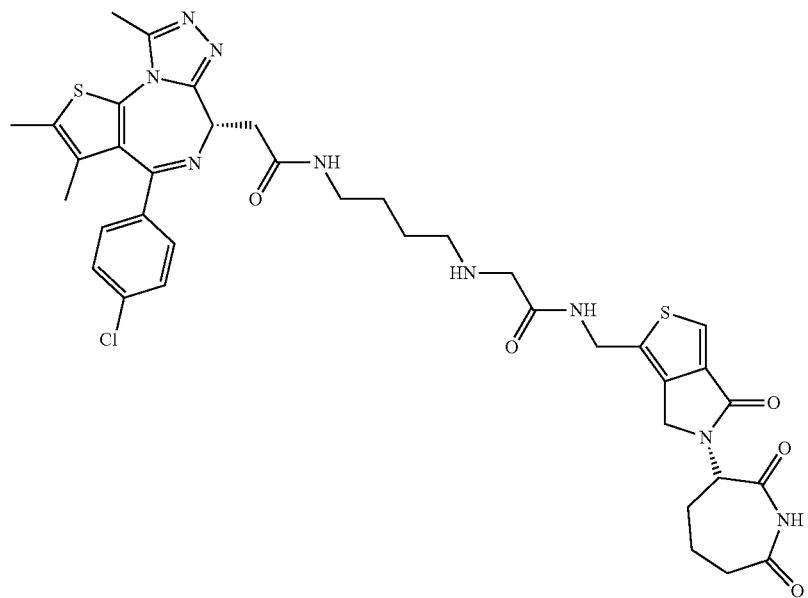

To a solution of (S)-2-bromo-N-((5-(2,7-dioxoazepan-3-yl)-4-oxo-5,6-dihydro-4H-thieno[3,4-c]pyrrol-1-yl)methyl)acetamide (42 mg, 0.088 mmol) in DMF (4 mL) was added $K_2CO_3$ (36.4 mg, 0.264 mmol), followed by (S)—N-(4-aminobutyl)-2-(4-(4-chlorophenyl)-2,3,9-trimethyl-6H-thieno[3,2-f][1,2,4]triazolo[4,3-a][1,4]diazepin-6-yl)acetamide (44 mg, 0.106 mmol). The suspension was heated at 50° C. for 4 h. The solvent was removed and the residue was purified by prep-TLC (DCM/MeOH=10/1) to give 2-((S)-4-(4-chlorophenyl)-2,3,9-trimethyl-6H-thieno[3,2-f][1,2,4]triazolo[4,3-a][1,4]diazepin-6-yl)-N-(4—((2-(((5-((S)-2,7-dioxoazepan-3-yl)-4-oxo-5,6-dihydro-4H-thieno[3,4-c]pyrrol-1-yl)methyl)amino)-2-oxoethyl)amino)butyl)acetamide (17 mg, 24.0%) as a white solid. MS (ESI) m/z 804.3[M+H]+ 1H NMR (400 MHz, DMSO-$d_6$) δ 10.72 (s, 1H), 8.57 (t, J=5.2 Hz, 1H), 8.20 (t, J=6.0 Hz, 1H), 7.85 (s, 1H), 7.49 (d, J=8.8 Hz, 2H), 7.41 (d, J=8.4 Hz, 2H), 5.13 (dd, J=5.2, 12.4 Hz, 1H), 4.51 (t, J=6.4 Hz, 1H), 4.44 (d, J=5.6 Hz, 2H), 4.36 (s, 2H), 3.28-3.22 (m, 4H), 3.17 (s, 2H), 3.09 (s, 2H), 3.05-3.00 (m, 1H), 2.61-2.50 (m, 2H), 2.58 (s, 3H), 2.40 (s, 3H), 2.19-2.13 (m, 1H), 2.07-1.98 (m, 2H), 1.82-1.75 (m, 1H), 1.61 (s, 3H), 1.46 (s, 4H).

Compound 64: 3-(3-Cyclopentyl-6-oxo-4H-thieno[2,3-c]pyrrol-5(6H)-yl)piperidine-2,6-dione

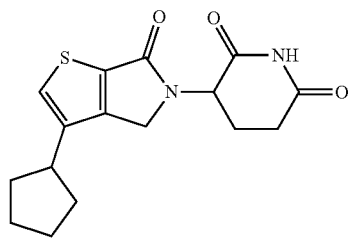 [SMILES: O=C1CCC(N2Cc3c(C4CCCC4)csc3C2=O)C(=O)N1]

To a solution of methyl 4-bromo-3-methylthiophene-2-carboxylate (5.0 g, 21.37 mmol) in carbon tetrachloride (90 mL) at RT was added N-bromosuccinimide (NBS) (4 g, 22.44 mmol) and dibenzoyl peroxide (BPO) (518 mg, 2.14 mmol). The mixture was stirred at 80° C. overnight. The reaction was cooled to RT and filtered. The filtrate was diluted with sat. aq. $NaHCO_3$, then extracted with dichloromethane. The combined organic layers were dried over $Na_2SO_4$, filtered, concentrated, and purified on silica gel eluting with petroleum to give methyl 4-bromo-3-(bromomethyl)thiophene-2-carboxylate (4.81 g, 72.1%) as a white solid 1H NMR (CDCl$_3$, 300 MHz) δ: 7.47 (s, 1H), 4.89 (s, 2H), 3.92 (s, 3H).

To a solution of methyl 4-bromo-3-(bromomethyl)thiophene-2-carboxylate (4.80 g, 15.35 mmol) and tert-butyl 4,5-diamino-5-oxopentanoate (4.41 g, 18.46 mmol) in DMF (80 mL) was added TEA (3.11 g, 30.770 mmol). The mixture was stirred at RT overnight then diluted with water and extracted with EA. The organic layers were concentrated, and the residue was purified on silica gel eluting with EA in petroleum (50%) to give methyl 3-(((1-amino-5-(tert-butoxy)-1,5-dioxopentan-2-yl)amino)methyl)-4-bromothiophene-2-carboxylate (5.92 g, 81.7%) as a white solid.

To a solution of methyl 3-(((1-amino-5-(tert-butoxy)-1,5-dioxopentan-2-yl)amino)methyl)-4-bromothiophene-2-carboxylate (1 g, 2.12 mmol) in tetrahydrofuran (20 mL) was added lithium hydroxide (5.3 mL, 0.56 N) slowly. The suspension was stirred at RT for 2 h then concentrated. Water was added, and the mixture was extracted with EA. The water phase was adjusted to a pH of 5-6 using HCl (1 N) dropwise then concentrated to give the crude 3-(((1-amino-5-(tert-butoxy)-1,5-dioxopentan-2-yl)amino)methyl)-4-bromothiophene-2-carboxylic acid (968 mg, 100%) as a white solid, used directly in the next step.

To a solution of 3-(((1-amino-5-(tert-butoxy)-1,5-dioxopentan-2-yl)amino)methyl)-4-bromothiophene-2-carboxylic acid (968 mg, 2.3 mmol) in DMF (20 mL) was added 2-(7-aza-1H-benzotriazole-1-yl)-1,1,3,3-tetramethyluronium hexafluorophosphate (HATU) (1.31 g, 3.45 mmol) and DIEA (590 mg, 4.60 mmol) at RT. The suspension was stirred at RT overnight. The mixture was diluted with water and extracted with EA. After removing the solvent under vacuum, the residue was washed with EA to give tert-butyl 5-amino-4-(3-bromo-6-oxo-4H-thieno[2,3-c]pyrrol-5(6H)-yl)-5-oxopentanoate (461 mg, 48.2%) as a white solid. $^1$H NMR (CDCl$_3$, 400 MHz) δ: 7.56 (s, 1H), 6.40 (s, 1H), 5.56 (s, 1H), 4.86-4.82 (m, 1H), 4.48 (d, J=18.4, 1H), 4.28 (d, J=18.0, 1H), 2.37-2.10 (m, 1H), 1.43 (s, 9H).

To a solution of tert-butyl 5-amino-4-(3-bromo-6-oxo-4H-thieno[2,3-c]pyrrol-5(6H)-yl)-5-oxopentanoate (400 mg, 0.99 mmol) in dioxane/water (12 mL/1.2 mL) was added 2-(cyclopent-1-en-1-yl)-4,4,5,5-tetramethyl-1,3,2-dioxaborolane (288 mg, 1.49 mmol), tetrakis(triphenylphosphine)palladium [Pd(PPh$_3$)$_4$] (232 mg, 0.20 mmol) and cesium carbonate (808 mg, 2.48 mmol). The atmosphere was replaced with nitrogen, and the mixture was stirred at 90° C. overnight. The mixture was then cooled to RT, concentrated, and diluted with water and extracted with DCM. The combined organic layers were dried over Na$_2$SO$_4$, filtered, and concentrated to give crude product, which was purified on silica gel eluting with EA in petroleum (50% to 100%) to give tert-butyl 5-amino-4-(3-(cyclopent-1-en-1-yl)-6-oxo-4H-thieno[2,3-c]pyrrol-5(6H)-yl)-5-oxopentanoate (302 mg, 77.8%) as a light-yellow solid. MS (ESI) m/z=391.0 [M+H]$^+$.

To a solution of tert-butyl 5-amino-4-(3-(cyclopent-1-en-1-yl)-6-oxo-4H-thieno[2,3-c]pyrrol-5(6H)-yl)-5-oxopentanoate (250 mg, 0.64 mmol) in THF (10 mL) at RT was added Pd/C (125 mg) and the suspension was stirred for 5 days. The mixture was filtered through celite then concentrated under vacuum to afford tert-butyl 5-amino-4-(3-cyclopentyl-6-oxo-4H-thieno[2,3-c]pyrrol-5(6H)-yl)-5-oxopentanoate (251 mg, 100%) as a yellow solid. MS (ESI) m/z=393.2 [M+H]$^+$.

To a solution of tert-butyl 5-amino-4-(3-cyclopentyl-6-oxo-4H-thieno[2,3-c]pyrrol-5(6H)-yl)-5-oxopentanoate (70 mg, 0.179 mmol) in DCM (6 mL) was added 2,2,2-trifluoroacetic acid (1.5 mL) at 0° C. then the mixture was stirred at RT for 1 h. The solvent was removed under vacuum to give 5-amino-4-(3-cyclopentyl-6-oxo-4H-thieno[2,3-c]pyrrol-5(6H)-yl)-5-oxopentanoic acid (60 mg, yield: 100%) as a crude solid.

To a solution of 5-amino-4-(3-cyclopentyl-6-oxo-4H-thieno[2,3-c]pyrrol-5(6H)-yl)-5-oxopentanoic acid (60 mg, 0.179 mmol) in ACN (6 mL) was added N,N'-carbonyldiimidazole (115.7 mg, 0.716 mmol) then the mixture was refluxed at 90° C. overnight. The solvent was removed under vacuum to give the crude product, which was purified on silica gel eluting with EA in petroleum (100%) to give 3-(3-cyclopentyl-6-oxo-4H-thieno[2,3-c]pyrrol-5(6H)-yl)piperidine-2,6-dione (47.1 mg, 82.9%) as a white solid. $^1$H NMR (DMSO-d$_6$, 400 MHz) δ: 10.97 (s, 1H), 7.65 (d, J=15.2, 1H), 5.00 (dd, J=12.8, 4.8 Hz, 1H), 4.41 (d, J=17.6, 1H), 4.25 (d, J=17.6, 1H), 3.09-3.00 (m, 1H), 3.00-2.84 (m, 1H), 2.58 (d, J=16.4, 1H), 2.43-2.32 (m, 1H), 2.03-1.98 (m, 3H), 1.78-1.50 (m, 6H). MS (ESI) m/z=393.2 [M+H]$^+$.

Compound 65: 1-(3-chloro-4-methylphenyl)-3-((5-(2,6-dioxopiperidin-3-yl)-4-oxo-5,6-dihydro-4H-thieno[2,3-c]pyrrol-2-yl)methyl)urea

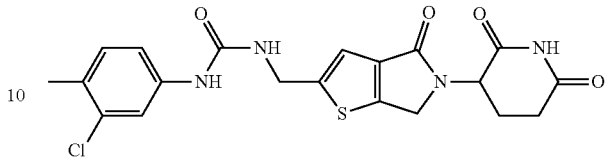

Compound 65 was prepared analogously to compounds previously described herein. $^1$H NMR (400 MHz, DMSO-d$_6$) δ 10.95 (s, 1H), 8.75 (s, 1H), 7.66 (s, 1H), 7.19-7.02 (m, 3H), 6.83 (t, J=6.0 Hz, 1H), 5.04-4.99 (m, 1H), 4.49 (d, J=6.0 Hz, 2H), 4.33 (m, 2H), 2.89 (m, 1H), 2.58 (d, J=16.4, 1H), 2.32-2.28 (m, 1H), 2.23 (s, 3H), 2.00-1.95 (m, 1H). MS (ESI) m/z=447 [M+H]$^+$.

Compound 66: 3-(1-cyclopentyl-4-oxo-4H-thieno[3,4-c]pyrrol-5(6H)-yl)piperidine-2,6-dione

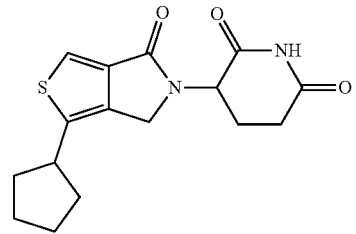 [SMILES: O=C1CCC(N2Cc3c(csc3C3CCCC3)C2=O)C(=O)N1]

Compound 66 was prepared analogously to compounds previously described herein. $^1$H NMR (400 MHz, DMSO-d$_6$) δ 10.96 (s, 1H), 7.79 (s, 1H), 5.00 (m, 1H), 4.32 (m, 2H), 3.23 (m, 1H), 2.89 (m, 1H), 2.56 (m, 1H), 2.36 (m, 1H), 2.10 (m, 2H), 1.96 (m, 1H), 1.75 (m, 2H), 1.55-1.65 (m, 4H). MS (ESI) m/z=319 [M+H]$^+$.

Cell-Based Assays

Frozen primary blood mononuclear cells (PBMCs) and frozen CD14+ mobilized peripheral blood monocytes were purchased from AllCells. Cells were quick thawed, and washed 1-time with RPMI-1640/10% FBS/1% Penicillin/1% Streptomycin and plated in 96-well plates at 200,000 cells per well. Cells were pretreated with DMSO only, Compound 5013 (lenolidamide) or the indicated compound for 1 h and then induced with 100 ng/mL lipopolysaccharide (LPS) for 18-24 h. The supernatant was analyzed for IL-1 beta, IL-6, and TNF-α using Meso Scale assay according to manufacturer's protocol. The negative control wells were treated with DMSO.

For the IL-2 analysis, 96 well plates were precoated with 1 ug/mL anti-human CD3 antibody (OKT3, eBioscience Inc.). After washing with PBS, compounds were added to the wells (50 μL/well) followed by PBMCs diluted at 3-4 million cells/mL (150 μL/well). Plates were incubated for 24 h and the supernatants collected for Mesoscale IL-2 analysis.

Figure 2:
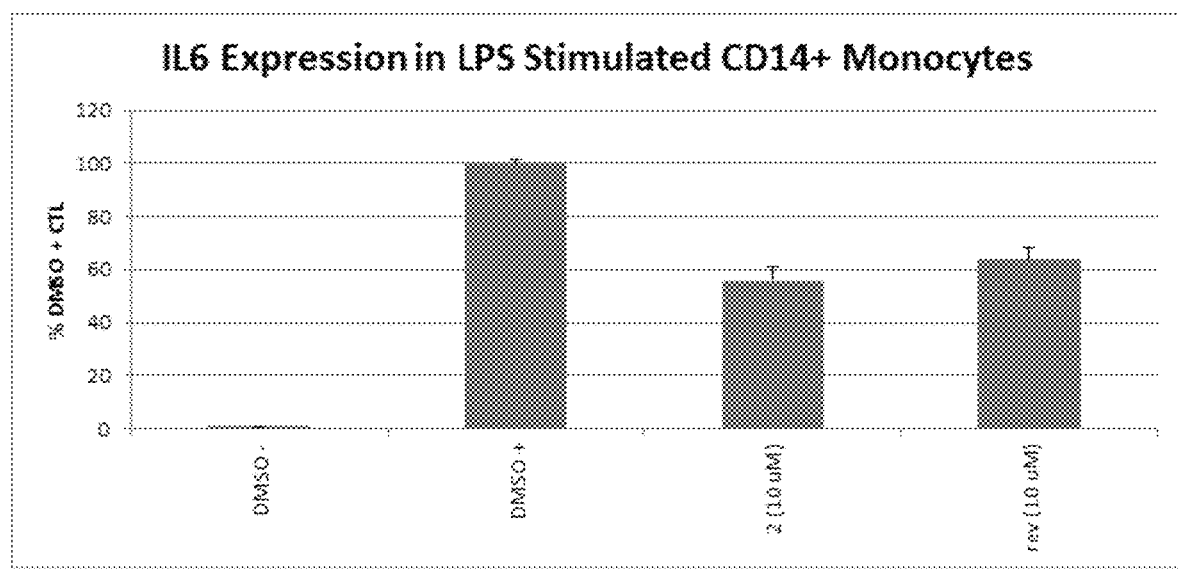
FIG. 2 is a graph showing IL-6 expression in LPS stimulated CD14+ monocytes. CD14+ monocytes were plated in 96-well plates and pretreated with compound (10 µM Compound 2 or 10 µM lenalidomide (rev)) for 1 h, and then induced with 100 ng/mL LPS for 18-24 h. Cytokines were measured according to MesoScale protocol. Negative control wells were treated with DMSO. Compound activity was measured as a percentage of LPS-induced activity.
Figure 3:
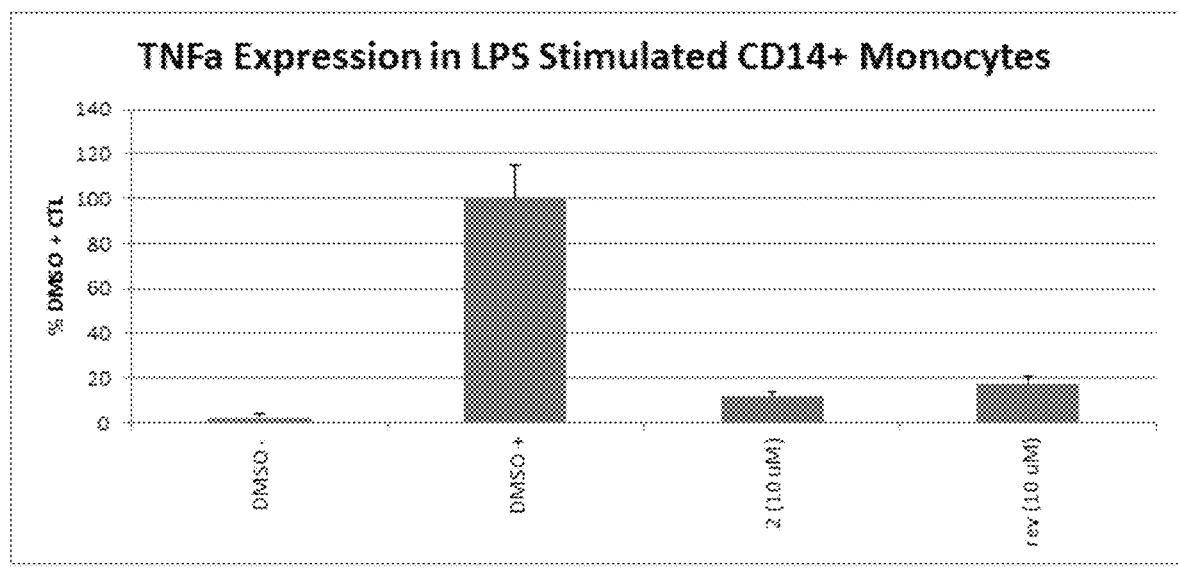
FIG. 3 is a graph showing TNF-α expression in LPS stimulated CD14+ monocytes. CD14+ monocytes were plated in 96-well plates and pretreated with compound (10 µM Compound 2 or 10 µM lenalidomide (rev)) for 1 h, and then induced with 100 ng/mL LPS for 18-24 h. Cytokines were measured according to MesoScale protocol. The negative control wells were treated with DMSO. Compound activity was measured as a percentage of LPS-induced activity.
Figure 4:
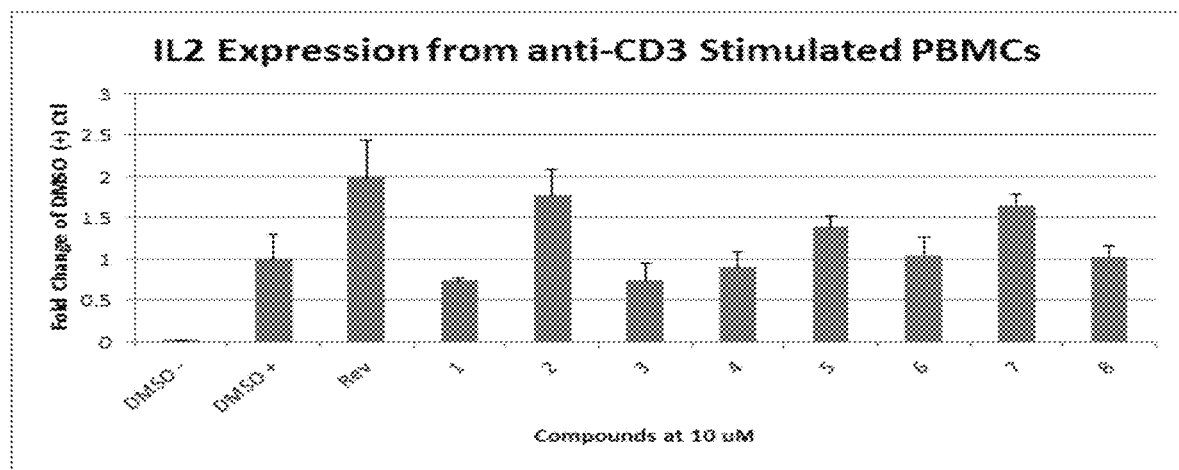
FIGS. 4 and 9D are graphs showing anti-CD3-induced IL-2 secretion in PBMCs. 1 ug/mL anti-CD3 (OKT-3) antibody in PBS were coated onto 96-well plates overnight at 4° C. Approximately 550,000 PBMCs were added to each well, followed by addition of DMSO only, Compound 1-8 at 10 µM (FIG. 4) or Compound 9 at 0.1 µM or 1 µM (FIG. 9D), or 10 µM lenalidomide (rev). Induction was measured after 24 h as fold difference from the DMSO stimulated control.

Compound activity was measured as fold difference from the DMSO control. IL-1-beta activity is shown in FIG. 1; IL-6 activity is shown in FIG. 2; TNF-α activity is shown in FIG. 3; and IL-2 activity is shown in FIG. 4.

PBMCs: AllCells PB003F, Normal Peripheral Blood MNC.

Media: RPMI 1640/10% FBS/1% Pen-Strep.

Figure 5:
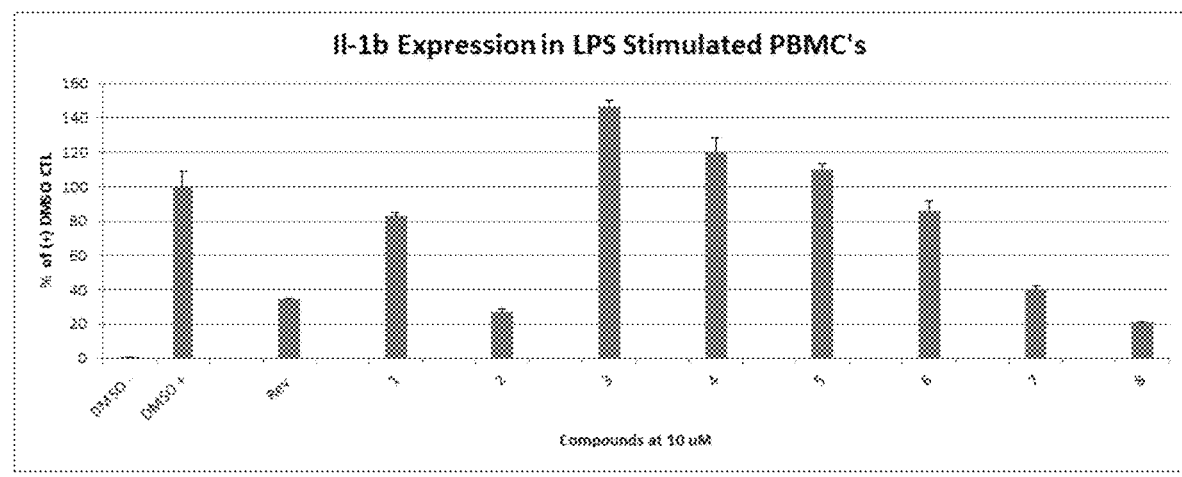
FIGS. 5 and 9A are graphs showing IL-1-beta expression in LPS stimulated peripheral blood mononuclear cells (PBMCs). PBMCs were plated in 96-well plates and pretreated with compound (Compound 1-9 individually) for 1 h, and then induced with 100 ng/mL LPS for 18-24 h. Cytokines in the media were measured according to MesoScale protocol. Negative control wells were treated with DMSO. Compound activity is measured as a percentage of LPS-induced activity. "Rev" is lenalidomide.
Figure 6:
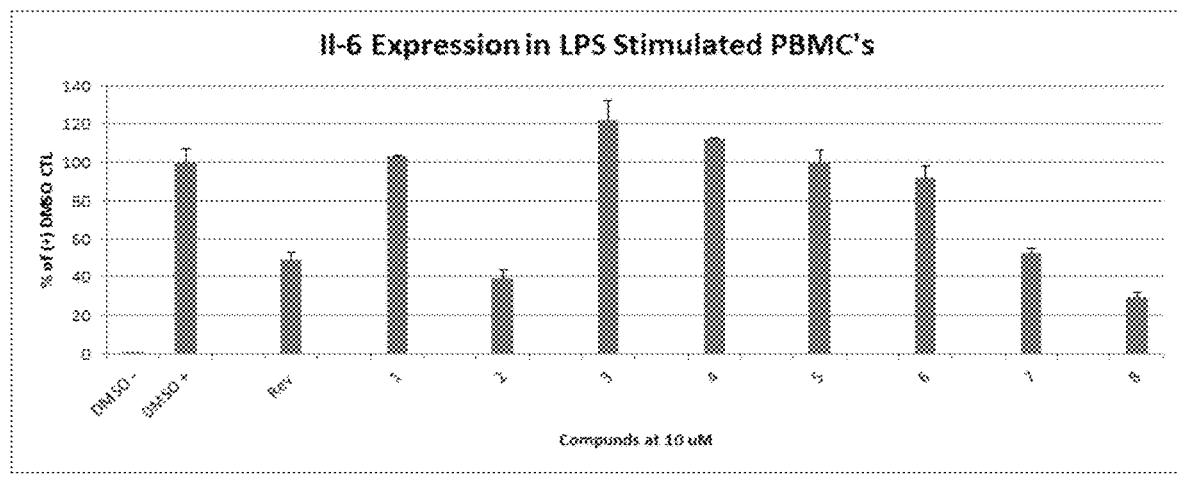
FIGS. 6 and 9B are graphs showing IL-6 expression in LPS stimulated peripheral blood mononuclear cells (PBMCs). PBMCs were plated in 96-well plates and pretreated with compound (Compound 1-9 individually) for 1 h, and then induced with 100 ng/mL LPS for 18-24 h. Cytokines were measured according to MesoScale protocol. Negative control wells were treated with DMSO. Compound activity was measured as a percentage of LPS-induced activity. "Rev" is lenalidomide.
Figure 7:
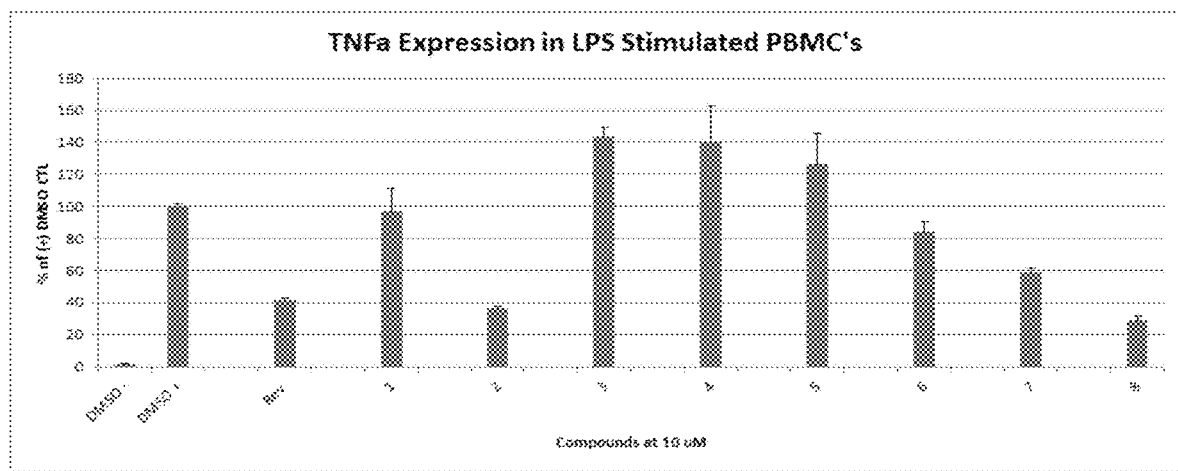
FIGS. 7 and 9C are graphs showing TNF-α expression in LPS stimulated peripheral blood mononuclear cells (PBMCs). PBMCs were plated in 96-well plates and pretreated with compound (Compound 1-9 individually) for 1 h, and then induced with 100 ng/mL LPS for 18-24 h. Cytokines in the media were measured according to MesoScale protocol. The negative control wells were treated with DMSO. Compound activity is measured as a percentage of LPS-induced activity. "Rev" is lenalidomide.
Figure 8A:
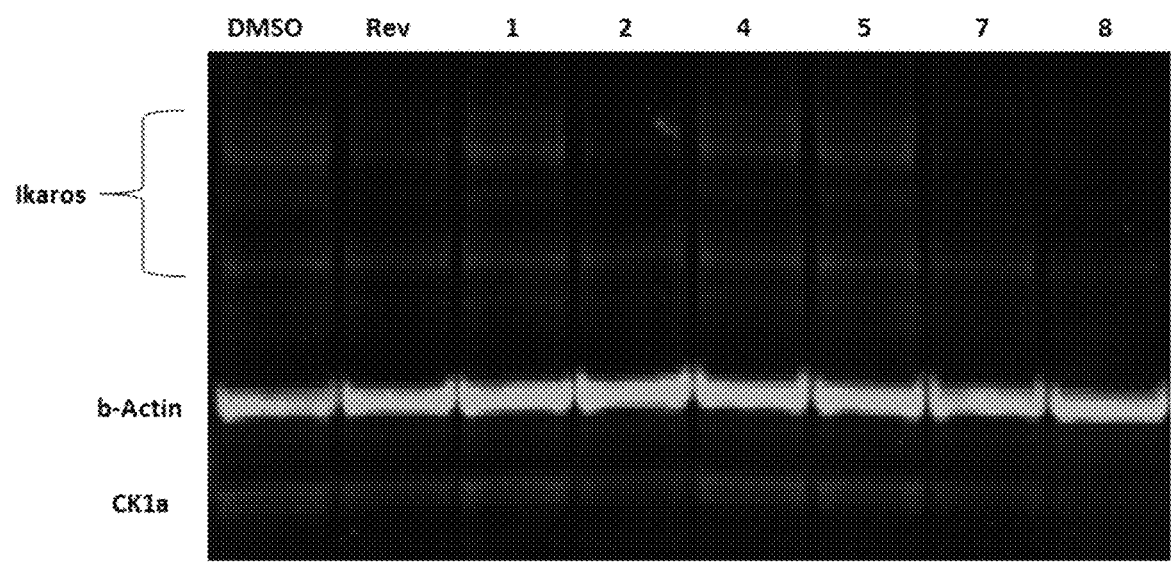
FIG. 8A shows the results of a Western Blot analysis of Jurkat cells treated with Control (DMSO only), or 10 µM compound (Compound 1, 2, 4, 5, 7, and 8) or lenalidomide (Rev). Cells were lysed using RIPA Buffer (Pierce) and a Western Blot analysis was performed using anti-ikaros, anti-CK1α, and anti-β-actin antibodies.
Figure 8B:
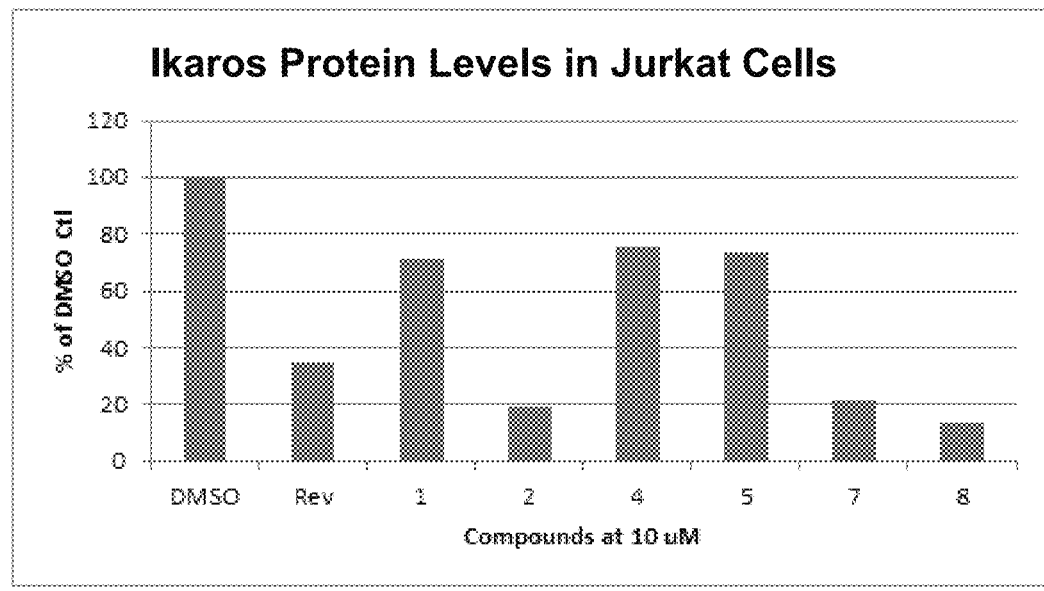
FIG. 8B is a graph showing the expression of ikaros protein in Jurkat cells after being treated with DMSO, compound, or Rev.
Figure 8C:
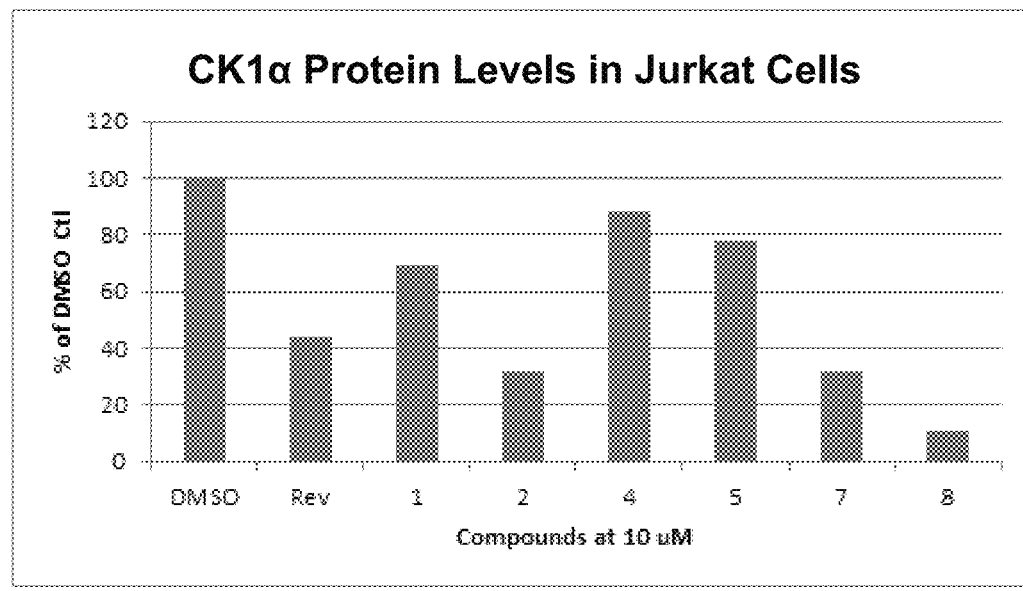
FIG. 8C is a graph showing the expression of CK1α protein in Jurkat cells after being treated with DMSO, compound, or Rev. Protein expression levels were measured using the LiCor Odyssey instrumentation and methods.
Figure 9A:
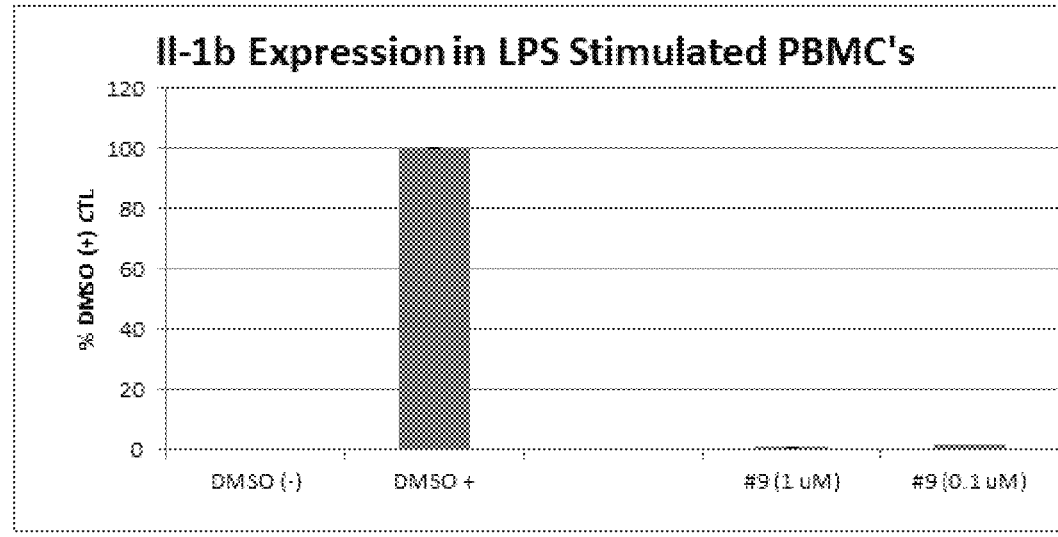
Figure 9B:
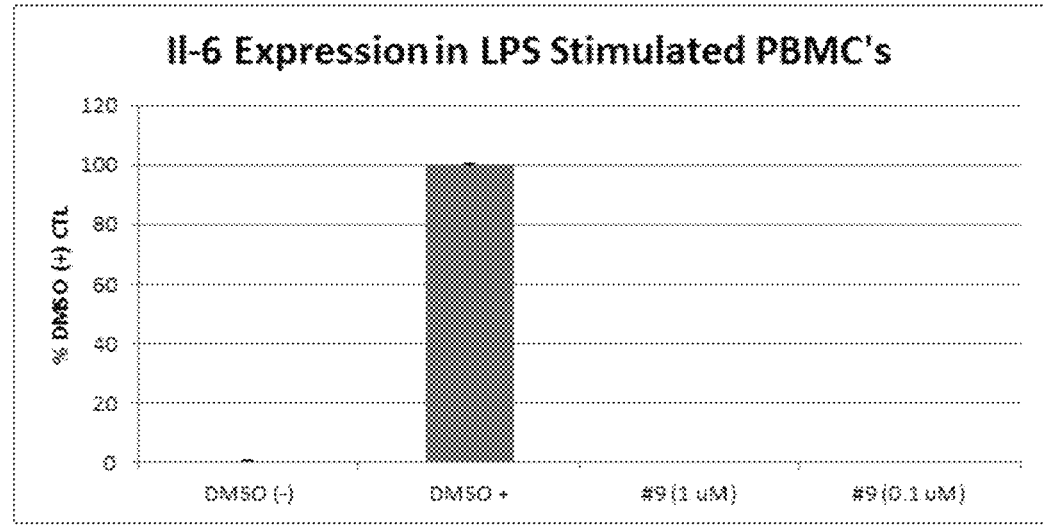
Figure 9C:
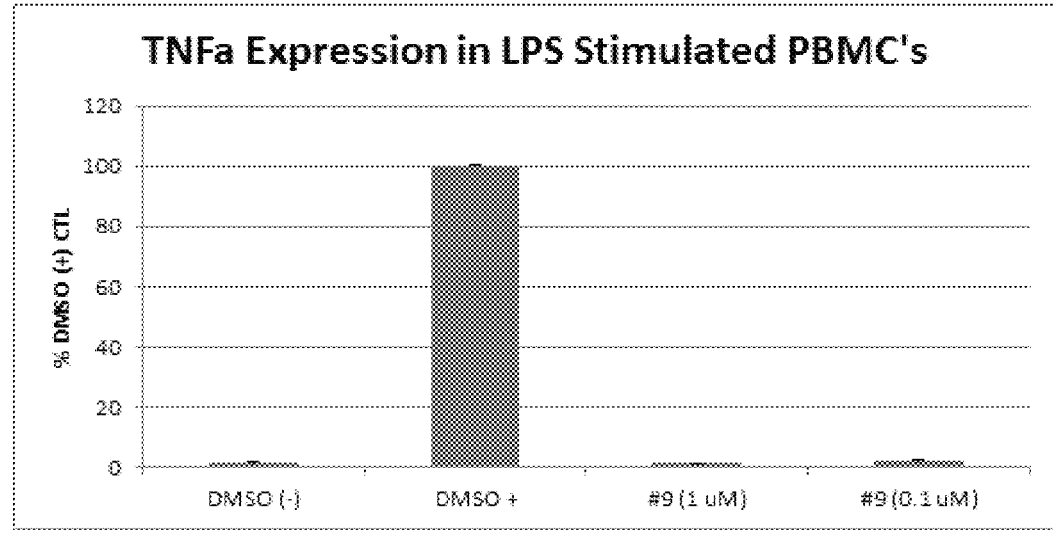
Figure 9D:
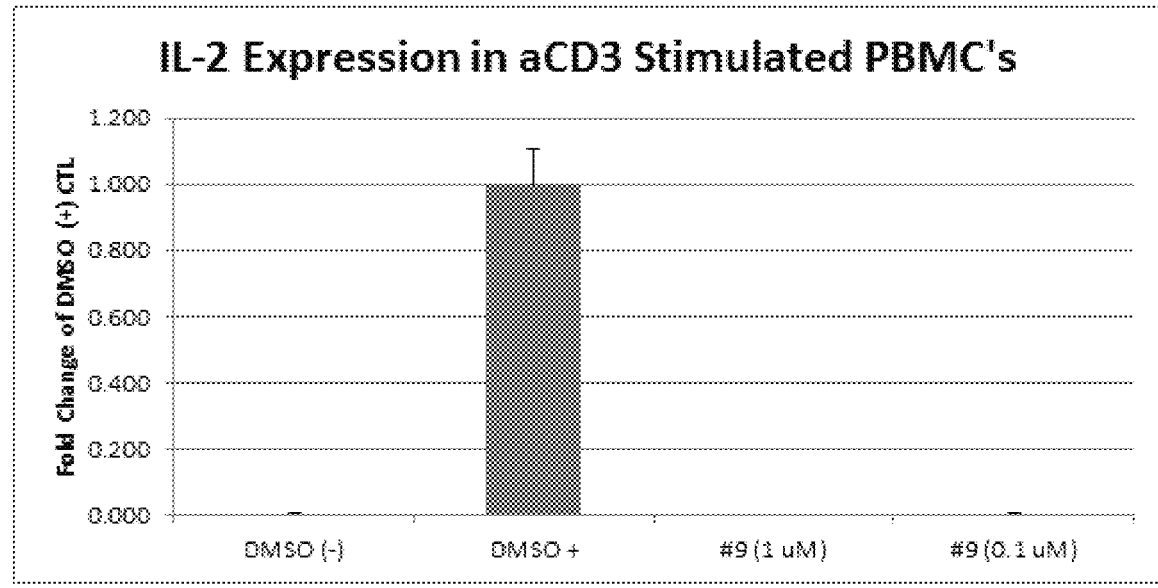

Compounds 2 and 8 reduced expression of IL-1-b in LPS-stimulated PBMCs by over 80%, relative to a just over 60% reduction with an equimolar concentration of lenalidomide (FIG. 5). Compounds 2 and 8 also reduced IL-6 levels in LPS-stimulated PBMCs by 60-75%, compared with a below 60% reduction in expression for cells treated with lenalidomide (FIG. 6). Compounds 2 and 8 also reduced expression of TNF-α in LPS-stimulated PBMCs by 60-75%, relative to a less than 60% reduction with an equimolar concentration of lenalidomide (FIG. 7). Inhibition data for additional compounds are shown in Table 1.

TABLE 1

Protein Levels at Indicated Compound Concentration

| Compound No. | Concentration (μM) | % Inhibition IL-1β | % Inhibition IL-6 | % Inhibition TNF-α | Fold Change IL-2 |
|---|---|---|---|---|---|
| DMSO | 0.1% | 0% | 0% | 0% | 1.0 |
| 1 | 5 | 25 | 0 | 22 | 0.8 |
| 2 | 5 | 88 | 31 | 65 | 1.9 |
| 3 | 10 | 0 | 0 | 0 | 0.9 |
| 4 | 10 | 0 | 0 | 0 | 0.7 |
| 5 | 10 | 0 | 1 | 0 | 1.4 |
| 6 | 10 | 14 | 8 | 16 | 1 |
| 7 | 10 | 60 | 47 | 41 | 1.7 |
| 8 | 10 | 80 | 71 | 71 | 1 |
| 9 | 0.1 | 98 | 100 | 98 | 0 |
| 10 | 10 | 21 | 13 | 37 | 0.6 |
| 11 | 10 | 65 | 26 | 46 | 2.6 |
| 12 | 10 | 52 | 0 | 56 | 0.8 |
| 13 | 10 | 90 | 66 | 84 | 1.2 |
| 14 | 10 | 88 | 65 | 85 | 1.5 |
| 15 | 10 | 67 | 56 | 55 | 0.7 |
| 16 | 10 | 80 | 51 | 78 | 2.2 |
| 17 | 10 | 4 | 14 | 26 | 1 |
| 18 | 10 | 36 | 32 | 48 | 0.9 |
| 19 | 10 | 79 | 78 | 59 | 4 |
| 20 | 10 | 50 | 19 | 58 | 2.2 |
| 21 | 10 | 74 | 73 | 74 | 2.9 |
| 22 | 10 | 0 | 16 | 26 | 0.8 |
| 23 | 10 | 69 | 45 | 82 | 2 |
| 24 | 10 | 11 | 6 | 23 | 0.7 |
| 25 | 10 | 45 | 22 | 41 | 1.3 |
| 26 | 10 | 2 | 14 | 31 | 0.9 |
| 27 | 10 | 21 | 3 | 22 | 0.8 |
| 28 | 10 | 0 | 9 | 0 | 0.9 |
| 29 | 10 | 57 | 19 | 60 | — |
| 30 | 1 | 81 | 98 | 84 | 0.4 |
| 31 | 1 | 76 | 40 | 80 | 1.7 |
| 32 | 0.1 | 67 | 65 | 62 | 0.8 |
| 33 | 0.1 | 95 | 99 | 95 | 0.3 |
| 34 | 1 | 70 | 39 | 69 | 1.6 |
| 35 | 1 | 44 | 16 | 39 | 1.4 |
| 36 | 1 | 40 | 38 | 33 | 0.8 |
| 37 | 1 | 4 | 3 | 6 | 1.1 |
| 38 | 1 | 84 | 94 | 87 | 0.6 |
| 39 | 1 | 24 | 0 | 18 | 1.4 |
| 40 | 1 | 37 | 17 | 34 | 0.3 |
| 41 | 1 | 89 | 95 | 90 | 0.3 |
| 42 | 1 | 91 | 97 | 90 | 0.4 |
| 43 | 1 | 73 | 88 | 77 | 0.5 |
| 44 | 1 | 45 | 6 | 41 | 1 |
| 45 | 1 | 19 | 18 | 22 | — |
| 46 | 0.1 | 54 | 85 | 58 | — |
| 47 | 0.1 | 99 | 100 | 97 | — |
| 48 | 0.1 | 96 | 100 | 92 | — |
| 49 | 0.1 | 61 | 87 | 62 | — |
| 50 | 1 | 14 | 0 | 1 | — |
| 51 | 1 | 38 | 5 | 49 | — |
| 52 | 0.1 | 98 | 100 | 95 | — |
| 53 | 0.1 | 60 | 90 | 65 | — |
| 54 | 0.1 | 96 | 100 | 93 | — |
| 55 | 0.1 | 99 | 100 | 96 | — |
| 56 | 1 | 55 | 12 | 59 | — |
| 57 | 1 | 42 | 32 | 44 | — |
| 58 | 10 | 82 | 53 | 92 | 1.9 |
| 59 | 10 | 45 | 10 | 81 | 1.8 |
| 60 | 1 | 91 | 95 | 93 | 0.2 |
| 61 | 10 | 53 | 11 | 66 | 0.8 |
| 62 | 10 | 51 | 15 | 63 | — |
| 63 | 10 | 27 | 1 | 34 | — |
| 64 | 10 | 22 | 8 | 45 | — |

TABLE 2

GSPT1 Protein Levels at 100 nM Compound Concentration

| Compound No. | GSPT1 Protein Levels |
|---|---|
| DMSO | 100.00 |
| 30 | 42.68 |
| 9 | 6.77 |
| 31 | 131.32 |
| 32 | 61.69 |
| 33 | 5.90 |
| 34 | 84.88 |
| 35 | 112.06 |
| 37 | 123.56 |
| 38 | 49.00 |
| 39 | 87.44 |
| 40 | 46.04 |
| 41 | 55.24 |
| 42 | 50.70 |
| 43 | 56.02 |
| 36 | 92.87 |
| 44 | 57.33 |
| 45 | 90.35 |
| 52 | 0.58 |
| 46 | 65.15 |
| 53 | 23.47 |
| 47 | 0.64 |
| 54 | 2.25 |
| 48 | 1.46 |
| 55 | 1.51 |
| 49 | 11.93 |
| 57 | 265.24 |

TABLE 3

GSPT1 Protein Levels at 1 μM Compound Concentration

| Compound No. | GSPT1 Protein Levels |
|---|---|
| DMSO | 100.00 |
| 30 | 5.28 |
| 9 | 5.31 |
| 31 | 107.70 |
| 32 | 29.34 |
| 33 | 5.50 |
| 34 | 37.47 |
| 35 | 44.46 |
| 37 | 153.84 |
| 38 | 5.52 |
| 39 | 95.98 |
| 40 | 39.98 |
| 41 | 6.40 |
| 42 | 8.44 |
| 43 | 14.23 |
| 36 | 32.62 |

TABLE 3-continued

GSPT1 Protein Levels at 1 µM Compound Concentration

| Compound No. | GSPT1 Protein Levels |
|---|---|
| 44 | 53.61 |
| 45 | 22.34 |
| 52 | 1.05 |
| 46 | 4.73 |
| 53 | 6.18 |
| 47 | 2.61 |
| 54 | 2.72 |
| 48 | 3.85 |
| 55 | 2.86 |
| 49 | 20.01 |
| 57 | 28.42 |

Western Blot Analysis

Western Blot Protocol: Cell lines were grown in RPMI 1640 supplemented with streptomycin, penicillin and 10% fetal bovine serum.

Cells were cultured at approximately $10^6$ cells per mL and incubated in DMSO or each of the indicated compounds for 6-8 h. Whole cell extracts were prepared using RIPA buffer according to manufacturer's protocol (Pierce). Briefly, $2\times10^6$ cells were washed once in PBS, the cell pellets were resuspended in RIPA buffer and allowed to incubate for 15 minutes on ice. Cells debris was removed by centrifugation and the cleared whole cell lysates were transferred to new tubes for further analysis.

For Western blot analysis, whole cell protein extracts were separated on 4-12% SDS-polyacrylamide gels, transferred to nitrocellulose, and probed with the indicated primary antibodies. Membranes were subsequently washed and probed with the appropriate IRDye secondary antibodies (LI-COR). The signal was detected using the Odyssey Imaging System (LI-COR).

The following antibodies were used in these studies:
β-actin: Mouse anti-b-Actin was obtained from Cell Signaling, 8H10D10 (Danvers, Mass.)
GSPT1: Rabbit anti-GSPT1 was obtained from Abcam, ab126090 (Cambridge, Eng.) CK1α goat polyclonal antibody: Santa Cruz Biotechnology, sc-6477 (Santa Cruz, Calif.) Casein kinase 1 epsilon goat polyclonal antibody: Santa Cruz Biotechnology, sc-6471 (Santa Cruz, Calif.)
Ikaros rabbit monoclonal antibody: Cell Signaling, #9034, D10E5 (Danvers, Mass.)
Donkey anti-goat IgG-HRP: Santa Cruz Biotechnology, sc-2056 (Santa Cruz, Calif.)
Goat anti-rabbit IgG-HRP: Cell Signaling, #7074 (Danvers, Mass.)
Goat anti-mouse IgG-HRP: Sigma, A4416 (St. Louis, Mo.)
Anti-eRF3/GSPT1 antibody: Abcam, ab126090 (Cambridge, Mass.)
β-Actin (8H10D10) mouse monoclonal antibody: Cell Signaling Technology, #3700 (Danvers, Mass.)
IRDye 680RD Goat anti-rabbit antibody: LI-COR, 926-68071 (Lincoln, Nebr.)
IRDye 800CW Goat anti-mouse antibody: LI-COR, 926-32210 (Lincoln, Nebr.)

Cell Viability Assays

Molm-13 cells were cultivated in RPMI-1640 (10% FBS/1% pen-strep) and were plated in white walled 96-well plates at 20,000 cells/well. H1048 cells were cultured in DMEM:F12 media supplemented with 5% fetal bovine serum, insulin, transferrin, sodium selenite, hydrocortisone, β-estradiol, penicillin and streptomycin, and were plated in white walled 96-well plates at 20,000 cells/well. MDA-MB-231 cells were cultured in DMEM media supplemented with 10% fetal bovine serum, penicillin and streptomycin, and were plated in white walled 96-well plates at 10,000 cells/well. Cells were treated with compound or DMSO (0.1%, control) and the cultures were incubated for 3 days at 37° C. and 5% $CO_2$. Following the incubation period, 100 µL of CellTiterGlow (CTG) reagent (CellTiter-Glo® Luminescent Cell Viability Assay, Promega (Madison, Wis.)) was added to each well. Following a 10 min incubation with shaking, luminescence was measured using a Victor Wallac Luminometer.

Figure 10A:
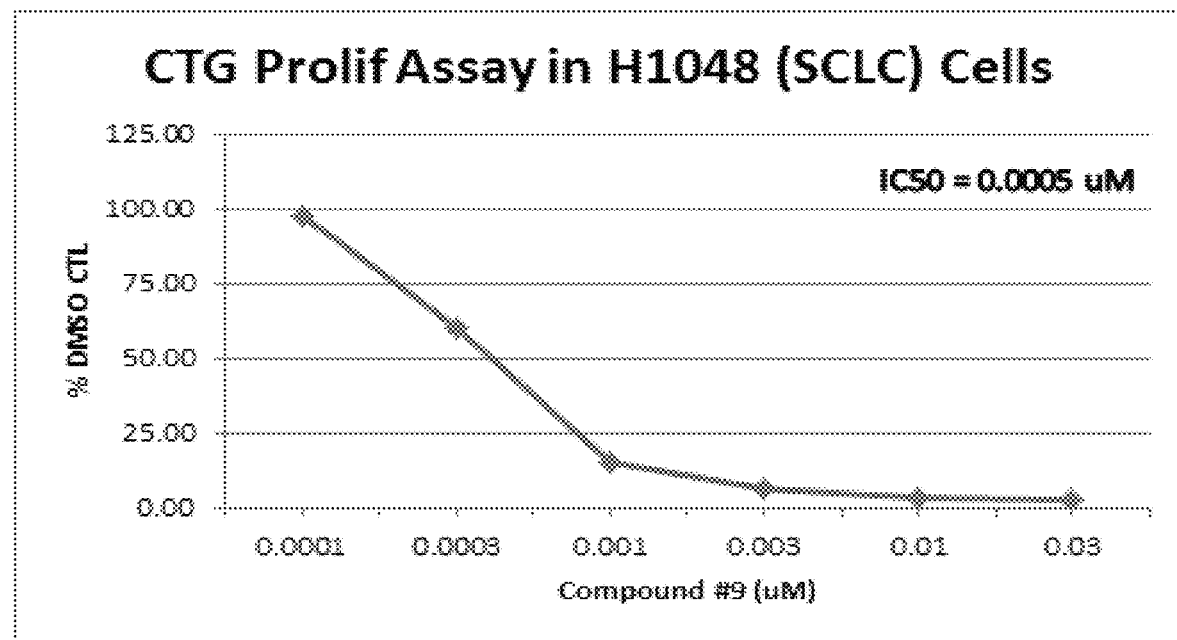
FIG. 10A is a graph showing antiproliferative activity in H1048 (SCLC) cells.
Figure 10B:
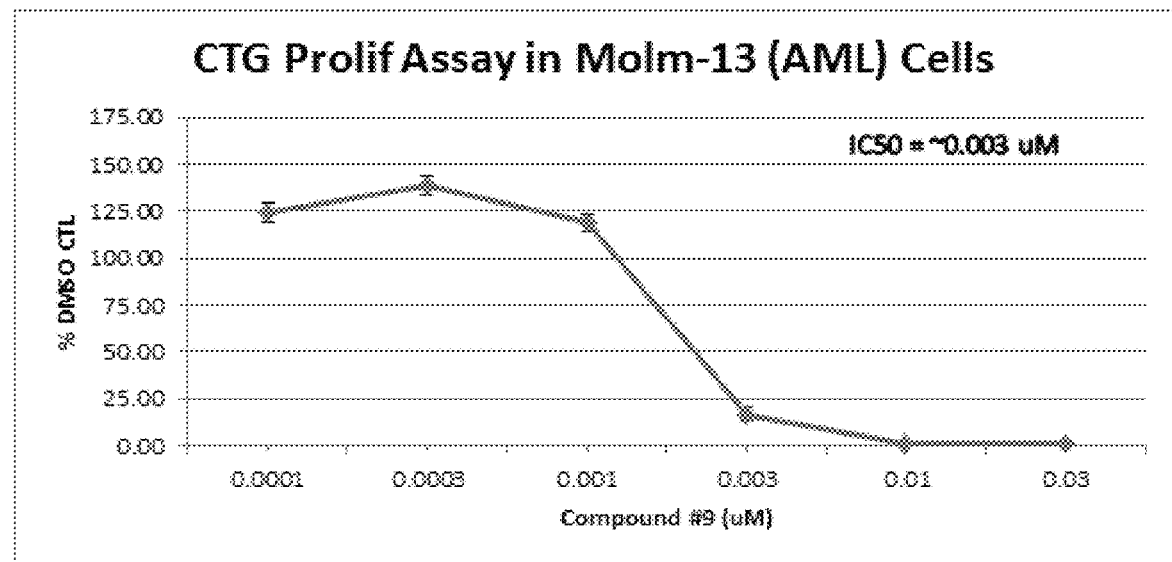
FIG. 10B is a graph showing antiproliferative activity in Molm-13 (AML) cells.
Figure 11A:
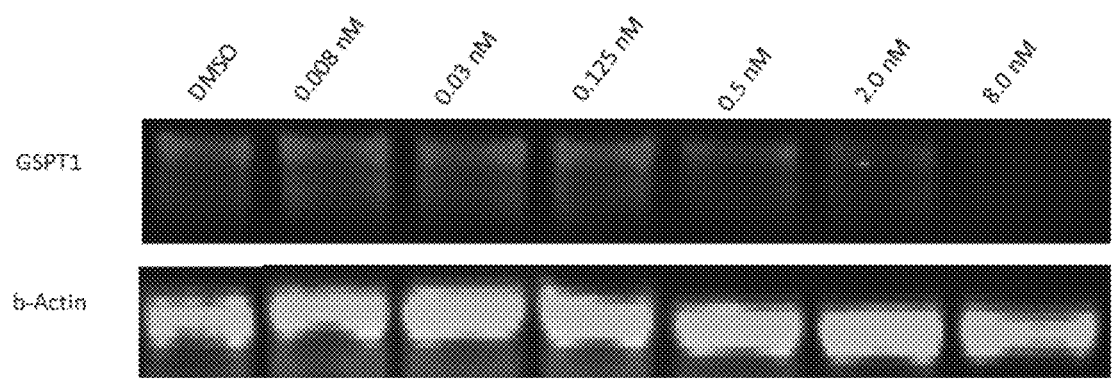
FIG. 11A shows the result of a Western Blot analysis of Molm-13 cells treated with Control (DMSO only), or the indicated concentration of Compound 9. Cells were lysed using RIPA Buffer (Pierce) and a Western Blot analysis was performed using anti-GSPT1 and anti-β-actin antibodies.
Figure 11B:
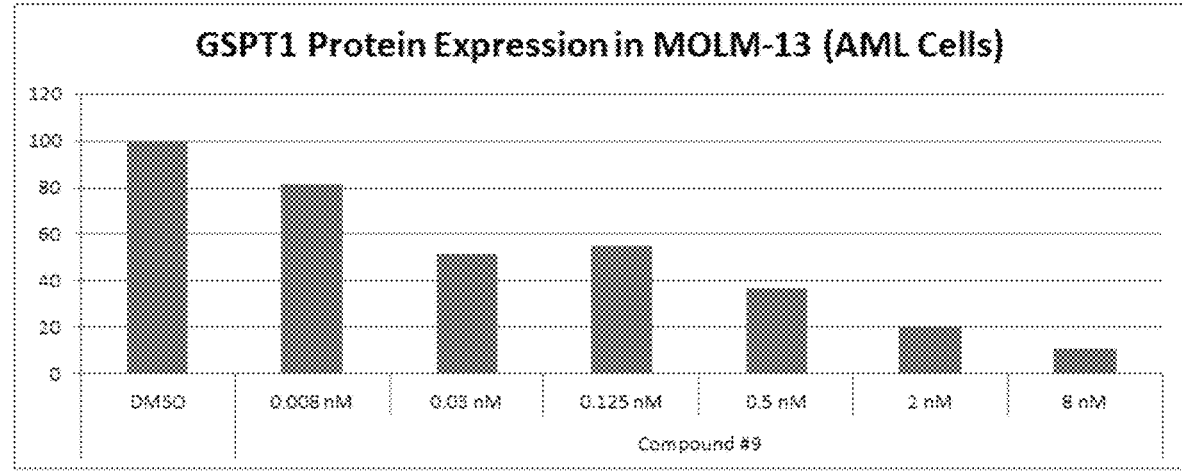
FIG. 11B is a graph showing the expression levels of GSPT1 protein in Molm-13 (AML) cells. Protein expression levels were measured using the LiCor Odyssey instrumentation and methods.

Compound 9 reduced cell viability in H1048 cells at an $IC_{50}$ concentration of 0.5 nM (FIG. 10A) and in Molm-13 at an approximate $IC_{50}$ concentration of 3 nM (FIG. 10B). Cell viability data for additional compounds are shown in Tables 4-8.

TABLE 4

H1048 Cell Viability at 1 µM Compound Concentration

| Compound No. | Cell Viability |
|---|---|
| DMSO | 100.00 |
| 9 | 7.50 |
| 30 | 8.55 |
| 31 | 84.29 |
| 32 | 10.62 |
| 33 | 8.76 |
| 34 | 12.95 |
| 35 | 15.49 |
| 36 | 10.64 |
| 37 | 55.04 |
| 38 | 8.35 |
| 39 | 58.32 |
| 40 | 12.95 |
| 41 | 9.42 |
| 42 | 8.70 |
| 43 | 7.97 |
| 44 | 13.82 |
| 45 | 12.70 |
| 46 | 9.35 |
| 47 | 8.91 |
| 48 | 9.03 |
| 49 | 7.67 |
| 50 | 15.83 |
| 51 | 94.94 |
| 52 | 9.22 |
| 53 | 8.51 |
| 54 | 8.11 |
| 55 | 7.63 |
| 56 | 29.12 |
| 57 | 12.36 |

TABLE 5

H1048 Cell Viability at 10 µM Compound Concentration

| Compound No. | Cell Viability |
|---|---|
| DMSO | 100.00 |
| 9 | 7.93 |
| 30 | 8.34 |
| 31 | 26.82 |
| 32 | 10.77 |
| 33 | 8.21 |
| 34 | 8.34 |
| 35 | 12.40 |
| 36 | 7.51 |
| 37 | 10.48 |
| 38 | 7.89 |
| 39 | 19.88 |

TABLE 5-continued

H1048 Cell Viability at 10 μM Compound Concentration

| Compound No. | Cell Viability |
|---|---|
| 40 | 13.64 |
| 41 | 9.37 |
| 42 | 8.68 |
| 43 | 7.63 |
| 44 | 14.28 |
| 45 | 9.89 |
| 46 | 11.46 |
| 47 | 8.58 |
| 48 | 6.89 |
| 49 | 6.10 |
| 50 | 13.40 |
| 52 | 10.30 |
| 51 | 24.09 |
| 53 | 8.09 |
| 54 | 6.12 |
| 55 | 7.94 |
| 56 | 26.33 |
| 57 | 8.70 |

TABLE 6

MOLM-13 Cell Viability at Indicated Compound Concentrations

| Compound No. | Concentration (μM) | % Inhibition |
|---|---|---|
| DMSO | 0.1% | 0 |
| 1 | 10 | 6 |
| 2 | 10 | 32 |
| 3 | 10 | 0 |
| 4 | 10 | 0 |
| 5 | 10 | 24 |
| 6 | 10 | 0 |
| 7 | 10 | 24 |
| 8 | 10 | 42 |
| 9 | 0.003 | 50 |
| 10 | 10 | 18 |
| 11 | 10 | 18 |
| 12 | 10 | 31 |
| 13 | 10 | 0 |
| 14 | 10 | 0 |
| 15 | 10 | 19 |
| 16 | 10 | 23 |
| 17 | 10 | 21 |
| 18 | 10 | 3 |
| 19 | 10 | 29 |
| 20 | 10 | 19 |
| 21 | 10 | 16 |
| 22 | 10 | 23 |
| 23 | 10 | 34 |
| 24 | 10 | 26 |
| 25 | 10 | 20 |
| 26 | 10 | 0 |
| 27 | 10 | 0 |
| 28 | 10 | 0 |
| 29 | 10 | 10 |
| 30 | 1 | 50 |
| 31 | 10 | 12 |
| 32 | 0.5 | 25 |
| 33 | 0.003 | 50 |
| 34 | 10 | 99 |
| 35 | 10 | 93 |
| 36 | 10 | 100 |
| 37 | 10 | 51 |
| 38 | 0.3 | 50 |
| 39 | 10 | 9 |
| 40 | 0.02 | 50 |
| 41 | 0.3 | 50 |
| 42 | 0.8 | 50 |
| 43 | 10 | 100 |
| 44 | 0.1 | 50 |
| 45 | 1 | 59 |
| 46 | 0.1 | 100 |
| 47 | 0.1 | 100 |
| 48 | 0.1 | 100 |
| 49 | 0.1 | 100 |
| 50 | 1 | 41 |
| 51 | 1 | 0 |
| 52 | 0.1 | 99 |
| 53 | 0.1 | 100 |
| 54 | 0.1 | 100 |
| 55 | 0.1 | 100 |
| 56 | 0.1 | 10 |
| 57 | 1 | 45 |
| 58 | 6 | 50 |
| 59 | 2.8 | 50 |
| 60 | 0.2 | 50 |
| 61 | 2.8 | 50 |
| 62 | 1 | 71 |
| 63 | >1* | 50 |
| 64 | 10 | 13 |

*predicted value

TABLE 7

MDA-MB-231 Cell Viability at 1 μM Compound Concentration

| Compound No. | Cell Viability |
|---|---|
| DMSO | 100.00 |
| 30 | 52.87 |
| 9 | 19.57 |
| 31 | 102.66 |
| 32 | 91.23 |
| 33 | 21.72 |
| 34 | 102.35 |
| 35 | 99.01 |
| 37 | 105.62 |
| 38 | 54.70 |
| 39 | 105.43 |
| 40 | 57.72 |
| 41 | 58.21 |
| 42 | 57.58 |
| 43 | 55.17 |
| 36 | 100.69 |
| 44 | 64.61 |
| 45 | 100.54 |
| 52 | 22.40 |
| 46 | 29.04 |
| 53 | 27.59 |
| 47 | 21.76 |
| 54 | 22.60 |
| 48 | 22.17 |
| 55 | 20.16 |
| 49 | 24.33 |
| 56 | 107.79 |
| 50 | 107.95 |
| 57 | 107.01 |
| 51 | 107.95 |

TABLE 8

MDA-MB-231 Cell Viability at 10 μM Compound Concentration

| Compound No. | Cell Viability |
|---|---|
| DMSO | 100.00 |
| 30 | 26.30 |
| 9 | 19.05 |
| 31 | 107.39 |
| 32 | 44.33 |
| 33 | 19.76 |
| 34 | 44.37 |
| 35 | 64.83 |
| 37 | 97.71 |

TABLE 8-continued

MDA-MB-231 Cell Viability at 10 μM Compound Concentration

| Compound No. | Cell Viability |
|---|---|
| 38 | 27.60 |
| 39 | 100.75 |
| 40 | 49.96 |
| 41 | 29.98 |
| 42 | 30.53 |
| 43 | 23.74 |
| 36 | 53.36 |
| 44 | 56.46 |
| 45 | 46.69 |
| 52 | 20.54 |
| 46 | 24.07 |
| 53 | 21.34 |
| 47 | 19.30 |
| 54 | 22.38 |
| 48 | 21.67 |
| 55 | 19.04 |
| 49 | 19.73 |
| 56 | 101.24 |
| 50 | 95.73 |
| 57 | 51.97 |
| 51 | 102.80 |

Pharmaceutical Compositions

Parenteral Pharmaceutical Composition

To prepare a parenteral pharmaceutical composition suitable for administration by injection (subcutaneous, intravenous, or the like), 0.1 mg to 100 mg of a water-soluble salt/soluble material itself/solubilized complex of a compound of a preferred embodiment is dissolved in sterile water and then mixed with 10 mL of 0.9% sterile saline. The mixture is incorporated into a dosage unit form suitable for administration by injection.

Injectable Pharmaceutical Composition

To prepare an injectable formulation, 0.1 mg to 100 mg of a compound of Formula II, 2.0 mL of NaOAc buffer solution (0.4 M), HCl (1 N) or NaOH (1 M) (q.s. to suitable pH), water (distilled, sterile) (q.s. to 20 mL) are mixed. All of the above ingredients, except water, are combined and stirred and if necessary, with slight heating if necessary. A sufficient quantity of water is then added.

Oral Pharmaceutical Composition

To prepare a pharmaceutical composition for oral delivery, 0.1 mg to 100 mg of a compound of a preferred embodiment is mixed with 750 mg of starch. The mixture is incorporated into an oral dosage unit, such as a hard gelatin capsule, or 0.1 mg to 100 mg of compound is granulated with binder solution such as starch solution along with suitable diluents such as microcrystalline cellulose or like, disintegrants such as croscaramellose sodium, dry the resultant mixture and add lubricant and compress into tablet which is suitable for oral administration.

Sublingual (Hard Lozenge) Pharmaceutical Composition

To prepare a pharmaceutical composition for buccal delivery, such as a hard lozenge, 0.1 mg to 100 mg of a compound of a preferred embodiment is mixed with 420 mg of powdered sugar/mannitol/xylitol or such sugars that provide negative heat of solution to the system, 1.6 mL of light corn syrup, 2.4 mL distilled water, and 0.42 mL mint extract or other flavorants. The mixture is blended and poured into a mold to form a lozenge suitable for buccal administration.

Fast-Disintegrating Sublingual Tablet

A fast-disintegrating sublingual tablet is prepared by mixing 48.5% by weigh of a compound of a preferred embodiment, 20% by weight of microcrystalline cellulose (KG-802), 24.5% by weight of either mannitol or modified dextrose or combination that help dissolve the compressed tablet faster in the mouth, 5% by weight of low-substituted hydroxypropyl cellulose (50 μM), and 2% by weight of magnesium stearate. Tablets are prepared by direct compression (AAPS PharmSciTech. 2006; 7(2):E41). The total weight of the compressed tablets is maintained at 150 mg. The formulation is prepared by mixing the amount of the compound of a preferred embodiment with the total quantity of microcrystalline cellulose (MCC) and mannitol/modified dextrose or combination, and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Inhalation Pharmaceutical Composition

To prepare a pharmaceutical composition for inhalation delivery, 0.1 mg to 100 mg of a compound of a preferred embodiment is mixed with 50 mg of anhydrous citric acid and 100 mL of 0.9% aq. NaCl. The mixture is incorporated into an inhalation delivery unit, such as a nebulizer, which is suitable for inhalation administration.

Nebulizer Suspension Pharmaceutical Composition

In another embodiment, a compound of a preferred embodiment (0.1 mg to 100 mg) is suspended in sterile water (100 mL); Span 85 (1 g) is added followed by addition of dextrose (5.5 g) and ascorbic acid (10 mg). Benzalkonium chloride (3 mL of a 1:750 aqueous solution) is added and the pH is adjusted to 7 with phosphate buffer. The suspension is packaged in sterile nebulizers.

Transdermal Patch Pharmaceutical Composition

To prepare a pharmaceutical composition for transdermal delivery, 0.1 mg to 100 mg of a compound of a preferred embodiment is embedded in, or deposited on, a patch with a single adhesive face. The resulting patch is then attached to the skin via the adhesive face for transdermal administration.

Topical Gel Pharmaceutical Composition

To prepare a pharmaceutical topical gel composition, 0.1 mg to 100 mg of a compound of a preferred embodiment is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution

To prepare a pharmaceutical ophthalmic solution composition, 0.1 mg to 100 mg of a compound of a preferred embodiment is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 0.1 mg to 100 mg of a compound of a preferred embodiment is mixed with 30 mL of a 0.05M phosphate buffer solution (pH 4.4). The solution is placed in a nasal administrator designed to deliver 100 μl of spray for each application.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Moreover, any one of the above described embodiments can be used alone or in combination with any one or more of the above described embodiments. Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of treating cancer associated with a cytokine, aiolos, ikaros, helios, CKla, or GSPT1, comprising administering a compound of Formula (IIa) or a pharmaceutically acceptable salt thereof to a subject in need thereof,

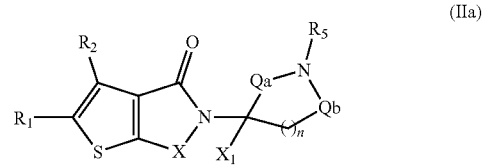

(IIa)

wherein:
$R_1$ and $R_2$ are each independently H, deuterium, hydroxyl, halogen, cyano, nitro, optionally substituted amino, optionally substituted $C_1$-$C_6$ alkoxy, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_6$-$C_{10}$ aryl, optionally substituted 3 to 10-membered heterocyclyl, or optionally substituted 5 to 10-membered heteroaryl; or one of $R_1$ and $R_2$ is H, deuterium, hydroxyl, halogen, cyano, nitro, optionally substituted amino, optionally substituted $C_1$-$C_6$ alkoxy, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_6$-$C_{10}$ aryl, optionally substituted 3 to 10-membered

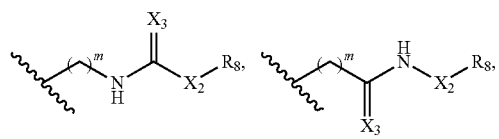

heterocyclyl, optionally substituted 5 to 10-membered heteroaryl, or L-Y; and the other of $R_1$ and $R_2$ is optionally substituted $C_3$-$C_8$ cycloalkyl, optionally substituted $C_6$-$C_{10}$ aryl, optionally substituted 3 to 10-membered heterocyclyl, optionally substituted 5 to 10-membered heteroaryl, or L-Y;

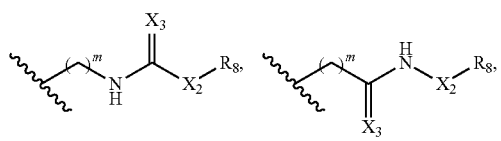

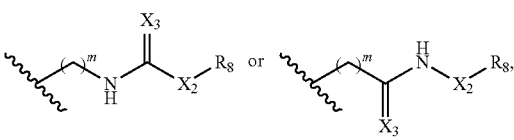

provided that when one of $R_1$ and R2 is then the other $R_1$ and $_{R2}$ is not L-Y;

$R_5$ is H, deuterium, or optionally substituted $C_1$-$C_6$ alkyl;

n is 2 or 3;

each of Qa and Qb is independently C=O, C=S, or $CH_2$;

X is $CH_2$ or C(=O);

$X_1$ is H, deuterium, halogen, or optionally substituted $C_1$-$C_6$ alkyl;

m is 1, 2, 3, 4, or 5;

$X_2$ is $(CH_2)_a$, C=O, NH, or N—(optionally substituted $C_1$-$C_6$ alkyl);

$X_3$ is 0, $NI_2$ or S;

a is 0, 1, 2, 3, 4, 5, 6, 7, 8, 9, or 10;

$R_8$ is optionally substituted $C_3$-$C_{10}$ cycloalkyl, optionally substituted $C_6$-$C_{10}$ aryl, optionally substituted 5 to 10-membered heteroaryl, optionally substituted 3 to 10-membered heterocyclyl, optionally substituted $C_3$-$C_{10}$ cycloalkyl($C_1$-$C_6$ alkyl), optionally substituted $C_6$-$C_{10}$ aryl($C_1$-$_{C6}$ alkyl), optionally substituted 5 to 10 membered heteroaryl($C_1$-$C_6$ alkyl), or optionally substituted 3 to 10 membered heterocyclyl($C_1$-$C_6$ alkyl);

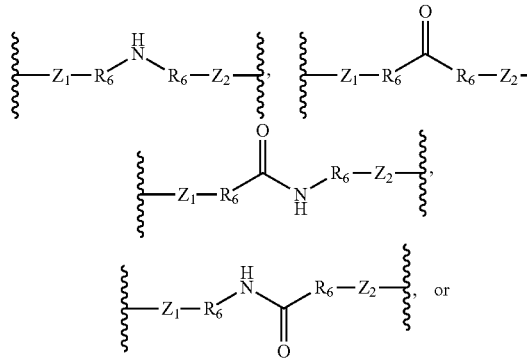

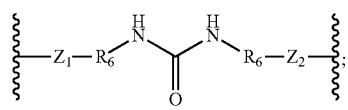

L is each $Z_1$ and $Z_2$ arc each is —$CH_2$-;

each $R_6$ is absent or independently absent or $C_1$-$C_6$ alkyl; and each Y is independently selected from a group consisting of

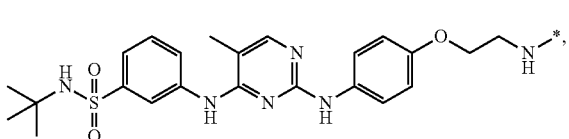

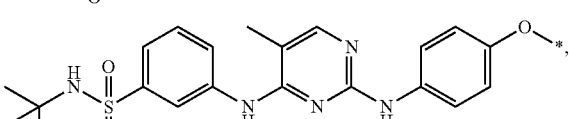

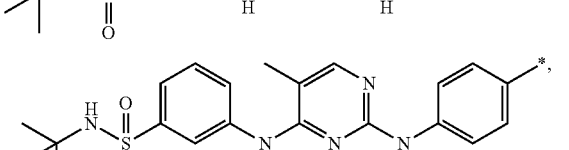

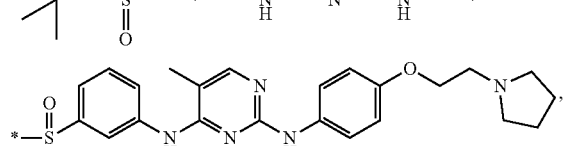

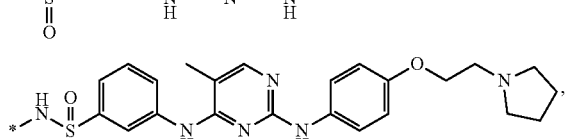

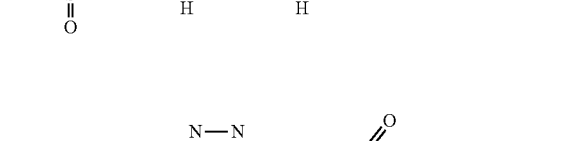

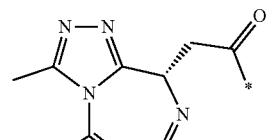

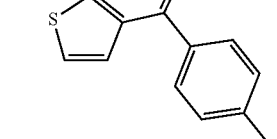

-continued

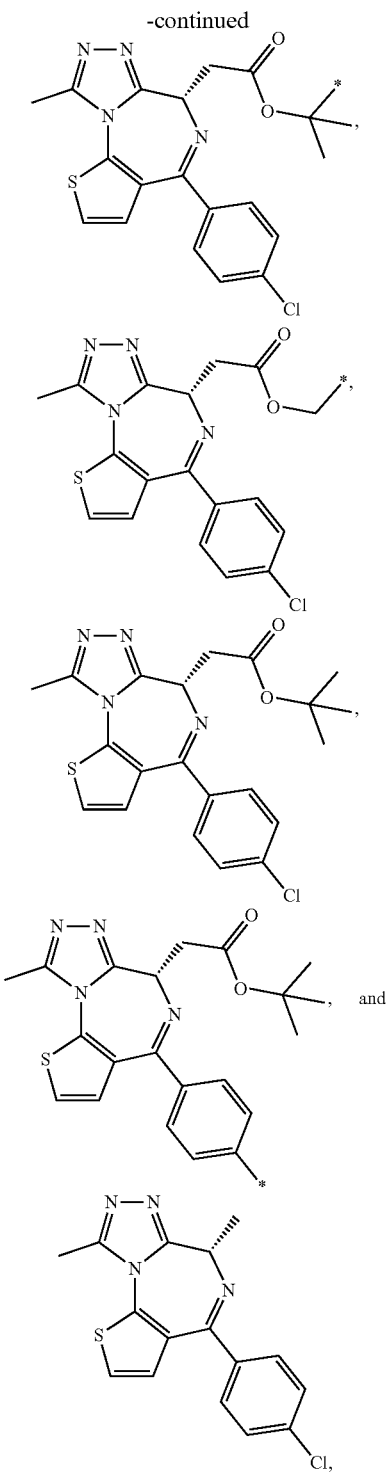

wherein * represents the point of attachment to L.

2. The method of claim 1, wherein n is 2; $X_1$ is H; $R_5$ is H; and Qa and Qb are each C=O.

3. The method of claim 2, wherein one of $R_1$ and $R_2$ is hydrogen and the other of $R_1$ and $R_2$ is optionally substituted $C_1$-$C_6$ alkyl or optionally substituted $C_3$-$C_8$ cycloalkyl.

4. The method of claim 2, wherein one of $R_1$ and R2 is optionally substituted $C_1$-$C_6$ alkyl or H; and the other of $R_1$ and $R_2$ is chloro, bromo, nitro, cyano, or optionally substituted amino.

5. The method of claim 1, wherein the cancer is leukemia, lymphoma, multiple myeloma, breast cancer, or lung cancer.

6. A method of treating cancer associated with a cytokine, aiolos, ikaros, helios, CK1α, or GSPT1, comprising administering a compound of Formula (IIb), or a pharmaceutically acceptable salt thereof to a subject in need thereof, (IIb)

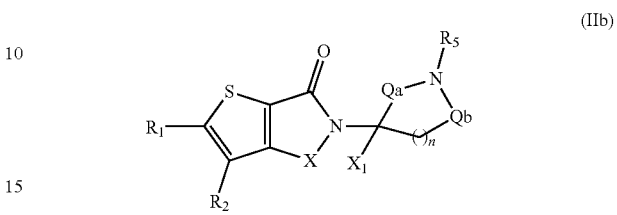

wherein:
one of $R_1$ and $R_2$ is H, deuterium, hydroxyl, halogen, cyano, nitro, optionally substituted amino, optionally substituted $C_1$-$C_6$ alkoxy, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_6$-$C_{10}$ aryl, optionally substituted 3 to 10-membered

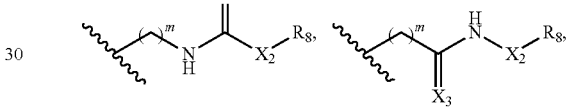

heterocyclyl, optionally substituted 5 to 10-membered heteroaryl, or L-Y; and
the other of $R_1$ and $R_2$ is optionally substituted $C_3$-$C_8$ cycloalkyl, optionally substituted $C_6$-$C_{10}$ aryl, optionally substituted 3 to 10-membered heterocyclyl, optionally substituted 5 to 10-membered heteroaryl, or L-Y;

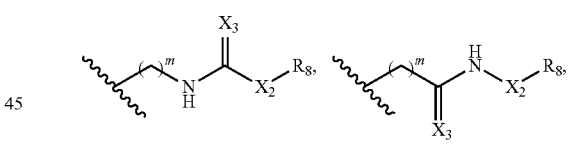

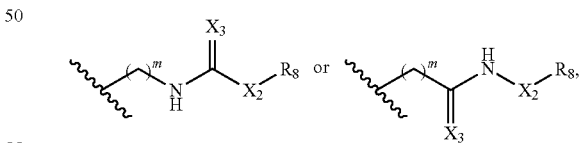

provided that when one of $R_1$ and $R_2$ is then the other $R_1$ and $R_2$ is not L-Y;
$R_5$ is H, deuterium, or optionally substituted $C_1$-$C_6$ alkyl;
n is 2 or 3;
each of Qa and Qb is independently C=O, C=S, or $CH_2$;
X is $CH_2$ or C(=O);
$X_1$ is H, deuterium, halogen, or optionally substituted $C_1$-$C_6$ alkyl;
m is 1, 2, 3, 4, or 5;
$X_2$ is $(CH_2)\alpha$, C=O, NH, or N—(optionally substituted $C_1$-$C_6$ alkyl);

X$_3$ is O, NH, or S;

a is 0, 1, 2, 3, 4, 5, 6, 7, 8, 9, or 10;

R$_8$ is optionally substituted C$_3$-C$_{10}$ cycloalkyl, optionally substituted C$_6$-C$_{10}$ aryl, optionally substituted 5 to 10-membered heteroaryl, optionally substituted 3 to 10-membered heterocyclyl, optionally substituted C$_3$-C$_{10}$ cycloalkyl(C$_1$-C$_6$ alkyl), optionally substituted C$_6$-C$_{10}$ aryl(C$_1$-C$_6$ alkyl), optionally substituted 5 to 10 membered heteroaryl(C$_1$-C$_6$ alkyl), or optionally substituted 3 to 10 membered heterocyclyl(C$_1$-C$_6$ alkyl);

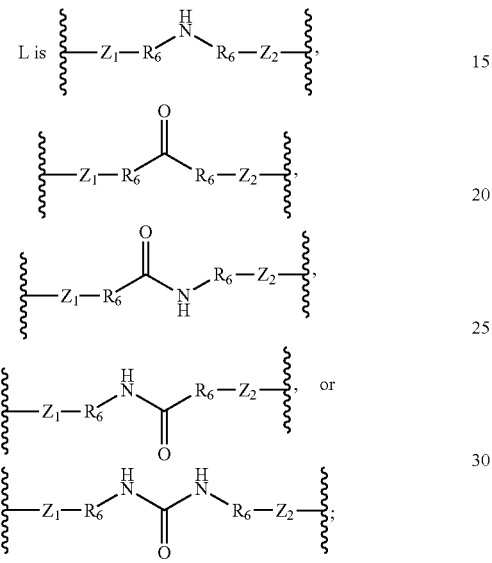

each Z$_1$ and Z$_2$ are each is CH$_2$—;

each R$_6$ is independently absent or C$_1$-C$_6$ alkyl; and each Y is independently selected from a group consisting of

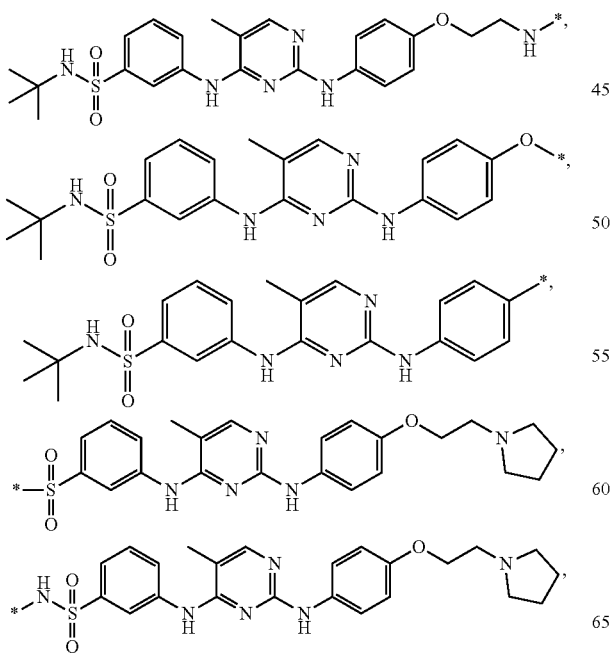

-continued

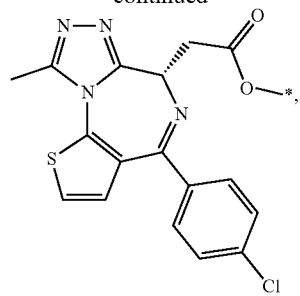

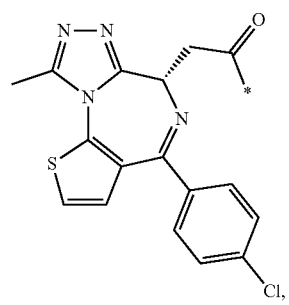

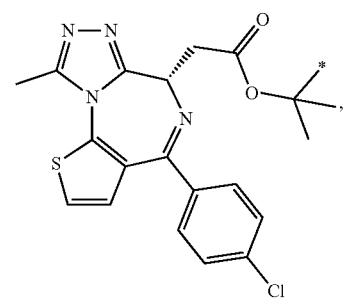

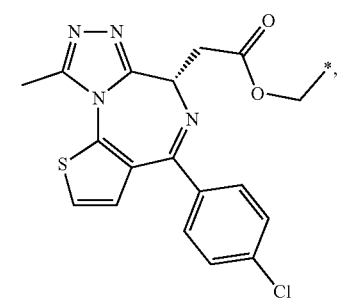

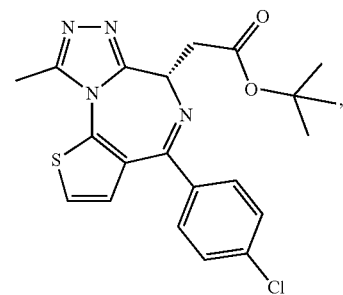

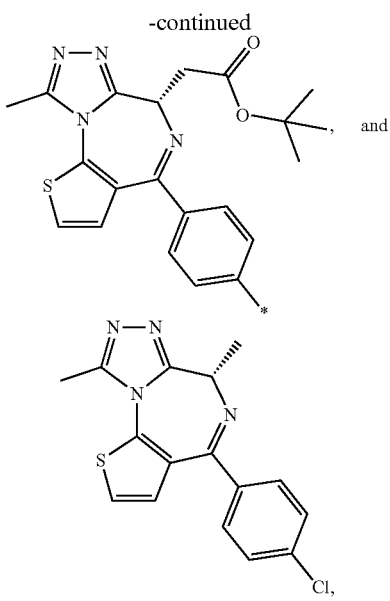

wherein * represents the point of attachment to the L group.

7. The method of claim 6, wherein n is 2; $X_1$ is H; $R_5$ is H; and Qa and Qb are each C=O.

8. The method of claim 7, wherein one of $R_1$ and $R_2$ is

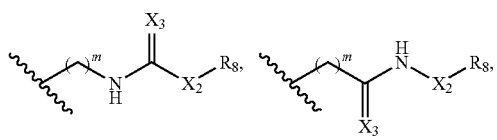

hydrogen and the other $R_1$ and $R_2$ is or L-Y.

9. The method of claim 7, wherein $R_1$ is

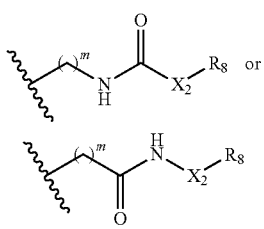

and $R_2$ is H.

10. The method of claim 9, wherein $R_1$ is and X2 is NH.

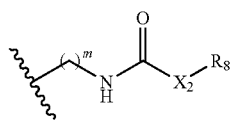

11. The method of claim 10, wherein $R_8$ is a phenyl group substituted with one or more substituents, each of which is independently selected from the group consisting of halogen, unsubstituted $C_1$-$C_6$ alkyl, $C_1$-$C_3$ alkoxy, and unsubstituted di($C_1$-$C_3$ alkyl)amino; or a 5-6 membered heteroaryl group substituted with one or more substituents each of which is independently selected from the group consisting of halogen, unsubstituted $C_1$-$C_6$ alkyl, $C_1$-$C_3$ alkoxy, and unsubstituted di($C_1$-$C_3$ alkyl)amino.

12. The method of claim 11, wherein $R_8$ is a phenyl group substituted with unsubstituted $C_1$-$C_6$ alkyl and halogen, a phenyl group substituted with unsubstituted $C_1$-$C_6$ alkyl and unsubstituted $C_1$-$C_3$ alkoxy, a phenyl group substituted with unsubstituted $C_1$-$C_3$ alkoxy and halogen, a phenyl group substituted with unsubstituted $C_1$-$C_6$ alkyl and unsubstituted di($C_1$-$C_3$ alkyl)amino, or a phenyl group substituted with unsubstituted di($C_1$-$C_3$ alkyl)amino and halogen.

13. The method of claim 7, wherein $R_1$ is L-Y and $R_2$ is H.

14. The method of claim 13, wherein L is

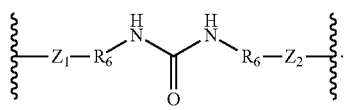

15. The method of claim 7, wherein one of $R_1$ and $R_2$ is hydrogen and the other of $R_1$ and $R_2$ is optionally substituted $C_3$-$C_8$ cycloalkyl.

16. The method of claim 6, wherein the cancer is leukemia, lymphoma, multiple myeloma, breast cancer, or lung cancer.

17. A method of treating cancer associated with a cytokine, aiolos, ikaros, helios, CK1a, or GSPT1, comprising administering a compound of Formula (IIc) or a pharmaceutically acceptable salt thereof to a subject in need thereof,

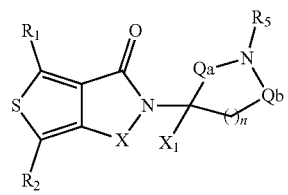

(IIc)

wherein:
one of $R_1$ and $R_2$ is H, deuterium, hydroxyl, halogen, cyano, nitro, optionally substituted amino, optionally substituted $C_1$-$C_6$ alkoxy, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_6$-$C_{10}$ aryl, optionally substituted 3 to 10-membered

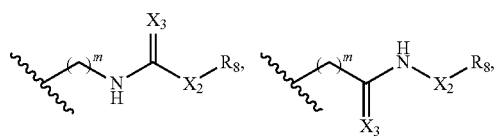

heterocyclyl, optionally substituted 5 to 10-membered heteroaryl, or L-Y; and
the other of $R_1$ and $R_2$ is optionally substituted $C_3$-$C_8$ cycloalkyl, optionally substituted $C_6$-$C_{10}$ aryl, optionally substituted 3 to 10-membered heterocyclyl, optionally substituted 5 to 10-membered heteroaryl, or L-Y;

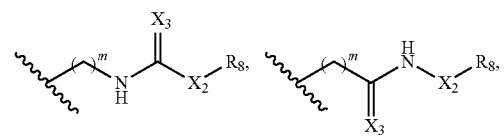

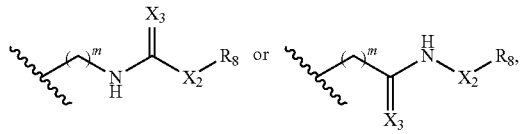

provided that when one of R₁ and R₂ is then the other R₁ and R₂ is not L-Y;
R$_5$ is H, deuterium, or optionally substituted C$_1$-C$_6$ alkyl;
n is 2 or 3;
each of Qa and Qb is independently C=O, C=S, or CH$_2$;
X is CH$_2$ or C(=O);
X$_1$ is H, deuterium, halogen, or optionally substituted C$_1$-C$_6$ alkyl;
m is 1, 2, 3, 4, or 5;
X$_2$ is (CH$_2$)$_a$, C=0, NH, or N—(optionally substituted C$_1$-C$_6$ alkyl);
X$_3$ is O, NH, or S;
a is 0, 1, 2, 3, 4, 5, 6, 7, 8, 9, or 10;
R$_8$ is optionally substituted C$_3$-C$_{10}$ cycloalkyl, optionally substituted C$_6$-C$_{10}$ aryl, optionally substituted 5 to 10-membered heteroaryl, optionally substituted 3 to 10-membered heterocyclyl, optionally substituted C$_3$-C$_{10}$ cycloalkyl(C$_1$-C$_6$ alkyl), optionally substituted C$_6$-C$_{10}$ aryl(C$_1$-C$_6$ alkyl), optionally substituted 5 to 10 membered heteroaryl(C$_1$-C$_6$ alkyl), or optionally substituted 3 to 10 membered heterocyclyl(C$_1$-C$_6$ alkyl);

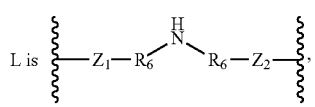

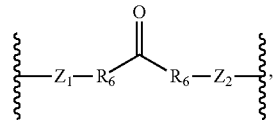

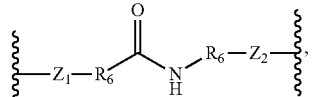

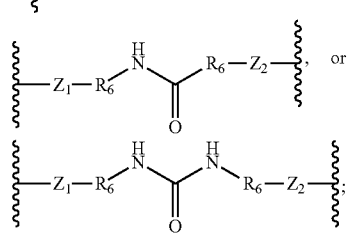

each Z$_1$ and Z$_2$ is —CH$_2$—;
each R$_6$ is independently absent or C$_1$-C$_6$ alkyl; and
each Y is independently selected from a group consisting of wherein * represents the point of attachment to the L group.

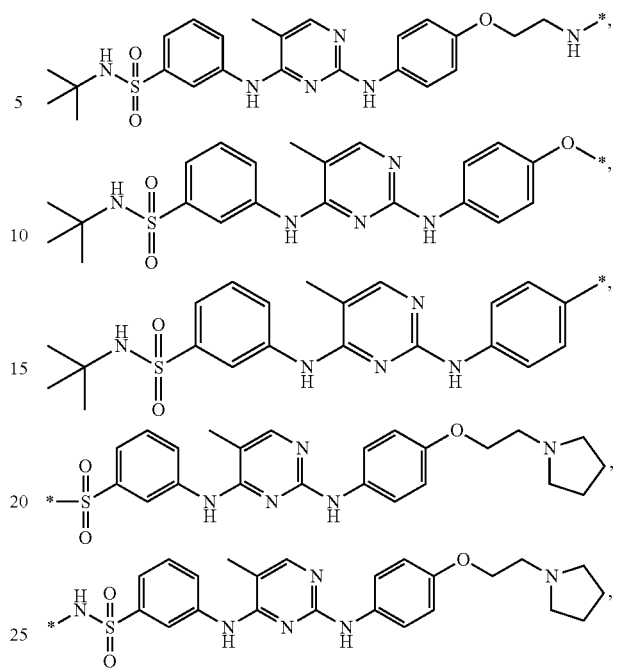

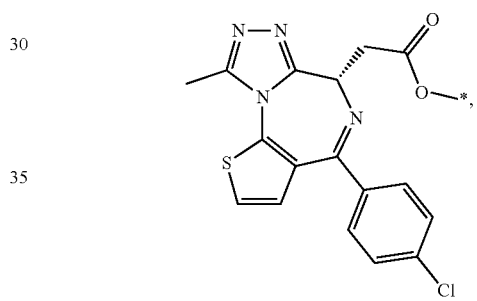

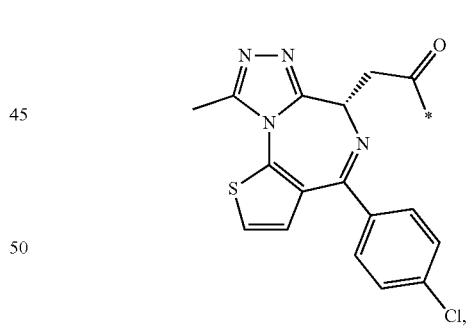

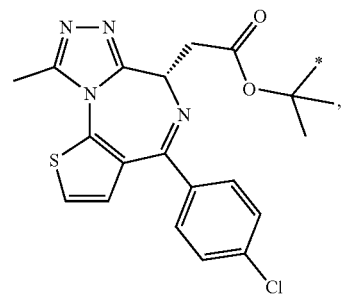

-continued

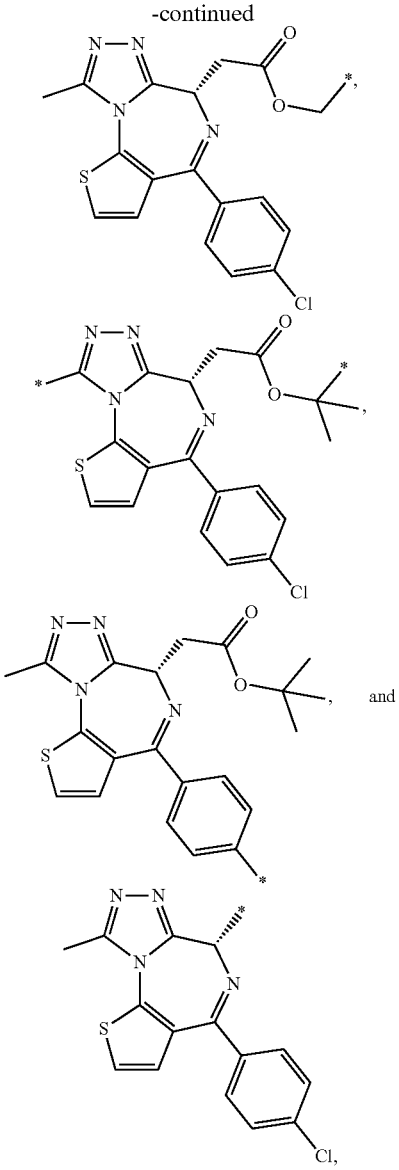

18. The method of claim 17, wherein n is 2; $X^1$ is H; $R_5$ is H; and Qa and Qb are each C=O.

19. The method of claim 18, wherein one of $R_1$ and $R_2$ is

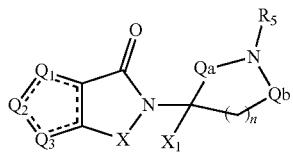
(II)

hydrogen, and the other $R_1$ and $R_2$ is L-Y.

20. The method of claim 18, wherein $R_1$ is H and $R_2$ is

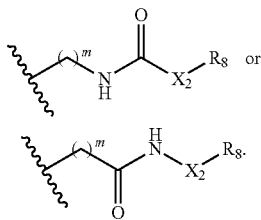

21. The method of claim 20, wherein $R_2$ is

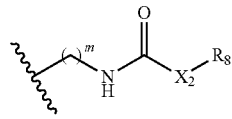

and $X_2$ is NH.

22. The method of claim 21, wherein $R_8$ is a phenyl group substituted with one or more substituents, each of which is independently selected from the group consisting of halogen, unsubstituted $C_1$-$C_6$ alkyl, $C_1$-$C_3$ alkoxy, and unsubstituted di($C_1$-$C_3$ alkyl)amino; or a 5-6 membered heteroaryl group substituted with one or more substituents each of which is independently selected from the group consisting of halogen, unsubstituted $C_1$-$C_6$ alkyl, $C_1$-$C_3$ alkoxy, and unsubstituted di($C_1$-$C_3$ alkyl)amino.

23. The method of claim 22, wherein $R_8$ is a phenyl group substituted with unsubstituted $C_1$-$C_6$ alkyl and halogen, a phenyl group substituted with unsubstituted $C_1$-$C_6$ alkyl and unsubstituted $C_1$-$C_3$ alkoxy, a phenyl group substituted with unsubstituted $C_1$-$C_3$ alkoxy and halogen, a phenyl group substituted with unsubstituted $C_1$-$C_6$ alkyl and unsubstituted di($C_1$-$C_3$ alkyl)amino, or a phenyl group substituted with unsubstituted di($C_1$-$C_3$ alkyl)amino and halogen.

24. The method of claim 18, wherein $R_1$ is H and $R_2$ is L-Y.

25. The method of claim 24, wherein L is

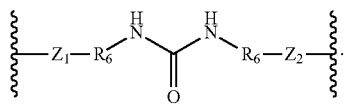

26. The method of claim 18, wherein one of $R_1$ and $R_2$ is hydrogen and the other of $R_1$ and $R_2$ is optionally substituted $C_3$-$C_8$ cycloalkyl.

27. The method of claim 17, wherein the cancer is leukemia, lymphoma, multiple myeloma, breast cancer, or lung cancer.

* * * * *